(12) United States Patent
Malandain et al.

(10) Patent No.: US 8,679,161 B2
(45) Date of Patent: Mar. 25, 2014

(54) PERCUTANEOUS SPINAL IMPLANTS AND METHODS

(75) Inventors: Hugues F. Malandain, Mountain View, CA (US); Janna G. Clark, Belmont, CA (US); Andrew C. Kohm, Burlingame, CA (US)

(73) Assignee: Warsaw Orthopedic, Inc., Warsaw, IN (US)

(*) Notice: Subject to any disclaimer, the term of this patent is extended or adjusted under 35 U.S.C. 154(b) by 1370 days.

(21) Appl. No.: 11/929,165

(22) Filed: Oct. 30, 2007

(65) Prior Publication Data

US 2008/0051906 A1 Feb. 28, 2008

Related U.S. Application Data

(63) Continuation of application No. 11/752,981, filed on May 24, 2007, which is a continuation-in-part of application No. 11/356,302, filed on Feb. 17, 2006, now Pat. No. 7,988,709, and a continuation-in-part of application No. 11/252,879, filed on Oct. 19, 2005, now Pat. No. 8,038,698, and a continuation-in-part of application No. 11/252,880, filed on Oct. 19, 2005, now abandoned, which is a continuation-in-part of application No. 11/059,526, filed on Feb. 17, 2005, now abandoned, said application No. 11/252,879 is a continuation-in-part of application No. 11/059,526, filed on Feb. 17, 2005, now abandoned, said application No. 11/752,981 is a continuation-in-part of application No. 11/356,301, filed on Feb. 17, 2006, now Pat. No. 8,057,513, and a continuation-in-part of application No. 11/252,879, filed on Oct. 19, 2005, now Pat. No. 8,038,698, and a continuation-in-part of application No. 11/252,880, filed on Oct. 19, 2005, now abandoned, which is a continuation-in-part of application No. 11/059,526, filed on Feb. 17, 2005, now abandoned, said application No. 11/252,879 is a continuation-in-part of application No. 11/059,526, filed on Feb. 17, 2005, now abandoned, said application No. 11/752,981 is a continuation-in-part of application No. 11/693,496, filed on Mar. 29, 2007, now Pat. No. 8,096,994, which is a continuation-in-part of application No. 11/454,153, filed on Jun. 16, 2006, now Pat. No. 7,993,342, which is a continuation-in-part of application No. PCT/US2006/005580, filed on Feb. 17, 2006, and a continuation-in-part of application No. 11/059,526, filed on Feb. 17, 2005, now abandoned, and a continuation-in-part of application No. 11/252,879, filed on Oct. 19, 2005, now Pat. No. 8,038,698, said application No. 11/454,153 is a continuation-in-part of application No. 11/252,880, filed on Oct. 19, 2005, now abandoned.

(60) Provisional application No. 60/695,836, filed on Jul. 1, 2005.

(51) Int. Cl.
*A61B 17/70* (2006.01)
*A61F 2/44* (2006.01)

(52) U.S. Cl.
USPC ............................................ 606/249; 623/17.13

(58) Field of Classification Search
USPC ......... 606/246, 248, 249, 75, 324; 623/17.11, 623/17.16, 17.13; 411/341–343
See application file for complete search history.

(56) References Cited

U.S. PATENT DOCUMENTS 624,969 A 5/1899 Peterson
(Continued)

FOREIGN PATENT DOCUMENTS

DE 2821678 A1 11/1979
(Continued)

OTHER PUBLICATIONS

Anasetti et al., "Spine Stability After Implantation of an Interspinous Device: an In Vitro and Finite Element Biomechanical Study," J. Neurosurg. Spine, Nov. 2010, vol. 13, pp. 568-575.
(Continued)

*Primary Examiner* — Michael T Schaper

(57) ABSTRACT

An apparatus includes a support member and a retention member. The support member has at least a portion configured to be disposed between a first spinous process and a second spinous process. The retention member is movably coupled to an end portion of the support member. The retention member is configured to displace a bodily tissue. The retention member is configured to move relative to the support member from a first position to a second position. The retention member is configured to limit movement of the support member along the longitudinal axis and relative to the first spinous process and the second spinous process when in the second position.

17 Claims, 79 Drawing Sheets

(56) References Cited

U.S. PATENT DOCUMENTS

| | | | |
|---|---|---|---|
| 1,153,797 | A | 9/1915 | Kegreisz |
| 1,516,347 | A | 11/1924 | Pataky |
| 1,870,942 | A | 8/1932 | Beatty |
| 2,077,804 | A | 4/1937 | Morrison |
| 2,299,308 | A | 10/1942 | Creighton |
| 2,485,531 | A | 10/1949 | Dzus et al. |
| 2,607,370 | A | 8/1952 | Anderson |
| 2,677,369 | A | 5/1954 | Knowles |
| 2,685,877 | A | 8/1954 | Dobelle |
| 3,065,659 | A | 11/1962 | Eriksson et al. |
| 3,108,595 | A | 10/1963 | Overment |
| 3,397,699 | A | 8/1968 | Kohl |
| 3,426,364 | A | 2/1969 | Lumb |
| 3,648,691 | A | 3/1972 | Lumb et al. |
| 3,779,239 | A | 12/1973 | Fischer et al. |
| 3,807,394 | A * | 4/1974 | Attenborough ............... 606/60 |
| 4,011,602 | A | 3/1977 | Rybicki et al. |
| 4,237,875 | A | 12/1980 | Termanini |
| 4,245,545 | A * | 1/1981 | Freeman ..................... 411/342 |
| 4,257,409 | A | 3/1981 | Bacal et al. |
| 4,274,324 | A | 6/1981 | Giannuzzi |
| 4,289,123 | A | 9/1981 | Dunn |
| 4,327,736 | A | 5/1982 | Inoue |
| 4,401,112 | A | 8/1983 | Rezaian |
| 4,499,636 | A | 2/1985 | Tanaka |
| 4,519,100 | A | 5/1985 | Wills et al. |
| 4,553,273 | A | 11/1985 | Wu |
| 4,554,914 | A | 11/1985 | Kapp et al. |
| 4,573,454 | A | 3/1986 | Hoffman |
| 4,592,341 | A | 6/1986 | Omagari et al. |
| 4,599,086 | A | 7/1986 | Doty |
| 4,604,995 | A | 8/1986 | Stephens et al. |
| 4,611,582 | A | 9/1986 | Duff |
| 4,632,101 | A | 12/1986 | Freedland |
| 4,636,217 | A | 1/1987 | Ogilvie et al. |
| 4,646,998 | A | 3/1987 | Pate |
| 4,657,550 | A | 4/1987 | Daher |
| 4,662,808 | A | 5/1987 | Camilleri |
| 4,686,970 | A | 8/1987 | Dove et al. |
| 4,704,057 | A | 11/1987 | McSherry |
| 4,721,103 | A | 1/1988 | Freedland |
| 4,759,769 | A | 7/1988 | Hedman et al. |
| 4,787,378 | A | 11/1988 | Sodhi |
| 4,822,226 | A | 4/1989 | Kennedy |
| 4,827,918 | A | 5/1989 | Olerud |
| 4,834,600 | A | 5/1989 | Lemke |
| 4,863,476 | A | 9/1989 | Shepperd |
| 4,886,405 | A | 12/1989 | Blomberg |
| 4,892,545 | A | 1/1990 | Day et al. |
| 4,913,144 | A | 4/1990 | Del Medico |
| 4,931,055 | A | 6/1990 | Bumpus et al. |
| 4,932,975 | A | 6/1990 | Main et al. |
| 4,969,887 | A | 11/1990 | Sodhi |
| 5,000,166 | A | 3/1991 | Karpf |
| 5,011,484 | A | 4/1991 | Breard |
| 5,035,712 | A | 7/1991 | Hoffman |
| 5,047,055 | A | 9/1991 | Bao et al. |
| 5,059,193 | A | 10/1991 | Kuslich |
| 5,092,866 | A | 3/1992 | Breard et al. |
| 5,098,433 | A * | 3/1992 | Freedland ..................... 606/63 |
| 5,171,278 | A | 12/1992 | Pisharodi |
| 5,201,734 | A | 4/1993 | Cozad et al. |
| 5,267,999 | A | 12/1993 | Olerud |
| 5,290,312 | A | 3/1994 | Kojimoto et al. |
| 5,306,275 | A | 4/1994 | Bryan |
| 5,306,310 | A | 4/1994 | Siebels |
| 5,312,405 | A | 5/1994 | Korotko et al. |
| 5,316,422 | A | 5/1994 | Coffman |
| 5,356,423 | A | 10/1994 | Tihon et al. |
| 5,360,430 | A | 11/1994 | Lin |
| 5,366,455 | A | 11/1994 | Dove |
| 5,370,697 | A | 12/1994 | Baumgartner |
| 5,390,683 | A | 2/1995 | Pisharodi |
| 5,395,370 | A | 3/1995 | Muller et al. |
| 5,401,269 | A | 3/1995 | Buttner-Janz et al. |
| 5,403,316 | A | 4/1995 | Ashman |
| 5,415,661 | A | 5/1995 | Holmes |
| 5,437,672 | A | 8/1995 | Alleyne |
| 5,437,674 | A | 8/1995 | Worcel et al. |
| 5,439,463 | A | 8/1995 | Lin |
| 5,454,812 | A | 10/1995 | Lin |
| 5,456,689 | A | 10/1995 | Kresch et al. |
| 5,458,641 | A | 10/1995 | Ramirez Jimenez |
| 5,480,442 | A | 1/1996 | Bertagnoli |
| 5,496,318 | A | 3/1996 | Howland et al. |
| 5,518,498 | A | 5/1996 | Lindenberg et al. |
| 5,540,689 | A | 7/1996 | Sanders et al. |
| 5,554,191 | A | 9/1996 | Lahille et al. |
| 5,562,662 | A | 10/1996 | Brumfield et al. |
| 5,562,735 | A | 10/1996 | Margulies |
| 5,571,192 | A | 11/1996 | Schonhoffer |
| 5,609,634 | A | 3/1997 | Voydeville |
| 5,609,635 | A | 3/1997 | Michelson |
| 5,628,756 | A | 5/1997 | Barker, Jr. et al. |
| 5,630,816 | A | 5/1997 | Kambin |
| 5,645,599 | A | 7/1997 | Samani |
| 5,653,762 | A | 8/1997 | Pisharodi |
| 5,653,763 | A | 8/1997 | Errico et al. |
| 5,658,335 | A | 8/1997 | Allen |
| 5,665,122 | A | 9/1997 | Kambin |
| 5,674,295 | A | 10/1997 | Ray et al. |
| 5,676,702 | A | 10/1997 | Ratron |
| 5,685,826 | A | 11/1997 | Bonutti |
| 5,690,649 | A | 11/1997 | Li |
| 5,693,100 | A | 12/1997 | Pisharodi |
| 5,702,391 | A | 12/1997 | Lin |
| 5,702,395 | A | 12/1997 | Hopf |
| 5,702,452 | A | 12/1997 | Argenson et al. |
| 5,702,455 | A | 12/1997 | Saggar |
| 5,707,390 | A | 1/1998 | Bonutti |
| 5,716,416 | A | 2/1998 | Lin |
| 5,723,013 | A | 3/1998 | Jeanson et al. |
| 5,725,341 | A | 3/1998 | Hofmeister |
| 5,746,762 | A | 5/1998 | Bass |
| 5,749,916 | A | 5/1998 | Richelsoph |
| 5,755,797 | A | 5/1998 | Baumgartner |
| 5,800,547 | A | 9/1998 | Schafer et al. |
| 5,810,815 | A | 9/1998 | Morales |
| 5,836,948 | A | 11/1998 | Zucherman et al. |
| 5,849,004 | A | 12/1998 | Bramlet |
| 5,860,977 | A | 1/1999 | Zucherman et al. |
| 5,888,196 | A | 3/1999 | Bonutti |
| 5,941,881 | A | 8/1999 | Barnes |
| 5,976,186 | A | 11/1999 | Bao et al. |
| 5,980,523 | A | 11/1999 | Jackson |
| 6,022,376 | A | 2/2000 | Assell et al. |
| 6,048,342 | A | 4/2000 | Zucherman et al. |
| 6,068,630 | A | 5/2000 | Zucherman et al. |
| 6,074,390 | A | 6/2000 | Zucherman et al. |
| 6,102,922 | A | 8/2000 | Jakobsson et al. |
| 6,126,689 | A | 10/2000 | Brett |
| 6,126,691 | A | 10/2000 | Kasra et al. |
| 6,127,597 | A | 10/2000 | Beyar et al. |
| 6,132,464 | A | 10/2000 | Martin |
| 6,190,413 | B1 | 2/2001 | Sutcliffe |
| 6,190,414 | B1 | 2/2001 | Young |
| 6,214,037 | B1 | 4/2001 | Mitchell et al. |
| 6,214,050 | B1 | 4/2001 | Huene |
| 6,245,107 | B1 | 6/2001 | Ferree |
| 6,293,949 | B1 | 9/2001 | Justis et al. |
| 6,336,930 | B1 | 1/2002 | Stalcup et al. |
| 6,348,053 | B1 | 2/2002 | Cachia |
| 6,352,537 | B1 | 3/2002 | Strnad |
| 6,364,883 | B1 | 4/2002 | Santilli |
| 6,371,987 | B1 | 4/2002 | Weiland et al. |
| 6,375,682 | B1 | 4/2002 | Fleischmann et al. |
| 6,402,750 | B1 | 6/2002 | Atkinson et al. |
| 6,402,751 | B1 | 6/2002 | Hoeck et al. |
| 6,419,676 | B1 * | 7/2002 | Zucherman et al. .......... 606/249 |
| 6,419,703 | B1 | 7/2002 | Fallin et al. |
| 6,419,704 | B1 | 7/2002 | Ferree |
| 6,432,130 | B1 | 8/2002 | Hanson |
| 6,436,140 | B1 | 8/2002 | Liu et al. |

| | | |
|---|---|---|
| 6,440,169 B1 | 8/2002 | Elberg et al. |
| 6,447,513 B1 | 9/2002 | Griggs |
| 6,447,546 B1 * | 9/2002 | Bramlet et al. ............ 623/17.16 |
| 6,451,019 B1 | 9/2002 | Zucherman et al. |
| 6,500,178 B2 | 12/2002 | Zucherman et al. |
| 6,511,508 B1 | 1/2003 | Shahinpoor et al. |
| 6,514,256 B2 | 2/2003 | Zucherman et al. |
| 6,520,991 B2 | 2/2003 | Huene |
| 6,527,803 B1 | 3/2003 | Crozet et al. |
| 6,554,833 B2 | 4/2003 | Levy |
| 6,572,653 B1 | 6/2003 | Simonson |
| 6,582,433 B2 | 6/2003 | Yun |
| 6,582,467 B1 | 6/2003 | Teitelbaum et al. |
| 6,592,585 B2 | 7/2003 | Lee et al. |
| 6,626,944 B1 | 9/2003 | Taylor |
| 6,645,207 B2 | 11/2003 | Dixon et al. |
| 6,669,729 B2 | 12/2003 | Chin |
| 6,685,742 B1 | 2/2004 | Jackson |
| 6,695,842 B2 | 2/2004 | Zucherman et al. |
| 6,699,246 B2 | 3/2004 | Zucherman et al. |
| 6,709,435 B2 | 3/2004 | Lin |
| 6,723,126 B1 | 4/2004 | Berry |
| 6,730,126 B2 | 5/2004 | Boehm, Jr. et al. |
| 6,733,531 B1 | 5/2004 | Trieu |
| 6,733,534 B2 | 5/2004 | Sherman |
| 6,736,818 B2 | 5/2004 | Perren et al. |
| 6,743,257 B2 | 6/2004 | Castro |
| 6,758,863 B2 | 7/2004 | Estes et al. |
| 6,761,720 B1 | 7/2004 | Senegas |
| 6,770,096 B2 | 8/2004 | Bolger et al. |
| 6,783,530 B1 | 8/2004 | Levy |
| 6,835,205 B2 | 12/2004 | Atkinson et al. |
| 6,902,580 B2 | 6/2005 | Fallin et al. |
| 6,905,512 B2 | 6/2005 | Paes et al. |
| 6,946,000 B2 | 9/2005 | Senegas et al. |
| 6,981,975 B2 | 1/2006 | Michelson |
| 7,011,685 B2 | 3/2006 | Arnin et al. |
| 7,041,136 B2 | 5/2006 | Goble et al. |
| 7,048,736 B2 | 5/2006 | Robinson et al. |
| 7,070,598 B2 | 7/2006 | Lim et al. |
| 7,081,120 B2 | 7/2006 | Li et al. |
| 7,087,055 B2 | 8/2006 | Lim et al. |
| 7,087,083 B2 | 8/2006 | Pasquet et al. |
| 7,097,648 B1 | 8/2006 | Globerman et al. |
| 7,097,654 B1 | 8/2006 | Freedland |
| 7,101,375 B2 | 9/2006 | Zucherman et al. |
| 7,163,558 B2 | 1/2007 | Senegas et al. |
| 7,201,751 B2 | 4/2007 | Zucherman et al. |
| 7,217,293 B2 | 5/2007 | Branch, Jr. |
| 7,238,204 B2 | 7/2007 | Le Couedic et al. |
| 7,306,628 B2 | 12/2007 | Zucherman et al. |
| 7,335,203 B2 | 2/2008 | Winslow et al. |
| 7,377,942 B2 | 5/2008 | Berry |
| 7,431,735 B2 | 10/2008 | Liu et al. |
| 7,442,208 B2 | 10/2008 | Mathieu et al. |
| 7,445,637 B2 | 11/2008 | Taylor |
| 7,458,981 B2 | 12/2008 | Fielding et al. |
| 7,582,106 B2 | 9/2009 | Teitelbaum et al. |
| 7,604,652 B2 | 10/2009 | Arnin et al. |
| 7,611,316 B2 | 11/2009 | Panasik et al. |
| 7,621,950 B1 | 11/2009 | Globerman et al. |
| 7,641,673 B2 | 1/2010 | Le Couedic et al. |
| 7,658,752 B2 | 2/2010 | Labrom et al. |
| 7,749,252 B2 | 7/2010 | Zucherman et al. |
| 7,771,456 B2 | 8/2010 | Hartman et al. |
| 7,862,615 B2 | 1/2011 | Carli et al. |
| 7,901,430 B2 | 3/2011 | Matsuura et al. |
| 7,927,354 B2 | 4/2011 | Edidin et al. |
| 2001/0016743 A1 | 8/2001 | Zucherman et al. |
| 2001/0049527 A1 | 12/2001 | Cragg |
| 2002/0143331 A1 | 10/2002 | Zucherman et al. |
| 2003/0040746 A1 | 2/2003 | Mitchell et al. |
| 2003/0045940 A1 | 3/2003 | Eberlein et al. |
| 2003/0065330 A1 | 4/2003 | Zucherman et al. |
| 2003/0153915 A1 | 8/2003 | Nekozuka et al. |
| 2003/0176925 A1 | 9/2003 | Paponneau |
| 2004/0010312 A1 | 1/2004 | Enayati |
| 2004/0010316 A1 | 1/2004 | William et al. |
| 2004/0064094 A1 | 4/2004 | Freyman |
| 2004/0087947 A1 | 5/2004 | Lim et al. |
| 2004/0097931 A1 | 5/2004 | Mitchell |
| 2004/0106995 A1 | 6/2004 | LeCoudeic et al. |
| 2004/0117017 A1 | 6/2004 | Pasquet et al. |
| 2004/0133204 A1 | 7/2004 | Davies |
| 2004/0133280 A1 | 7/2004 | Trieu |
| 2004/0158248 A1 | 8/2004 | Ginn |
| 2004/0167625 A1 | 8/2004 | Beyar et al. |
| 2004/0172029 A1 | 9/2004 | Lerch |
| 2004/0186577 A1 | 9/2004 | Ferree |
| 2004/0199255 A1 | 10/2004 | Mathieu et al. |
| 2004/0260397 A1 | 12/2004 | Lambrecht et al. |
| 2005/0010293 A1 | 1/2005 | Zucherman et al. |
| 2005/0033434 A1 | 2/2005 | Berry |
| 2005/0049590 A1 | 3/2005 | Alleyne et al. |
| 2005/0049708 A1 | 3/2005 | Atkinson et al. |
| 2005/0056292 A1 | 3/2005 | Cooper |
| 2005/0085814 A1 | 4/2005 | Sherman et al. |
| 2005/0143827 A1 | 6/2005 | Globerman et al. |
| 2005/0165398 A1 | 7/2005 | Reiley |
| 2005/0203512 A1 | 9/2005 | Hawkins et al. |
| 2005/0203519 A1 | 9/2005 | Harms et al. |
| 2005/0203624 A1 | 9/2005 | Serhan et al. |
| 2005/0228391 A1 | 10/2005 | Levy et al. |
| 2005/0245937 A1 * | 11/2005 | Winslow .................... 606/90 |
| 2005/0261768 A1 | 11/2005 | Trieu |
| 2005/0267579 A1 | 12/2005 | Reiley et al. |
| 2005/0273166 A1 | 12/2005 | Sweeney |
| 2005/0288672 A1 | 12/2005 | Ferree |
| 2006/0004447 A1 | 1/2006 | Mastrorio et al. |
| 2006/0004455 A1 | 1/2006 | Leonard et al. |
| 2006/0015181 A1 | 1/2006 | Elberg |
| 2006/0047282 A1 | 3/2006 | Gordon |
| 2006/0064165 A1 | 3/2006 | Zucherman et al. |
| 2006/0084983 A1 | 4/2006 | Kim |
| 2006/0084985 A1 | 4/2006 | Kim |
| 2006/0084987 A1 | 4/2006 | Kim |
| 2006/0084988 A1 | 4/2006 | Kim |
| 2006/0085069 A1 | 4/2006 | Kim |
| 2006/0085070 A1 | 4/2006 | Kim |
| 2006/0085074 A1 | 4/2006 | Raiszadeh |
| 2006/0089654 A1 | 4/2006 | Lins et al. |
| 2006/0089719 A1 | 4/2006 | Trieu |
| 2006/0095136 A1 | 5/2006 | McLuen |
| 2006/0106381 A1 | 5/2006 | Ferree et al. |
| 2006/0106397 A1 | 5/2006 | Lins |
| 2006/0111728 A1 | 5/2006 | Abdou |
| 2006/0116690 A1 | 6/2006 | Pagano |
| 2006/0122620 A1 | 6/2006 | Kim |
| 2006/0129239 A1 | 6/2006 | Kwak |
| 2006/0136060 A1 | 6/2006 | Taylor |
| 2006/0142858 A1 | 6/2006 | Colleran et al. |
| 2006/0149242 A1 | 7/2006 | Kraus et al. |
| 2006/0182515 A1 | 8/2006 | Panasik et al. |
| 2006/0184247 A1 | 8/2006 | Edidin et al. |
| 2006/0184248 A1 | 8/2006 | Edidin et al. |
| 2006/0195102 A1 | 8/2006 | Malandain |
| 2006/0217726 A1 | 9/2006 | Maxy et al. |
| 2006/0224159 A1 | 10/2006 | Anderson |
| 2006/0224241 A1 | 10/2006 | Butler et al. |
| 2006/0235387 A1 | 10/2006 | Peterman |
| 2006/0235532 A1 | 10/2006 | Meunier et al. |
| 2006/0241601 A1 | 10/2006 | Trautwein et al. |
| 2006/0241613 A1 | 10/2006 | Bruneau et al. |
| 2006/0241643 A1 | 10/2006 | Lim et al. |
| 2006/0241757 A1 | 10/2006 | Anderson |
| 2006/0247623 A1 | 11/2006 | Anderson et al. |
| 2006/0247640 A1 | 11/2006 | Blackwell et al. |
| 2006/0264938 A1 | 11/2006 | Zucherman et al. |
| 2006/0265074 A1 | 11/2006 | Krishna et al. |
| 2006/0271044 A1 | 11/2006 | Petrini et al. |
| 2006/0271049 A1 | 11/2006 | Zucherman et al. |
| 2006/0271061 A1 | 11/2006 | Beyar et al. |
| 2006/0282075 A1 | 12/2006 | Labrom et al. |
| 2006/0282079 A1 | 12/2006 | Labrom et al. |
| 2006/0293662 A1 | 12/2006 | Boyer, II et al. |
| 2006/0293663 A1 | 12/2006 | Walkenhorst et al. |
| 2007/0005064 A1 | 1/2007 | Anderson et al. |
| 2007/0010813 A1 | 1/2007 | Zucherman et al. |

| | | |
|---|---|---|
| 2007/0032790 A1 | 2/2007 | Aschmann et al. |
| 2007/0043362 A1 | 2/2007 | Malandain et al. |
| 2007/0043363 A1 | 2/2007 | Malandain et al. |
| 2007/0049935 A1 | 3/2007 | Edidin et al. |
| 2007/0073289 A1 | 3/2007 | Kwak et al. |
| 2007/0100340 A1 | 5/2007 | Lange et al. |
| 2007/0123861 A1 | 5/2007 | Dewey et al. |
| 2007/0142915 A1 | 6/2007 | Altarac et al. |
| 2007/0151116 A1 | 7/2007 | Malandain |
| 2007/0162000 A1 | 7/2007 | Perkins |
| 2007/0167945 A1 | 7/2007 | Lange et al. |
| 2007/0173822 A1 | 7/2007 | Bruneau et al. |
| 2007/0173823 A1 | 7/2007 | Dewey et al. |
| 2007/0191833 A1 | 8/2007 | Bruneau et al. |
| 2007/0191834 A1 | 8/2007 | Bruneau et al. |
| 2007/0191837 A1 | 8/2007 | Trieu |
| 2007/0191838 A1 | 8/2007 | Bruneau et al. |
| 2007/0198091 A1 | 8/2007 | Boyer et al. |
| 2007/0225807 A1 | 9/2007 | Phan et al. |
| 2007/0225810 A1 | 9/2007 | Colleran et al. |
| 2007/0233068 A1 | 10/2007 | Bruneau et al. |
| 2007/0233074 A1 | 10/2007 | Anderson et al. |
| 2007/0233076 A1 | 10/2007 | Trieu |
| 2007/0233081 A1 | 10/2007 | Pasquet et al. |
| 2007/0233084 A1 | 10/2007 | Betz et al. |
| 2007/0233089 A1 | 10/2007 | DiPoto et al. |
| 2007/0250060 A1 | 10/2007 | Anderson et al. |
| 2007/0270823 A1 | 11/2007 | Trieu et al. |
| 2007/0270824 A1 | 11/2007 | Lim et al. |
| 2007/0270825 A1 | 11/2007 | Carls et al. |
| 2007/0270826 A1 | 11/2007 | Trieu et al. |
| 2007/0270827 A1 | 11/2007 | Lim et al. |
| 2007/0270828 A1 | 11/2007 | Bruneau et al. |
| 2007/0270829 A1 | 11/2007 | Carls et al. |
| 2007/0270834 A1 | 11/2007 | Bruneau et al. |
| 2007/0270874 A1 | 11/2007 | Anderson |
| 2007/0272259 A1 | 11/2007 | Allard et al. |
| 2007/0276368 A1 | 11/2007 | Trieu et al. |
| 2007/0276369 A1 | 11/2007 | Allard et al. |
| 2007/0276493 A1 | 11/2007 | Malandain et al. |
| 2007/0276496 A1 | 11/2007 | Lange et al. |
| 2007/0276497 A1 | 11/2007 | Anderson |
| 2007/0282443 A1 | 12/2007 | Globerman et al. |
| 2008/0021457 A1 | 1/2008 | Anderson et al. |
| 2008/0021460 A1 | 1/2008 | Bruneau et al. |
| 2008/0058934 A1 | 3/2008 | Malandain et al. |
| 2008/0097446 A1 | 4/2008 | Reiley et al. |
| 2008/0114357 A1 | 5/2008 | Allard et al. |
| 2008/0114358 A1 | 5/2008 | Anderson et al. |
| 2008/0114456 A1 | 5/2008 | Dewey et al. |
| 2008/0147190 A1 | 6/2008 | Dewey et al. |
| 2008/0161818 A1 | 7/2008 | Kloss et al. |
| 2008/0167685 A1 | 7/2008 | Allard et al. |
| 2008/0177306 A1 | 7/2008 | Lamborne et al. |
| 2008/0183209 A1 | 7/2008 | Robinson et al. |
| 2008/0183211 A1 | 7/2008 | Lamborne et al. |
| 2008/0183218 A1 | 7/2008 | Mueller et al. |
| 2008/0195152 A1 | 8/2008 | Altarac et al. |
| 2008/0215094 A1 | 9/2008 | Taylor |
| 2008/0221685 A9 | 9/2008 | Altarac et al. |
| 2008/0234824 A1 | 9/2008 | Youssef et al. |
| 2008/0243250 A1 | 10/2008 | Seifert et al. |
| 2008/0262617 A1 | 10/2008 | Froehlich et al. |
| 2008/0281359 A1 | 11/2008 | Abdou |
| 2008/0281360 A1 | 11/2008 | Vittur et al. |
| 2008/0281361 A1 | 11/2008 | Vittur et al. |
| 2009/0062915 A1 | 3/2009 | Kohm et al. |
| 2009/0099610 A1 | 4/2009 | Johnson et al. |
| 2009/0105766 A1 | 4/2009 | Thompson et al. |
| 2009/0105773 A1 | 4/2009 | Lange et al. |
| 2009/0234389 A1 | 9/2009 | Chuang et al. |
| 2009/0240283 A1 | 9/2009 | Carls et al. |
| 2009/0264927 A1 | 10/2009 | Ginsberg et al. |
| 2009/0270918 A1 | 10/2009 | Attia et al. |
| 2009/0292316 A1 | 11/2009 | Hess |
| 2009/0326538 A1 | 12/2009 | Sennett et al. |
| 2010/0036419 A1 | 2/2010 | Patel et al. |
| 2010/0121379 A1 | 5/2010 | Edmond |
| 2010/0191241 A1 | 7/2010 | McCormack et al. |
| 2010/0204732 A1 | 8/2010 | Aschmann et al. |
| 2010/0211101 A1 | 8/2010 | Blackwell et al. |
| 2011/0054531 A1 | 3/2011 | Lamborne et al. |
| 2011/0144692 A1 | 6/2011 | Saladin et al. |
| 2011/0166600 A1 | 7/2011 | Lamborne et al. |

FOREIGN PATENT DOCUMENTS

| | | |
|---|---|---|
| DE | 3922044 A1 | 2/1991 |
| DE | 4012622 C1 | 7/1991 |
| DE | 202006018978 U1 | 2/2007 |
| EP | 0322334 B1 | 2/1992 |
| EP | 0767636 B1 | 1/1999 |
| EP | 1004276 A1 | 5/2000 |
| EP | 1011464 B1 | 6/2000 |
| EP | 1138268 A1 | 10/2001 |
| EP | 1148850 B1 | 10/2001 |
| EP | 1148851 B1 | 10/2001 |
| EP | 1302169 A1 | 4/2003 |
| EP | 1330987 A1 | 7/2003 |
| EP | 1552797 A2 | 7/2005 |
| EP | 1854433 A1 | 11/2007 |
| EP | 1905392 A1 | 4/2008 |
| EP | 1982664 A1 | 10/2008 |
| FR | 2623085 A1 | 5/1989 |
| FR | 2625097 A1 | 6/1989 |
| FR | 2681525 A1 | 3/1993 |
| FR | 2700941 A1 | 8/1994 |
| FR | 2703239 A1 | 10/1994 |
| FR | 2707864 A1 | 1/1995 |
| FR | 2717675 A1 | 9/1995 |
| FR | 2722087 A1 | 1/1996 |
| FR | 2722088 A1 | 1/1996 |
| FR | 2724554 A1 | 3/1996 |
| FR | 2725892 A1 | 4/1996 |
| FR | 2730156 A1 | 8/1996 |
| FR | 2731643 A1 | 9/1996 |
| FR | 2775183 A1 | 8/1999 |
| FR | 2799948 A1 | 4/2001 |
| FR | 2816197 A1 | 5/2002 |
| JP | 02-224660 | 9/1990 |
| JP | 09-075381 | 3/1997 |
| JP | 2003079649 | 3/2003 |
| SU | 988281 | 1/1983 |
| SU | 1484348 A1 | 6/1989 |
| WO | WO 94/26192 | 11/1994 |
| WO | WO 94/26195 | 11/1994 |
| WO | WO 97/18769 | 5/1997 |
| WO | WO 98/20939 | 5/1998 |
| WO | WO 99/26562 | 6/1999 |
| WO | WO 00/44319 | 8/2000 |
| WO | WO 01/54598 A1 | 8/2001 |
| WO | WO 03/057055 A1 | 7/2003 |
| WO | WO 2004/047689 A1 | 6/2004 |
| WO | WO 2004/047691 A1 | 6/2004 |
| WO | WO 2004/084743 A1 | 10/2004 |
| WO | WO 2004/084768 A2 | 10/2004 |
| WO | WO 2004/110300 A2 | 12/2004 |
| WO | WO 2005/009300 A1 | 2/2005 |
| WO | WO 2005/011507 A1 | 2/2005 |
| WO | WO 2005009300 A1 * | 2/2005 ............... A61F 2/44 |
| WO | WO 2005/044118 A1 | 5/2005 |
| WO | WO 2005/048856 A1 | 6/2005 |
| WO | WO 2005/110258 A1 | 11/2005 |
| WO | WO 2006/064356 A1 | 6/2006 |
| WO | WO 2006064356 A1 * | 6/2006 ............. A61B 17/70 |
| WO | WO 2007/034516 A1 | 3/2007 |
| WO | WO 2007052975 A1 | 5/2007 |
| WO | WO 2009/083276 A1 | 7/2009 |
| WO | WO 2009/083583 A1 | 7/2009 |
| WO | WO 2009/098536 A1 | 8/2009 |

OTHER PUBLICATIONS

Bellini et al., "Biomechanics of the Lumbar Spine Afer Dynamic Stabilization," J. Spinal Discord Tech., 2006, vol. 00, No. 00, pp. 1-7.
Buric et al., "DIAM Device for Low Back Pain in Degenerative Disc Disease 24 Months Follow-up," Advances in Minimally Invasive Surgery and Therapy for Spine and Nerves, Alexandre et al., eds., 2011, pp. 177-182, Spinger-Verlat/Wien.

Phillips et al., "Biomechanics of Posterior Dynamic Stabiling Device (DIAM) After Facetectomy and Disectomy," The Spine Journal, 2006, vol. 6, pp. 714-722.

Taylor et al., "Device for Intervertebral Assisted Motion: Technique and Intial Results," 22 Neurosurg. Focus, Jan. 2007, vol. 22, No. 1, pp. 1-6.

Wilke et al., "Biomedical Effect of Different Lumbar Interspinous Implants on Flexibilty and Intradiscal Pressure," Eur Spine J., Vo. 17, published online Jun. 27, 2008, pp. 1049-1056.

Zhao et al., "Efficacy of the Dynamic Interspinous Assisted Motion System in Clinical Treatment of Degenerative Lumbar Disease," Chin. Med. J., 2010, vol. 123, No. 21, pp. 2974-2977.

Benzel et al., "Posterior Cervical Interspinous Compression Wiring and Fusion for Mid to Low Cervical Spinal Injuries," J. Neurosurg., Jun. 1989, pp. 893-899, vol. 70.

Caserta et al., "Elastic Stabilization Alone or Combined with Rigid Fusion in Spinal Surgery: a Biomechanical Study and Clinical Experience Based on 82 Cases," Eur. Spine J., Oct. 2002, pp. S192-S197, vol. 11, Suppl. 2.

Christie et al., "Dynamic Interspinous Process Technology," SPINE, 2005, pp. S73-S78, vol. 30, No. 16S.

Cousin Biotech, Dispositif Intervertébral Amortissant, Jun. 1998, pp. 1-4.

Dickman et al., "The Interspinous Method of Posterior Atlantoaxial Arthrodesis," J. Neurosurg., Feb. 1991, pp. 190-198, vol. 74.

Dubois et al., "Dynamic Neutralization: A New Concept for Restabilization of the Spine," Lumbar Segmental Insability, Szpalski et al., eds., 1999, pp. 233-240, Lippincott Williams & Wilkins, Philadelphia, Pennsylvania.

Ebara et al., "Inoperative Measurement of Lumbar Spinal Instability," SPINE, 1992, pp. S44-S50, vol. 17, No. 3S.

Fassio et al., "Treatment of Degenerative Lumbar Spinal Instability L4-L5 by Interspinous Ligamentoplasty," Rachis, Dec. 1991, pp. 465-474, vol. 3, No. 6.

Fassio, "Mise au Point Sur la Ligamentoplastie Inter-Epineuse Lombaire Dans les Instabilites," Maîtrise Orthopédique, Jul. 1993, pp. 18, No. 25.

Garner et al., "Development and Preclinical Testing of a New Tension-Band Device for the Spine: the Loop System," Eur. Spine J., Aug. 7, 2002, pp. S186-S191, vol. 11, Suppl. 2.

Guang et al., "Interspinous Process Segmental Instrumentation with Bone-Button-Wire for Correction of Scoliosis," Chinese Medical J., 1990, pp. 721-725, vol. 103.

Guizzardi et al., "The Use of DIAM (Interspinous Stress-Breaker Device) in the Prevention of Chronic Low Back Pain in Young Patients Operated on for Large Dimension Lumbar Disc Herniation," 12th Eur. Cong. Neurosurg., Sep. 7-12, 2003, pp. 835-839, Port.

Hambly et al., "Tension Band Wiring-Bone Grafting for Spondylolysis and Spondylolisthesis," SPINE, 1989, pp. 455-460, vol. 14, No. 4.

Kiwerski, "Rehabilitation of Patients with Thoracic Spine Injury Treated by Spring Alloplasty," Int. J. Rehab. Research, 1983, pp. 469-474, vol. 6, No. 4.

Kramer et al., "Intervetertebral Disk Diseases: Causes, Diagnosis, Treatment and Prophylaxis," pp. 244-249, Medical, 1990.

Laudet et al., "Comportement Bio-Mécanique D'Un Ressort Inter-Apophysaire Vertébral Postérieur Analyse Expérimentale Due Comportement Discal En Compression Et En Flexion/Extension," Rachis, 1993, vol. 5, No. 2.

Mah et al., "Threaded K-Wire Spinous Process Fixation of the Axis for Modified Gallie Fusion in Children and Adolescents," J. Pediatric Othopaedics, 1989, pp. 675-679, vol. 9.

Mariottini et al., "Preliminary Results of a Soft Novel Lumbar Intervertebral Prothesis (DIAM) in the Degenerative Spinal Pathology," Acta Neurochir., Adv. Peripheral Nerve Surg. and Minimal Invas. Spinal Surg., 2005, pp. 129-131, vol. 92, Suppl.

McDonnell et al., "Posterior Atlantoaxial Fusion: Indications and Techniques," Techniques in Spinal Fusion and Stabilization, Hitchon et al., eds., 1995, pp. 92-106, Ch. 9, Thieme, New York.

Minns et al., "Preliminary Design and Experimental Studies of a Novel Soft Implant for Correcting Sagittal Plane Instability in the Lumbar Spine," SPINE, 1997, pp. 1819-1825, vol. 22, No. 16.

Müller, "Restauration Dynamique de la Stabilité Rachidienne," Tiré de la Sulzer Technical Review, Jan. 1999, Sulzer Management Ltd, Winterthur, Switzerland.

Pennal et al., "Stenosis of the Lumbar Spinal Canal," Clinical Neurosurgery: Proceedings of the Congress of Neurological Surgeons, St. Louis, Missouri, 1970, Tindall et al., eds., 1971, Ch. 6, pp. 86-105, vol. 18.

Petrini et al., "Analisi Di Un'Esperienza Clinica Con Un Impianto Posteriore Ammortizzante," S.O.T.I.M.I. Società di Ortopedia e Traumatologia dell'Italia Meridionale e Insulare 90 ° Congresso, Jun. 21-23, 2001, Paestum.

Petrini et al., "Stabilizzazione Elastica," Patologia Degenerativa del Rachide Lombare, Oct. 5-6, 2001, Rimini.

Porter, "Spinal Stenosis and Neurogenic Claudication," SPINE, Sep. 1, 1996, pp. 2046-2052, vol. 21, No. 17.

Pupin et al., "Clinical Experience with a Posterior Shock-Absorbing Implant in Lumbar Spine," World Spine 1: First Interdisciplinary World Congress on Spinal Surgery and Related Disciplines, Aug. 27-Sep. 1, 2000, Berlin, Germany.

Rengachary et al., "Cervical Spine Stabilization with Flexible, Multistrand Cable System," Techniques in Spinal Fusion and Stabilization, Hitchon et al., eds., 1995, pp. 79-81, Ch. 7, Thieme, New York.

Richards et al., "The Treatment Mechanism of an Interspinous Process Implant for Lumbar Neurogenic Intermittent Claudication," SPINE, 2005, pp. 744-749, vol. 30, No. 7.

Schiavone et al., "The Use of Disc Assistance Prosthesis (DIAM) in Degenerative Lumbar Pathology: Indications, Technique, Results," Italian J. Spinal Disorders, 2003, pp. 213-220, vol. 3, No. 2.

Schlegel et al., "The Role of Distraction in Improving the Space Available in the Lumbar Stenotic Canal and Foramen," SPINE, 1994, pp. 2041-2047, vol. 19, No. 18.

Senegas et al., "Le Recalibrage du Canal Lombaire, Alternative à la Laminectomie dans le Traitement des Sténoses du Canal Lombaire," Revue de Chirurgie Orthopédique, 1988, pp. 15-22.

Senegas et al., "Stabilisation Lombaire Souple," Instabilité Vertébrales Lombaires, Gastambide, ed., 1995, pp. 122-132, Expansion Scientifique Française, Paris, France.

Senegas, "La Ligamentoplastie Inter Vertébrale Lombaire, Alternative a L'Arthrodese," La Revue de Medécine Orthopédique, Jun. 1990, pp. 33-35, No. 20.

Senegas, "La Ligamentoplastie Intervertébrale, Alternative à L'arthrodèse dans le Traitement des Instabilités Dégénératives," Acta Othopaedica Belgica, 1991, pp. 221-226, vol. 57, Suppl. I.

Senegas, "Mechanical Supplementation by Non-Rigid Fixation in Degenerative Intervertebral Lumbar Segments: the Wallis System," Eur. Spine J., 2002, p. S164-S169, vol. 11, Suppl. 2.

Senegas, "Rencontre," Maîtrise Orthopédique, May 1995, pp. 1-3, No. 44.

Serhan, "Spinal Implants: Past, Present, and Future," 19th International IEEE/EMBS Conference, Oct. 30-Nov. 2, 1997, pp. 2636-2639, Chicago, Illinois.

Spadea et al., "Interspinous Fusion for the Treatment of Herniated Intervertebral Discs: Utilizing a Lumbar Spinous Process as a Bone Graft," Annals of Surgery, 1952, pp. 982-986, vol. 136, No. 6.

Taylor et al., "Analyse d'une experience clinique d'un implant postérieur amortissant," Rachis Revue de Pathologie Vertébrate, Oct./Nov. 1999, vol. 11, No. 4-5, Gieda Inter Rachis.

Taylor et al., "Technical and Anatomical Considerations for the Placement of a Posterior Interspinous Stabilizer," 2004, pp. 1-10, Medtronic Sofamor Danek USA, Inc., Memphis, Tennessee.

Taylor, "Biomechanical Requirements for the Posterior Control of the Centers of Rotation," Swiss Spine Institute International Symposium: Progress in Spinal Fixation, Jun. 21-22, 2002, pp. 1-2, Swiss Spine Institute, Bern, Switzerland.

Taylor, "Non-Fusion Technologies of the Posterior Column: A New Posterior Shock Absorber," International Symposium on Intervertebral Disc Replacement and Non-Fusion-Technology, May 3-5, 2001, Spine Arthroplasty.

Taylor, "Présentation à un an d'un dispositif amortissant d'assistance discale," 5èmes journées Avances & Controverses en pathologie rachidienne, Oct. 1-2, 1998, Faculté Libre de Médecine de Lille.

Tsuji et al., "Ceramic Interspinous Block (CISB) Assisted Anterior Interbody Fusion," J. Spinal Disorders, 1990, pp. 77-86, vol. 3, No. 1.

Vangilder, "Interspinous, Laminar, and Facet Posterior Cervical Bone Fusions," Techniques in Spinal Fusion and Stabilization, Hitchon et al., eds., 1995, pp. 135-146, Ch. 13, Thieme, New York.

Voydeville et al., "Experimental Lumbar Instability and Artificial Ligament," Eur. J. Orthop. Surg. Traumatol., Jul. 15, 2000, pp. 167-176, vol. 10.

Voydeville et al., "Lumbar Instability Treated by Intervertebral Ligamentoplasty with Smooth Wedges," Orthopédie Traumatologie, 1992, pp. 259-264, vol. 2, No. 4.

Waldemar Link, "Spinal Surgery: Instrumentation and Implants for Spinal Surgery," 1981, Link America Inc., New Jersey.

Wiltse et al., "The Treatment of Spinal Stenosis," Clinical Orthopaedics and Related Research, Urist, ed., Mar.-Apr. 1976, pp. 83-91, No. 115.

Wisneski et al., "Decompressive Surgery for Lumbar Spinal Stenosis," Seminars in Spine Surgery, Wiesel, ed., Jun. 1994, pp. 116-123, vol. 6, No. 2.

Zdeblick et al., "Two-Point Fixation of the Lumbar Spine Differential Stability in Rotation," SPINE, 1991, pp. S298-S301, vol. 16, No. 6, Supplement.

Zucherman et al., "Clinical Efficacy of Spinal Instrumentation in Lumbar Degenerative Disc Disease," SPINE, Jul. 1992, pp. 834-837, vol. 17, No. 7.

Bini et al., "Minimally Invasive Treatment of Moderate Lumbar Spinal Stenosis with the Superion® Interspinous Spacer," The Open Orthopaedics Journal, May 27, 2011, pp. 361-367, vol. 5.

* cited by examiner

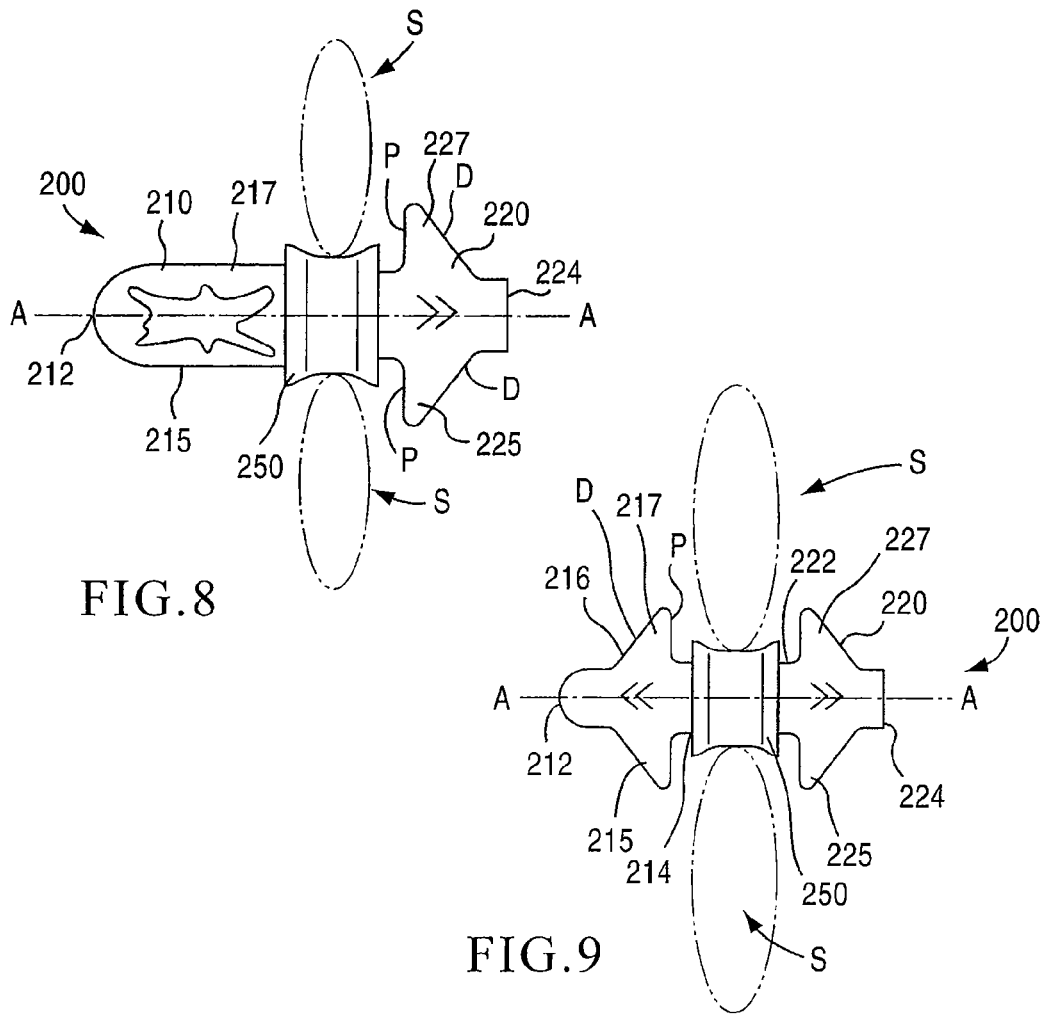
FIG.8
FIG.9
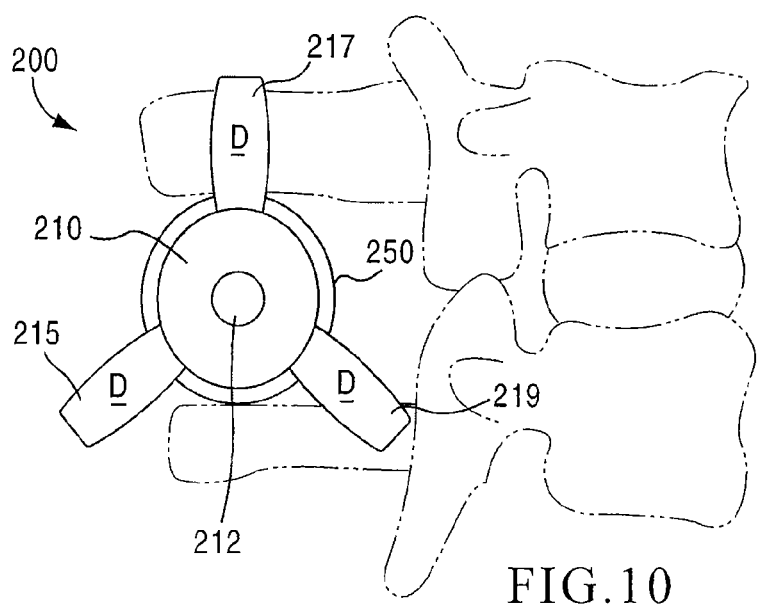
FIG.10

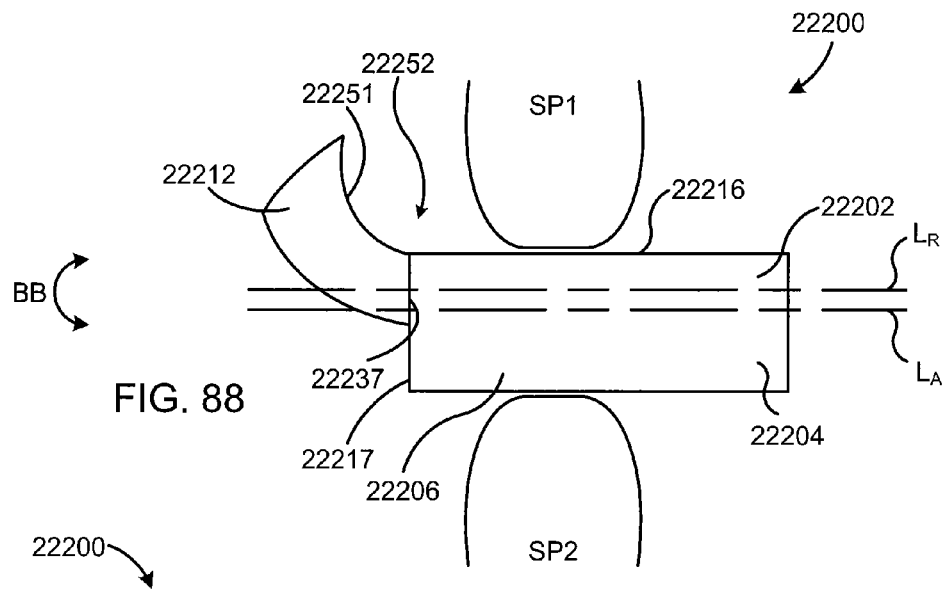
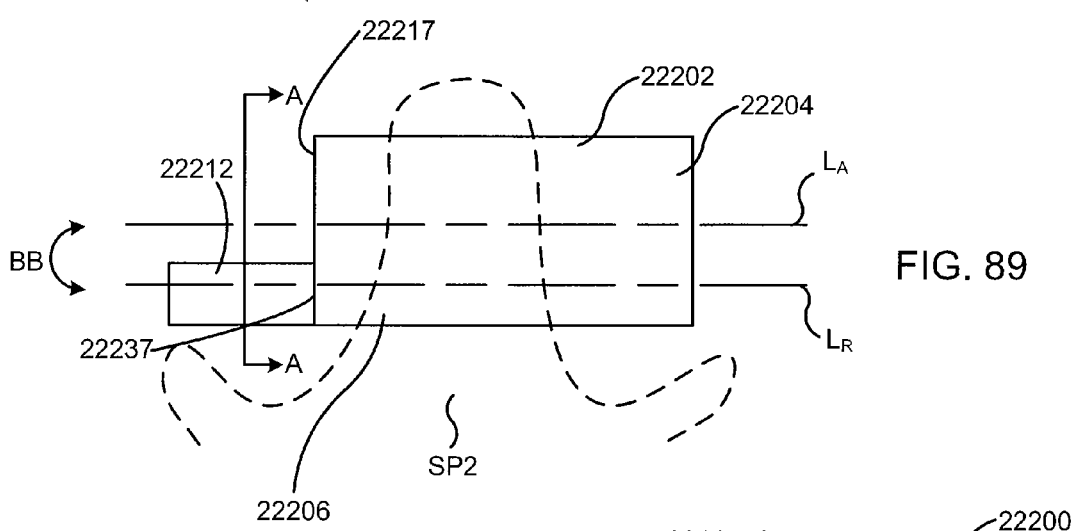
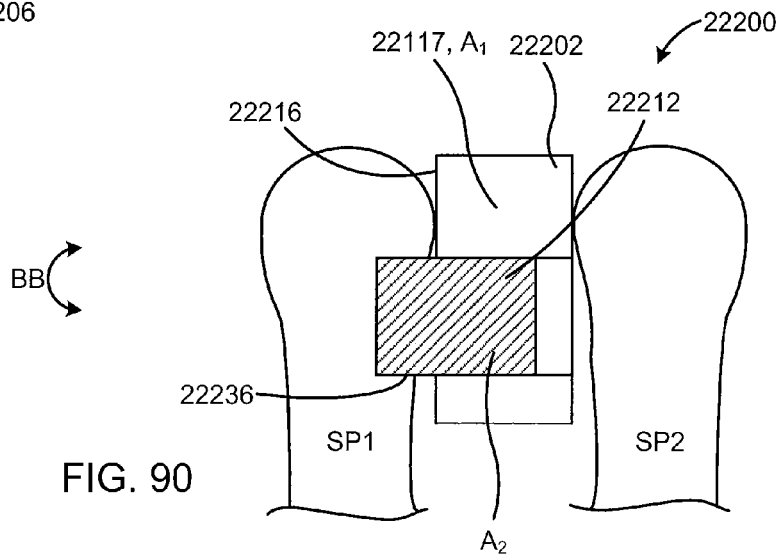

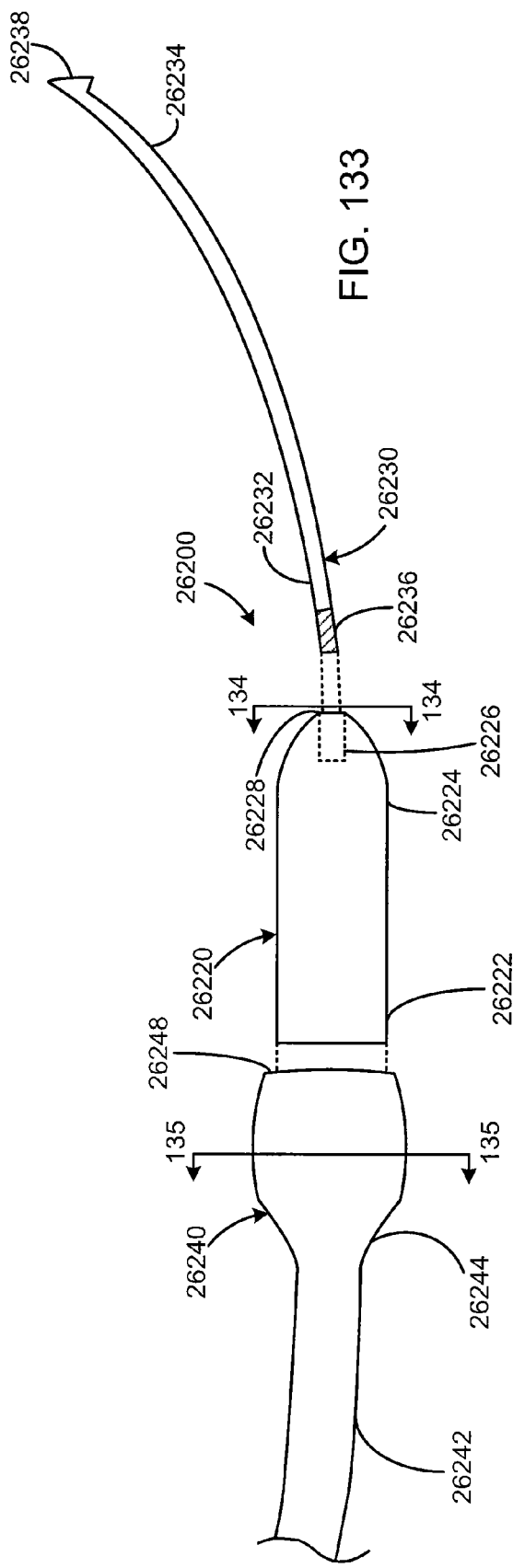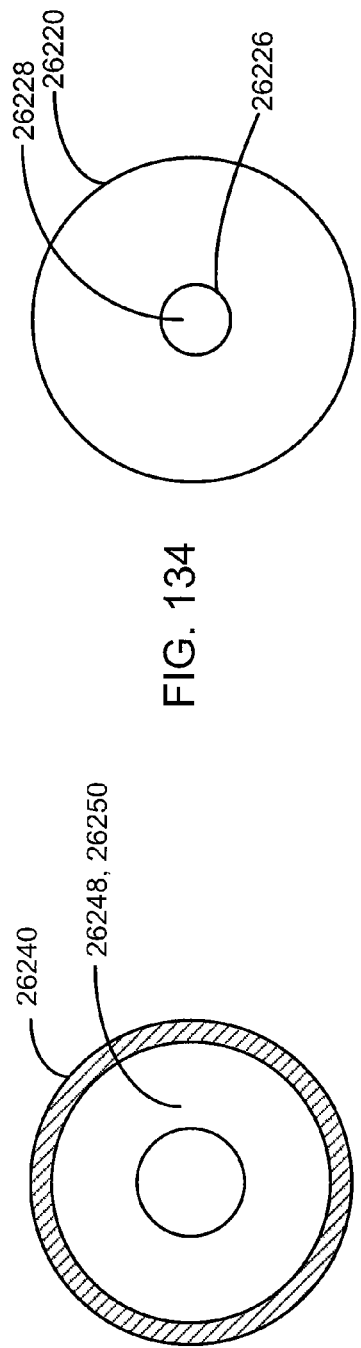

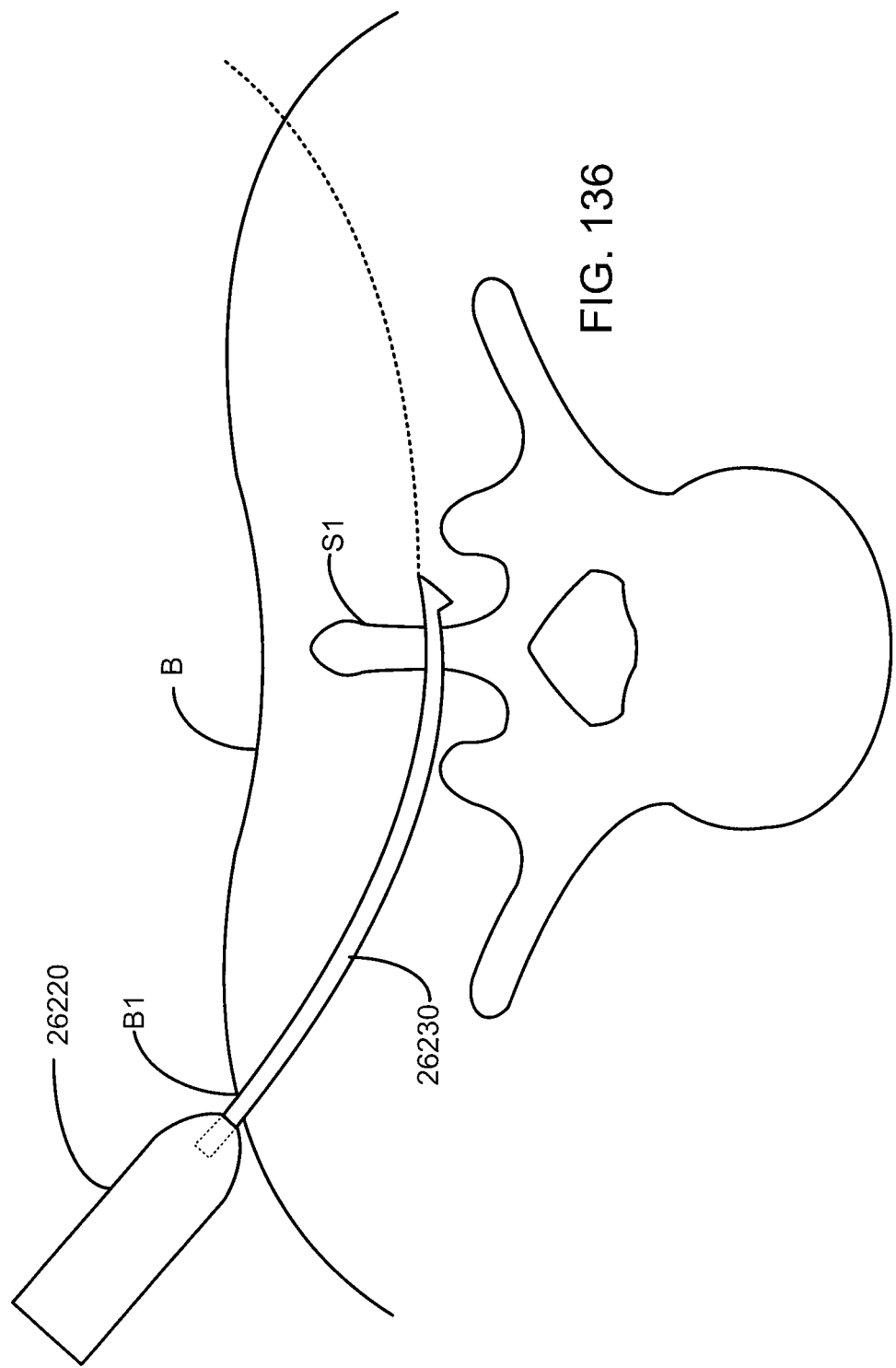

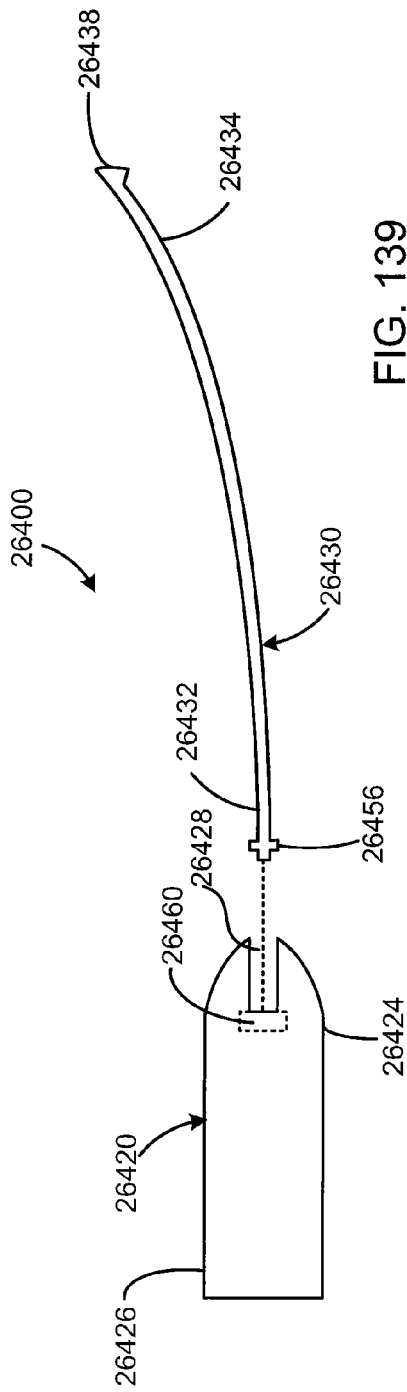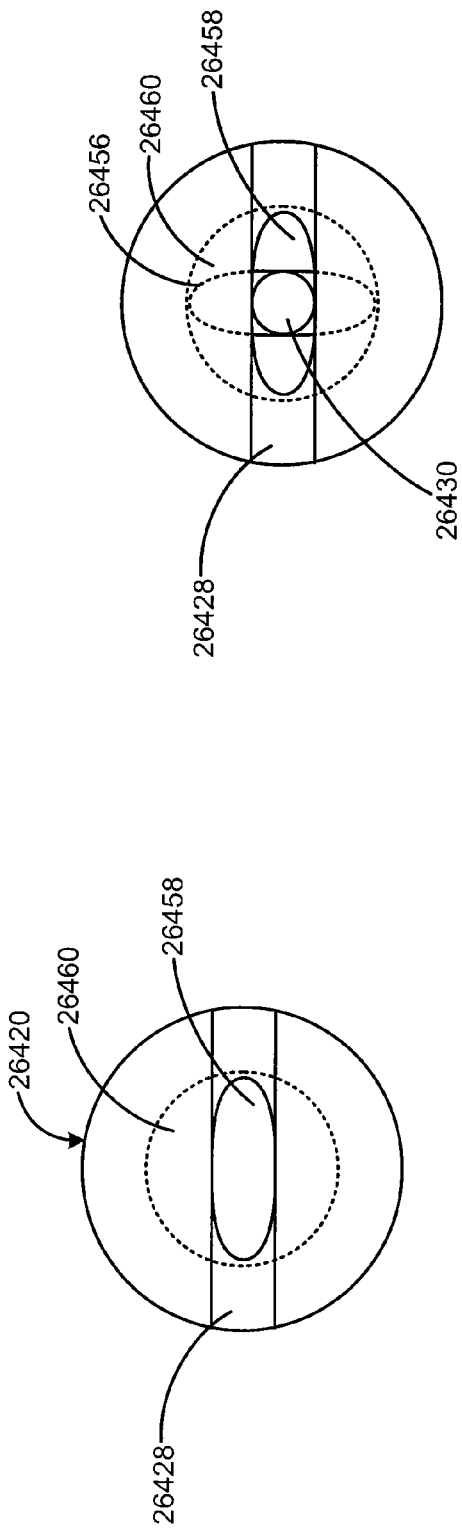

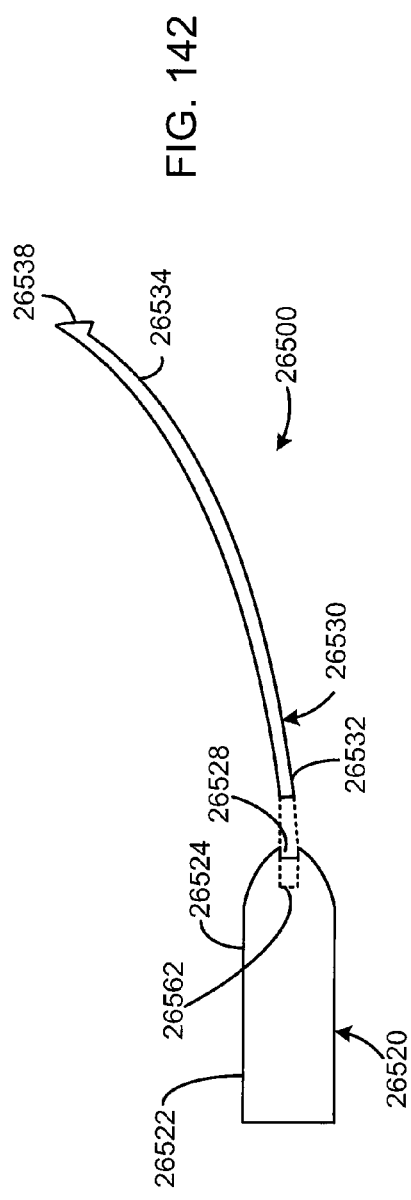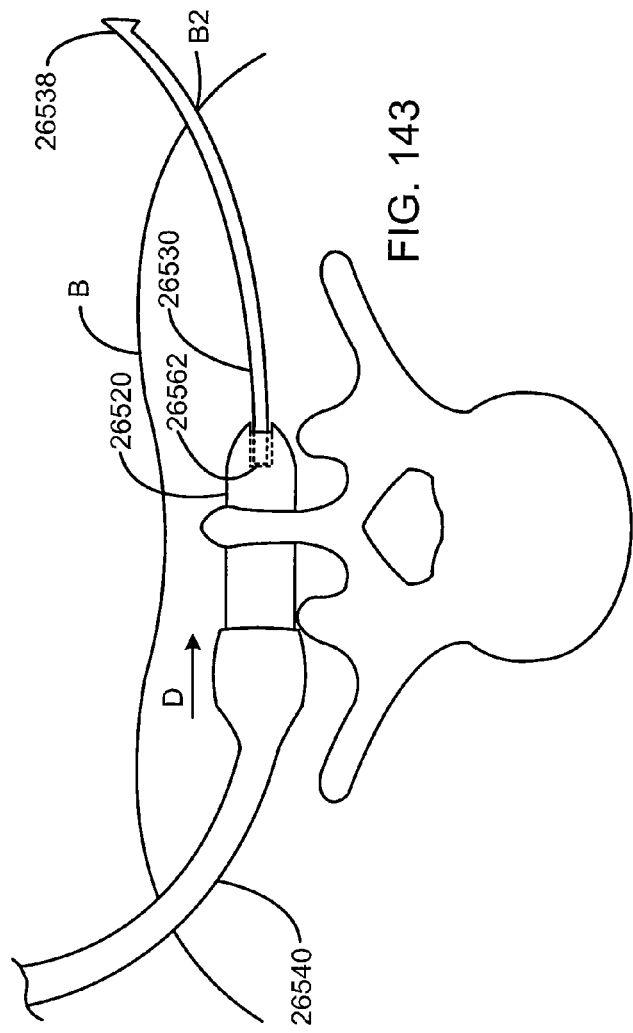
FIG. 142
FIG. 143

PERCUTANEOUS SPINAL IMPLANTS AND METHODS

CROSS-REFERENCE TO RELATED APPLICATIONS

This application is a continuation of U.S. patent application Ser. No. 11/752,981 entitled "Percutaneous Spinal Implants and Methods," filed May 24, 2007, which is a continuation-in-part of U.S. patent application Ser. No. 11/356,302, entitled "Percutaneous Spinal Implants and Methods," filed Feb. 17, 2006 now U.S. Pat. No. 7,988,709, which claims priority to U.S. Provisional Application Ser. No. 60/695,836, entitled "Percutaneous Spinal Implants and Methods," filed Jul. 1, 2005, and which is a continuation-in-part of each of U.S. patent application Ser. No. 11/252,879 now U.S. Pat. No. 8,038,698 and Ser. No. 11/252,880 now abandoned, each entitled "Percutaneous Spinal Implants and Methods," filed Oct. 19, 2005, each of which is a continuation-in-part of U.S. patent application Ser. No. 11/059,526, entitled "Apparatus and Method for Treatment of Spinal Conditions," filed Feb. 17, 2005 now abandoned, and each of which claims priority to U.S. Provisional Application Ser. No. 60/695,836, entitled "Percutaneous Spinal Implants and Methods," filed Jul. 1, 2005. Each of the above-identified applications is incorporated herein by reference in its entirety.

U.S. patent application Ser. No. 11/752,981 is also a continuation-in-part of U.S. patent application Ser. No. 11/356,301, entitled "Percutaneous Spinal Implants and Methods," filed Feb. 17, 2006 now U.S. Pat. No. 8,057,513, which claims priority to U.S. Provisional Application Ser. No. 60/695,836, entitled "Percutaneous Spinal Implants and Methods," filed Jul. 1, 2005, and which is a continuation-in-part of each of U.S. patent application Ser. No. 11/252,879 now U.S. Pat. No. 8,038,698 and Ser. No. 11/252,880 now abandoned, each entitled "Percutaneous Spinal Implants and Methods," and filed October 19, each of which is a continuation-in-part of U.S. patent application Ser. No. 11/059,526, entitled "Apparatus and Method for Treatment of Spinal Conditions," filed Feb. 17, 2005 now abandoned and each of which claims priority to U.S. Provisional Application Ser. No. 60/695,836, entitled "Percutaneous Spinal Implants and Methods," filed Jul. 1, 2005. Each of the above-identified applications is incorporated herein by reference in its entirety.

U.S. patent application Ser. No. 11/752,981 is a continuation-in-part of U.S. patent application Ser. No. 11/693,496 entitled "Percutaneous Spinal Implants and Methods," filed Mar. 29, 2007, which is a continuation-in-part of U.S. patent application Ser. No. 11/454,153, entitled "Percutaneous Spinal Implants and Methods," filed Jun. 16, 2006, which is a continuation-in-part of International Patent Application No. PCT/US2006/005580, entitled "Percutaneous Spinal Implants and Methods," filed Feb. 17, 2006, and which is a continuation-in-part of U.S. patent application Ser. No. 11/059,526, entitled "Apparatus and Method for Treatment of Spinal Conditions," filed Feb. 17, 2005, and which is a continuation-in-part of U.S. patent application Ser. No. 11/252,879, entitled "Percutaneous Spinal Implants and Methods," filed Oct. 19, 2005, which claims priority to U.S. Provisional Application Ser. No. 60/695,836, entitled "Percutaneous Spinal Implants and Methods," filed Jul. 1, 2005, and which is a continuation-in-part of U.S. patent application Ser. No. 11/252,880, entitled "Percutaneous Spinal Implants and Methods," filed Oct. 19, 2005, which claims priority to U.S. Provisional Application Ser. No. 60/695,836, entitled "Percutaneous Spinal Implants and Methods," filed Jul. 1, 2005. Each of the above-identified applications is incorporated herein by reference in its entirety.

This application is related to U.S. patent application Ser No. 11/928,827, Ser. No. 11/928,841, and Ser. No. 11/929,173, each entitled "Percutaneous Spinal Implants and Methods," filed on the same date herewith, each of which is incorporated herein by reference in its entirety.

BACKGROUND

The invention relates generally to the treatment of spinal conditions, and more particularly, to the treatment of spinal compression using percutaneous spinal implants for implantation between adjacent spinous processes.

A back condition that impacts many individuals is spinal stenosis. Spinal stenosis is a progressive narrowing of the spinal canal that causes compression of the spinal cord. Each vertebra in the spinal column has an opening that extends through it. The openings are aligned vertically to form the spinal canal. The spinal cord runs through the spinal canal. As the spinal canal narrows, the spinal cord and nerve roots extending from the spinal cord and between adjacent vertebrae are compressed and may become inflamed. Spinal stenosis can cause pain, weakness, numbness, burning sensations, tingling, and in particularly severe cases, may cause loss of bladder or bowel function, or paralysis. The legs, calves and buttocks are most commonly affected by spinal stenosis, however, the shoulders and arms may also be affected.

Mild cases of spinal stenosis may be treated with rest or restricted activity, non-steroidal anti-inflammatory drugs (e.g., aspirin), corticosteroid injections (epidural steroids), and/or physical therapy. Some patients find that bending forward, sitting or lying down may help relieve the pain. This may be due to bending forward creates more vertebral space, which may temporarily relieve nerve compression. Because spinal stenosis is a progressive disease, the source of pressure may have to be surgically corrected (decompressive laminectomy) as the patient has increasing pain. The surgical procedure can remove bone and other tissues that have impinged upon the spinal canal or put pressure on the spinal cord. Two adjacent vertebrae may also be fused during the surgical procedure to prevent an area of instability, improper alignment or slippage, such as that caused by spondylolisthesis. Surgical decompression can relieve pressure on the spinal cord or spinal nerve by widening the spinal canal to create more space. This procedure requires that the patient be given a general anesthesia as an incision is made in the patient to access the spine to remove the areas that are contributing to the pressure. This procedure, however, may result in blood loss and an increased chance of significant complications, and usually results in an extended hospital stay.

Minimally-invasive procedures have been developed to provide access to the space between adjacent spinous processes such that major surgery is not required. Such known procedures, however, may not be suitable in conditions where the spinous processes are severely compressed. Moreover, such procedures typically involve large or multiple incisions.

Thus, a need exists for improvements in the treatment of spinal conditions such as spinal stenosis.

SUMMARY OF THE INVENTION

Medical devices and related methods for the treatment of spinal conditions are described herein. In some embodiments, an apparatus includes a support member and a retention member. The support member has at least a portion configured to be disposed between a first spinous process and a second spinous process. The retention member is movably coupled to an end portion of the support member. The retention member is configured to displace a bodily tissue. The retention member is configured to move relative to the support member from a first position to a second position. The retention member is configured to limit movement of the support member along a longitudinal axis of the support member and relative to the first spinous process and the second spinous process when in the second position. In some embodiments, for example, the retention member and a portion of the support member collectively form a portion of a saddle configured to receive a portion of the first spinous process when the retention member is in the second position.

BRIEF DESCRIPTION OF THE DRAWINGS

FIG. 8 is a posterior view of a medical device according to an embodiment of the invention, a portion of which is in a second configuration.

FIG. 9 is a posterior view of the medical device illustrated in FIG. 7 fully deployed in the second configuration.

FIG. 10 is a front plan view of the medical device illustrated in FIG. 7 in the second configuration.

FIG. 88 is a schematic illustration of a posterior view of the implant shown in FIG. 85 in a second configuration.

FIG. 89 is a schematic illustration of a side view of the implant shown in FIG. 85 in the second configuration.

FIG. 90 is a schematic illustration of a lateral cross-sectional view of the implant shown in FIG. 85 in the second configuration taken along line A-A as shown in FIG. 89.

FIG. 133 is an exploded side view of a medical device according to an embodiment of the invention.

FIG. 134 is a distal end view of the implant shown in FIG. 133 taken along line 134-134 in FIG. 133.

FIG. 135 is a cross-sectional view of the insertion tool shown in FIG. 133 taken along line 135-135 in FIG. 133.

FIG. 136 is a top view of a portion of the medical device of FIG. 133 shown partially disposed within a body in a first position.

FIG. 139 is an exploded side view of a medical device according to another embodiment of the invention.

FIG. 140 is a distal end view of the implant shown in FIG. 139.

FIG. 141 is a distal end view of the implant shown in FIG. 139 illustrating a portion of the guide member of FIG. 139 disposed within a distal end portion of the implant.

FIG. 142 is a side exploded view of a medical device according to another embodiment of the invention.

FIG. 143 is a top view of the medical device of FIG. 142 and an insertion tool shown partially disposed within a body.

FIG. 144 is a flowchart of a method according to an embodiment of the invention.

FIG. 145 is a side view of a measurement device according to an embodiment of the invention.

FIG. 146 is a side view of the measurement device of FIG. 145 shown partially disposed within a body and illustrating a first position and a second position of the measurement device.

FIG. 147 is a side perspective view of a measurement device according to another embodiment of the invention.

FIG. 148 is a side view of the measurement device of FIG. 147 shown adjacent to an image of a portion of a spine.

FIG. 149 is a schematic illustration of a posterior view of an implant in a first configuration according to an embodiment of the invention.

FIG. 150 is a schematic illustration of a posterior view of the implant shown in FIG. 149 in a second configuration disposed between a first spinous process and second spinous process.

FIG. 151 is a schematic illustration of a posterior view of the implant shown in FIG. 149 in a third configuration.

FIG. 152 is a schematic illustration of a posterior view of the implant shown in FIG. 149 in a fourth configuration.

Figure 153:
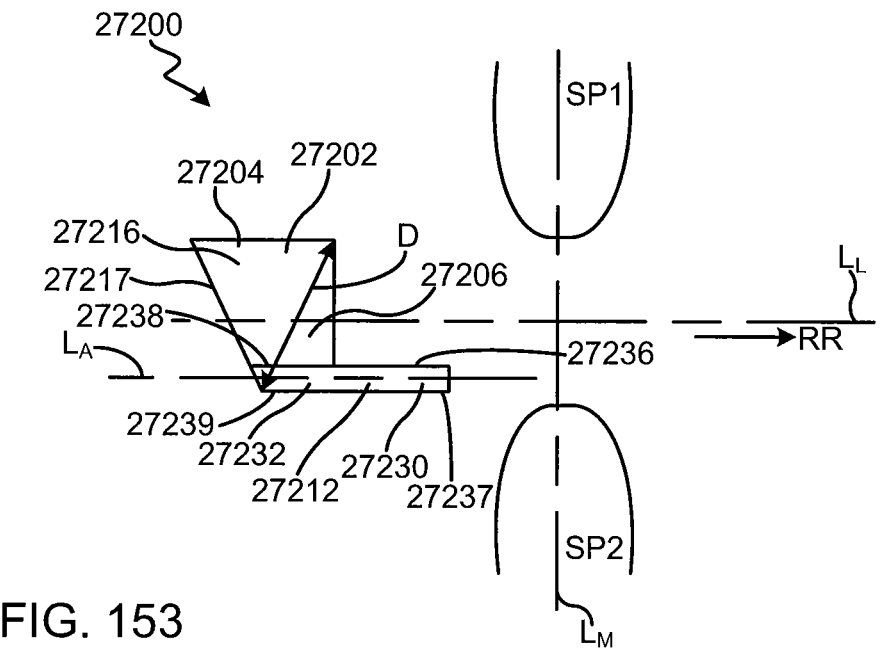

FIG. 153 is a schematic illustration of a posterior view of an implant in a first configuration according to an embodiment of the invention.

Figure 154:
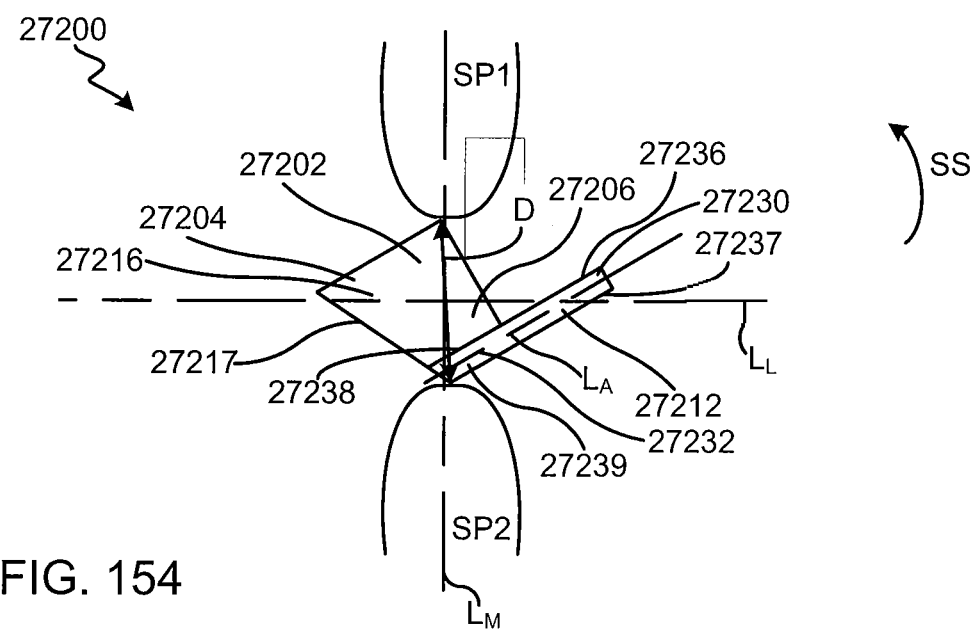

FIG. 154 is a schematic illustration of a posterior view of the implant shown in FIG. 153 in a second configuration disposed between a first spinous process and second spinous process.

Figure 155:
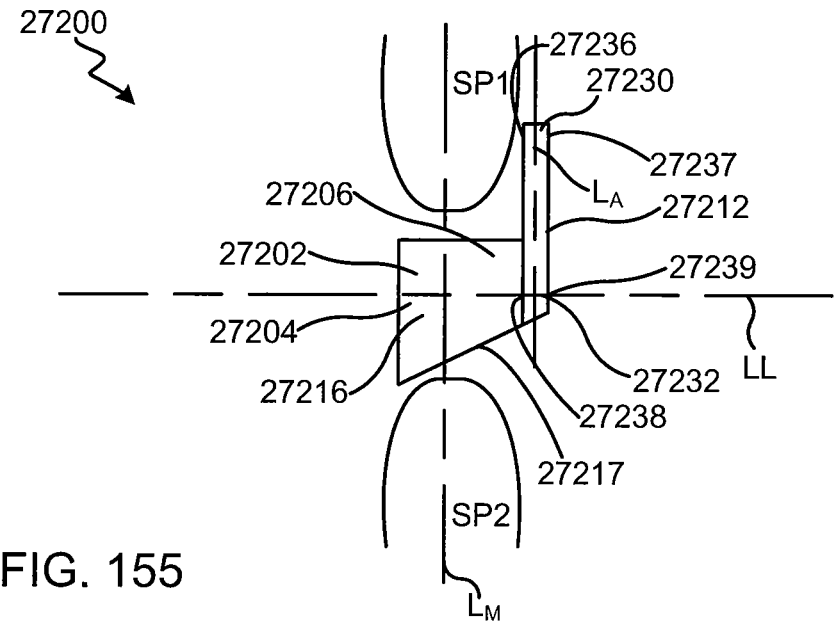

FIG. 155 is a schematic illustration of a posterior view of the implant shown in FIG. 153 in a third configuration.

Figure 156:
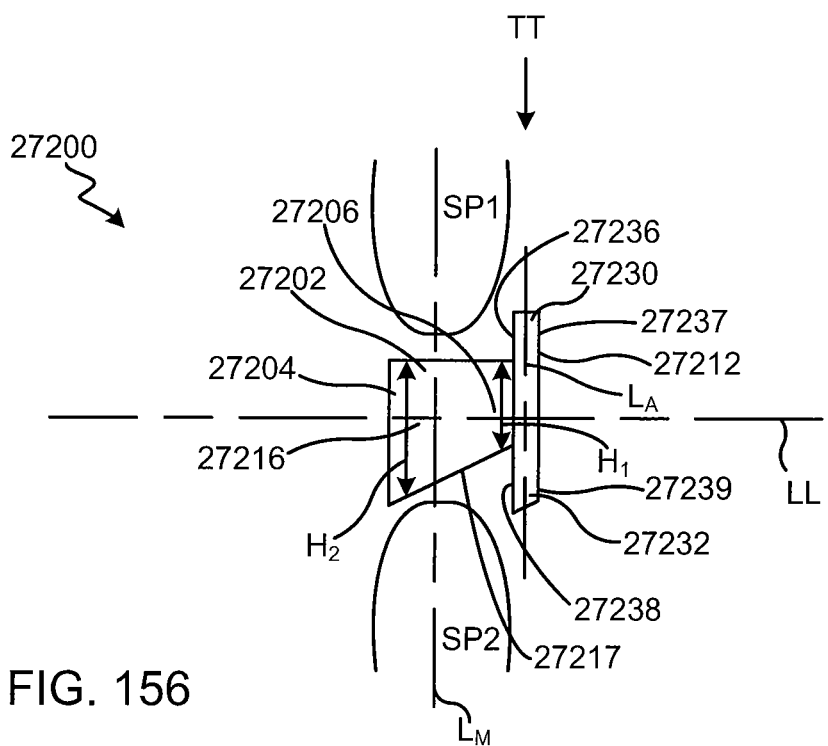

FIG. 156 is a schematic illustration of a posterior view of the implant shown in FIG. 153 in a fourth configuration.

Figure 157:
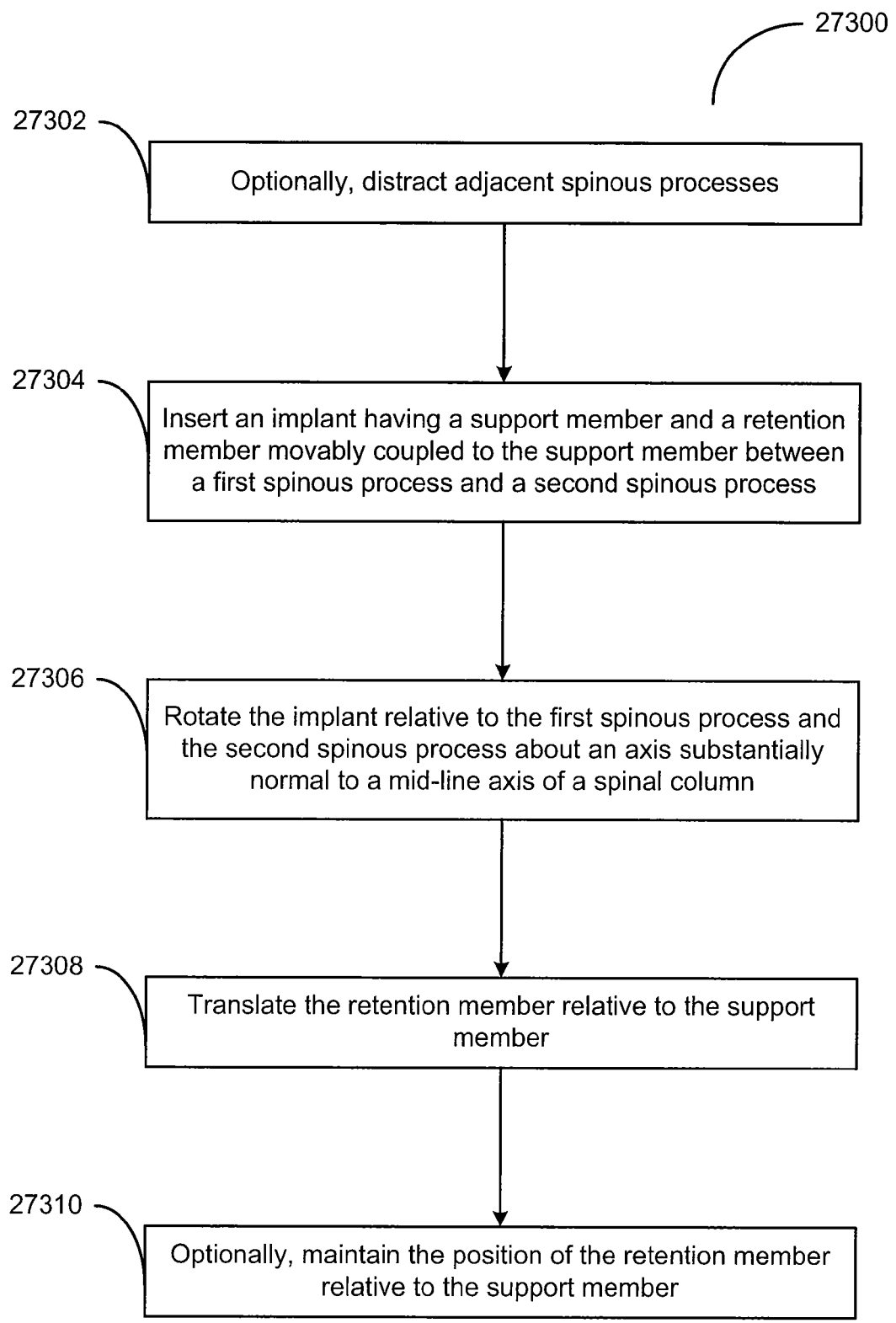

FIG. 157 is a flow chart illustrating a method of treating a spinal condition according to an embodiment of the invention.

Figure 158:
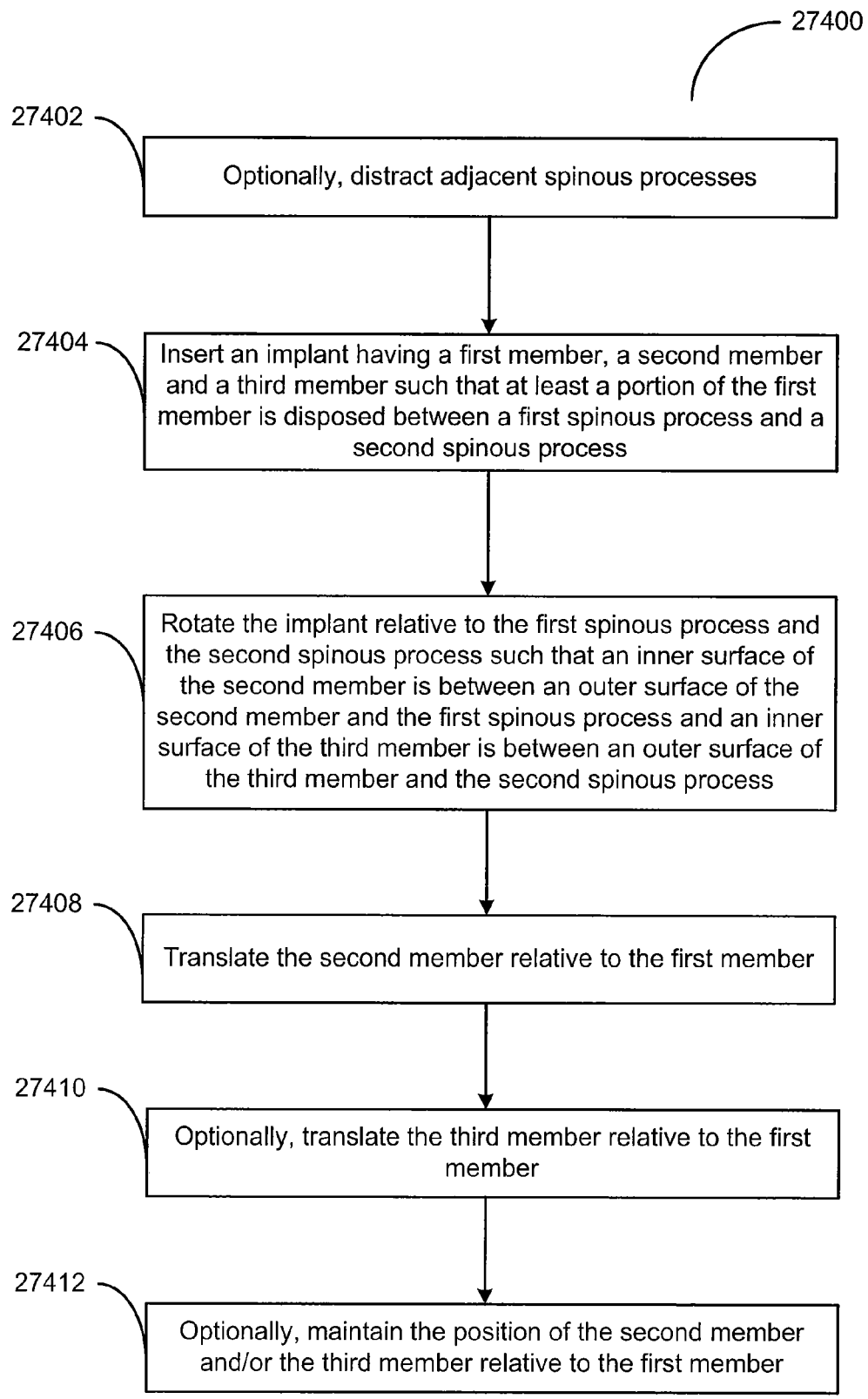

FIG. 158 is a flow chart illustrating a method of treating a spinal condition according to an embodiment of the invention.

DETAILED DESCRIPTION

As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the implant end first inserted inside the patient's body would be the distal end of the implant, while the implant end to last enter the patient's body would be the proximal end of the implant.

In some embodiments, an apparatus includes a support member and a retention member. The support member has at least a portion configured to be disposed between a first spinous process and a second spinous process. The retention member is movably coupled to an end portion of the support member. The retention member is configured to displace a bodily tissue. The retention member is configured to move relative to the support member from a first position to a second position. The retention member is configured to limit movement of the support member along a longitudinal axis of the support member and relative to the first spinous process and the second spinous process when in the second position. In some embodiments, for example, the retention member and a portion of the support member collectively form a portion of a saddle configured to receive a portion of the first spinous process when the retention member is in the second position.

In some embodiments, an apparatus includes a first member and a second member. The first member has a longitudinal axis, a first surface, and a second surface offset from the longitudinal axis by a non-zero angle. At least a portion of the first surface is configured to engage a spinous process. The second member is rotatably coupled to a distal end of the first member. The second member is configured to move relative to the first member between a first position and a second position. In some embodiments, for example, the second member is configured to rotate relative to the first member about an axis substantially parallel to the longitudinal axis of the first member. When the second member is in the first position, at least a portion of a surface of the second member is disposed adjacent at least a portion of the second surface of the first member. In some embodiments, for example, the surface of the second member is in contact with the portion of the second surface of the first member when the second member is in the first position. When the second member is in the second position, the portion of the second surface of the second member is spaced apart from the portion of the second surface of the first member. The portion of the surface of the second member is configured to limit movement of the first member along the longitudinal axis and relative to the spinous process when the second member is in the second position.

In some embodiments, an apparatus includes a support member and a retention member rotatably coupled to the distal end of the support member. The support member has at least a portion configured to engage adjacent spinous processes. A distal end of the support member has a cross-sectional area normal to a longitudinal axis of the support member. The retention member has a cross-sectional area normal to the longitudinal axis of the support member. The retention member is configured to rotate relative to the support member about an axis substantially parallel to the longitudinal axis of the support member from a first position to a second position. When the retention member is in the second position, the retention member is configured to limit movement of the support member along the longitudinal axis and relative to the first spinous process and the second spinous process. When the retention member is in the first position, the cross-sectional area of the retention member is within the cross-sectional area of the distal end of the support member when projected on a plane substantially normal to the longitudinal axis. When the retention member is in the second position, a portion of the cross-sectional area of the retention member is outside of the cross-sectional area of the distal end of the support member when projected on the plane substantially normal to the longitudinal axis.

In some embodiments, an apparatus includes a support member and a retention member movably coupled to the distal end of the support member. The support member has at least a portion configured to engage adjacent spinous processes. A distal end of the support member has a first dimension along a first axis substantially normal to a longitudinal axis of the support member and a second dimension along a second axis that is normal to both the longitudinal axis and the first axis. The second dimension is greater than the first dimension (e.g., the distal end of the support member is rectangular). The retention member has a first dimension along the first axis and a second dimension along the second axis. The first dimension of the retention member is greater than the second dimension of the support member and is no greater than the first dimension of the support member. The second dimension of the retention member is no greater than the second dimension of the support member. The retention member is configured to displace a bodily tissue. The retention member is configured to move relative to the support member from a first position to a second position. In some embodiments, for example, when the retention member is in the first position, the first dimension of the retention member is aligned with the first dimension of the support member. When the retention member is in the second position, the first dimension of the retention member is aligned with the second dimension of the support member. In this manner, the retention member can limit movement of the support member along a longitudinal axis and relative to the spinous processes.

In some embodiments, an apparatus includes a support member, a retention member and a locking member. The support member is configured to be disposed between a first spinous process and a second spinous process. The retention member is movably coupled to a distal end of the support member. The retention member is configured to move from a first position to a second position to limit movement of the support member along a longitudinal axis and relative to the first spinous process and the second spinous process. The locking member is disposed within the support member and is configured to engage a first surface of the retention member when the retention member is in the first position such that the retention member is maintained in the first position. At least a portion of the locking member is disposed outside of the support member and is configured to engage a second surface of the retention member when the retention member is in the second position such that the retention member is maintained in the second position. The second surface is different than the first surface.

In some embodiments, a method includes disposing at least a portion of an implant between adjacent spinous processes. The implant includes a support member and a retention member movably coupled to the support member. The retention member is rotated from a first position to a second position such that the retention member retains a portion of the implant between the adjacent spinous processes. In some embodiments, the retention member can be rotated about an axis substantially parallel to a longitudinal axis of the support member. The retention member is reversibly locked in the second position.

In some embodiments, an apparatus includes a support member, a first retention member and a second retention member. The support member has at least a portion configured to be disposed between a first spinous process and a second spinous process. The first retention member is movably coupled to a first end portion of the support member. The second retention member is movably coupled to a second end portion of the support member. The second retention member is coupled to the first retention member such that the first retention member and the second retention member are configured to collectively move relative to the support member from a first position to a second position. The first retention member and the second retention member are configured to limit movement of the support member relative to the first spinous process and the second spinous process when in the second position.

In some embodiments, an apparatus includes a support member and a retention member rotatably coupled to the support member. The support member has an outer surface configured to be disposed between a first spinous process and a second spinous process. The retention member has a first end portion and a second end portion. The first end portion of the retention member is spaced apart from the outer surface of the support member by a first distance along an axis substantially normal to a longitudinal axis of the support member when the outer surface of the support member is disposed between the first spinous process and the second spinous process. The second end portion of the retention member is spaced apart from the outer surface of the support member by a second distance along the axis substantially normal to the longitudinal axis of the support member when the outer surface of the support member is disposed between the first spinous process and the second spinous process. The first end portion of the retention member and the second end portion of the retention member are configured to cooperatively limit movement of the support member along the longitudinal axis of the support member and relative to the first spinous process and the second spinous process. In some embodiments, for example, the first end portion of the retention member is configured to engage the first spinous process when the outer surface of the support member is disposed between the first spinous process and the second spinous process. In some embodiments, for example, the second end portion of the retention member is configured to engage the second spinous process when the outer surface of the support member is disposed between the first spinous process and the second spinous process.

In some embodiments, an apparatus includes a support member and a retention member rotatably coupled to the support member about an axis substantially normal to a longitudinal axis of the support member. The support member has a portion configured to be disposed between a first spinous process and a second spinous process. The retention member has a first end portion, a second end portion, and a central portion. The central portion of the retention member is disposed within the support member. The first end portion of the retention member is disposed outside of a distal end portion of the support member and is configured to engage the first spinous process when the portion of the support member is disposed between the first spinous process and the second spinous process. The second end portion of the retention member is disposed outside of a proximal end portion of the support member and is configured to engage the second spinous process when the portion of the support member is disposed between the first spinous process and the second spinous process.

In some embodiments, an apparatus includes a support member and a retention member rotatably coupled to the support member between a first position and a second position. The support member has a portion configured to be disposed between a first spinous process and a second spinous process. A distal end portion of the support member has a cross-sectional area normal to a longitudinal axis of the support member. The retention member has an end portion and a central portion. The central portion is disposed within the support member. The end portion of the retention member is configured to displace a bodily tissue, such as for example, a supraspinous ligament. The end portion of the retention member has a cross-sectional area normal to the longitudinal axis of the support member. The cross-sectional area of the end portion of the retention member is within the cross-sectional area of the distal end portion of the support member when projected on a plane substantially normal to the longitudinal axis and when the retention member is in the first position. At least a portion of the cross-sectional area of the end portion of retention member is outside of the cross-sectional area of the distal end of the support member when projected on the plane substantially normal to the longitudinal axis and when the retention member is in the second position.

In some embodiments, an apparatus includes a first elongate member and a second elongate member rotatably coupled to the first elongate member. The first elongate member and the second elongate member collectively have a first configuration and a second configuration. When the first elongate member and the second elongate member are in the first configuration, a longitudinal axis of the second elongate member is substantially parallel to a longitudinal axis of the first elongate member. When the first elongate member and the second elongate member are in the second configuration, the longitudinal axis of the second elongate member is angularly offset from the longitudinal axis of the first elongate member. When the first elongate member and the second elongate member are in the second configuration, a portion of the first elongate member is configured to contact a first side of a spinous process and a portion of the second elongate member is configured to contact a second side of the spinous process opposite the first side to cooperatively limit movement of the first elongate member relative to the spinous process.

In some embodiments, a method includes disposing at least a portion of an implant between a first spinous process and a second spinous process. The implant includes a support member and a retention member rotatably coupled to the support member. The retention member is rotated relative to the support member from a first position to a second position such that a first end portion of the retention member is disposed outside of a proximal end portion of the support member and a second end portion of the retention member is disposed outside a distal end portion of the support member. The first end portion of the retention member and the second end portion of the retention member cooperatively limit movement of the support member along a longitudinal axis of the support member and relative to the first spinous process and the second spinous process. In some embodiments, the method can optionally include locking the retention member in the second position after the rotating.

In some embodiments, a method includes disposing at least a portion of an implant between a first spinous process and a second spinous process. The implant includes a first elongate member and a second elongate member rotatably coupled to the first elongate member. The second elongate member is rotated relative to the first elongate member about an axis substantially normal to a longitudinal axis of the support member from a first position to a second position such that a portion of the first elongate member is engagable with a first surface of the first spinous process and a portion of the second elongate member is engagable with a second surface of the first spinous process opposite the first surface to limit lateral movement of the implant.

In one variation, a method provides for the insertion of an implant between adjacent bone structures. For example, an implant is inserted between adjacent spinous processes. The implant can be advanced within a body to a location between adjacent bone structures with an insertion tool and guided by a path defined by a guide member releasably coupled to the guide member. For example, the guide member can define a curved path through the body and a portion of the path goes between the adjacent bone structures.

In one embodiment, a method includes inserting at least a portion of a guide member between adjacent spinous processes. An implant that is coupled to the guide member is advanced such that the guide member is advanced along a curved path until at least a portion of the implant is positioned between the adjacent spinous processes. An apparatus according to an embodiment of the invention includes an implant configured to be disposed between adjacent spinous processes and a guide member having a proximal end releasably couplable to the implant. The implant is stationary relative to the guide member when the guide member is releasably coupled to the implant. The guide member has a curved shape and a distal tip configured to be percutaneously inserted into a body.

In another embodiment, a method includes percutaneously inserting a guide member at a first exterior location of a body. An implant coupled to a proximal end of the guide member is advanced along a path defined by the guide member such that during the advancing, a proximal end of the implant is at a fixed distance from the proximal end of the guide member. A distal end of the guide member is advanced through a second exterior location of the body.

In another embodiment, an apparatus includes an implant configured to be inserted into a body and a guide member. The guide member has a proximal end releasably couplable to the implant such that a distance between a proximal end of the implant and the proximal end of the guide member is fixed during insertion of the implant into the body. The guide member has a distal tip configured to be percutaneously inserted into the body at a first location and exit the body at a second location different than the first location.

In some embodiments, a method includes inserting an implant having a support member and a retention member movably coupled to the support member such that at least a portion of the support member of the implant is disposed between a first spinous process and a second spinous process. The implant is rotated relative to the first spinous process and the second spinous process about an axis substantially normal to a mid-line axis of a spinal column while the portion of the support member is disposed between the first spinous process and the second spinous process. In some embodiments, the implant is rotated such that an inner surface of an end portion of the retention member is between an outer surface of the end portion of the retention member and the first spinous process. The retention member is translated relative to the support member.

In some embodiments, a method includes inserting an implant having a first member, a second member and a third member such that at least a portion of the first member of the implant is disposed between a first spinous process and a second spinous process. The implant is rotated relative to the first spinous process and the second spinous process such that an inner surface of the second member is between an outer surface of the second member and the first spinous process and an inner surface of the third member is between an outer surface of the third member and the second spinous process. The second member is translated relative to the first member after the implant is rotated. In some embodiments, the third member is translated relative to the first member after the implant is rotated.

In some embodiments, an apparatus includes a support member and a retention member movably coupled to an end portion of the support member. The support member is configured to have at least a portion disposed between a first spinous process and a second spinous process. The retention member is configured to translate relative to the support member from a first position to a second position along a longitudinal axis of the retention member. The retention member is configured to limit movement of the support member relative to the first spinous process and the second spinous process when in the second position.

In some embodiments, an apparatus includes a support member, a first retention member and a second retention member. The support member is configured to have at least a portion disposed between a first spinous process and a second spinous process. The first retention member is movably coupled to a first end portion of the support member. The first retention member is configured to translate relative to the support member from a first position to a second position along a longitudinal axis of the first retention member. The second retention member is movably coupled to a second end portion of the support member. The second retention member is configured to translate relative to the support member from a first position to a second position along a longitudinal axis of the second retention member. In some embodiments, the support member, the first retention member and the second retention member are collectively configured to rotate about an axis normal to a mid-line axis of a spinal column when the portion of the support member is disposed between the first spinous process and the second spinous process, the first retention member is in its first position and the second retention member is in its first position.

The term "body" is used here to mean a mammalian body. For example, a body can be a patient's body, or a cadaver, or a portion of a patient's body or a portion of a cadaver.

The term "parallel" or is used herein to describe a relationship between two geometric constructions (e.g., two lines, two planes, a line and a plane, two curved surfaces, a line and a curved surface or the like) in which the two geometric constructions are substantially non-intersecting as they extend substantially to infinity. For example, as used herein, a line is said to be parallel to a curved surface when the line and the curved surface do not intersect as they extend to infinity. Similarly, when a planar surface (i.e., a two-dimensional surface) is said to be parallel to a line, every point along the line is spaced apart from the nearest portion of the surface by a substantially equal distance. Two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

The term "normal" is used herein to describe a relationship between two geometric constructions (e.g., two lines, two planes, a line and a plane, two curved surfaces, a line and a curved surface or the like) in which the two geometric constructions intersect at an angle of approximately 90 degrees within at least one plane. For example, as used herein, a line is said to be normal to a curved surface when the line and the curved surface intersect at an angle of approximately 90 degrees within a plane. Two geometric constructions are described herein as being "normal" or "substantially normal" to each other when they are nominally normal to each other, such as for example, when they are normal to each other within a tolerance. Such tolerances can include, for example, manufacturing tolerances, measurement tolerances or the like.

Figure 1:
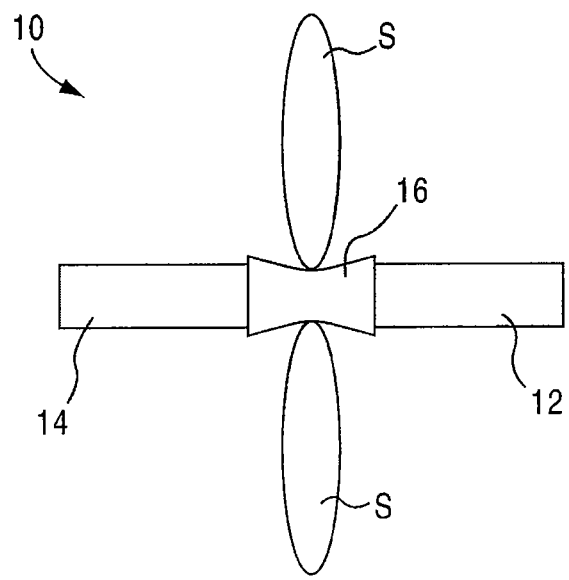
FIG. 1 is a schematic illustration of a posterior view of a medical device according to an embodiment of the invention in a first configuration adjacent two adjacent spinous processes.

FIG. 1 is a schematic illustration of a medical device according to an embodiment of the invention adjacent two adjacent spinous processes. The medical device 10 includes a proximal portion 12, a distal portion 14 and a central portion 16. The medical device 10 has a first configuration in which it can be inserted between adjacent spinous processes S. The central portion 16 is configured to contact the spinous processes S to prevent over-extension/compression of the spinous processes S. In some embodiments, the central portion 16 does not substantially distract the adjacent spinous processes S. In other embodiments, the central portion 16 does not distract the adjacent spinous processes S.

In the first configuration, the proximal portion 12, the distal portion 14 and the central portion 16 are coaxial (i.e., share a common longitudinal axis). In some embodiments, the proximal portion 12, the distal portion 14 and the central portion 16 define a tube having a constant inner diameter. In other embodiments, the proximal portion 12, the distal portion 14 and the central portion 16 define a tube having a constant outer diameter and/or inner diameter.

Figure 2:
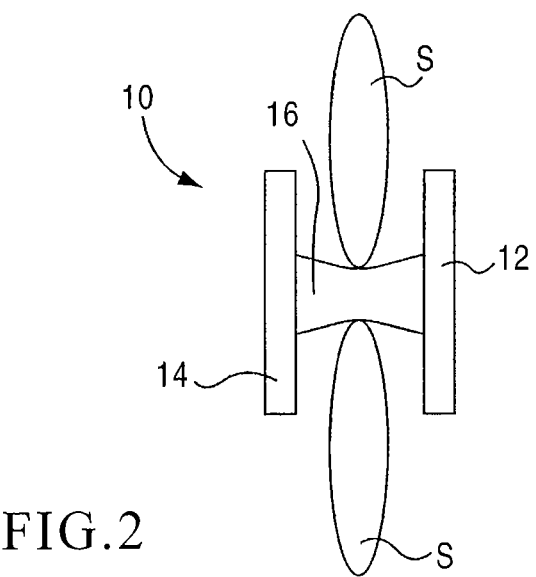
FIG. 2 is a schematic illustration of a posterior view of a medical device according to an embodiment of the invention in a second configuration adjacent two adjacent spinous processes.

The medical device 10 can be moved from the first configuration to a second configuration as illustrated in FIG. 2. In the second configuration, the proximal portion 12 and the distal portion 14 are positioned to limit lateral movement of the device 10 with respect to the spinous processes S. The proximal portion 12 and the distal portion 14 are configured to engage the spinous process (i.e., either directly or through surrounding tissue) in the second configuration. For purposes of clarity, the tissue surrounding the spinous processes S is not illustrated.

In some embodiments, the proximal portion 12, the distal portion 14 and the central portion 16 are monolithically formed. In other embodiments, one or more of the proximal portion 12, the distal portion 14 and the central portion 16 are separate components that can be coupled together to form the medical device 10. For example, the proximal portion 12 and distal portion 14 can be monolithically formed and the central portion can be a separate component that is coupled thereto.

In use, the spinous processes S can be distracted prior to inserting the medical device 10. Distraction of spinous processes is discussed below. When the spinous processes are distracted, a trocar can be used to define an access passage for the medical device 10. In some embodiments, the trocar can be used to define the passage as well as distract the spinous processes S. Once an access passage is defined, the medical device 10 is inserted percutaneously and advanced between the spinous processes, distal end 14 first, until the central portion 16 is located between the spinous processes S. Once the medical device 10 is in place between the spinous processes, the proximal portion 12 and the distal portion 14 are moved to the second configuration, either serially or simultaneously.

In some embodiments, the medical device 10 is inserted percutaneously (i.e., through an opening in the skin) and in a minimally-invasive manner. For example, as discussed in detail herein, the size of portions of the implant is expanded after the implant is inserted between the spinous processes. Once expanded, the size of the expanded portions of the implant is greater than the size of the opening. For example, the size of the opening/incision in the skin may be between 3 millimeters in length and 25 millimeters in length. In some embodiments, the size of the implant in the expanded configuration is between 3 and 25 millimeters.

Figure 3:
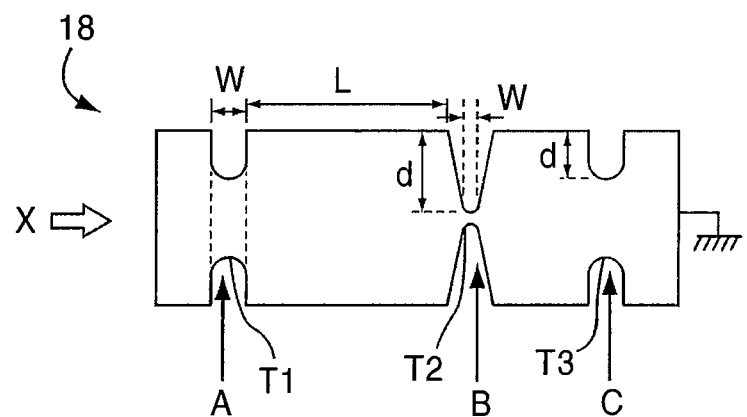
FIG. 3 is a schematic illustration of a deforming element according to an embodiment of the invention in a first configuration.

FIG. 3 is a schematic illustration of a deformable element 18 that is representative of the characteristics of, for example, the distal portion 14 of the medical device 10 in a first configuration. The deformable member 18 includes cutouts A, B, C along its length to define weak points that allow the deformable member 18 to deform in a predetermined manner. Depending upon the depth d of the cutouts A, B, C and the width w of the throats T1, T2, T3, the manner in which the deformable member 18 deforms under an applied load can be controlled and varied. Additionally, depending upon the length L between the cutouts A, B, C (i.e., the length of the material between the cutouts) the manner in which the deformable member 18 deforms can be controlled and varied.

Figure 4:
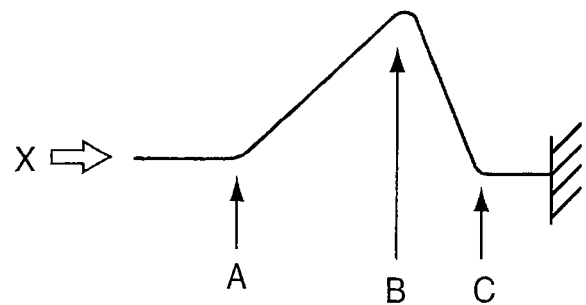
FIG. 4 is a schematic illustration of a side view of the expanding element illustrated in FIG. 3.

FIG. 4 is a schematic illustration of the expansion properties of the deformable member 18 illustrated in FIG. 3. When a load is applied, for example, in the direction indicated by arrow X, the deformable member 18 deforms in a predetermined manner based on the characteristics of the deformable member 18 as described above. As illustrated in FIG. 4, the deformable member 18 deforms most at cutouts B and C due to the configuration of the cutout C and the short distance between cutouts B and C. In some embodiments, the length of the deformable member 18 between cutouts B and C is sized to fit adjacent a spinous process.

The deformable member 18 is stiffer at cutout A due to the shallow depth of cutout A. As indicated in FIG. 4, a smooth transition is defined by the deformable member 18 between cutouts A and B. Such a smooth transition causes less stress on the tissue surrounding a spinous process than a more drastic transition such as between cutouts B and C. The dimensions and configuration of the deformable member 18 can also determine the timing of the deformation at the various cutouts. The weaker (i.e., deeper and wider) cutouts deform before the stronger (i.e., shallower and narrower) cutouts.

Figures 5, 6:
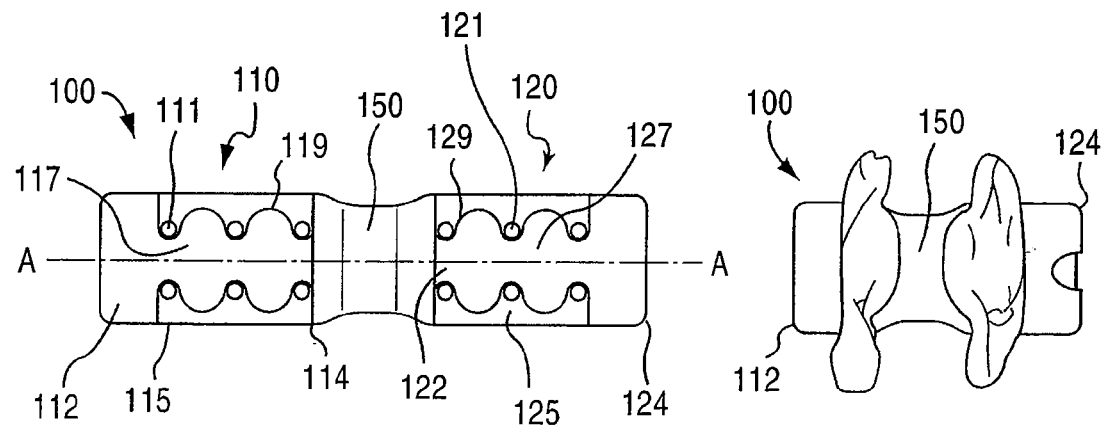
FIG. 5 is a side view of a medical device according to an embodiment of the invention in a first configuration.
FIG. 6 is a side view of the medical device illustrated in FIG. 5 in a second configuration.

FIGS. 5 and 6 illustrate a spinal implant 100 in a first configuration and second configuration, respectively. As shown in FIG. 5, the spinal implant 100 is collapsed in a first configuration and can be inserted between adjacent spinous processes. The spinal implant 100 has a first expandable portion 110, a second expandable portion 120 and a central portion 150. The first expandable portion 110 has a first end 112 and a second end 1140. The second expandable portion 120 has a first end 122 and a second end 124. The central portion 150 is coupled between second end 1140 and first end 122. In some embodiment, the spinal implant 100 is monolithically formed.

The first expandable portion 110, the second expandable portion 120 and the central portion 150 have a common longitudinal axis A along the length of spinal implant 100. The central portion 150 can have the same inner diameter as first expandable portion 110 and the second expandable portion 120. In some embodiments, the outer diameter of the central portion 150 is smaller than the outer diameter of the first expandable portion 110 and the second expandable portion 120.

In use, spinal implant 100 is inserted percutaneously between adjacent spinous processes. The first expandable portion 110 is inserted first and is moved past the spinous processes until the central portion 150 is positioned between the spinous processes. The outer diameter of the central portion 150 can be slightly smaller than the space between the spinous processes to account for surrounding ligaments and tissue. In some embodiments, the central portion directly contacts the spinous processes between which it is positioned. In some embodiments, the central portion of spinal implant 100 is a fixed size and is not compressible or expandable.

The first expandable portion 110 includes expanding members 115, 117 and 119. Between the expanding members 115, 117, 119, openings 111 are defined. As discussed above, the size and shape of the openings 111 influence the manner in which the expanding members 115, 117, 119 deform when an axial load is applied. The second expandable portion 120 includes expanding members 125, 127 and 129. Between the expanding members 125, 127, 129, openings 121 are defined. As discussed above, the size and shape of the openings 121 influence the manner in which the expanding members 125, 127, 129 deform when an axial load is applied.

When an axial load is applied to the spinal implant 100, the spinal implant 100 expands to a second configuration as illustrated in FIG. 6. In the second configuration, first end 112 and second end 1140 of the first expandable portion 110 move towards each other and expanding members 115, 117, 119 project substantially laterally away from the longitudinal axis A. Likewise, first end 122 and second end 124 of the second expandable portion 120 move towards one another and expanding members 125, 127, 129 project laterally away from the longitudinal axis A. The expanding members 115, 117, 119, 125, 127, 129 in the second configuration form projections that extend to positions adjacent to the spinous processes between which the spinal implant 100 is inserted. In the second configuration, the expanding members 115, 117, 119, 125, 127, 129 inhibit lateral movement of the spinal implant 100, while the central portion 150 prevents the adjacent spinous processes from moving together any closer than the distance defined by the diameter of the central portion 150.

Figure 7:
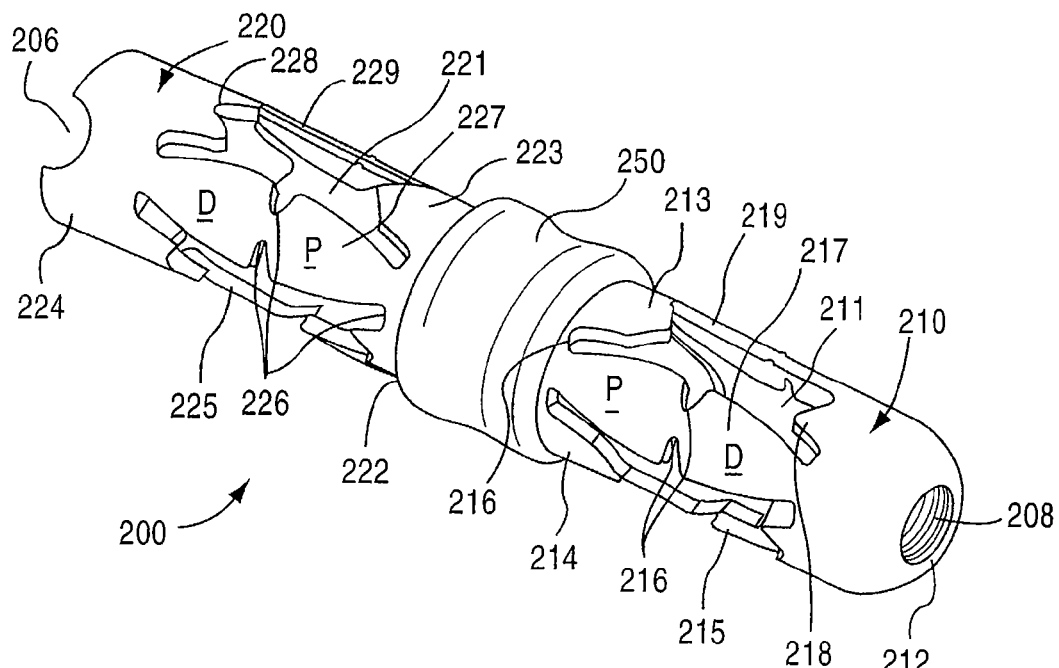
FIG. 7 is a perspective view of a medical device according to an embodiment of the invention in a first configuration.
Figure 11:
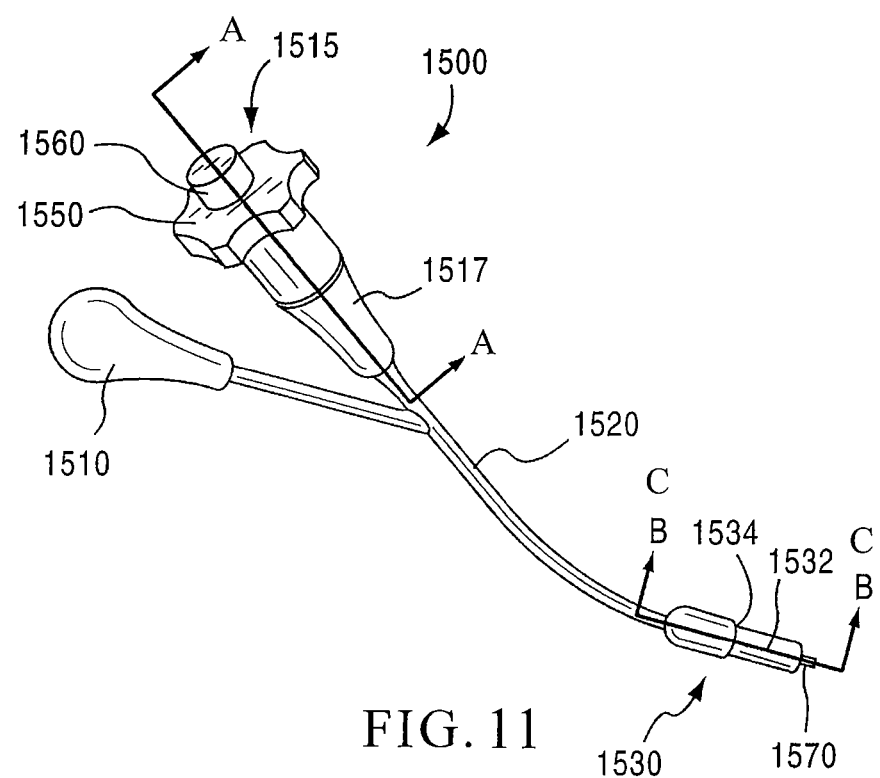
FIG. 11 is a perspective view of an implant expansion device according to an embodiment of the invention.
Figure 12:
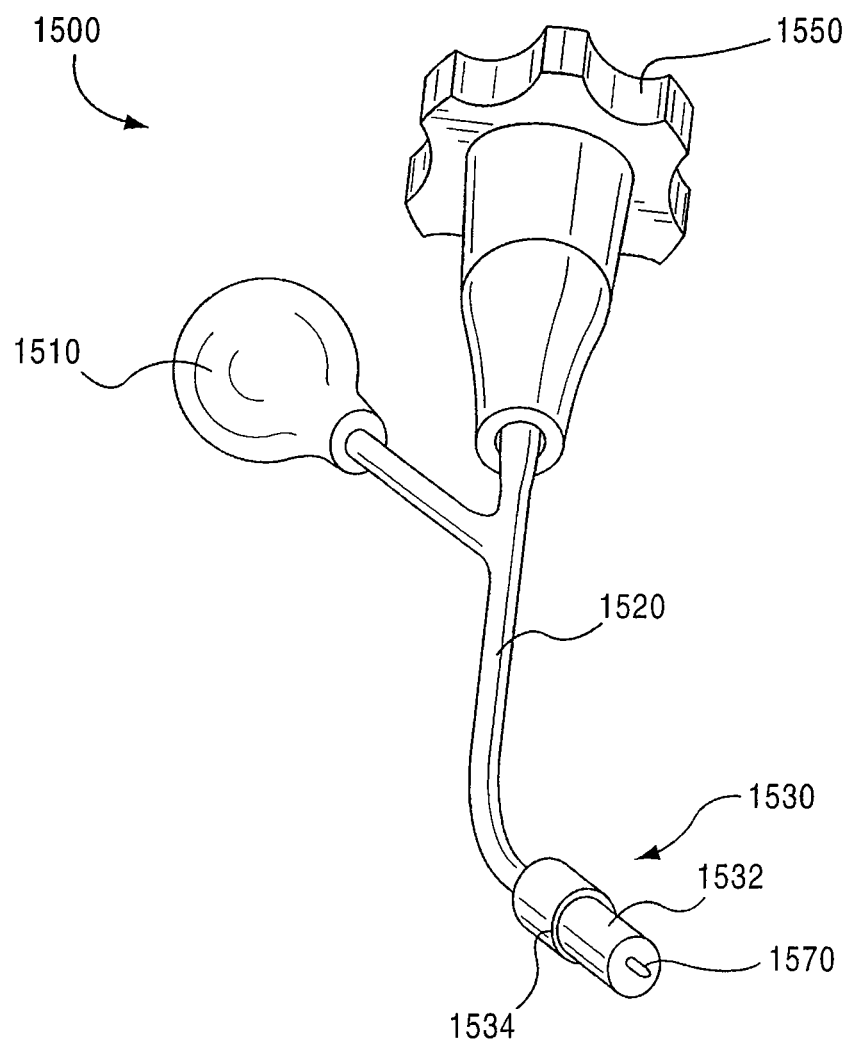
FIG. 12 is an alternative perspective view of the implant expansion device illustrated in FIG. 11.
Figure 13:
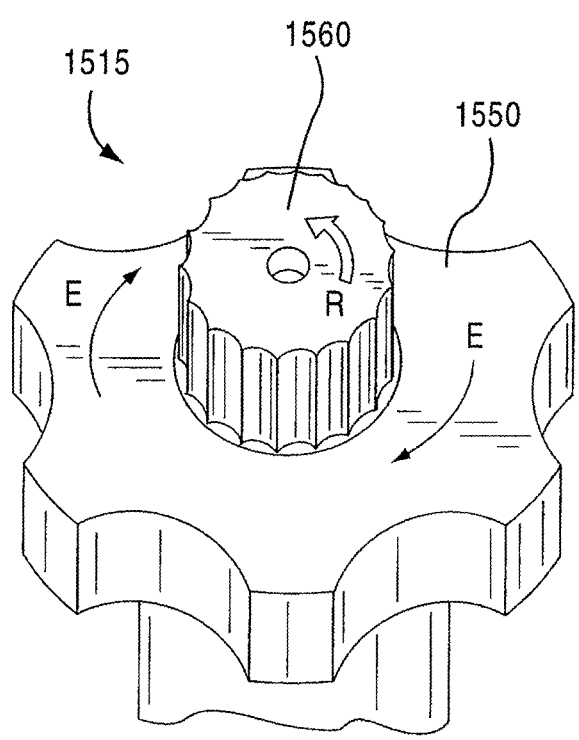
FIG. 13 is a perspective view of a portion of the implant expansion device illustrated in FIG. 11.

A spinal implant 200 according to an embodiment of the invention is illustrated in FIGS. 7-9 in various configurations. Spinal implant 200 is illustrated in a completely collapsed configuration in FIG. 7 and can be inserted between adjacent spinous processes. The spinal implant 200 has a first expandable portion 210, a second expandable portion 220 and a central portion 250. The first expandable portion 210 has a first end 212 and a second end 214. The second expandable portion 220 has a first end 222 and a second end 224. The central portion 250 is coupled between second end 214 and first end 222.

The first expandable portion 210, the second expandable portion 220 and the central portion 250 have a common longitudinal axis A along the length of spinal implant 200. The central portion 250 can have the same inner diameter as first expandable portion 210 and the second expandable portion 220. The outer diameter of the central portion 250 is greater than the outer diameter of the first expandable portion 210 and the second expandable portion 220. The central portion 250 can be monolithically formed with the first expandable portion 210 and the second expandable portion 220 or can be a separately formed sleeve coupled thereto or thereupon.

In use, spinal implant 200 is inserted percutaneously between adjacent spinous processes S. The first expandable portion 210 is inserted first and is moved past the spinous processes S until the central portion 250 is positioned between the spinous processes S. The outer diameter of the central portion 250 can be slightly smaller than the space between the spinous processes S to account for surrounding ligaments and tissue. In some embodiments, the central portion 250 directly contacts the spinous processes S between which it is positioned. In some embodiments, the central portion 250 of spinal implant 200 is a fixed size and is not compressible or expandable. In other embodiments, the central portion 250 can compress to conform to the shape of the spinous processes.

The first expandable portion 210 includes expanding members 215, 217 and 219. Between the expanding members 215, 217, 219, openings 211 are defined. As discussed above, the size and shape of the openings 211 influence the manner in which the expanding members 215, 217, 219 deform when an axial load is applied. Each expanding member 215, 217, 219 of the first expandable portion 210 includes a tab 213 extending into the opening 211 and an opposing mating slot 218. In some embodiments, the first end 212 of the first expandable portion 210 is rounded to facilitate insertion of the spinal implant 200.

The second expandable portion 220 includes expanding members 225, 227 and 229. Between the expanding members 225, 227, 229, openings 221 are defined. As discussed above, the size and shape of the openings 221 influence the manner in which the expanding members 225, 227, 229 deform when an axial load is applied. Each expanding member 225, 227, 229 of the second expandable portion 220 includes a tab 223 extending into the opening 221 and an opposing mating slot 228.

When an axial load is applied to the spinal implant 200, the spinal implant moves to a partially expanded configuration as illustrated in FIG. 8. In the partially expanded configuration, first end 222 and second end 224 of the second expandable portion 220 move towards one another and expanding members 225, 227, 229 project laterally away from the longitudinal axis A. To prevent the second expandable portion 220 from over-expanding, the tab 223 engages slot 228 and acts as a positive stop. As the axial load continues to be imparted to the spinal implant 200 after the tab 223 engages slot 228, the load is transferred to the first expandable portion 210. Accordingly, the first end 212 and the second end 214 then move towards one another until tab 213 engages slot 218 in the fully expanded configuration illustrated in FIG. 9. In the second configuration, expanding members 215, 217, 219 project laterally away from the longitudinal axis A. In some alternative embodiments, the first expandable portion and the second expandable portion expand simultaneously under an axial load.

The order of expansion of the spinal implant 200 can be controlled by varying the size of openings 211 and 221. For example, in the embodiments shown in FIGS. 7-9, the opening 221 is slightly larger than the opening 211. Accordingly, the notches 226 are slightly larger than the notches 216. As discussed above with respect to FIGS. 3 and 4, for this reason, the second expandable portion 220 will expand before the first expandable portion 210 under an axial load.

In the second configuration, the expanding members 215, 217, 219, 225, 227, 229 form projections that extend adjacent the spinous processes S. Once in the second configuration, the expanding members 215, 217, 219, 225, 227, 229 inhibit lateral movement of the spinal implant 200, while the central portion 250 prevents the adjacent spinous processes from moving together any closer than the distance defined by the diameter of the central portion 250.

The portion P of each of the expanding members 215, 217, 219, 225, 227, 229 proximal to the spinous process S expands such that portion P is substantially parallel to the spinous process S. The portion D of each of the expanding members 215, 217, 219, 225, 227, 229 distal from the spinous process S is angled such that less tension is imparted to the surrounding tissue.

In the second configuration, the expanding members 225, 227, 229 are separate by approximately 120 degrees from an axial view as illustrated in FIG. 10. While three expanding members are illustrated, two or more expanding members may be used and arranged in an overlapping or interleaved fashion when multiple implants 200 are inserted between multiple adjacent spinous processes. Additionally, regardless of the number of expanding members provided, the adjacent expanding members need not be separated by equal angles or distances.

The spinal implant 200 is deformed by a compressive force imparted substantially along the longitudinal axis A of the spinal implant 200. The compressive force is imparted, for example, by attaching a rod (not illustrated) to the first end 212 of the first expandable portion 210 and drawing the rod along the longitudinal axis while imparting an opposing force against the second end 224 of the second expandable portion 220. The opposing forces result in a compressive force causing the spinal implant 200 to expand as discussed above.

The rod used to impart compressive force to the spinal implant 200 can be removably coupled to the spinal implant 200. For example, the spinal implant 200 can include threads 208 at the first end 212 of the first expandable portion 210. The force opposing that imparted by the rod can be applied by using a push bar (not illustrated) that is removably coupled to the second end 224 of the second expandable portion 220. The push rod can be aligned with the spinal implant 200 by an alignment notch 206 at the second end 224. The spinal implant 200 can also be deformed in a variety of other ways, using a variety of expansion devices (also referred to herein as insertion tools, deployment tools and/or removal tools). While various types of implants are illustrated with various types of expansion devices, the expansion devices described herein can be used with any of the implants described herein.

FIGS. 11-16 illustrate an expansion device 1500 (also referred to herein as an insertion tool or a deployment tool) according to an embodiment of the invention. Although no particular implant is illustrated in FIGS. 11-16, any of the implants described herein, such as, for example, implant 200 (see FIG. 7), can be used with the expansion device 1500. The expansion device 1500 includes a guide handle 1510, a knob assembly 1515, a shaft 1520, a rod 1570 and an implant support portion 1530. The expansion device 1500 is used to insert an implant (not illustrated) in between adjacent spinous processes and expand the implant such that it is maintained in position between the spinous processes as described above. Both the guide handle 1510 and the knob assembly 1515 can be grasped to manipulate the expansion device 1500 to insert the implant. As described in more detail herein, the knob assembly 1515 is configured such that as the knob assembly 1515 is actuated, the rod 1570 translates and/or rotates within the shaft 1520; when the rod 1570 translates, the implant (not illustrated) is moved between its collapsed configuration and its expanded configuration; when the rod 1570 rotates, the implant is disengaged from the rod 1570.

Figure 15:
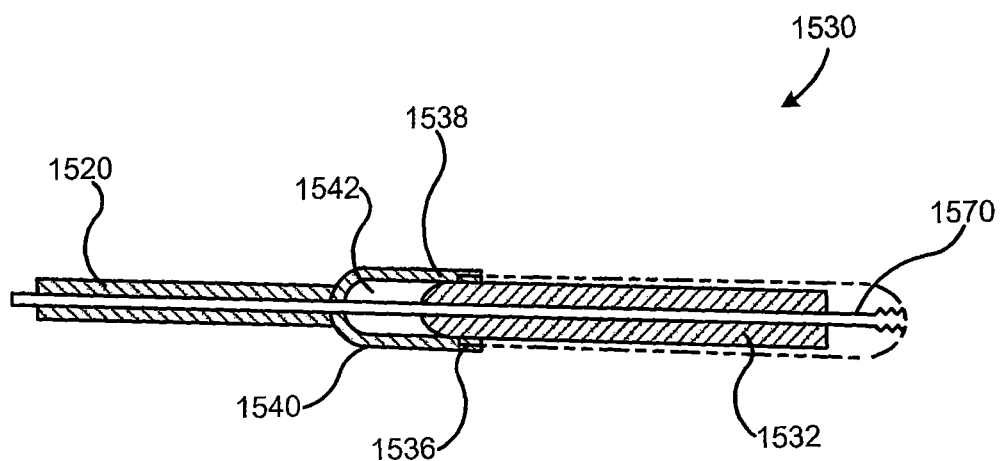
FIG. 15 is a cross-sectional view of a portion of the device illustrated in FIG. 11 in a first configuration, taken along line B-B in FIG. 11.
Figure 16:
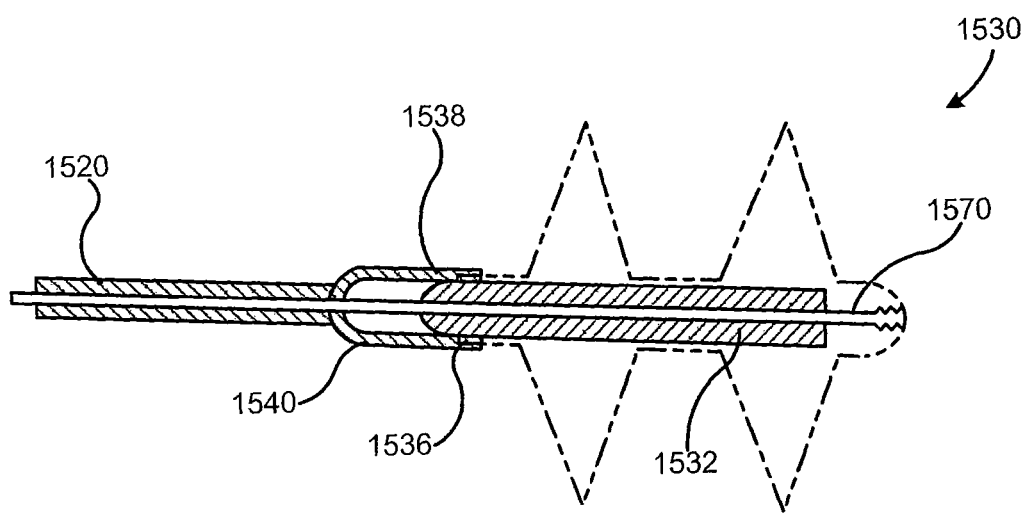
FIG. 16 is a cross-sectional view of a portion of the device illustrated in FIG. 11 in a second configuration, taken along line C-C in FIG. 11.

As best illustrated in FIGS. 15 and 16, the implant support portion 1530 includes a receiving member 1538 and a spacer 1532. The receiving member 1538 includes a side wall 1540 that is coupled to and supported by the distal end of the shaft 1520. The side wall 1540 defines an alignment protrusion 1536 and a receiving area 1542 configured to receive a portion of the spacer 1532. The implant slides over spacer 1532 until its proximal end is received within a recess 1534 defined by the side wall 1540 and the outer surface of the spacer 1532. The alignment protrusion 1536 is configured to mate with a corresponding notch on the implant (see, e.g., alignment notch 206 in FIG. 7) to align the implant with respect to the expansion device. Once the implant is aligned within the implant support portion 1530, the distal end of the implant is threadedly coupled to the distal end of rod 1570.

As illustrated, the spacer 1532 ensures that the implant is aligned longitudinally during the insertion and expansion process. The spacer 1532 can also be configured to maintain the shape of the implant during insertion and to prevent the expandable portions of the implant from extending inwardly during deployment of the implant. For example, in some embodiments, the spacer 1532 can be constructed from a solid, substantially rigid material, such as stainless steel, having an outer diameter and length corresponding to the inner diameter and length of the implant. In other embodiments, the expansion device can be configured to be used with implants that include an inner core configured to provide structural support to the implant (see, for example, FIGS. 17-23). In such embodiments, as described in more detail herein, the spacer of the insertion tool can be configured to cooperate with the inner core of the implant to provide the alignment and structural support of the implant during insertion and expansion.

Figure 14:
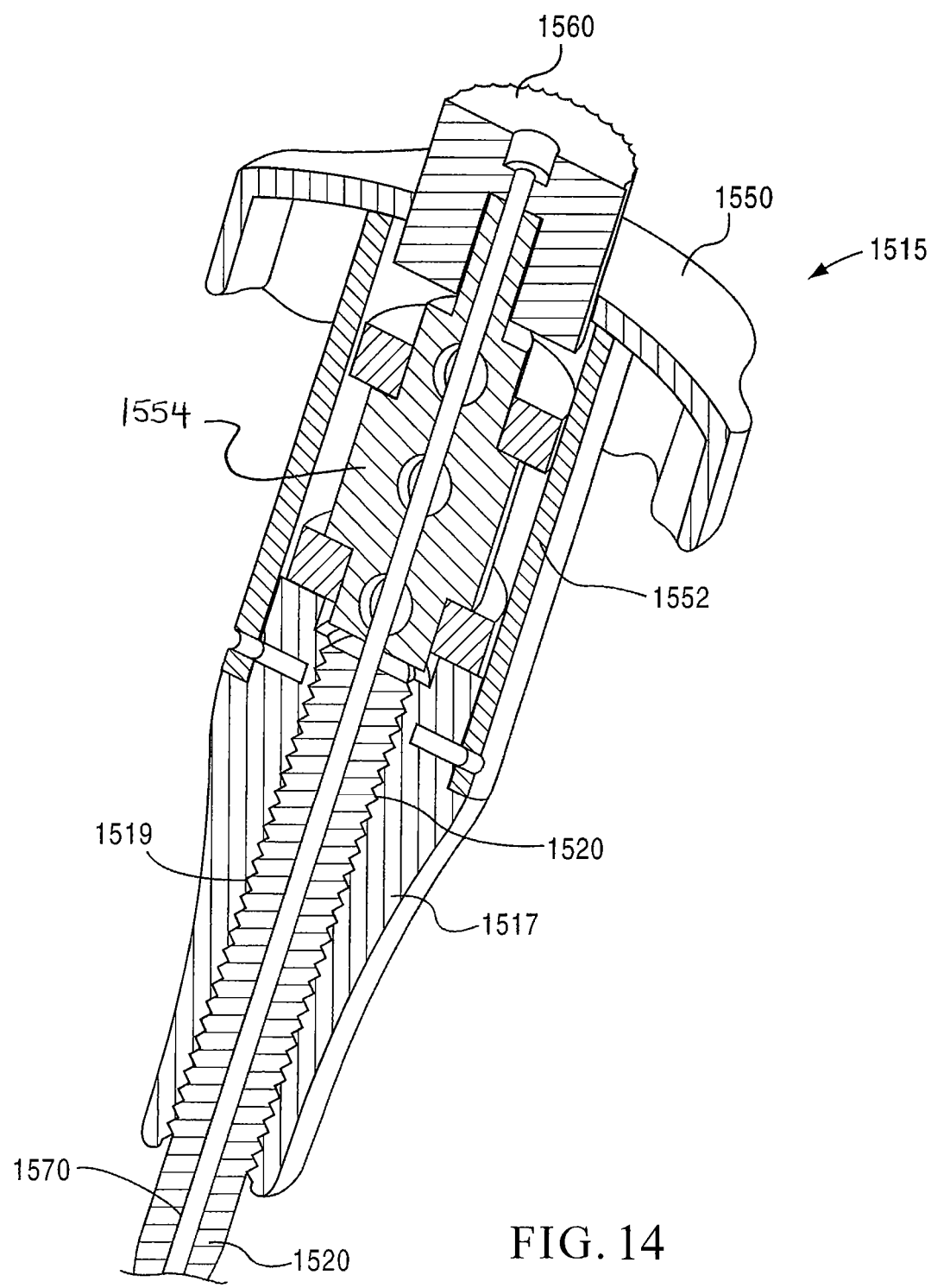
FIG. 14 is a cross-sectional view of a portion of the device illustrated in FIG. 11, taken along line A-A in FIG. 11.

The knob assembly 1515 includes an upper housing 1517 that threadedly receives the shaft 1520, an actuator knob 1550 and a release knob 1560 as best illustrated in FIG. 14. Upper housing 1517 includes internal threads 1519 that mate with external threads 1521 on shaft 1520. The proximal end of rod 1570 is coupled to the knob assembly 1515 by an adapter 1554, which is supported by two thrust bearings 1552. Actuator knob 1550 is coupled to the upper housing 1517 and is engaged with the adapter 1554 such that when actuator knob 1550 is turned in the direction indicated by arrows E (see FIG. 13), the rod 1570 translates axially relative to the shaft 1520 towards the proximal end of the device 1500, thereby acting as a draw bar and opposing the movement of the implant in the distal direction. In other words, when the implant is inserted between adjacent spinous processes and the actuator knob 1515 is turned, the distal end of the implant support portion 1530 imparts an axial force against the proximal end of the implant, while the rod 1570 causes an opposing force in the proximal direction. In this manner, the forces imparted by the implant support portion and the rod 1570 cause portions of the implant to expand in a transverse configuration such that the implant is maintained in position between the spinous processes as described above. The expansion device 1500 can also be used to move the implant from its expanded configuration to its collapsed configuration by turning the actuator knob 1550 in the opposite direction.

Once the implant is in position and fully expanded, the release knob 1560 is turned in the direction indicated by arrow R (see FIG. 13) thereby causing the rod 1570 to rotate within the shaft 1520. In this manner, the implant can be disengaged from the rod 1570. During this operation, the implant is prevented from rotating by the alignment protrusion 1536, which is configured to mate with a corresponding notch on the implant. Once the implant is decoupled from the rod 1570, the expansion tool 1500 can then be removed from the patient.

Although the knob assembly 1515 is shown and described as including an actuator knob 1550 and a release knob 1560 that are coaxially arranged with a portion of the release knob 1560 being disposed within the actuator knob 1550, in some embodiments, the release knob is disposed apart from the actuator knob. In other embodiments, the release knob and the actuator knob are not coaxially located. In yet other embodiments, the knob assembly 1515 does not include knobs having a circular shape, but rather includes levers, handles or any other device suitable for actuating the rod relative to the shaft as described above.

Figure 17:
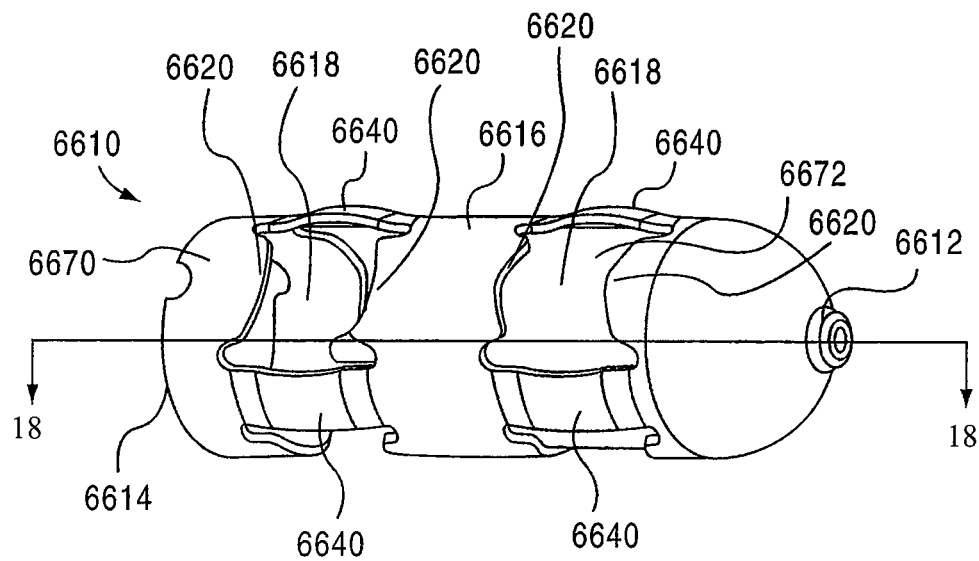
FIG. 17 is a side perspective view of an implant according to an embodiment of the invention shown in a collapsed configuration.
Figure 18:
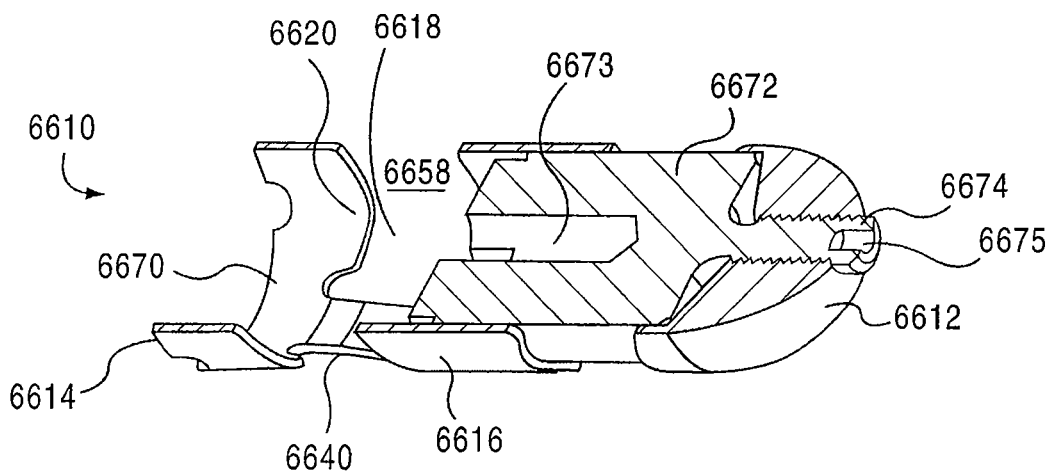
FIG. 18 is a cross-sectional view of the implant of FIG. 17 taken along line 18-18.
Figure 19:
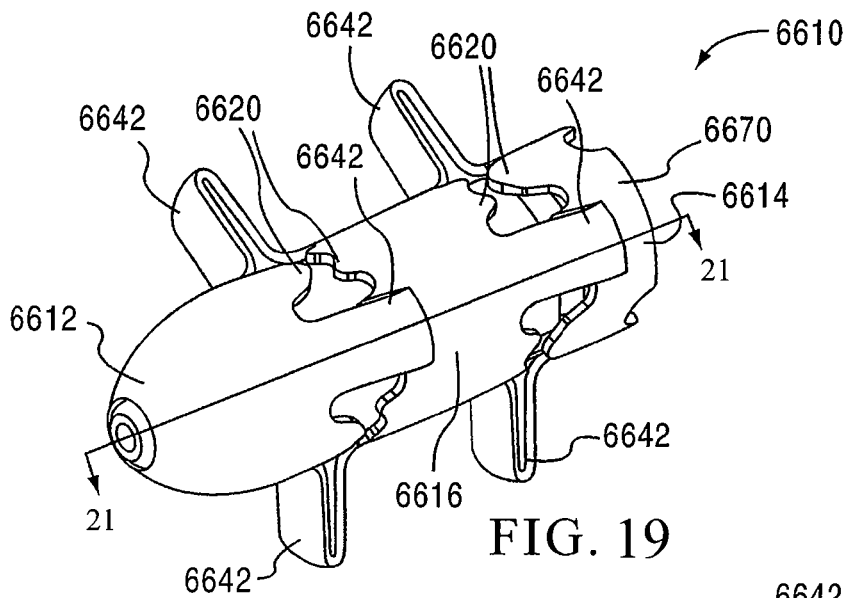
FIG. 19 is a side perspective view of the implant of FIG. 17 shown in an expanded configuration.
Figure 20:
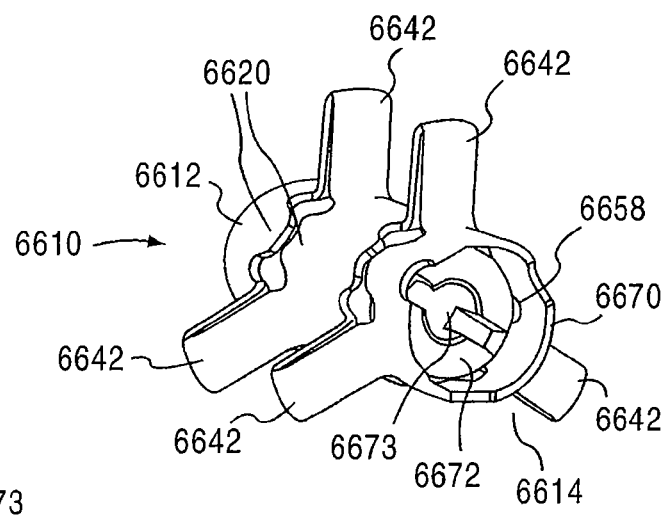
FIG. 20 is a rear perspective view of the implant of FIG. 17 shown in a collapsed configuration.
Figure 21:
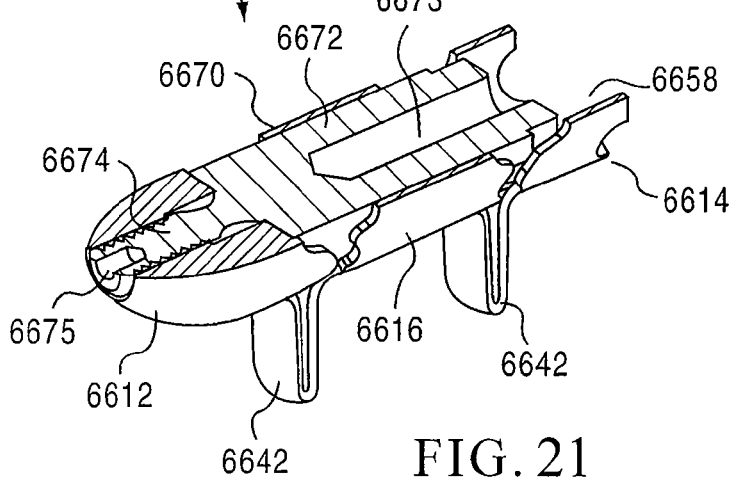
FIG. 21 is cross-sectional view of the implant of FIG. 19 shown in a collapsed configuration taken along line 21-21.
Figure 22:
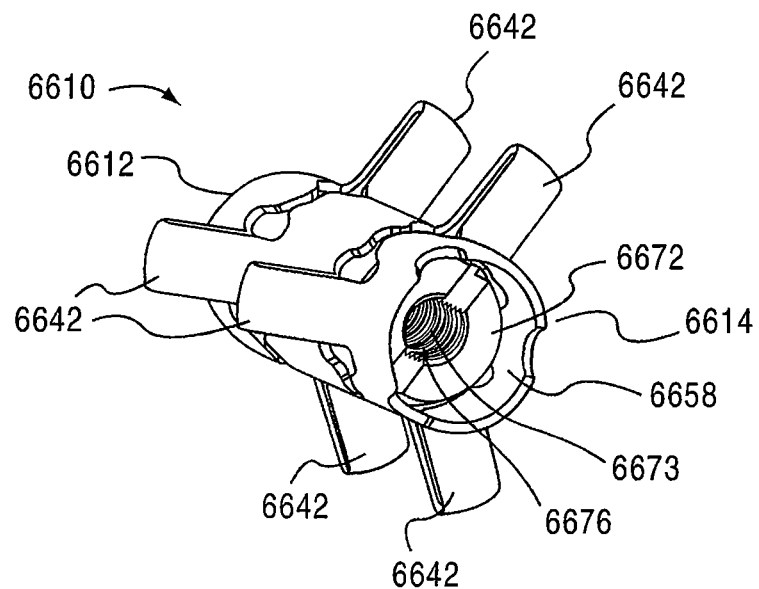
FIG. 22 is a rear perspective view of an implant according to an embodiment of the invention shown in an expanded configuration.
Figure 23:
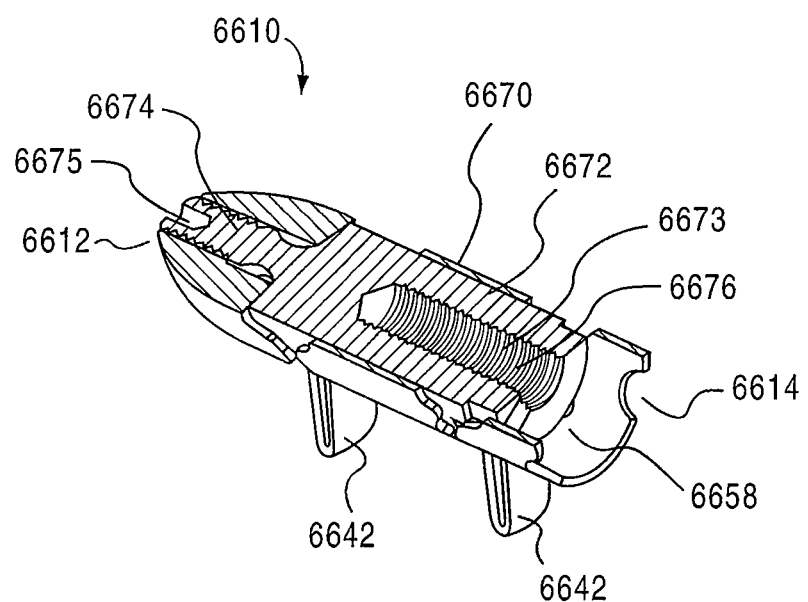
FIG. 23 is a cross-sectional view of the implant of FIG. 22 shown in an expanded configuration.
Figure 24:
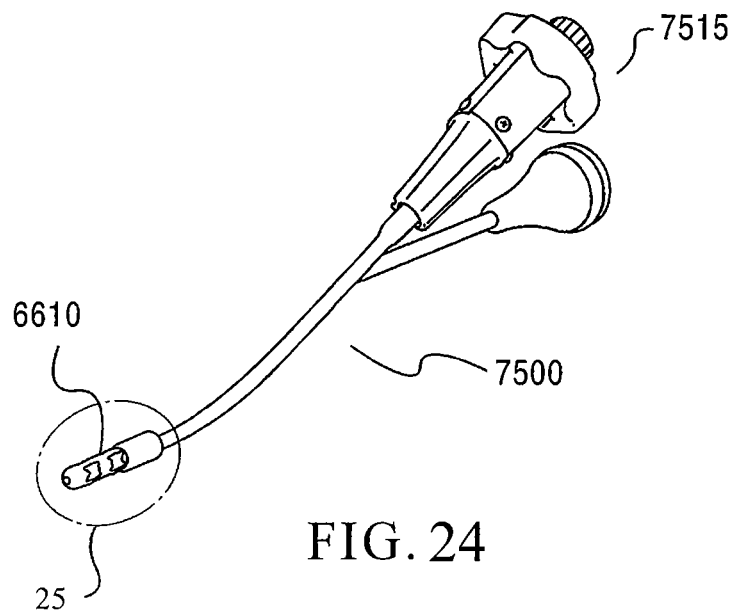
FIG. 24 is a perspective view of the implant of FIG. 22 in a collapsed configuration disposed on an expansion tool according to an embodiment of the invention.
Figure 25:
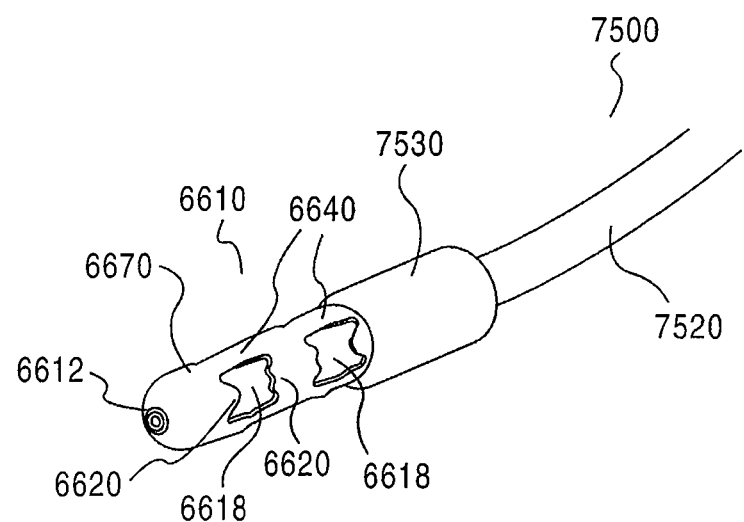
FIG. 25 is a perspective view of the implant and the expansion tool of FIG. 24 taken along region 25.
Figure 26:
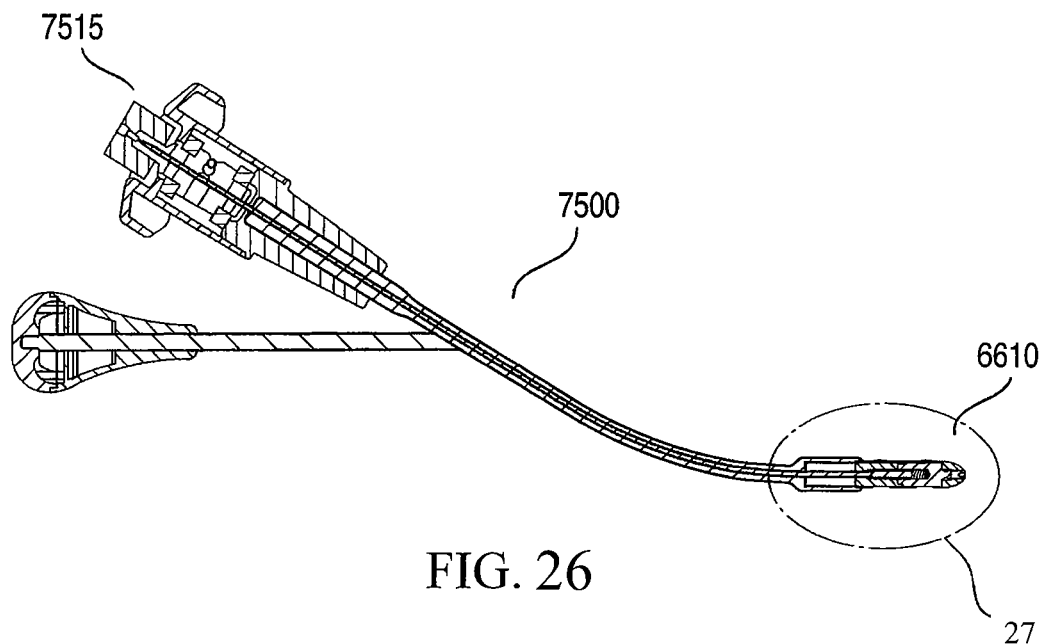
FIG. 26 is a side cross-sectional view of the implant and the expansion tool of FIG. 24.
Figure 27:
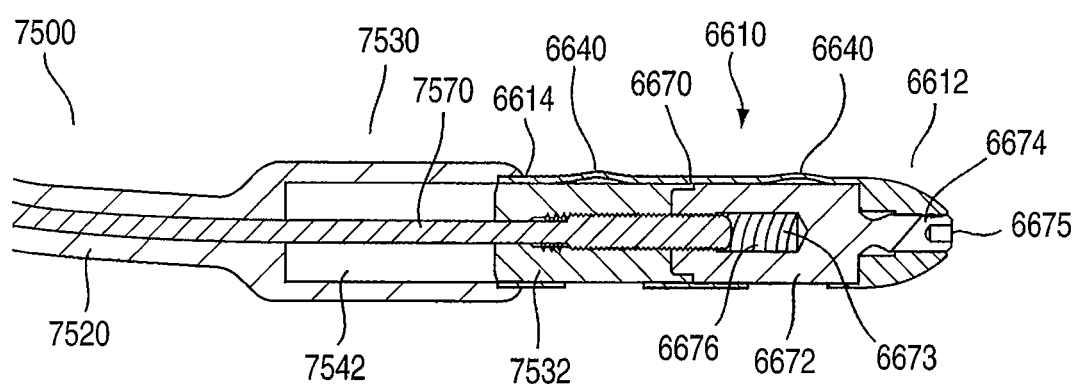
FIG. 27 is a side cross-sectional view of the implant and the expansion tool as shown in FIG. 26 taken along region 27.
Figure 28:
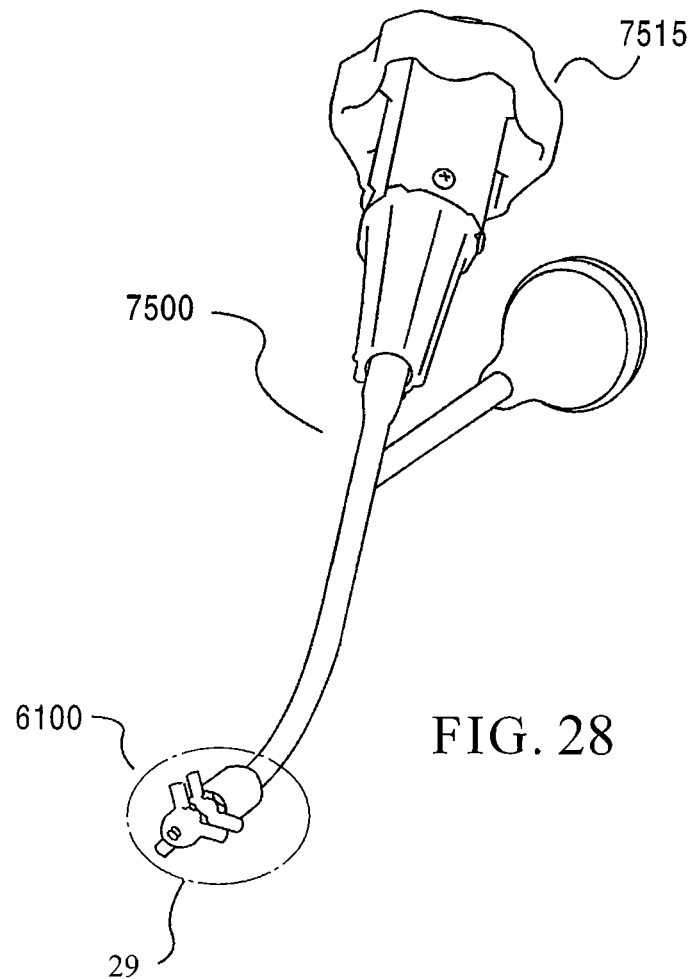
FIG. 28 is a perspective view of the implant of FIG. 22 in an expanded configuration disposed on an expansion tool according to an embodiment of the invention.

FIGS. 17-23 illustrate an implant 6610 according to another embodiment of the invention. The implant 6610 can be moved between a collapsed configuration, as shown in FIGS. 17 and 18, and an expanded configuration, as shown in FIGS. 19-23. The implant 6610 includes an outer shell 6670 having a distal portion 6612, a proximal portion 6614, and a central portion 6616. The outer shell 6670 defines a series of openings 6618 disposed between the distal portion 6612 and the central portion 6616, and the proximal portion 6614 and the central portion 6616. The outer shell 6670 includes a series of tabs 6620, a pair of which are disposed opposite each other, along the longitudinal axis of the implant 6610, on either side of each opening 6618. The outer shell 6670 also includes expandable portions 6640, which form extensions 6642 that extend radially from the outer shell 6670 when the implant 6610 is in the expanded configuration. As illustrated best in FIGS. 19-23, the arrangement of the openings 6618 and the tabs 6620 effect the shape and/or size of the extensions 6642. In some embodiments, the opposing tabs 6620 can be configured to engage each other when the implant 6610 is in the expanded configuration, thereby serving as a positive stop to limit the amount of expansion. In other embodiments, for example, the opposing tabs 6620 can be configured to engage each other during the expansion process, thereby serving as a positive stop, but remain spaced apart when the implant 6610 is in the expanded configuration (see, for example, FIGS. 19-23). In such embodiments, the elastic properties of the extensions 6642 can cause a slight "spring back," thereby causing the opposing tabs 6620 to be slightly spaced apart when the expansion device (also referred to as an insertion tool or a deployment tool) is disengaged from the implant 6610.

As illustrated best in FIG. 17, when the implant is in the collapsed configuration, the expandable portions 6640 are contoured to extend slightly radially from remaining portions of the outer shell 6670. In this manner, the expandable portions 6640 are biased such that when a compressive force is applied, the expandable portions 6640 will extend outwardly from the outer shell 6670. The expandable portions 6640 can be biased using any suitable mechanism. In some embodiments, for example, the expandable portions can be biased by including a notch in one or more locations along the expandable portion, as previously described. In other embodiments, the expandable portions can be biased by varying the thickness of the expandable portions in an axial direction. In yet other embodiments, the expandable portions can be stressed or bent prior to insertion such that the expandable portions are predisposed to extend outwardly when a compressive force is applied to the implant. In such embodiments, the radius of the expandable portions is greater than that of the remaining portions of the implant (e.g., the remaining cylindrical portions of the implant).

The implant 6610 also includes an inner core 6672 disposed within a lumen 6658 defined by the outer shell 6670. The inner core 6672 is configured to maintain the shape of the implant 6610 during insertion, to prevent the expandable portions from extending inwardly into a region inside of the outer shell 6670 during deployment and/or to maintain the shape of the central portion 6616 once the implant is in its desired position. As such, the inner core 6670 can be constructed to provide increased compressive strength to the outer shell 6670. In other words, the inner core 6672 can provide additional structural support to outer shell 6670 (e.g., in a direction transverse to the axial direction) by filling at least a portion of the region inside outer shell 6670 (e.g., lumen 6658) and contacting the walls of outer shell 6670. This can increase the amount of compressive force that can be applied to the implant 6610 while the implant 6610 still maintains its shape and, for example, the desired spacing between adjacent spinous processes. In some embodiments, the inner core 6672 can define a lumen 6673, while in other embodiments, the inner core 6672 can have a substantially solid construction. As illustrated, the inner core 6672 is fixedly coupled to the outer shell 6670 with a coupling portion 6674, which is configured to be threadedly coupled to the distal portion 6612 of the outer shell 6670. The distal end of the coupling portion 6674 of the inner core 6672 includes an opening 6675 configured to receive a tool configured to deform the distal end of the coupling portion 6674. In this manner once the inner core 6672 is threadedly coupled to the outer shell 6670, the coupling portion 6674 can be deformed or peened to ensure that the inner core 6672 does not become inadvertently decoupled from the outer shell 6670. In some embodiments, an adhesive, such as a thread-locking compound can be applied to the threaded portion of the coupling portion 6674 to ensure the that the inner core 6672 does not inadvertently become decoupled from the outer shell 6670.

Although illustrated as being threadedly coupled, the inner core 6672 can be coupled to the outer shell 6670 by any suitable means. In some embodiments, for example, the inner core 6672 can be coupled to the central portion 6616 of the outer shell 6670 by, for example, a friction fit. In other embodiments, the inner core 6672 can be coupled to the outer shell 6670 by an adhesive. The inner core 6672 can have a length such that the inner core 6672 is disposed within the lumen 6658 along substantially the entire length of the outer shell 6670 or only a portion of the length of the outer shell 6670.

The proximal portion of the inner core 6672 includes an opening 6673 configured to receive a portion of an expansion device 7500 (also referred to as an insertion tool or a deployment tool), as shown in FIGS. 24-31. The expansion device 7500 is similar to the expansion device 1500 shown and described above (see e.g. FIGS. 11-16). The expansion device 7500 differs, however, from expansion device 1500 in that the expansion device 7500 includes spacer 7532 configured to cooperate with the inner core 6672 of the implant 6610. In such an arrangement, the threaded portion of rod 7570 of the expansion device 7500 removably engages to the internal threads 6676 of the inner core 6672 of the implant 6610, rather than coupling directly to the distal portion of the implant (as shown in FIGS. 15 and 16). Although the inner core 6672 is shown as being threadedly coupled to the expansion device 7500, the inner core 6672 can be removably coupled to the expansion device 7500 by any suitable means, such as a protrusion and detent arrangement.

Figure 29:
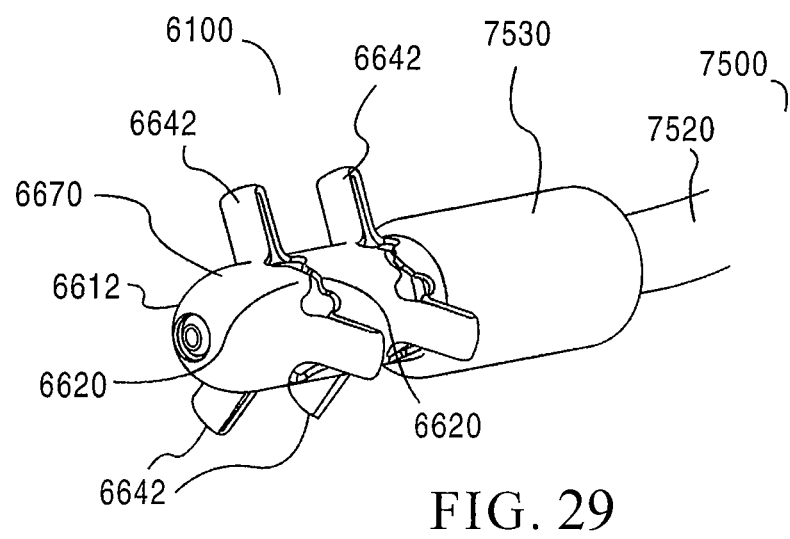
FIG. 29 is a perspective view of the implant and the expansion tool of FIG. 28 taken along region 29.
Figure 30:
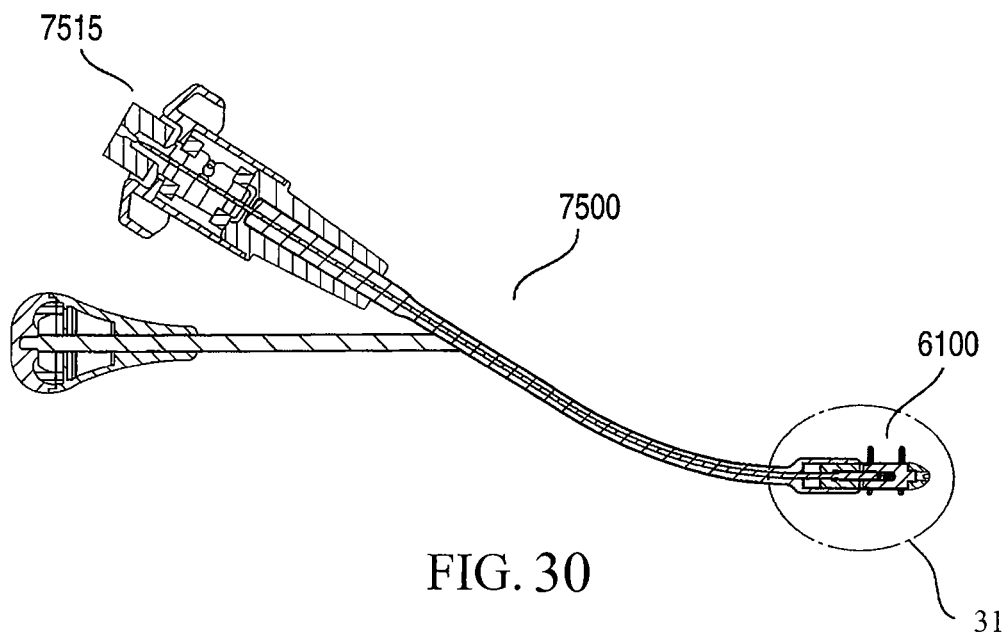
FIG. 30 is a side cross-sectional view of the implant and the expansion tool of FIG. 28.
Figure 31:
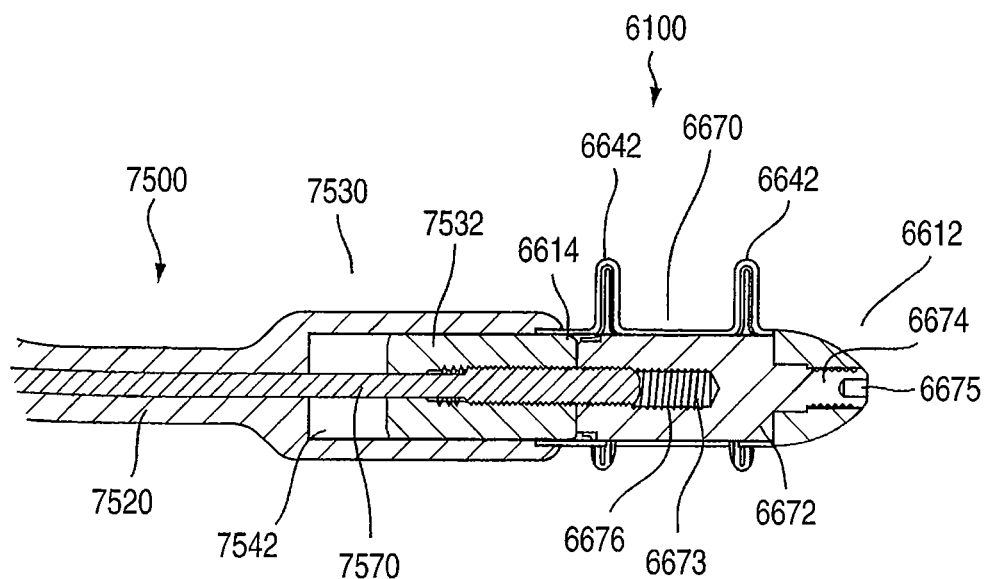
FIG. 31 is a side cross-sectional view of the implant and the expansion tool as shown in FIG. 30 taken along region 31.

In use, once the implant 6610 is positioned on the implant support portion 7530 of the expansion tool 7500 (see FIGS. 24 and 25), the implant is inserted into the patient's body and disposed between adjacent spinous processes. Once disposed between adjacent spinous processes, the expansion device can be used to move the inner core 6672 axially towards the proximal portion 6614 of the implant 6610 while simultaneously maintaining the position of the proximal portion 6614 of the implant 6610, as shown in FIGS. 29 and 31. In this manner, a compressive force is applied along the longitudinal axis of the outer shell 6670, thereby causing the outer shell 6670 to fold or bend to form extensions 6642 as described above. As illustrated, a portion of the spacer 7532 is received within the receiving area 7542 of the support portion 7530 as the implant 6610 is placed in the expanded configuration. Similarly, to move the implant 6610 from the expanded configuration to the collapsed configuration, the expansion device is actuated in the opposite direction to impart an axial force on the distal portion 6612 of the outer shell 6610 in a distal direction, moving the distal portion 6612 distally, and moving the implant 6610 to the collapsed configuration.

Once the implant 6610 is in its expanded configuration (see FIGS. 28-31), the implant 6610 can be disengaged from the expansion device 7500 by disengaging the distal portion of the rod 7570 from the opening 6673. The rod 7570 can be disengaged by actuating the knob assembly 7515 rotate the rod 7570 relative to the shaft 7520, as discussed above.

Although shown and described above without reference to any specific dimensions, in some embodiments, the outer shell 6670 can have a cylindrical shape having a length of approximately 34.5 mm (1.36 inches) and a diameter between 8.1 and 14.0 mm (0.32 and 0.55 inches). In some embodiments, the wall thickness of the outer shell can be approximately 5.1 mm (0.2 inches).

Similarly, in some embodiments, the inner core 6672 can have a cylindrical shape having an overall length of approximately 27.2 mm (1.11 inches) and a diameter between 8.1 and 14.0 mm (0.32 and 0.55 inches).

In some embodiments, the shape and size of the openings 6618 located adjacent the distal portion 6612 can be the same as that for the openings 6618 located adjacent the proximal portion 6614. In other embodiments, the openings 6618 can have different sizes and/or shapes. In some embodiments, the openings 6618 can have a length of approximately 11.4 mm (0.45 inches) and a width between 4.6 and 10 mm (0.18 and 0.40 inches).

Similarly, the shape and size of the tabs 6620 can be uniform or different as circumstances dictate. In some embodiments, for example, the longitudinal length of the tabs 6620 located adjacent the proximal portion 6614 can be shorter than the longitudinal length of the tabs 6620 located adjacent the distal portion 6612. In this manner, as the implant is moved from the collapsed configuration to the expanded configuration, the tabs adjacent the distal portion will engage each other first, thereby limiting the expansion of the expandable portions 6640 adjacent the distal portion 6612 to a greater degree than the expandable portions 6642 located adjacent the proximal portion 6614. In other embodiments, the longitudinal length of the tabs can be the same. In some embodiments, the longitudinal length of the tabs can be between 1.8 and 2.8 mm (0.07 and 0.11 inches). In some embodiments, the end portions of opposing tabs 6620 can have mating shapes, such as mating radii of curvature, such that the opposing tabs 6620 engage each other in a predefined manner.

Although illustrated as having a generally rectangular shape, the expandable portions 6640 and the resulting extensions 6642 can be of any suitable shape and size. In some embodiments, for example, the expandable portions can have a longitudinal length of approximately 11.4 mm (0.45 inches) and a width between 3.6 and 3.8 mm (0.14 and 0.15 inches). In other embodiments, size and/or shape of the expandable portions located adjacent the proximal portion 6614 can be different than the size and/or shape of the tabs 6620 located adjacent the distal portion 6612. Moreover, as described above, the expandable portions 6640 can be contoured to extend slightly radially from the outer shell 6670. In some embodiments, for example, the expandable portions can have a radius of curvature of approximately 12.7 mm (0.5 inches) along an axis normal to the longitudinal axis of the implant.

In some embodiments, the expandable portions 6640 and the outer shell 6670 are monolithically formed. In other embodiments, the expandable portions 6640 and the outer shell 6670 are formed from separate components having different material properties. For example, the expandable portions 6640 can be formed from a material having a greater amount of flexibility, while the outer shell 6670 can be formed from a more rigid material. In this manner, the expandable portions 6640 can be easily moved from the collapsed configuration to the expanded configuration, while the outer shell 6670 is sufficiently strong to resist undesirable deformation when in use.

In one embodiment, an apparatus includes a first body coupled to a second body. The first body and the second body collectively are configured to be releasably coupled to an implant device configured to be disposed between adjacent spinous processes. A first engaging portion is coupled to the first body, and a second engaging portion is coupled to the second body. The first engaging portion and/or the second engaging portion is configured to be received within a first opening defined by the implant device. The first body configured to be moved relative to the second body such that a distance between the first engaging portion and the second engaging portion is moved between a first distance and a second distance, and simultaneously a length of the implant device is moved between a first length and a second length.

In another embodiment, a kit includes an implant that is reconfigurable between an expanded configuration and a collapsed configuration while disposed between adjacent spinous processes. The implant has a longitudinal axis and defines an opening. A deployment tool is configured to be releasably coupled to the implant. The deployment tool includes an engaging portion configured to be removably received within the opening of the implant and extend in a transverse direction relative to the longitudinal axis when the deployment tool is coupled to the implant. The deployment tool is configured to move the implant between the collapsed configuration and the expanded configuration while the implant is disposed between the adjacent spinous processes.

Figure 32:
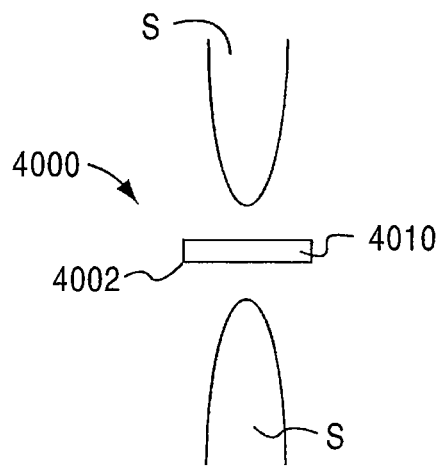
FIGS. 32-35 are schematic illustrations of a posterior view of a medical device according to an embodiment of the invention in a first configuration (FIG. 32), a second (FIGS. 33 and 35) configuration and a third configuration (FIG. 34).
Figure 33:
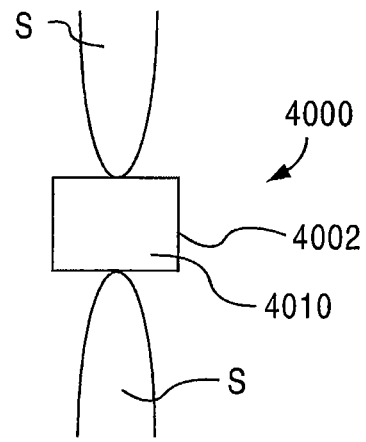
Figure 34:
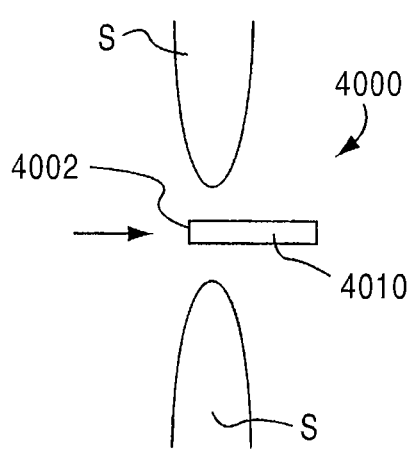

FIGS. 32-35 are schematic illustrations of a posterior view of a medical device 4000 according to an embodiment of the invention positioned adjacent two adjacent spinous processes S in a first configuration (FIG. 32), a second configuration (FIGS. 33 and 35) and a third configuration (FIG. 34). The medical device 4000 includes an expandable member 4002 having an inner area (not shown) and an outer surface 4010. The outer surface 4010 is configured to be disposed between the spinous processes S to prevent over-extension/compression of the spinous processes S. In some embodiments, the expandable member 4002 distracts the adjacent spinous processes S. In other embodiments, the expandable member 4002 does not distract the adjacent spinous processes S.

Figure 35:
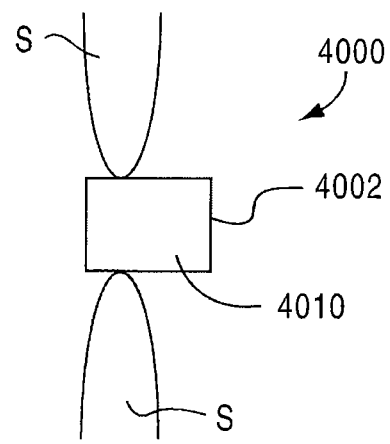

The expandable member 4002 has a first configuration, a second configuration and a third configuration. When in each configuration, the expandable member 4002 has an associated volume. As illustrated in FIG. 32, the first configuration represents a substantially contracted condition in which the expandable member 4002 has a minimal volume. When the expandable member 4002 is in the first configuration, the medical device 4000 is inserted between the adjacent spinous processes S. As illustrated in FIGS. 33 and 35, the second configuration represents an expanded condition in which the expandable member 4002 has a large volume. When the expandable member 4002 is in the second configuration, the outer surface 4010 of the medical device 4000 contacts the adjacent spinous processes S during at least a portion of the range of motion of the spinous processes. As illustrated in FIG. 34, the third configuration represents a partially expanded condition in which the expandable member 4002 has a volume between that associated with the first configuration and that associated with the second configuration. When the expandable member 4002 is in the third configuration, the medical device 4000 can be repositioned between the adjacent spinous processes, as indicated by the arrow in FIG. 34. The medical device can then be subsequently re-expanded into the second configuration, as illustrated in FIG. 35.

Figure 36:
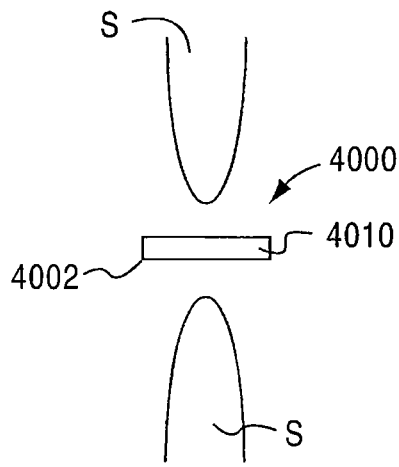
FIGS. 36-38 are schematic illustrations of a posterior view of a medical device according to an embodiment of the invention in a first configuration, a second configuration and a third configuration, respectively.
Figure 37:
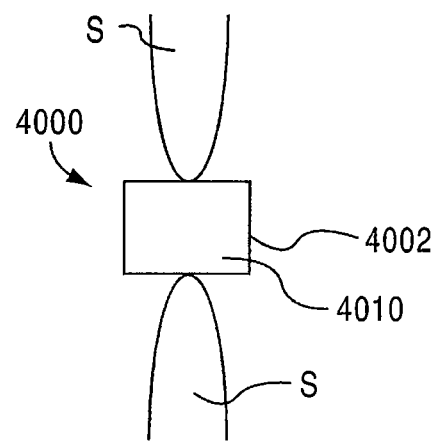
Figure 38:
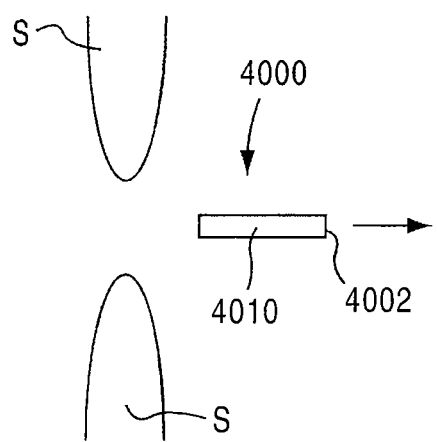
Figure 39:
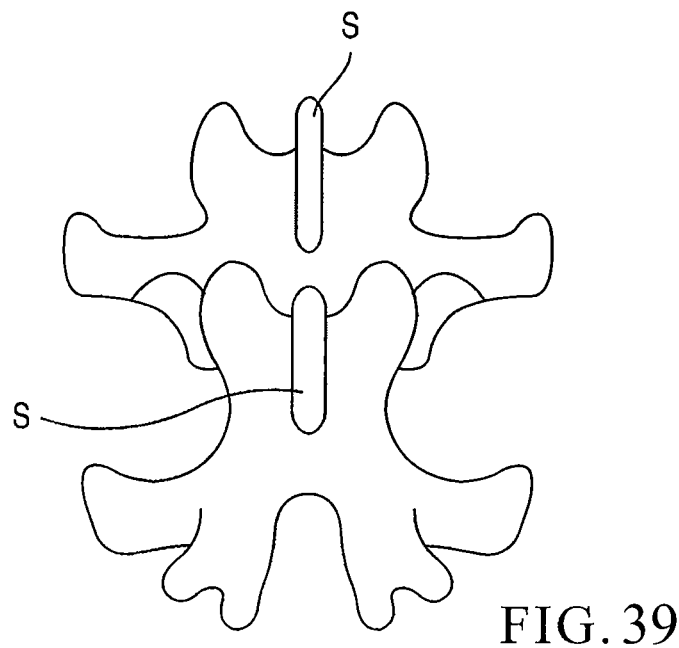
FIGS. 39-44 are posterior views of a medical device according to an embodiment of the invention inserted between adjacent spinous processes in a first lateral positions and a second lateral position.

FIGS. 36-38 are schematic illustrations of a posterior view of the medical device 4000 positioned adjacent two adjacent spinous processes S in a first configuration, a second configuration and a third configuration, respectively. As described above, when the expandable member 4002 is in the first configuration, the medical device 4000 is inserted between the adjacent spinous processes S. The expandable member 4002 is then expanded to the second configuration, in which the outer surface 4010 of the medical device 4000 is disposed between the adjacent spinous processes S. The expandable member 4002 is then contracted to the third configuration to facilitate removal of the medical device 4000, as shown in FIG. 38. In some embodiments, the third configuration can be the same as the first configuration.

In use, the adjacent spinous processes S can be distracted prior to inserting the medical device 4000 into a body, as described herein. When the spinous processes S are distracted, a trocar (not shown) can be used to define an access passageway (not shown) for the medical device 4000. In some embodiments, the trocar can be used to define the passage as well as to distract the spinous processes S. Once an access passageway is defined, the medical device 4000 is inserted percutaneously and advanced between the spinous processes S and placed in the desired position between the adjacent spinous processes S. Once the medical device 4000 is in the desired position, the expandable member is expanded to the second condition, causing the outer surface 4010 to engage the spinous processes S.

In some embodiments, the adjacent spinous processes can be distracted by a first expandable member (not shown) configured to distract bone. Upon distraction, the first expandable member is contracted and removed from the body. The medical device 4000 is then inserted percutaneously, advanced between the spinous processes S, placed in the desired position and expanded, as described above.

In some embodiments, the medical device 4000 is inserted percutaneously (i.e., through an opening in the skin) and in a minimally-invasive manner. For example, as discussed in detail herein, the overall sizes of portions of the medical device 4000 are increased by transitioning the expandable member 4002 from the first configuration to the second configuration after the medical device 4000 is inserted between the adjacent spinous processes S. When in the expanded second configuration, the sizes of portions of the medical device 4000 are greater than the size of the opening. For example, the size of the opening/incision in the skin can be between 3 millimeters in length and 25 millimeters in length across the opening. In some embodiments, the size of the medical device 4000 in the expanded second configuration is between 3 and 25 millimeters across the opening.

Figure 40:
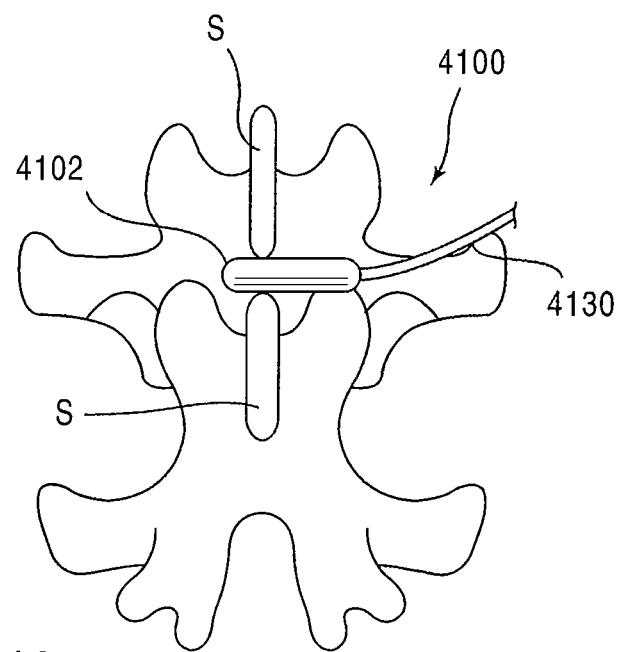
Figure 41:
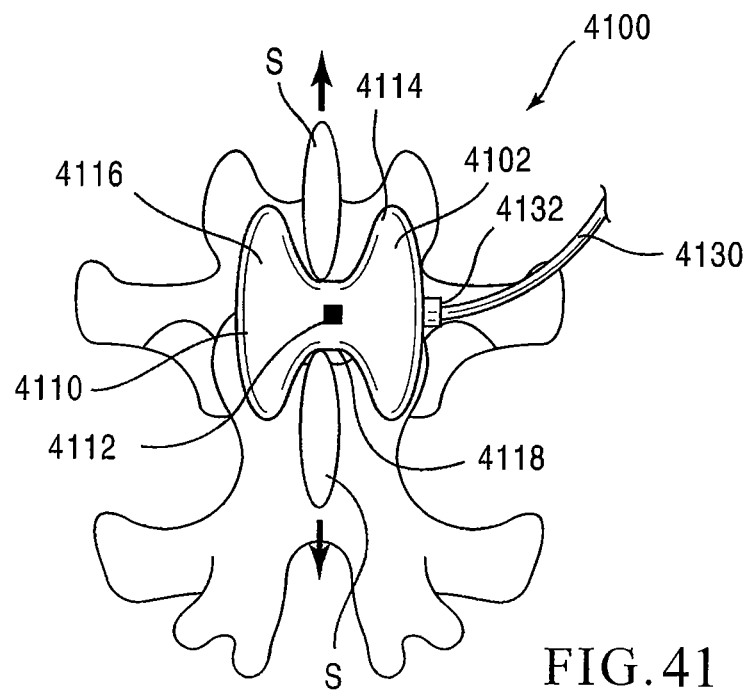
Figure 42:
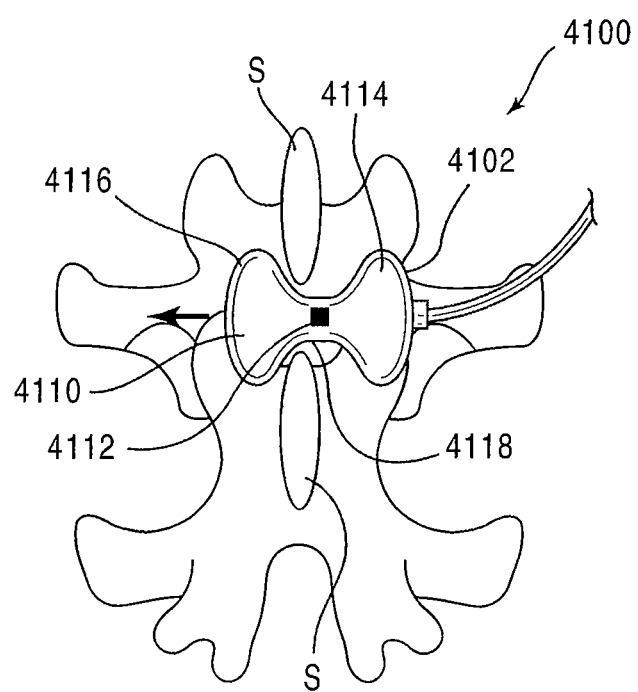
Figure 43:
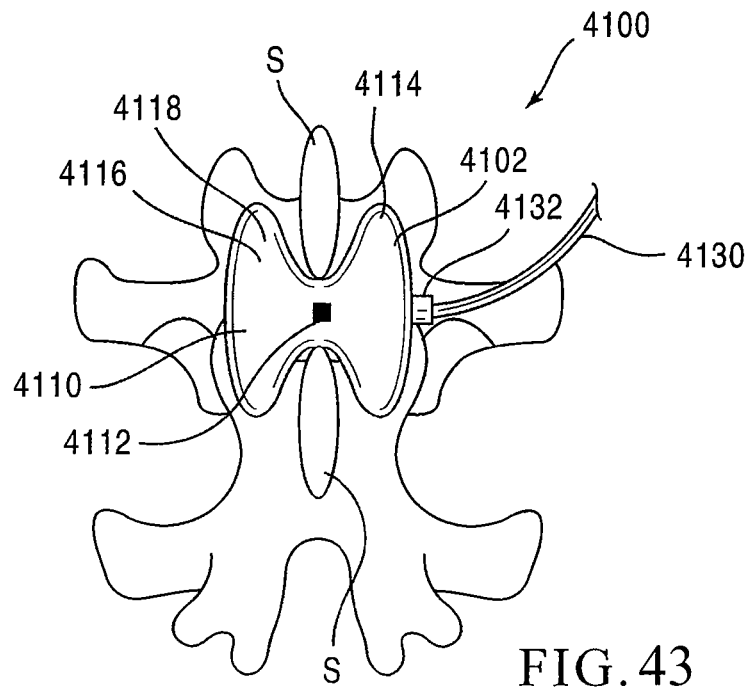

FIGS. 39-44 are posterior views of a spinal implant 4100 according to an embodiment of the invention inserted between adjacent spinous processes S in a first lateral position (FIG. 41) and a second lateral position (FIG. 43). The spinal implant 4100 includes an expandable member 4102, a sensor 4112 and a valve 4132. The expandable member 4102 has an inner area (not shown), an outer surface 4110, a support portion 4118, a proximal retention portion 4114 and a distal retention portion 4116. The expandable member 4102 is repeatably positionable in a first configuration (FIG. 40), a second configuration (FIGS. 41, 43 and 44) and a third configuration (FIG. 42). When in each configuration, the expandable member 4102 has an associated volume, as will be discussed below.

In use, the spinal implant 4100 is positioned in the substantially contracted first configuration during insertion and/or removal (see FIG. 40). As discussed above, the spinal implant 4100 is inserted percutaneously between adjacent spinous processes S. The distal retention portion 4116 of the expandable member 4102 is inserted first and is moved past the spinous processes S until the support portion 4118 is positioned between the spinous processes S. When in the first configuration, the support portion 4118 can be can be sized to account for ligaments and tissue surrounding the spinous processes S. For purposes of clarity, such surrounding ligaments and tissue are not illustrated.

As illustrated in FIG. 41, once in position, the expandable member 4102 is expanded into the second configuration by conveying a fluid (not shown) from an area outside of the expandable member 4102 to the inner area of the expandable member 4102. The fluid is conveyed by an expansion tool 4130, such as a catheter, that is matingly coupled to the valve 4132. The valve 4132 can be any valve suitable for sealably connecting the inner area of the expandable member 4102 to an area outside of the expandable member 4102. For example, in some embodiments, the valve 4132 can be, for example a poppet valve, a pinch valve or a two-way check valve. In other embodiments, the valve includes a coupling portion (not shown) configured to allow the expansion tool 4130 to be repeatably coupled to and removed from the valve 4132. For example, in some embodiments, the valve 4132 can include a threaded portion configured to matingly couple the expansion tool 4130 and the valve 4132.

The fluid is configured to retain fluidic properties while resident in the inner area of the expandable member 4102. In this manner, the spinal implant 4100 can be repeatably transitioned from the expanded second configuration to the first configuration and/or the third configuration by removing the fluid from the inner area of the expandable member 4102. In some embodiments, the fluid can be a biocompatible liquid having constant or nearly constant properties. Such liquids can include, for example, saline solution. In other embodiments, the fluid can be a biocompatible liquid configured to have material properties that change over time while still retaining fluidic properties sufficient to allow removal of the fluid. For example, the viscosity of a fluid can be increased by adding a curing agent or the like. In this manner, the fluid can provide both the requisite structural support while retaining the ability to be removed from the inner area of the expandable member 4102 via the valve 4132. In yet other embodiments, the fluid can be a biocompatible gas.

The outer surface 4110 of the support portion 4118 can distract the adjacent spinous processes S as the expandable member 4102 expands to the second configuration, as indicated by the arrows shown in FIG. 41. In some embodiments, the support portion 4118 does not distract the adjacent spinous processes S. For example, as discussed above, the adjacent spinous processes S can be distracted by a trocar and/or any other device suitable for distraction.

When in the second configuration, the outer surface 4110 of the support portion 4118 is configured to engage the spinous processes S for at least a portion of the range of motion of the spinous processes S to prevent over-extension/compression of the spinous processes S. In some embodiments, the engagement of the spinous processes S by the outer surface 4110 of the support portion 4118 is not continuous, but occurs upon spinal extension.

When in the second configuration, the proximal retention portion 4114 and the distal retention portion 4116 each have a size S1 (shown in FIG. 45) that is greater than the vertical distance D1 (shown in FIG. 45) between the spinous processes. In this manner, the proximal retention portion 4114 and the distal retention portion 4116 are disposed adjacent the sides of spinous processes S (i.e., either through direct contact or through surrounding tissue), thereby limiting movement of the spinal implant 4100 laterally along a longitudinal axis of the support portion 4118.

The expandable member 4102 can be made from any number of biocompatible materials, such as, for example, PET, Nylons, cross-linked Polyethylene, Polyurethanes, and PVC. In some embodiments, the chosen material can be substantially inelastic, thereby forming a low-compliant expandable member 4102. In other embodiments, the chosen material can have a higher elasticity, thereby forming a high-compliant expandable member 4102. In yet other embodiments, the expandable member 4102 can be made from a combination of materials such that one portion of the expandable member 4102, such as the support portion 4118, can be low-compliant while other portions of the expandable member 4102, such as the proximal retention portion 4114 and/or distal retention portion 4116 are more highly compliant. In yet other embodiments, a portion of the expandable member 4102 can include a rigid, inflexible material to provide structural stiffness. For example, the support portion 4118 can be constructed of a composite material that includes a rigid, inflexible material to facilitate distraction of the adjacent spinous processes.

In some embodiments, the expandable member 4102 includes a radiopaque material, such as bismuth, to facilitate tracking the position of the spinal implant 4100 during insertion and/or repositioning. In other embodiments, the fluid used to expand the expandable member 4102 includes a radiopaque tracer to facilitate tracking the position of the spinal implant 4100.

In the illustrated embodiment, the spinal implant 4100 includes a sensor 4112 coupled to the expandable member 4102. In some embodiments, the sensor 4112 is a strain gauge sensor that measures a force applied to the support portion 4118 of the expandable member 4102. The sensor 4112 can include multiple strain gauges to facilitate measuring multiple force quantities, such as a compressive force and/or a tensile force. In other embodiments, the sensor 4112 is a variable capacitance type pressure sensor configured to measure a force and/or a pressure of the fluid contained within the inner portion of the expandable member 4102. In yet other embodiments, the sensor 4112 is a piezoelectric sensor that measures a pressure of the fluid contained within the inner portion of the expandable member 4102. In still other embodiments, the spinal implant 4100 can include multiple sensors 4112 located at various locations to provide a spatial profile of the force and/or pressure applied to the expandable member 4102. In this manner, a practitioner can detect changes in the patient's condition, such those that may result in a loosening of the spinal implant 4100.

In some embodiments, the sensor 4112 can be remotely controlled by an external induction device. For example, an external radio frequency (RF) transmitter (not shown) can be used to supply power to and communicate with the sensor 4112. In other embodiments, an external acoustic signal transmitter (not shown) can be used to supply power to and communicate with the sensor 4112. In such an arrangement, for example, the sensor can include a pressure sensor, of the types described above, for measuring a pressure; an acoustic transducers, and an energy storage device. The acoustic transducer converts energy between electrical energy and acoustic energy. The energy storage device stores the electrical energy converted by the acoustic transducer and supplies the electrical energy to support the operation of the pressure sensor. In this manner, acoustic energy from an external source can be received and converted into electrical energy used to power the pressure sensor. Similarly, an electrical signal output from the pressure sensor can be converted into acoustic energy and transmitted to an external source.

Figure 44:
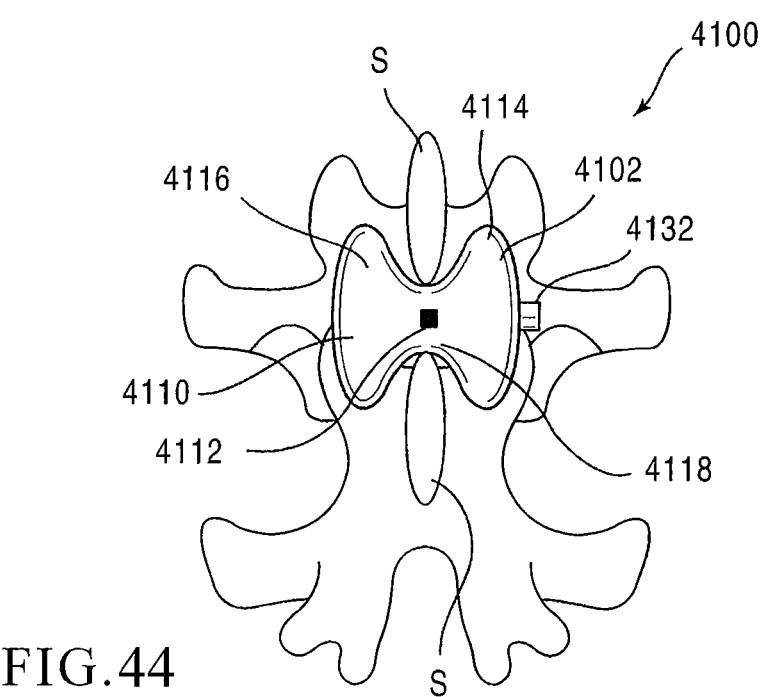

At times, the spinal implant 4100 may need to be repositioned. Such repositioning can be required, for example, to optimize the lateral position of the support portion 4118 during the insertion process. In other instances, the spinal implant 4100 can require repositioning subsequent to the insertion process to accommodate changes in the conditions of the patient. In yet other instances, the spinal implant 4100 can be removed from the patient. To allow for such repositioning and/or removal, the spinal implant is repeatably positionable in the first configuration, the second configuration and/or the third configuration. In FIG. 42, for example, the expandable member 4102 is contracted to the third configuration by removing all or a portion of the fluid contained in the inner area, as described above. In this manner, the spinal implant 4100 can be repositioned in a lateral direction, as indicated by the arrow. Once in the desired position, the expandable member is reexpanded to the second condition as described above. Finally, as shown in FIG. 44, the expansion tool 4130 is removed from the valve 4132.

Figure 45:
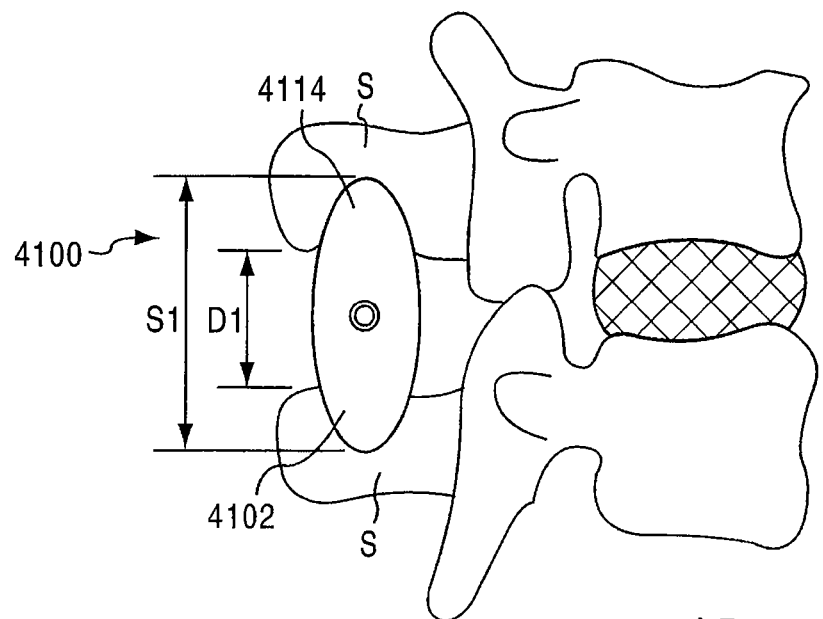
FIG. 45 is a lateral view of the medical device illustrated in FIGS. 39-44 inserted between adjacent spinous processes in a second configuration.

FIG. 45 is a lateral view of the spinal implant 4100 illustrated in FIGS. 39-44 inserted between adjacent spinous processes S in a second configuration. Although FIG. 45 only shows the proximal retention portion 4114 of the expandable member 4102, it should be understood that the distal retention portion 4116 has characteristics and functionality similar to those described below for proximal retention portion 4114. As illustrated, the proximal retention portion 4114 has a size S1 that is greater than the vertical distance D1 between the spinous processes S. In this manner, the proximal retention portion 4114 and the distal retention portion 4116 limit the lateral movement of the spinal implant 4100 when in the second configuration, as discussed above.

Figure 46:
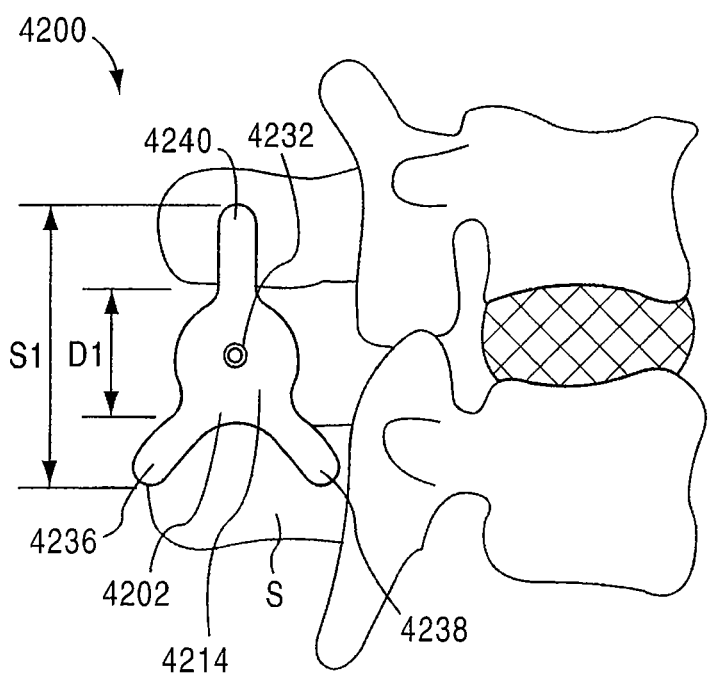
FIG. 46 is a lateral view of a medical device according to an embodiment of the invention inserted between adjacent spinous processes in a second configuration.

FIG. 46 is a lateral view of a spinal implant 4200 according to an embodiment of the invention inserted between adjacent spinous processes and in a second configuration. Similar to the spinal implant 4100 discussed above, the spinal implant 4200 includes an expandable member 4202 and a valve 4232. The expandable member 4202 has a support portion (not shown), a proximal retention portion 4214 and a distal retention portion (not shown). The expandable member 4202 is repeatably positionable in a first configuration, a second configuration and/or a third configuration. When in each configuration, the expandable member 4202 has an associated volume, as discussed above.

In the illustrated embodiment, the proximal retention portion 4214 of the expandable member 4202 has a first radial extension 4236, a second radial extension 4238 and a third radial extension 4240. As illustrated, the distance S1 between the ends of the radial extensions is greater than the vertical distance D1 between the spinous processes S. In this manner, the proximal retention portion 4214 and the distal retention portion limit the lateral movement of the spinal implant 4200 when in the second configuration. In some embodiments, the proximal retention portion and the distal retention portion can assume a variety of different shapes.

Figure 47:
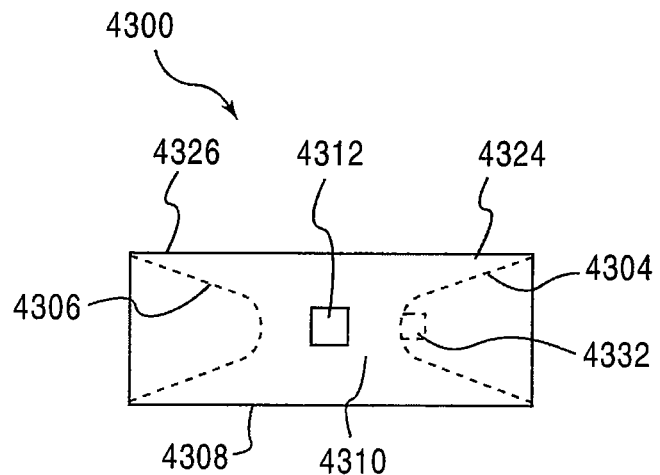
FIGS. 47 and 48 are front views of a medical device according to an embodiment of the invention in a first configuration and a second configuration, respectively.
Figure 48:
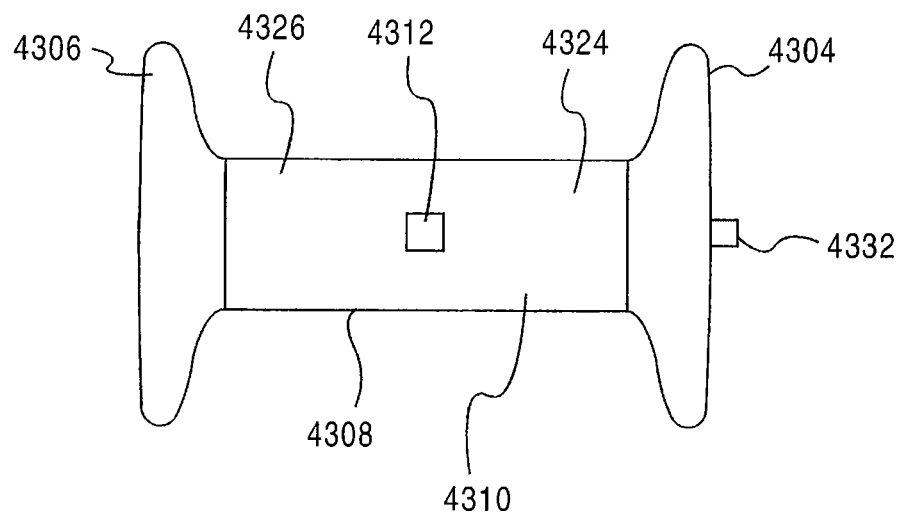

FIGS. 47 and 48 are front views of a spinal implant 4300 according to an embodiment of the invention in a first configuration and a second configuration, respectively. The spinal implant 4300 includes a proximal expandable member 4304, a distal expandable member 4306, a support member 4308, a sensor 4312 and a valve 4332. The support member 4308 has an inner area (not shown) and an outer surface 4310. The outer surface 4310 is configured to contact the spinous processes (not shown). In some embodiments, the support member 4308 distracts the adjacent spinous processes. In other embodiments, the support member 4308 does not distract the adjacent spinous processes. In yet other embodiments, the engagement of the spinous processes by the support member 4308 is not continuous, but occurs upon spinal extension.

The support member 4308 has a proximal portion 4324, to which the proximal expandable member 4304 is coupled, and a distal portion 4326, to which the distal expandable member 4306 is coupled. The proximal expandable member 4304 and the distal expandable member 4306 are each repeatably positionable in a first configuration (FIG. 47) and a second configuration (FIG. 48). As described above, the first configuration represents a substantially contracted condition in which the proximal expandable member 4304 and the distal expandable member 4306 each have a minimal volume. When the spinal implant 4300 is in the first configuration, it can be inserted, repositioned and/or removed. In the illustrated embodiment, the proximal expandable member 4304 and the distal expandable member 4306 are each contained within the inner area of the support member 4308 when the spinal implant 4300 is in the first configuration. In some embodiments, the proximal expandable member 4304 and the distal expandable member 4306 are not contained within the support member 4308.

Conversely, the second configuration represents an expanded condition in which the proximal expandable member 4304 and the distal expandable member 4306 each have a large volume. When the spinal implant 4300 is in the second configuration, the proximal expandable member 4304 and the distal expandable member 4306 each have a size that is greater than the vertical distance between the spinous processes, as described above. In this manner, the proximal expandable member 4304 and the distal expandable member 4306 engage the spinous processes, thereby limiting the lateral movement of the spinal implant 4300.

The proximal expandable member 4304 and the distal expandable member 4306 are expanded into the second configuration by conveying a fluid (not shown) from an area outside of each expandable member 4304, 4306 to an inner area defined by each expandable member 4304, 4306. The fluid is conveyed through a valve 4332, as described above. In the illustrated embodiment, the inner area of the proximal expandable member 4304, the inner area of the distal expandable member 4306 and the inner area of the support member 4308 are in fluid communication with each other to form a single inner area. As such, the fluid can be conveyed to both the inner area of the proximal expandable member 4304 and the inner area of the distal expandable member 4306 by a single valve 4332. In some embodiments, the inner areas of the proximal expandable member 4304 and the distal expandable member 4306 are not in fluid communication. In such an arrangement, each expandable member can be independently transformed between configurations.

The support member 4308 can be made from any number of biocompatible materials, such as, for example, stainless steel, plastic, polyetheretherketone (PEEK), carbon fiber, ultra-high molecular weight (UHMW) polyethylene, and the like. The material of the support member 4308 can have a tensile strength similar to or higher than that of bone. In some embodiments, the support member 4308 is substantially rigid. In other embodiments, the support member 4308 or portions thereof is elastically deformable, thereby allowing it to conform to the shape of the spinous processes. In yet other embodiments, the support member 4308 includes a radiopaque material, such as bismuth, to facilitate tracking the position of the spinal implant 4300 during insertion and/or repositioning.

The proximal expandable member 4304 and the distal expandable member 4306 can be made from any number of biocompatible materials, as discussed above. The proximal expandable member 4304 and the distal expandable member 4306 can be coupled to the support member by an suitable means, such as a biocompatible adhesive.

In the illustrated embodiment, the spinal implant 4300 includes a sensor 4312 coupled to the support member 4308. As described above, the sensor 4312 can be configured to measure multiple force quantities and/or a pressure of the fluid contained within the proximal expandable member 4304 and the distal expandable member 4306.

Although the spinal implants 4100, 4200 and 4300 are shown and described above as be movable from a retracted configuration to an expanded configuration by conveying a fluid to an inner area of an expandable member, in some embodiments, an implant can be configured to receive any suitable substance to move from a retracted configuration to an expanded configuration. For example, in some embodiments, an implant can include an expandable portion configured to receive a mixture of solid particles contained within a carrier fluid (e.g., a slurry). In other embodiments, an implant can include an expandable portion configured to be filled solely with solid particles to move from a retracted configuration to an expanded configuration. In this manner, the solid particles can form a substrate within the expandable portion that is incompressible and/or more rigid than a liquid or gas.

The solid particles can be of any suitable size and/or shape. In some embodiments, for example, the solid particles can be approximately spherical particles having a diameter of between 0.010 mm and 0.100 mm. In other embodiments, the solid particles can include one or more flat surfaces. In yet other embodiments, the solid particles can be irregularly shaped.

The solid particles can be constructed from any suitable biocompatible material, such as, for example, PET, Nylons, cross-linked Polyethylene, Polyurethanes, and PVC. In some embodiments, the solid particles can be substantially inelastic, thereby forming a low-compliant substrate within the expandable portion of the implant. In other embodiments, the solid particles can have a higher elasticity, thereby forming a high-compliant filler within the expandable portion of the implant. In yet other embodiments, the solid particles can be constructed from a combination of materials such that the characteristics of the filler within the expandable portion of the implant can vary spatially.

Similarly, in some embodiments, the solid particles can be constructed from a material having a high rigidity (i.e., a high shear modulus). In this manner, the solid particles can form a substrate within the expandable portion that has a high resistance to deformation when exposed to a shear stress. In other embodiments, the solid particles can be constructed from a material having a low rigidity. In such embodiments, for example, the solid particles can form a substrate with the expandable portion that can deform when compressed during extension of the spinal column.

In some embodiments, the materials from which the solid particles and the expandable portion are constructed can be selected cooperatively such that the implant, when filled, has suitable strength, rigidity, elasticity and the like. For example, in some embodiments, an implant includes an expandable portion constructed from a low-compliant material that is configured to be expanded by flexible solid particles. In other embodiments, an implant includes an expandable portion constructed from a low-compliant material that is configured to be expanded by rigid solid particles. In yet other embodiments, an implant includes an expandable portion constructed from a high-compliant material that is configured to be expanded by flexible solid particles. In yet other embodiments, an implant includes an expandable portion constructed from a high-compliant material that is configured to be expanded by rigid solid particles.

In some embodiments, the solid particles and/or mixture of solid particles and carrier fluid can be conveyed into and/or removed from the expandable portion of the implant by an expansion tool and via a valve, as described above. In other embodiments, the solid particles and/or mixture of solid particles and carrier fluid can be removed from the expandable portion of the implant by puncturing the expandable portion and applying a vacuum to withdraw the solid particles and/or mixture of solid particles and carrier fluid. In yet other embodiments, the solid particles and/or mixture of solid particles and carrier fluid can be removed from the expandable portion of the implant by puncturing the expandable portion and applying a pressure against an outer portion of the expandable portion to cause the solid particles and/or mixture of solid particles and carrier fluid to be expelled within the body.

In some embodiments, the solid particles can be configured to absorb liquid to expand the expandable portion of an implant. For example, in some embodiments, an expandable portion of an implant can include solid particles constructed from a hydrogel. When the implant is disposed between adjacent spinous processes, a liquid can be conveyed to the expandable portion of the implant, which is then absorbed by the hydrogel particles. Accordingly, the size of the hydrogel particles will increase, thereby expanding the expandable portion of the implant.

Similarly, in some embodiments, a kit can include an implant having an expandable portion, multiple sets of solid particles, and multiple different liquids. The different sets of solid particles can have different characteristics, such as, for example, a size, a shape, and/or an absorption coefficient. Similarly, the different liquids can have different characteristics, such as, for example, viscosity, density and/or an absorption coefficient. In this manner, a user can select a particular set of particles for inclusion in the expandable portion of the implant and a particular liquid for use in expanding the solid particles.

Figure 49:
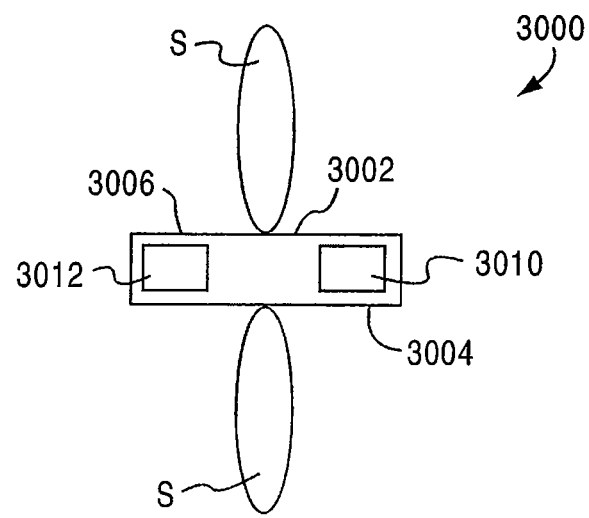
FIG. 49 is a schematic illustration of a posterior view of a medical device according to an embodiment of the invention in a first configuration disposed between two adjacent spinous processes.
Figure 50:
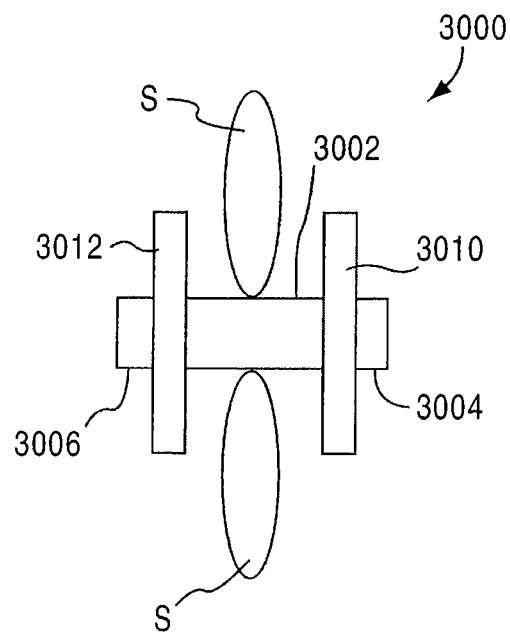
FIG. 50 is a schematic illustration of a posterior view of the medical device shown in FIG. 49 in a second configuration disposed between two adjacent spinous processes.

FIGS. 49 and 50 are schematic illustrations of a posterior view of a medical device 3000 according to an embodiment of the invention disposed between two adjacent spinous processes S in a first configuration and a second configuration, respectively. The medical device 3000 includes a support member 3002, a proximal retention member 3010 and a distal retention member 3012. The support member 3002 has a proximal portion 3004 and a distal portion 3006, and is configured to be disposed between the spinous processes S to prevent over-extension/compression of the spinous processes S. In some embodiments, the support member 3002 distracts the adjacent spinous processes S. In other embodiments, the support member 3002 does not distract the adjacent spinous processes S.

The proximal retention member 3010 has a first configuration in which it is substantially disposed within the proximal portion 3004 of the support member 3002, as illustrated in FIG. 49. Similarly, the distal retention member 3012 has a first configuration in which it is substantially disposed within the distal portion 3006 of the support member 3002. When the proximal retention member 3010 and the distal retention member 3012 are each in their respective first configuration, the medical device 3000 can be inserted between the adjacent spinous processes S.

The proximal retention member 3010 can be moved from the first configuration to a second configuration in which a portion of it is disposed outside of the support member 3002, as illustrated in FIG. 50. Similarly, the distal retention member 3012 can be moved from the first configuration to a second configuration. When each is in their respective second configuration, the proximal retention member 3010 and the distal retention member 3012 limit lateral movement of the support member 3002 with respect to the spinous processes S by contacting the spinous processes S (i.e., either directly or through surrounding tissue). For purposes of clarity, the tissue surrounding the spinous processes S is not illustrated.

In use, the adjacent spinous processes S can be distracted prior to inserting the medical device 3000 into the patient. When the spinous processes S are distracted, a trocar (not shown in FIG. 49 or 50) can be used to define an access passageway (not shown in FIGS. 49 and 50) for the medical device 3000. In some embodiments, the trocar can be used to define the passage as well as to distract the spinous processes S.

Once an access passageway is defined, the medical device 3000 is inserted percutaneously and advanced, distal portion 3006 first, between the spinous processes S. The medical device 3000 can be inserted from the side of the spinous processes S (i.e., a posterior-lateral approach). The use of a curved shaft assists in the use of a lateral approach to the spinous processes S. Once the medical device 3000 is in place between the spinous processes S, the proximal retention member 3010 and the distal retention member 3012 are moved to their second configurations, either serially or simultaneously. In this manner, lateral movement of the support member 3002 with respect to the spinous processes S is limited.

When it is desirable to change the position of the medical device 3000, the proximal retention member 3010 and the distal retention member 3012 are moved back to their first configurations, thereby allowing the support member 3002 to be moved laterally. Once the support member 3002 is repositioned, the medical device 3000 can be returned to the second configuration. Similarly, when it is desirable to remove the medical device 3000, proximal retention member 3010 and the distal retention member 3012 are moved to their first configurations, thereby allowing the support member 3002 to be removed.

In some embodiments, the medical device 3000 is inserted percutaneously (i.e., through an opening in the skin) and in a minimally-invasive manner. For example, as discussed in detail herein, the overall sizes of portions of the medical device 3000 can be increased by moving the proximal retention member 3010 and the distal retention member 3012 to their respective second configurations after the medical device 3000 is inserted between the adjacent spinous processes S. When in the expanded second configuration, the sizes of portions of the medical device 3000 can be greater than the size of the opening. For example, the size of the opening/incision in the skin can be between 3 millimeters in length and 25 millimeters in length across the opening. In some embodiments, the size of the medical device 3000 in the expanded second configuration is between 3 and 25 millimeters across the opening.

Figure 51:
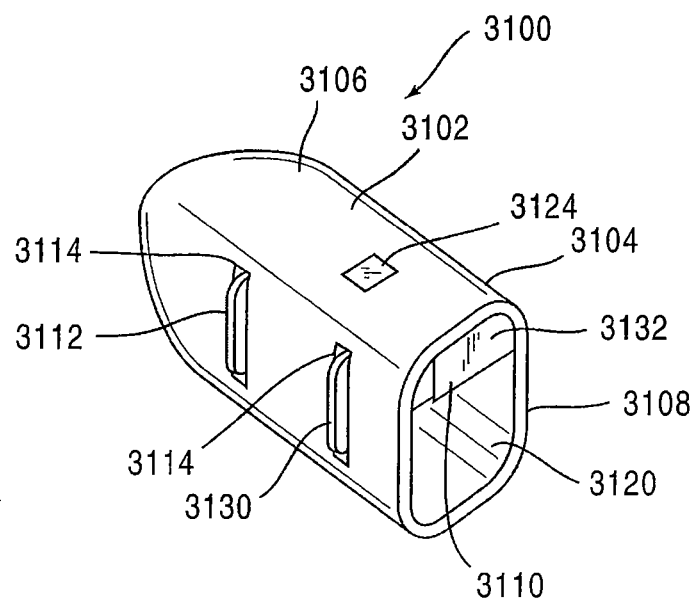
FIGS. 51 and 52 are perspective views of a medical device according to an embodiment of the invention in a first configuration and a second configuration, respectively.
Figure 52:
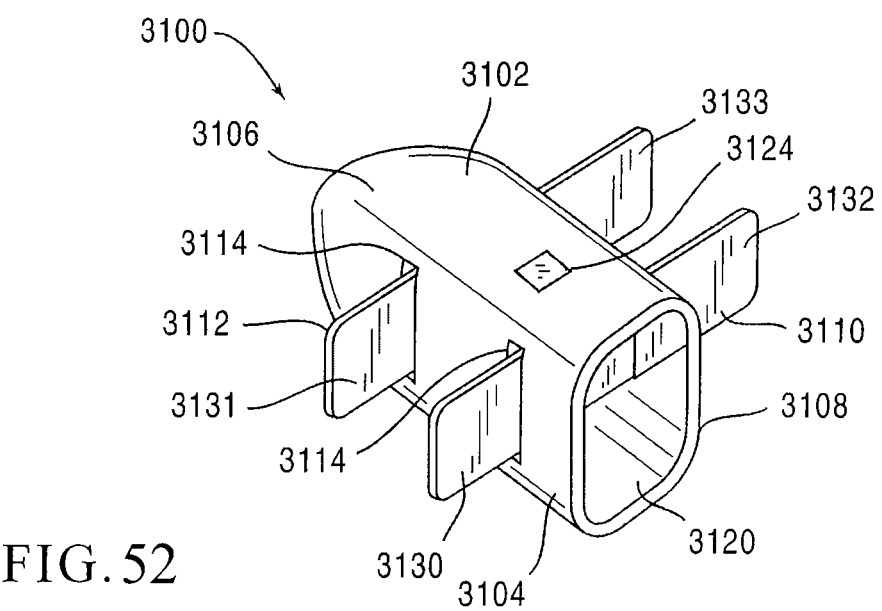
Figure 53:
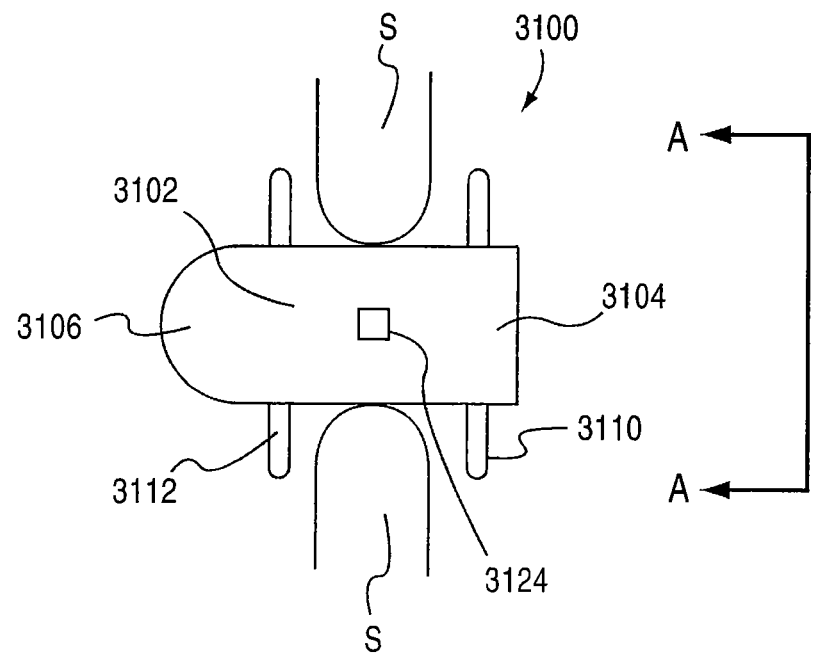
FIG. 53 is a posterior view of the medical device illustrated in FIGS. 51 and 52 disposed between adjacent spinous processes in a second configuration.
Figure 54:
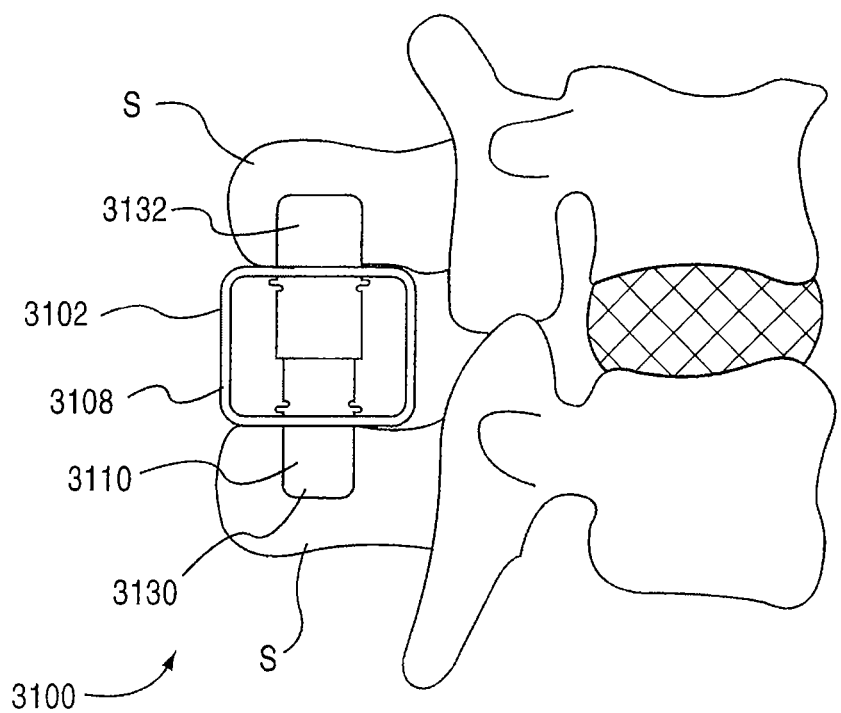
FIG. 54 is a lateral view taken from a proximal perspective A-A of the medical device illustrated in FIG. 53 disposed between adjacent spinous processes in a second configuration.

FIGS. 51-56 illustrate a spinal implant 3100 according to an embodiment of the invention. FIGS. 51 and 52 are perspective views of the spinal implant 3100 in a first configuration and a second configuration, respectively. The spinal implant 3100 includes a support member 3102, a proximal retention member 3110 and a distal retention member 3112. The support member 3102 is positioned between adjacent spinous processes S, as illustrated in FIGS. 53 and 54. As shown in FIGS. 51 and 52, the proximal retention member 3110 and the distal retention member 3112 are each repeatably positionable in a first configuration in which they are substantially disposed within the support member 3102 (FIG. 51), and a second configuration in which a portion of each retention member 3110, 3112 is disposed outside of the support member 3102 (FIG. 52). When the spinal implant 3100 is in the first configuration, it can be inserted between the adjacent spinous processes S, repositioned between the adjacent spinous processes and/or removed from the patient. When the spinal implant 3100 is in the second configuration, its lateral movement is limited, thereby allowing the desired position of the support member 3102 to be maintained.

In some embodiments, the support member 3102 distracts the adjacent spinous processes S. In other embodiments, the support member 3102 does not distract the adjacent spinous processes S. In yet other embodiments, the engagement of the spinous processes S by the support member 3102 is not continuous, but occurs upon spinal extension.

The support member 3102 can be made from any number of biocompatible materials, such as, for example, stainless steel, plastic, polyetheretherketone (PEEK), carbon fiber, ultra-high molecular weight (UHMW) polyethylene, and the like. The material of the support member 3102 can have a tensile strength similar to or higher than that of bone. In some embodiments, the support member 3102 is substantially rigid. In other embodiments, the support member 3102 or portions thereof is elastically deformable, thereby allowing it to conform to the shape of the spinous processes. In yet other embodiments, the support member 3102 includes a radiopaque material, such as bismuth, to facilitate tracking the position of the spinal implant 3100 during insertion and/or repositioning.

In the illustrated embodiment, the spinal implant 3100 includes a sensor 3124 coupled to the support member 3102. In some embodiments, the sensor 3124 is a strain gauge sensor that measures a force applied to the support member 3102. In some embodiments, the sensor 3124 can include multiple strain gauges to facilitate measuring multiple force quantities, such as a compressive force and/or a bending moment. In other embodiments, the sensor 3124 is a variable capacitance type pressure sensor configured to measure a force and/or a pressure applied to the support member 3102. In yet other embodiments, the sensor 3124 is a piezoelectric sensor that measures a force and/or a pressure applied to the support member 3102. In still other embodiments, the spinal implant 3100 can include multiple sensors located at various locations to provide a spatial profile of the force and/or pressure applied to the support member 3102. In this manner, a practitioner can detect changes in the patient's condition, such those that may result in a loosening of the spinal implant.

In some embodiments, the sensor 3124 can be remotely controlled by an external induction device. For example, an external radio frequency (RF) transmitter (not shown) can be used to supply power to and communicate with the sensor 3124. In other embodiments, an external acoustic signal transmitter (not shown) can be used to supply power to and communicate with the sensor 3124. In such an arrangement, for example, the sensor can include a pressure sensor, of the types described above, for measuring a pressure; an acoustic transducers, and an energy storage device. The acoustic transducer converts energy between electrical energy and acoustic energy. The energy storage device stores the electrical energy converted by the acoustic transducer and supplies the electrical energy to support the operation of the pressure sensor. In this manner, acoustic energy from an external source can be received and converted into electrical energy used to power the pressure sensor. Similarly, an electrical signal output from the pressure sensor can be converted into acoustic energy and transmitted to an external source.

The support member 3102 includes a sidewall 3108 that defines an inner area 3120 and multiple openings 3114 that connect the inner area 3120 to an area outside of the support member 3102. When the spinal implant 3100 is in the first configuration, the proximal retention member 3110 and the distal retention member 3112 are substantially disposed within the inner area 3120 of the support member 3102, as shown in FIG. 51. When the spinal implant 3100 is in the second configuration, a portion of each of the proximal retention member 3110 and the distal retention member 3112 extends through the openings 3114 to an area outside of the support member 3102. In the second configuration, the proximal retention member 3110 and the distal retention member 3112 engage the adjacent spinous processes, thereby limiting lateral movement of the spinal implant 3100.

Figure 56:
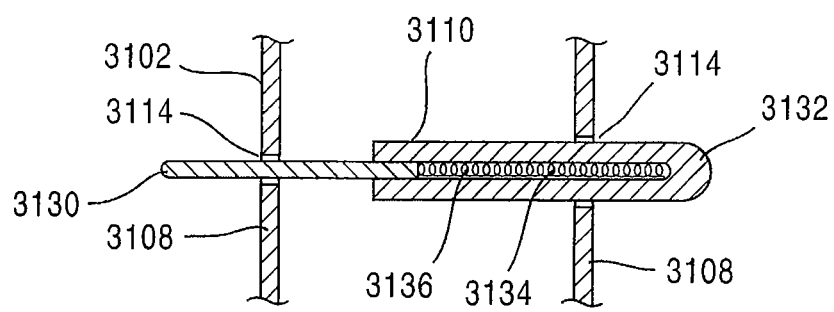
FIG. 56 is a cross-sectional plan view taken along section A-A in FIG. 55 of the medical device illustrated in FIGS. 52 and 55 in a second configuration.

The proximal retention member 3110 includes a first elongate member 3130 and a second elongate member 3132. Similarly, the distal retention member 3112 includes a first elongate member 3131 and a second elongate member 3133. As illustrated in FIG. 56, which shows is a cross-sectional plan view of the proximal portion 3104 of the support member 3102, the first elongate member 3130 is slidably disposed within a pocket 3134 defined by the second elongate member 3132. A biasing member 3136, such as a spring or an elastic member, is disposed within the pocket 3134 and is coupled to the first elongate member 3130 and the second elongate member 3132. In this manner, the retention members can be biased in the second configuration. In other embodiments, the biasing member 3136 can be configured to bias the retention members in the first configuration. In yet other embodiments, the retention members do not include a biasing member, but instead use other mechanisms to retain a desired configuration. Such mechanisms can include, for example, mating tabs and slots configured to lockably engage when the retention members are in a desired configuration.

In use, the spinal implant 3100 is positioned in the first configuration during insertion, removal or repositioning. As discussed above, the spinal implant 3100 is inserted percutaneously between adjacent spinous processes. The distal portion 3106 of the support member 3102 is inserted first and is moved past the spinous processes until the support member 3102 is positioned between the spinous processes. The support member 3102 can be sized to account for ligaments and tissue surrounding the spinous processes S. In some embodiments, the support member 3102 contacts the spinous processes between which it is positioned during a portion of the range of motion of the spinous processes S. In some embodiments, the support member 3102 of spinal implant 3100 is a fixed size and is not compressible or expandable. In yet other embodiments, the support member 3102 can compress to conform to the shape of the spinous processes S. Similarly, in some embodiments, the proximal retention member 3110 and the distal retention member 3112 are substantially rigid. In other embodiments, the retention members or portions thereof are elastically deformable, thereby allowing them to conform to the shape of the spinous processes.

Figure 55:
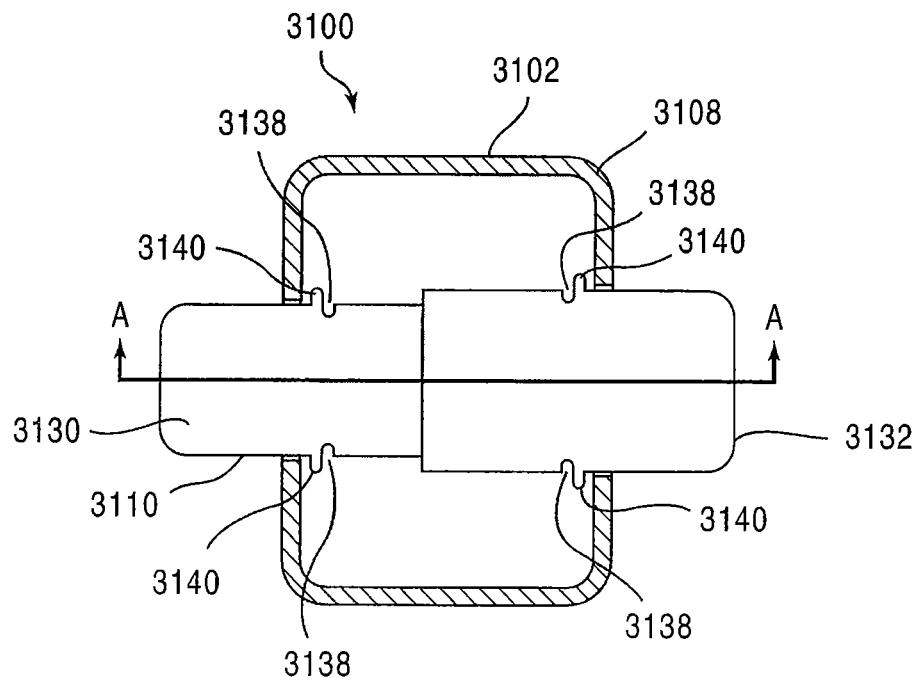
FIG. 55 is a cross-sectional front view of the medical device illustrated in FIGS. 51 and 52 in a second configuration.

In the illustrated embodiment, the spinal implant 3100 is held in the first configuration by an insertion tool (not shown) that overcomes the force exerted by the biasing member 3136, thereby disposing a portion of the first elongate member 3130 within the pocket 3134 of the second elongate member 3132. In this manner, the spinal implant 3100 can be repeatedly moved from the first configuration to the second configuration, thereby allowing it to be repositioned and/or removed percutaneously. As illustrated in FIG. 55, the first elongate member 3130 and the second elongate member 3132 each include notches 3138 configured to receive a portion of the insertion tool. When the insertion tool is released, the biasing member 3136 is free to extend, thereby displacing a portion of the first elongate member 3130 out of the pocket 3134 of the second elongate member 3132. In this manner, portions of both the first elongate member 3130 and the second elongate member 3132 are extended through the adjacent openings 3114 and to an area outside of the support member 3102. In some embodiments, the proximal retention member 3110 and the distal retention member 3112 are transitioned between their respective first and second configurations simultaneously. In other embodiments, the proximal retention member 3110 and the distal retention member 3112 are transitioned between their first and second configurations serially.

As illustrated, the first elongate member 3130 and the second elongate member 3132 each include one or more tabs 3140 that engage the side wall 3108 of the support member 3102 when in the second configuration, thereby ensuring that the first and second elongate members remain coupled to each other and that portions of the first and second elongate members remain suitably disposed within the support member 3102. In other embodiments, the first elongate member 3130 and the second elongate member 3132 are coupled to each other by other suitable mechanisms, such as mating tabs and slots configured to engage when the retention member reaches a predetermined limit of extension.

Figure 57:
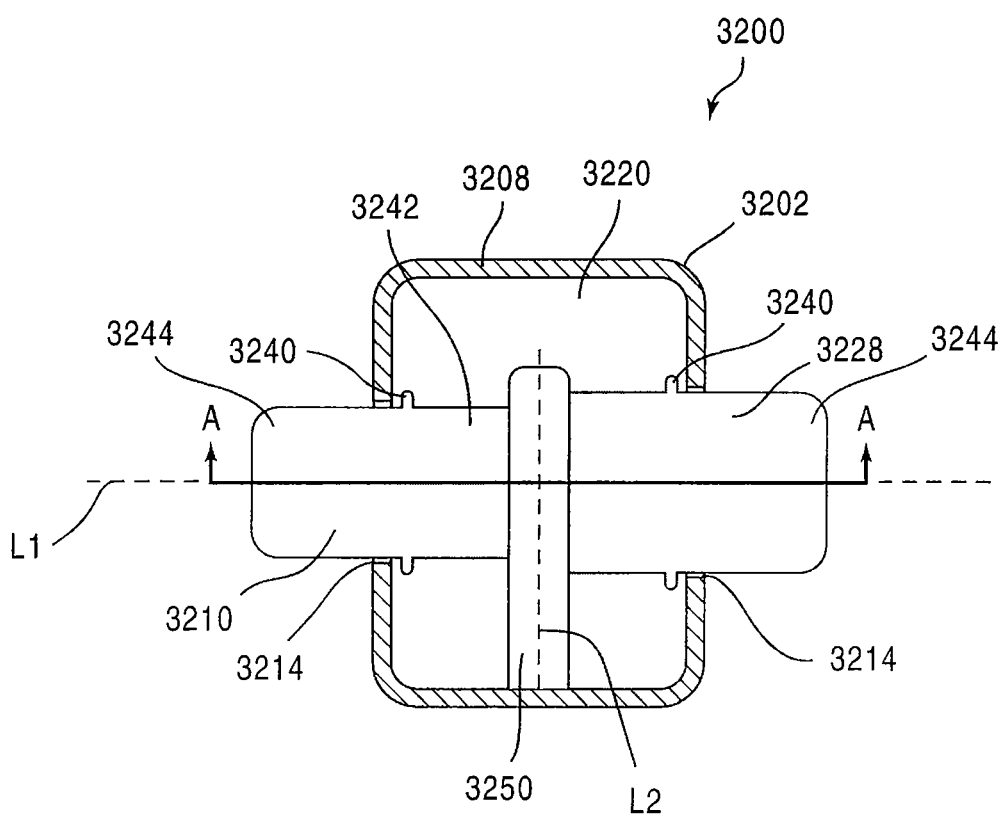
FIG. 57 is a cross-sectional front view of a medical device according to an embodiment of the invention in a second configuration.
Figure 58:
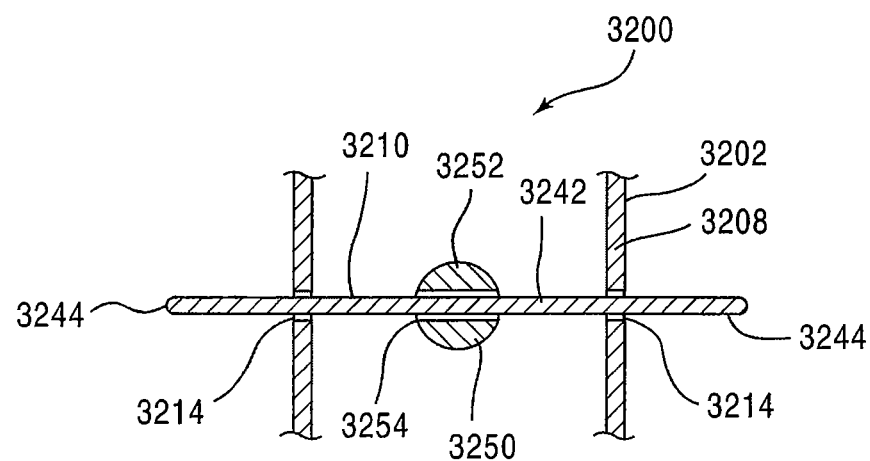
FIGS. 58 and 59 are cross-sectional plan views taken along section A-A of the medical device illustrated in FIG. 57 in a second configuration and a first configuration, respectively.
Figure 59:
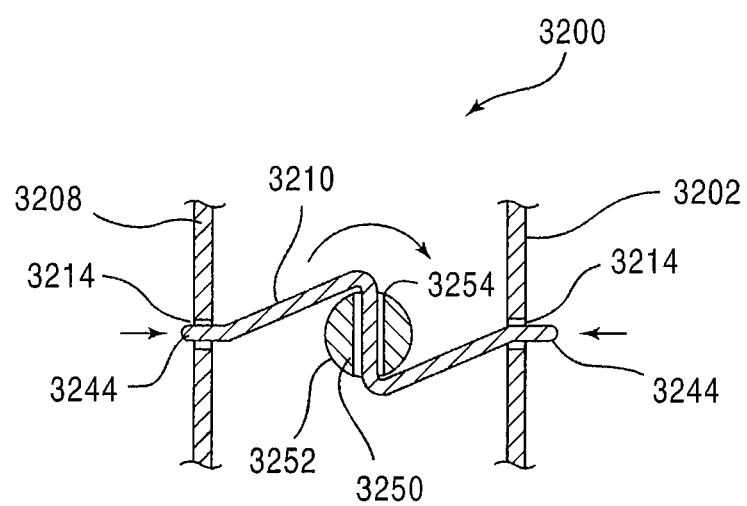

FIGS. 57-59 are cross-sectional views of a spinal implant 3200 according to an embodiment of the invention. FIG. 57 illustrates a cross-sectional front view of the spinal implant 3200 in a second configuration, while FIGS. 58 and 59 illustrate a cross-sectional plan view of the spinal implant 3200 in the second configuration and a first configuration, respectively. The illustrated spinal implant 3200 includes a support member 3202, a retention member 3210 and a rotating member 3250. Although shown and described as including only a single retention member 3210, some embodiments can include one or more additional retention members having characteristics and functionality similar to those described for the retention member 3210.

As shown in FIGS. 58 and 59, the retention member 3210 is repeatably positionable in a first configuration in which it is substantially disposed within the support member 3202, and a second configuration in which a portion the retention member 3210 is disposed outside of the support member 3102. When the spinal implant 3200 is in the first configuration, it can be inserted between adjacent spinous processes, repositioned between adjacent spinous processes and/or removed from the patient. When the spinal implant 3200 is in the second configuration, its lateral movement is limited, thereby allowing the desired position of the support member 3202 to be maintained.

The support member 3202 includes a sidewall 3208 that defines an inner area 3220 and multiple openings 3214 that connect the inner area 3220 to an area outside of the support member 3202. When the spinal implant 3200 is in the first configuration, the retention member 3210 is substantially disposed within the inner area 3220 of the support member 3202, as shown in FIG. 59. When the spinal implant 3200 is in the second configuration, a portion of the proximal retention member 3210 extends through the openings 3214 to an area outside of the support member 3202. In the second configuration, the retention member 3210 is disposed adjacent the spinous processes, thereby limiting lateral movement of the spinal implant 3200.

The retention member 3210 includes an elongate member 3228 having two end portions 3244, a central portion 3242, and a longitudinal axis L1 (shown in FIG. 57). A portion of the elongate member 3228 is flexible such that it can be wound along the rotating member 3250, as described below. In some embodiments, the elongate member 3228 is monolithically formed such that it is flexible enough to be wound along the rotating member 3250 yet rigid enough to limit lateral movement of the support member 3202 when positioned in the second configuration. In other embodiments, the elongate member 3228 includes separate components that are coupled together to form the elongate member 3228. For example, the central portion 3242 of the elongate member 3228 can be a distinct component having a greater amount of flexibility, while the end portions 3244 can be distinct components having a greater amount of rigidity.

In the illustrated embodiment, elongate member 3228 has one or more tabs 3240 that engage the side wall 3208 of the support member 3202 when in the second configuration, thereby ensuring that the elongate member 3228 does not freely extend entirely outside of the support member 3202. In other embodiments, a portion of the elongate member 3228 is retained within the support member 3202 by other suitable mechanisms. For example, the width of the central portion 3242 of the elongate member 3228 can be greater than the width of the openings 3214, thereby ensuring that a portion of the elongate member 3228 will remain within the support member 3202.

The rotating member 3250 defines an outer surface 3252 and a slot 3254 through which the elongate member 3228 is disposed. The rotating member 3250 has a longitudinal axis L2 (shown in FIG. 57) about which it rotates. As illustrated in FIG. 59, as the rotating member 3250 rotates, the elongate member 3228 is wound along the outer surface 3252 of the rotating member 3250. This causes the elongate member 3228 to move along its longitudinal axis L1, thereby causing the end portions 3244 of the elongate member 3228 to be retracted inwardly through the openings 3214. In this manner, the retention member 3210 can be repeatedly transitioned between the first configuration and the second configuration.

In some embodiments, the rotating member 3250 is rotated using an insertion tool (not shown) that includes a ratchet mechanism. The insertion tool can rotate the rotating member 3250 in a number of different ways, such as, for example, manually, pneumatically or electronically.

Figure 60:
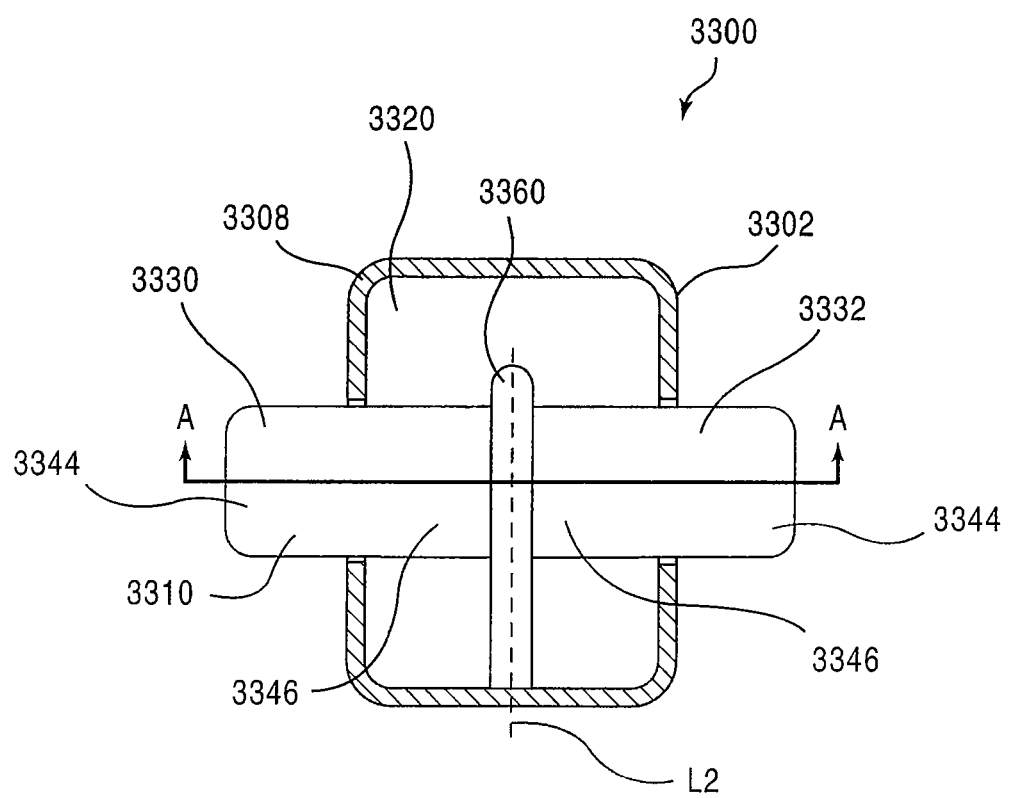
FIG. 60 is a cross-sectional front view of a medical device according to an embodiment of the invention in a second configuration.
Figure 61:
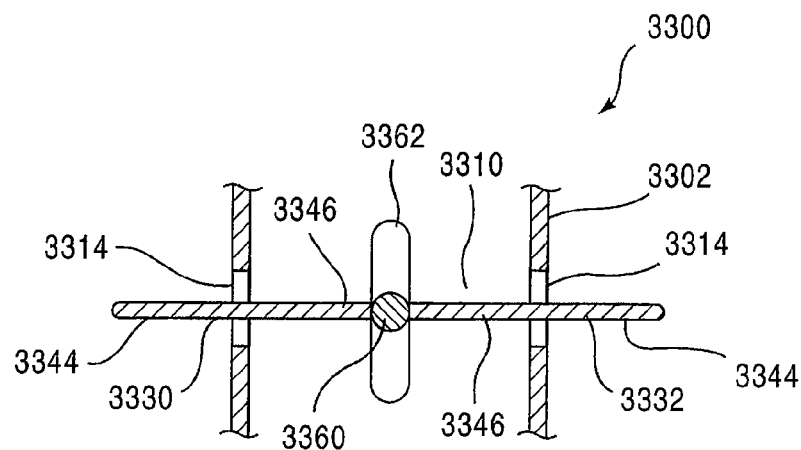
FIGS. 61 through 63 are cross-sectional plan views taken along section A-A of the medical device illustrated in FIG. 60 in a second configuration, a first configuration, and a third configuration respectively.
Figure 62:
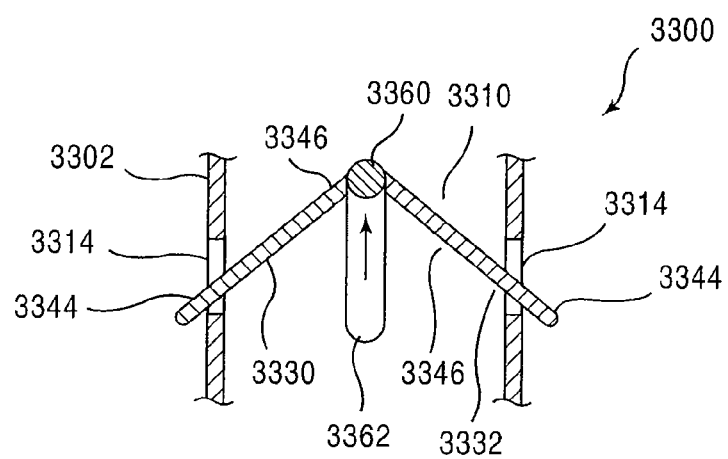
Figure 63:
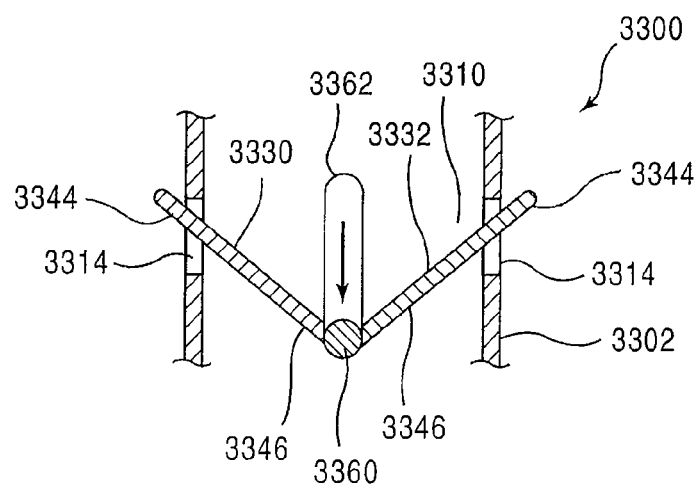

FIGS. 60-63 are cross-sectional views of a spinal implant 3300 according to an embodiment of the invention. FIG. 60 illustrates a cross-sectional front view of the spinal implant 3300 in a second configuration, while FIGS. 61-63 illustrate a cross-sectional plan view of the spinal implant 3300 in the second configuration, a first configuration, and a third configuration, respectively. The illustrated spinal implant 3300 includes a support member 3302 and a retention member 3310. Although shown and described as including only a single retention member 3310, some embodiments can include one or more additional retention members having characteristics and functionality similar to those described for the retention member 3310.

As shown in FIGS. 61-63, the retention member 3310 is repeatably positionable in a first configuration, a second configuration and a third configuration. A portion the retention member 3310 is disposed outside of the support member 3302 when positioned in the second configuration. The retention member 3310 is substantially disposed within the support member 3202 when positioned in each of the first and third configurations. As illustrated in FIGS. 62 and 63, the orientation of the retention member 3310 differs between the first and third configurations. In this manner, the position of the spinal implant 3300 can be positioned appropriately depending on the direction in which it is being moved. For example, the spinal implant 3300 may be positioned in the first configuration to facilitate lateral movement of the support member 3302 in a distal direction, such as during insertion. Conversely, the spinal implant 3300 may be positioned in the third configuration to facilitate lateral movement of the support member 3302 in a proximal direction, such as during removal.

The support member 3302 includes a sidewall 3308 that defines an inner area 3320 and multiple openings 3314 that connect the inner area 3320 to an area outside of the support member 3302. When the spinal implant 3300 is in the second configuration, a portion of the proximal retention member 3310 extends through the openings 3314 to an area outside of the support member 3302.

The retention member 3310 includes a first elongate member 3330, a second elongate member 3332, and a hinge 3360 having a longitudinal axis L2 (shown in FIG. 60). Each of the first elongate member 3330 and the second elongate member 3332 has a distal end portion 3344 that extends through the openings 3314 when the spinal implant 3300 is in the second configuration and a proximal end portion 3346 that is pivotally coupled to the hinge 3360. In use, the hinge 3360 moves in a direction normal to its longitudinal axis L2, as indicated by the arrows in FIGS. 62 and 63. The motion of the hinge is guided by a slot 3362 defined by the side wall 3308 of the support member 3302. The movement of the hinge 3360 allows the each of the first elongate member 3330 and the second elongate member 3332 to rotate about the longitudinal axis L2 of the hinge 3360, thereby positioning the distal end portion 3344 of each elongate member substantially within the inner area 3320 of the support member 3302.

In some embodiments, the slot 3362 includes detents or any other suitable mechanism (not shown) to maintain the hinge 3360 in the desired position. In other embodiments the hinge 3360 includes a biasing member (not shown) configured to bias the hinge 3360 in one of the first, second, or third configurations. In yet other embodiments, the elongate members include other suitable mechanisms to retain the retention member in a desired configuration. Such mechanisms can include, for example, mating tabs and slots configured to lockably engage when the elongate members are in a desired configuration.

In some embodiments, the first elongate member 3330 and the second elongate member 3332 are monolithically formed of a substantially rigid material. In other embodiments, the first elongate member 3330 and the second elongate member 3332 include separate components having different material properties. For example, the distal end portion 3344 can be formed from a material having a greater amount of flexibility, while the proximal end portion 3346 can be formed from a substantially rigid material. In this manner, movement of the spinal implant 3300 is not restricted when a portion of the distal end portion 3344 protrudes from the openings 3314 in either the first configuration or the third configuration.

Figure 64:
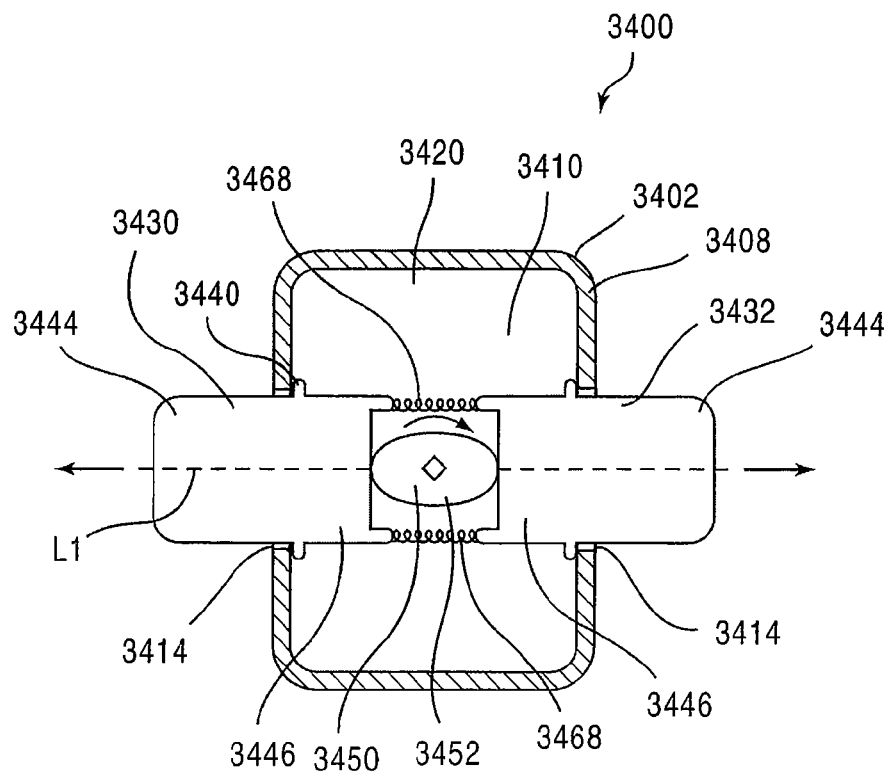
FIGS. 64 and 65 are cross-sectional front views of a medical device according to an embodiment of the invention in a second configuration and a first configuration, respectively.
Figure 65:
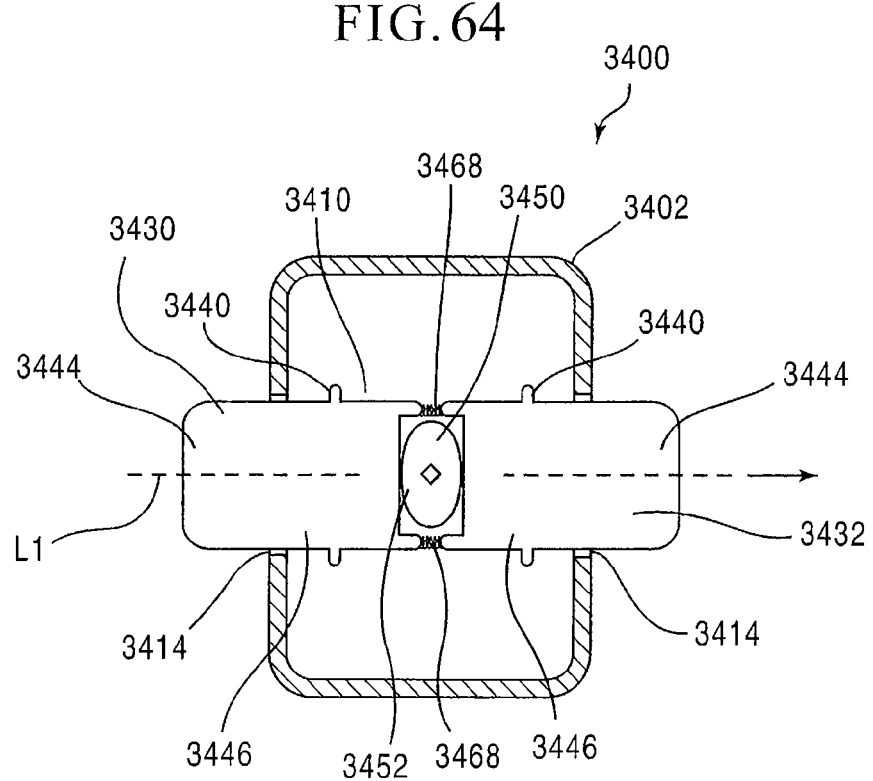

FIGS. 64 and 65 are cross-sectional front views of a spinal implant 3400 according to an embodiment of the invention. The illustrated spinal implant 3400 includes a support member 3402, a retention member 3410 and a rotating member 3450. As shown in FIGS. 64 and 65, the retention member 3410 is repeatably positionable in a first configuration in which it is substantially disposed within the support member 3402, and a second configuration in which a portion the retention member 3410 is disposed outside of the support member 3402. Although shown and described as including only a single retention member 3410, some embodiments include one or more additional retention members having characteristics and functionality similar to those described for the retention member 3410.

The support member 3402 includes a sidewall 3408 that defines an inner area 3420 and multiple openings 3414 that connect the inner area 3420 to an area outside of the support member 3402. When the spinal implant 3400 is in the second configuration, a portion of the proximal retention member 3410 extends through the openings 3414 to an area outside of the support member 3402.

The retention member 3410 includes a first elongate member 3430 and a second elongate member 3432, each having a distal end portion 3444 that extends through the openings 3414 when the spinal implant 3400 is in the second configuration, a proximal end portion 3446, and a longitudinal axis L1. As illustrated, the proximal end portions 3346 are coupled by two elastic members 3468, such as a spring or an elastic band. In some embodiments, the proximal end portions 3346 are coupled by a single elastic member. In other embodiments, the proximal end portions 3346 are indirectly coupled via the rotating member 3450. In such an arrangement, for example, a biasing member can be placed between the sidewall of the support member and each elongate member, thereby biasing each elongate member against the rotating member.

In the illustrated embodiment, the elongate members each include one or more tabs 3440 that engage the side wall 3408 of the support member 3402 when in the second configuration, thereby ensuring that the elongate members 3430, 3432 does not freely extend entirely outside of the support member 3402. In other embodiments, the elongate members do not include tabs, but are retained within the support member 3402 solely by the elastic members 3468. In yet other embodiments, the width of a portion of the elongate members can be greater than the width of the openings 3414, thereby ensuring that the elongate members will remain within the support member 3402.

The rotating member 3450 defines an outer surface 3452 having an eccentric shape and includes a longitudinal axis (not shown) about which it rotates. As illustrated in FIGS. 64 and 65, as the rotating member 3450 rotates about its longitudinal axis, a portion of the proximal end portion 3346 of the first elongate member 3430 and the second elongate member 3432 engage the outer surface 3452 of the rotating member 3250. This causes the first elongate member 3430 and the second elongate member 3432 to move along their respective longitudinal axes L1, thereby causing the end portions 3444 of each elongate member to be extended outwardly through the openings 3414, as indicated by the arrows in FIG. 64. In this manner, the retention member 3410 can be repeatedly transitioned between the first configuration and the second configuration.

In some embodiments, the rotating member 3450 is rotated using an insertion tool (not shown) that includes a ratchet mechanism. The insertion tool can rotate the rotating member 3450 in a number of different ways, such as, for example, manually, pneumatically or electronically.

Figure 66:
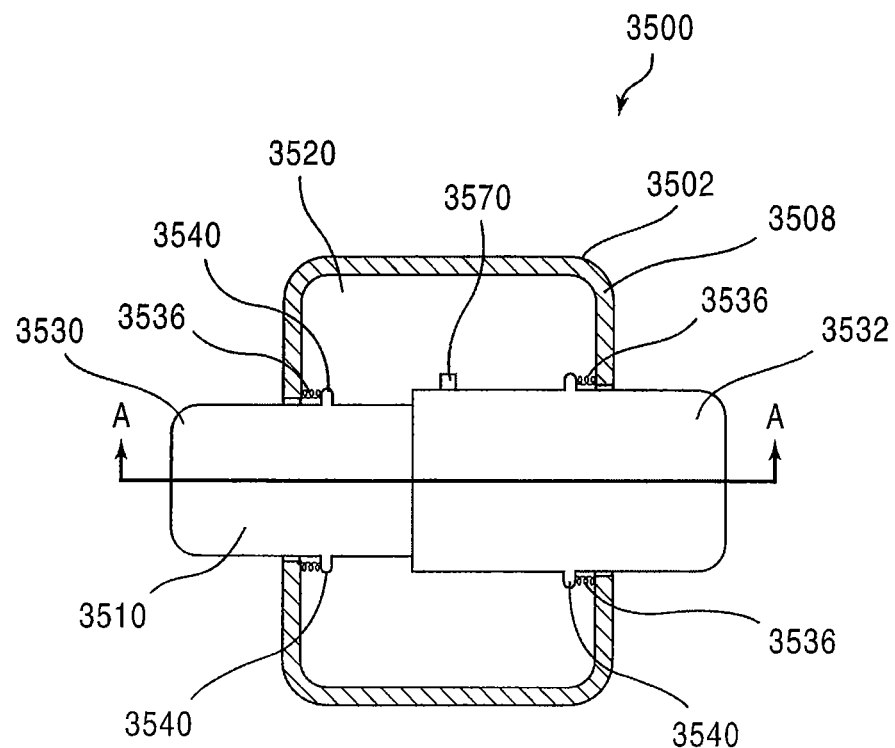
FIG. 66 is a cross-sectional front view of a medical device according to an embodiment of the invention in a second configuration.
Figure 67:
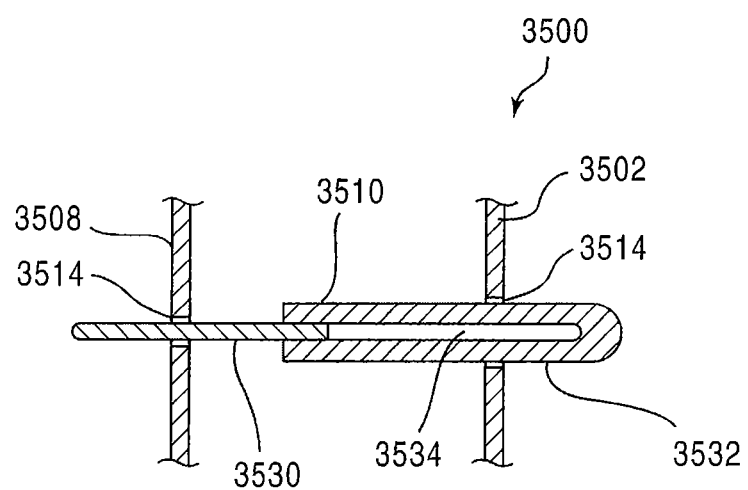
FIG. 67 is a cross-sectional plan view taken along section A-A of the medical device illustrated in FIG. 66 in a second configuration.

FIGS. 66 and 67 illustrate a spinal implant 3500 according to an embodiment of the invention. FIG. 66 is a cross-sectional front view of the spinal implant 3500 in a second configuration. FIG. 67 is a cross-sectional plan view of the spinal implant 3500 taken along section A-A. The spinal implant 3500 includes a support member 3502 and a retention member 3510. Although only shown as being in a second or expanded configuration, it is understood from the previous descriptions that the retention member 3510 is repeatably positionable in a first configuration in which it is substantially disposed within the support member 3502, and the second configuration in which a portion the retention member 3510 is disposed outside of the support member 3502.

As illustrated, the retention member 3510 includes a first elongate member 3530 and a second elongate member 3532. The first elongate member 3530 is slidably disposed within a pocket 3534 defined by the second elongate member 3532. The first elongate member 3530 and the second elongate member 3532 each include one or more tabs 3540 that are coupled to the side wall 3508 of the support member 3502 by one or more biasing members 3536. In this manner, the retention member 3510 is biased in the first or retracted configuration. In other embodiments, the biasing members 3536 can be configured to bias the retention member 3510 in the second configuration. In yet other embodiments, the retention member 3510 is not retained by a biasing member 3536, but rather uses other suitable mechanisms to retain the desired configuration.

In use, the retention member 3510 is transitioned from the first configuration to the second configuration by supplying a pressurized fluid (not shown) to the pocket 3534 via valve 3570. The pressure exerted by the fluid on each of the first elongate member 3530 and the second elongate member 3532 overcomes the force exerted by the biasing members 3536, thereby causing a portion the first elongate member 3530 to extend outwardly from the pocket 3534 of the second elongate member 3132, thereby allowing a portion of each elongate member to extend through the adjacent openings 3514 and to an area outside of the support member 3502. Similarly, the retention member 3510 is transitioned from the second configuration to the first configuration by opening the valve 3570 and relieving the pressure within the pocket 3534. In this manner, the spinal implant 3500 can be repeatedly moved from the first configuration to the second configuration, thereby allowing it to be repositioned and/or removed percutaneously.

Figure 68:
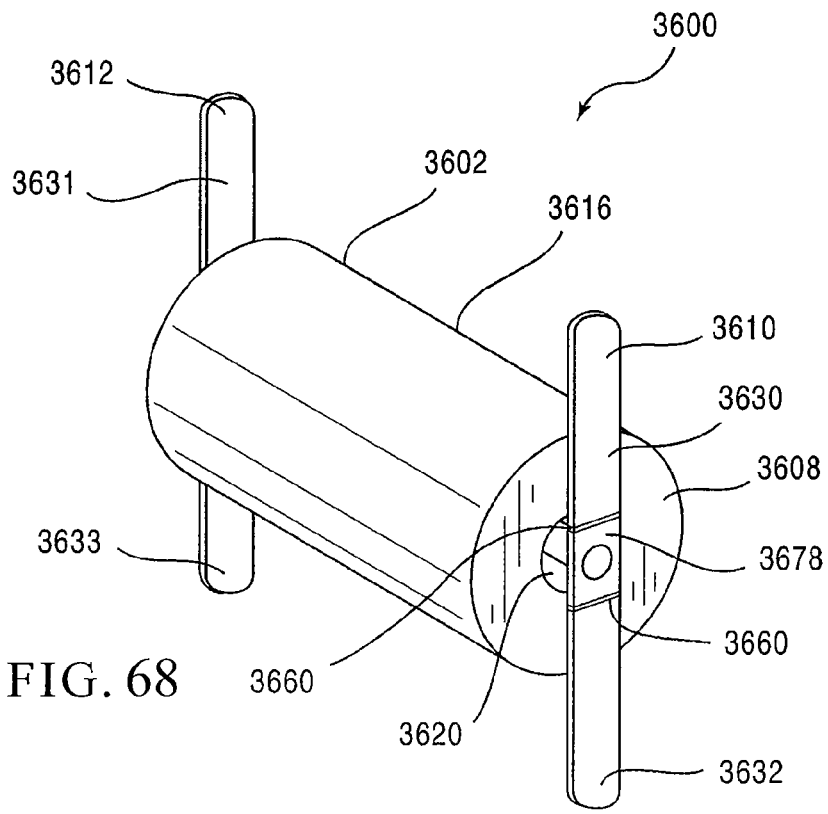
FIGS. 68 and 69 are perspective views of a medical device according to an embodiment of the invention in a second configuration and a first configuration, respectively.
Figure 69:
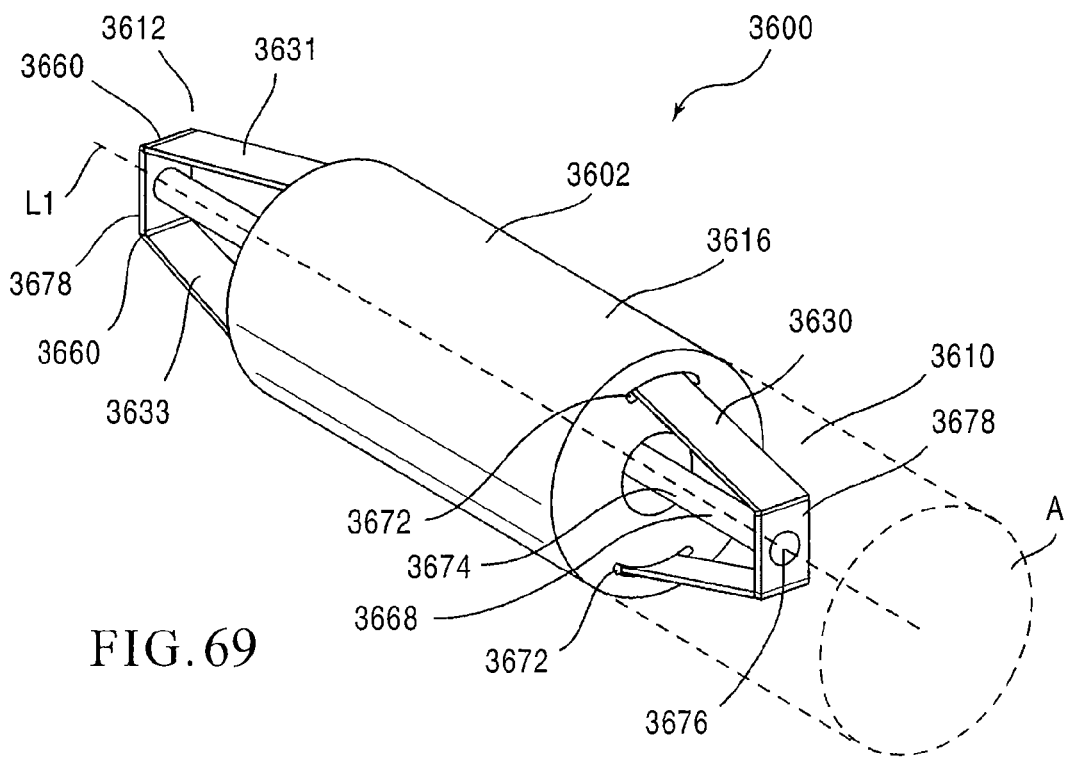
Figure 70:
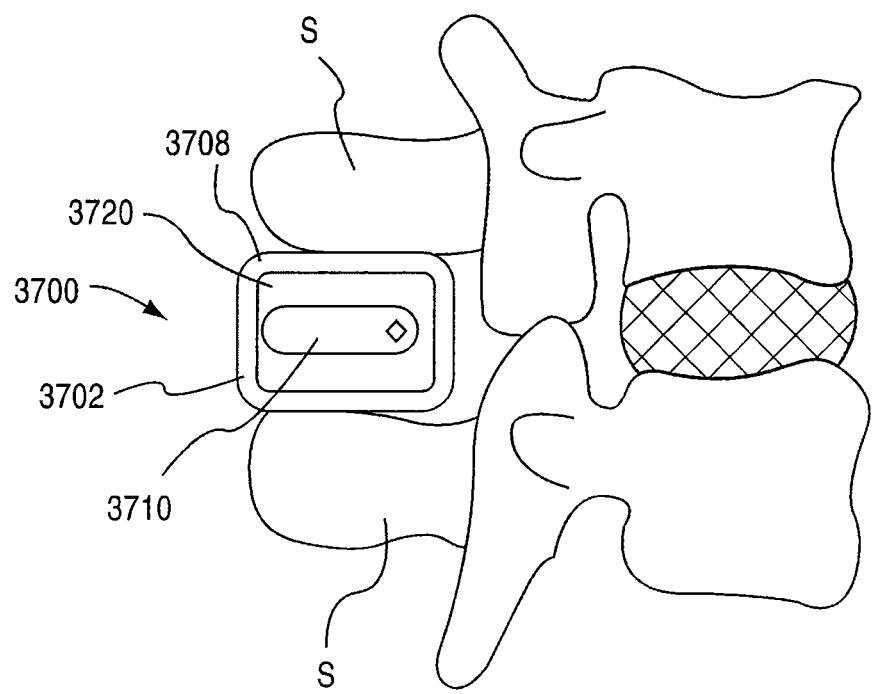
FIGS. 70 and 71 are lateral views of a medical device according to an embodiment of the invention in a first configuration and a second configuration, respectively.
Figure 71:
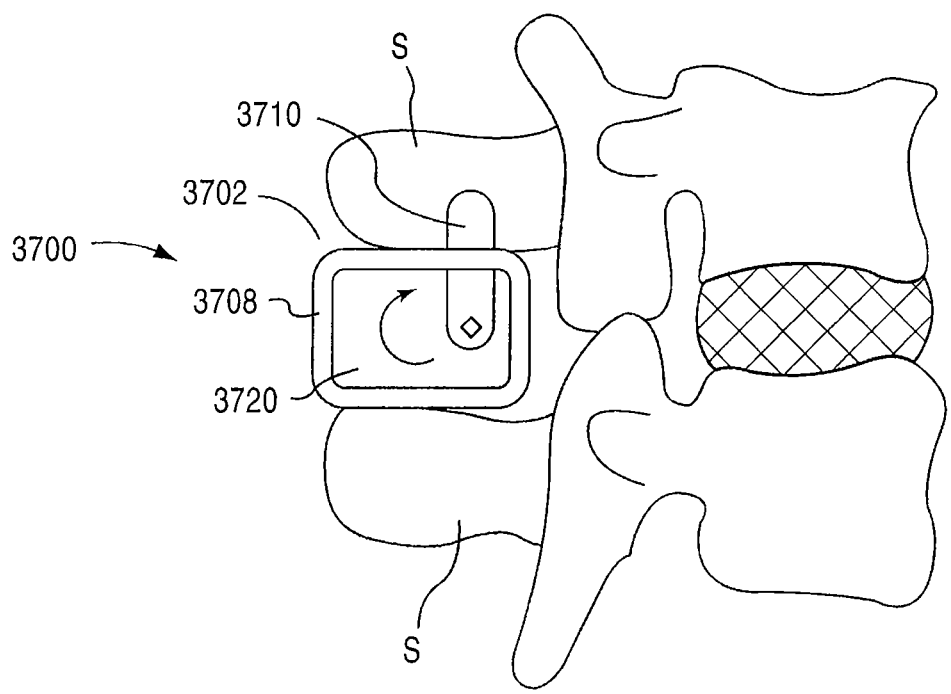
Figure 72:
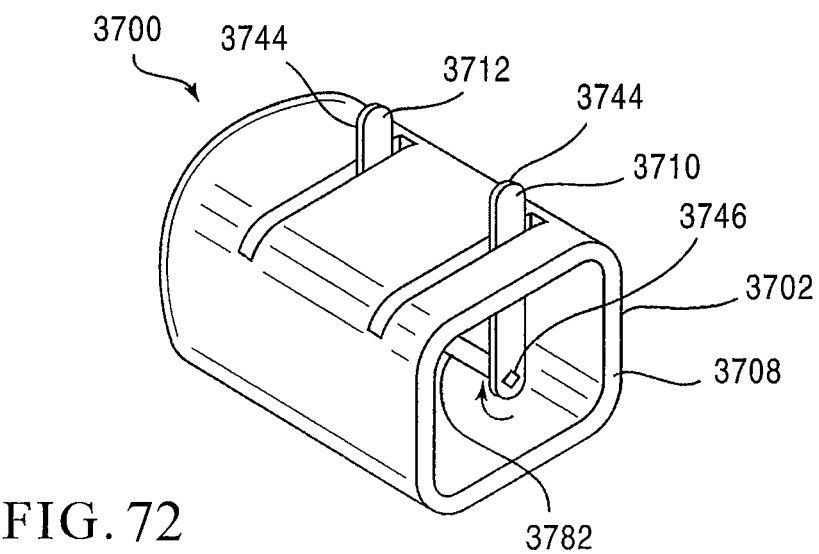
FIGS. 72 and 73 are perspective views of the medical device illustrated in FIGS. 70 and 71 in a first configuration and a second configuration, respectively.
Figure 73:
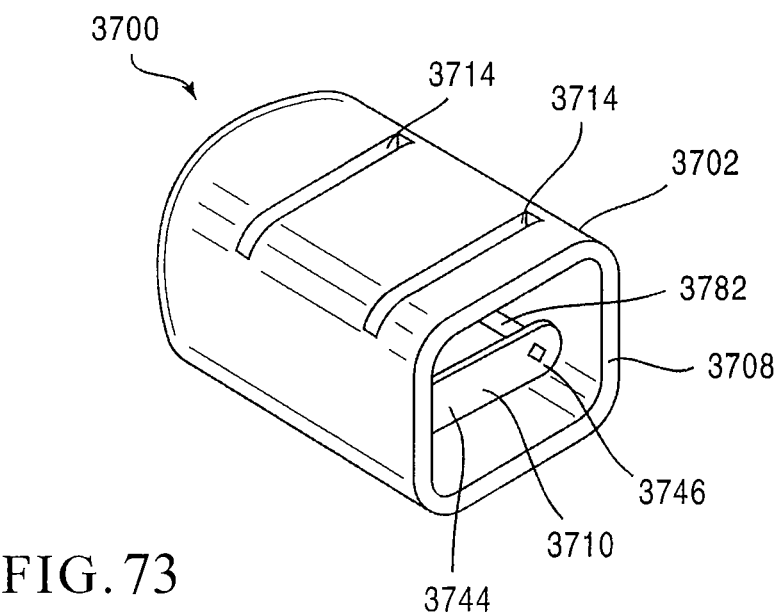
Figure 74:
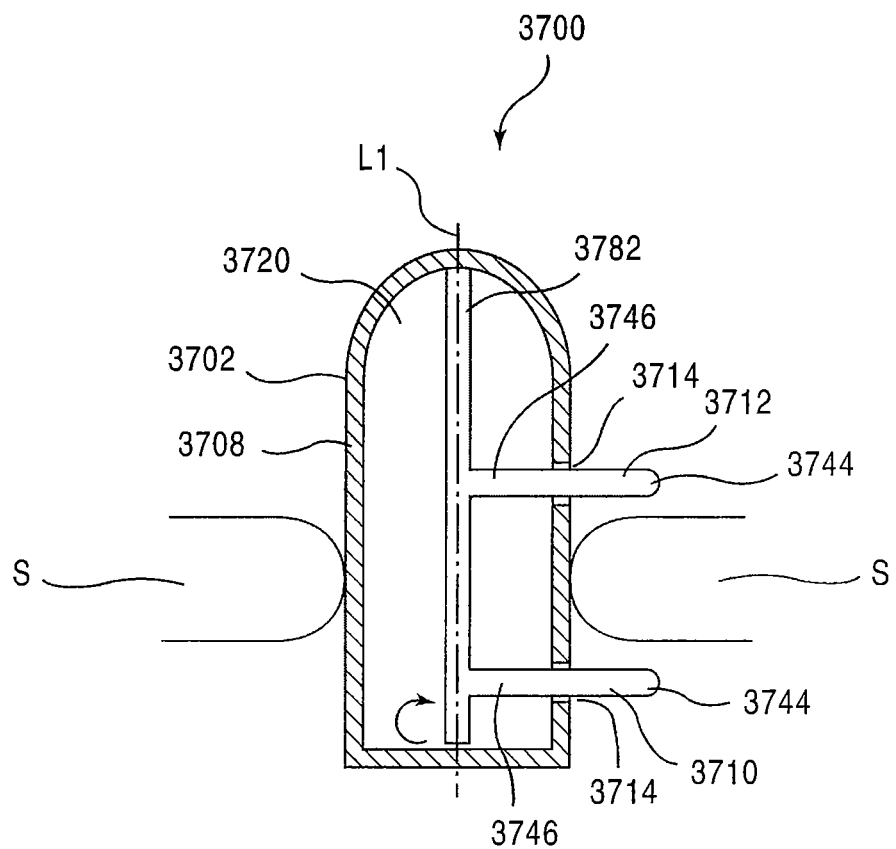
FIG. 74 is a cross-sectional plan view of the medical device illustrated in FIGS. 70 and 71 in a second configuration.

FIGS. 68 and 69 illustrate perspective views of a spinal implant 3600 according to an embodiment of the invention. The spinal implant 3600 includes a support member 3602, a proximal retention member 3610, a distal retention member 3612, and an elastic member 3668. The support member 3602 defines a longitudinal axis L1 and has a sidewall 3608 that defines an inner area 3620 and has an outer surface 3616. As illustrated in FIG. 69, the outer surface 3616 defines an area A normal to the longitudinal axis L1. As shown, the proximal retention member 3610 and the distal retention member 3612 are each repeatably positionable in a first configuration in which they are substantially disposed within the area A (FIG. 69), and a second configuration in which a portion of each retention member 3610, 3612 is disposed outside of the area A (FIG. 68).

As illustrated, the proximal retention member 3610 and the distal retention member 3612 are coupled by the elastic member 3668, a portion of which is disposed within the inner area 3620 of the support member 3602. In the illustrated embodiment, the elastic member 3668 has a sidewall 3674 that defines a lumen 3676. In other embodiments, the elastic member can be, for example, a spring, an elastic band, or any other suitable device for elastically coupling the proximal retention member 3610 and the distal retention member 3612.

The proximal retention member 3610 includes a first elongate member 3630 and a second elongate member 3632, each of which are pivotally coupled to a connection member 3678 by a hinge 3660. Similarly, the distal retention member 3612 includes a first elongate member 3631 and a second elongate member 3633 each of which are pivotally coupled to a connection member 3678 by a hinge 3660.

As illustrated in FIG. 68, when the spinal implant 3600 is in the second configuration, the elastic member 3668 exerts a biasing force on each connection member 3678, thereby causing the connection members 3678 to remain adjacent to the support member 3602. In this configuration, the first elongate member 3630 and the second elongate member 3632 are fully extended. The spinal implant 3600 is transitioned from the second configuration to the first configuration by stretching the elastic member 3668, which allows the connection members 3678 to be disposed apart from the support member 3602, thereby allowing the elongate members to move within the area A, as illustrated in FIG. 69. The support member 3602 includes slots 3672 in which the end portion of each elongate member can be disposed to maintain the spinal implant 3600 in the first configuration.

The elastic member 3668 can be stretched by an insertion tool (not shown), a portion of which can be configured to be disposed within the lumen 3676 of the elastic member 3668. For example, a first portion of an insertion tool can engage the connection member 3678 of the proximal retention member 3610 while a second portion of the insertion tool can engage the connection member 3678 of the distal retention member 3612. The tool can then be configured to exert an outward force on each of the connection members 3678, thereby stretching the elastic member 3668 and allowing the spinal implant to transition from the second configuration to the first configuration.

While the spinal implants are shown and described above as having one or more retention members that extend substantially symmetrically from a support member when in a second configuration, in some embodiments, a spinal implant includes a retention member that extends asymmetrically from a support member when in a second configuration. For example, FIGS. 70-74 illustrate a spinal implant 3700 according to an embodiment of the invention that includes a proximal retention member 3710 and a distal retention member 3712 that extend asymmetrically from a support member 3702. As shown in FIGS. 70-74, the proximal retention member 3710 and the distal retention member 3712 are each repeatably positionable in a first configuration in which they are substantially disposed within the support member 3702, and a second configuration in which a portion each is disposed outside of the support member 3702.

The support member 3702 includes a sidewall 3708 that defines an inner area 3720 and two openings 3714 that connect the inner area 3720 to an area outside of the support member 3702. When the spinal implant 3700 is in the second configuration, a portion of the proximal retention member 3710 and a portion of the distal retention member 3712 extend through the openings 3714 to an area outside of the support member 3702.

In the illustrated embodiment, the proximal retention member 3710 and the distal retention member 3712 each include a first end portion 3746 and a second end portion 3744. The first end portions 3746 of the proximal retention member 3710 and the distal retention member 3712 are coupled by a connecting member 3782 that has a longitudinal axis L1 (shown in FIG. 74). In some embodiments, the connecting member 3782, the proximal retention member 3710 and the distal retention member 3712 are separate components that are coupled together to form the illustrated structure. In other embodiments, the connecting member 3782, the proximal retention member 3710 and the distal retention member 3712 are monolithically formed.

The connecting member 3782 defines a longitudinal axis L1, about which it rotates. As illustrated, as the connecting member 3782 rotates, the proximal retention member 3710 and the distal retention member 3712 also rotate, thereby causing the end portions 3744 of the proximal retention member 3710 and the distal retention member 3712 to extend outwardly through the openings 3714. In this manner, the retention member 3210 can be repeatedly transitioned between the first configuration and the second configuration.

In some embodiments, the connecting member 3782 is rotated using an insertion tool (not shown) that includes a ratchet mechanism. The insertion tool can rotate the connecting member 3782 in a number of different ways, such as, for example, manually, pneumatically or electronically.

Figure 75:
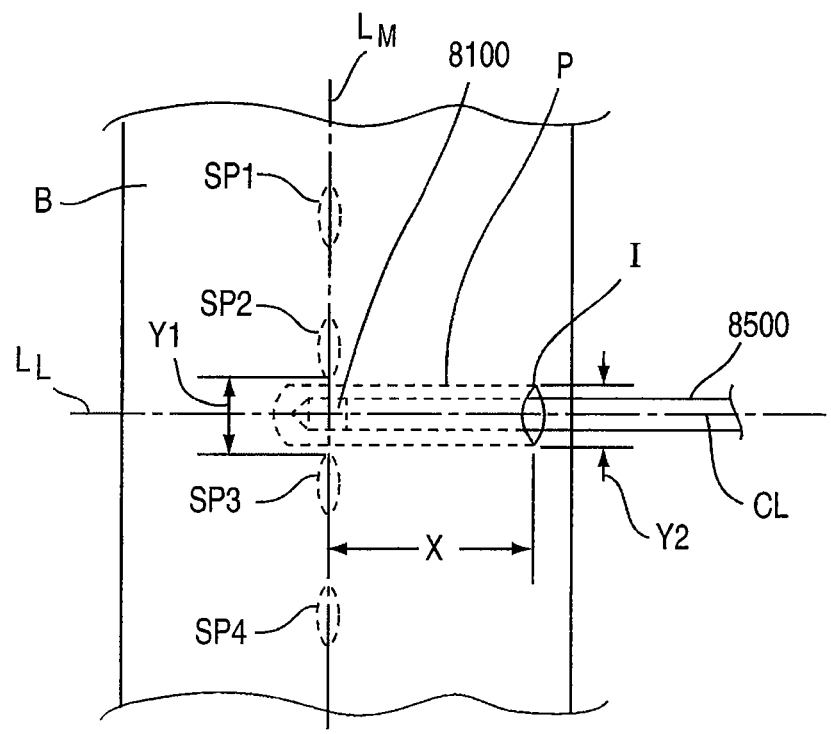
FIG. 75 is a posterior view of a portion of a medical device according to an embodiment of the invention disposed within a body between a pair of spinous processes.
Figure 76:
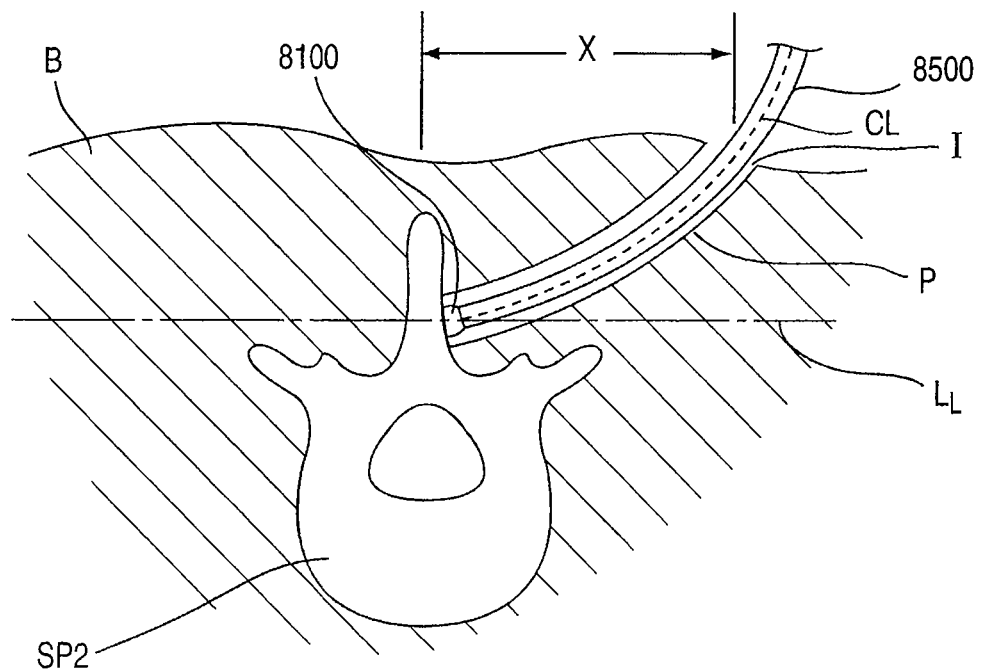
FIG. 76 is a side view of the portion of medical device shown in FIG. 75 taken along the lateral axis $L_L$.

As described herein, in some embodiments, the spinal implants shown and described above can be inserted between adjacent spinous processes percutaneously using a posterior-lateral approach. FIGS. 75 and 76 show an implant 8100 and a portion of an insertion tool 8500 being inserted into a body B using a posterior-lateral approach according to an embodiment of the invention. The body B includes spinous processes SP1-SP4, which define a mid-line axis $L_M$. A lateral axis $L_L$ is defined substantially normal to the mid-line axis $L_M$.

To position the implant 8100 between adjacent spinous processes SP2 and SP3, a lateral incision I having a length Y2 is made a distance X from the mid-line axis $L_M$. The length Y2 and the distance X can be selected to allow the implant to be inserted percutaneously in a minimally-invasive manner. In some embodiments, the distance X can be, for example, between 25 mm and 100 mm. In some embodiments, the incision I has a length Y2 that is no greater than the distance Y1 between the adjacent spinous processes, such as, for example, SP2 and SP3. In some embodiments, for example, the length Y2 is no greater than 15 mm and the distance Y1 is between 20 mm and 25 mm. In other embodiments, the length Y2 can exceed the distance Y1 between the adjacent spinous processes SP2 and SP3. In some embodiments, for example, the length Y2 can be as much as 50 mm.

A distraction tool (not shown in FIGS. 75 and 76) is then inserted through the incision I and is used to define the passageway P from the incision I to the adjacent spinous processes SP2 and SP3. The distraction tool can also distract the adjacent spinous processes SP2 and SP3 to define the desired space between, as described above. The distraction tool can be any suitable distraction tool of the type shown and described herein.

The insertion tool 8500 including the implant 8100 is then inserted through the incision I and via the passageway P to the space between the adjacent spinous processes SP2 and SP3. The implant 8100 is then disposed between the adjacent spinous processes SP2 and SP3 in any suitable manner, as described above. For example, in some embodiments, the implant 8100 can include one or more expandable portions that are adjacent to and/or engage portions of the spinous processes SP2 and/or SP3 to limit at least a lateral movement of the implant 8100.

As shown in FIGS. 75 and 76, during the insertion operation, the insertion tool 8500 is positioned such that when the implant 8100 is disposed between the adjacent spinous processes SP2 and SP3, the implant 8100 is substantially aligned with the lateral axis $L_L$. Said another way, during insertion, the insertion tool 8500 is positioned such that the longitudinal axis (not shown) of the implant 8100 is substantially coaxial with the lateral axis $L_L$. As described in more detail herein, the insertion tool 8500 is configured to ensure that the implant 8100 is aligned with the lateral axis $L_L$ during insertion.

Figure 77:
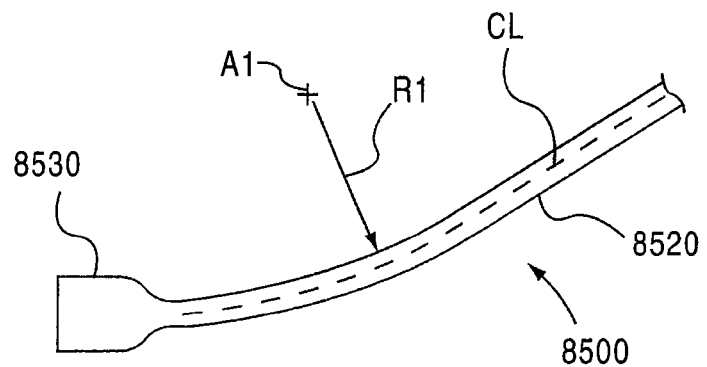
FIGS. 77 and 78 are a side view and a top plan view, respectively, of the portion of medical device shown in FIG. 75.
Figure 78:
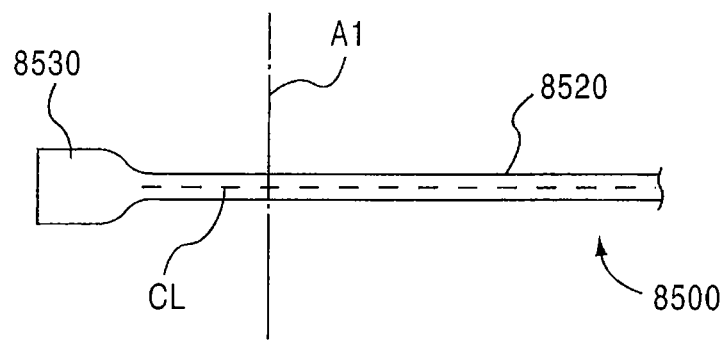

As shown in FIGS. 77 and 78, the insertion tool 8500, which can be similar to the insertion tools 1500 and 7500 shown and described above, includes a curved portion 8520 and an implant support portion 8530. The insertion tool 8500 defines a center line CL. As shown in FIGS. 77 and 78, which show a side view and a top plan view, respectively, of the insertion tool 8500, the center line CL of the curved portion 8520 defines a radius of curvature R1 about an axis A1 that is substantially normal to the center line CL. The radius of curvature R1 can be any value suitable to define and/or proceed along the passageway P such that the implant 8100 and/or a portion of the center line CL is aligned with the lateral axis $L_L$ during insertion. Moreover, the radius of curvature R1 can be selected to blend with the adjacent portions of the insertion tool 8500 to ensure that the surface of the insertion tool 8500 is continuous.

In some embodiments, for example, an insertion tool 8500 can have a small radius of curvature R1 (e.g., 20 mm to 50 mm), which corresponds to a relatively sharp curve. Such an embodiment can be appropriate, for example, when the distance X between the incision I and the mid-line axis $L_M$ is relatively small (e.g. 20 mm), requiring that passageway P have a relatively sharp curve to ensure that the implant 8100 is properly aligned. In other embodiments, for example, an insertion tool 8500 can have a large radius of curvature R1 (e.g., greater than 300 mm), which corresponds to less curvature. Such an embodiment can be appropriate, for example, when the distance X between the incision I and the mid-line axis $L_M$ is relatively great (e.g. greater than 50 mm). In yet other embodiments, an insertion tool 8500 can have a radius of curvature R1 that is between 50 mm and 300 mm. In some embodiments, for example, an insertion tool 8500 can have a radius of approximately 181 mm.

Figure 79:
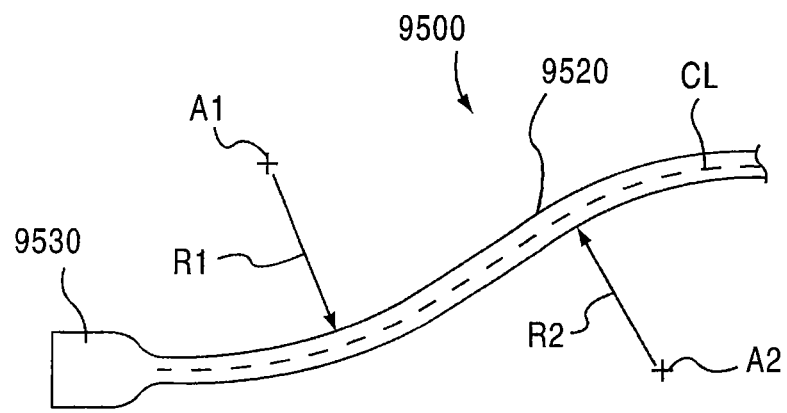
FIGS. 79 and 80 are a side view and a top plan view, respectively, of a portion of a medical device according to an embodiment of the invention.
Figure 80:
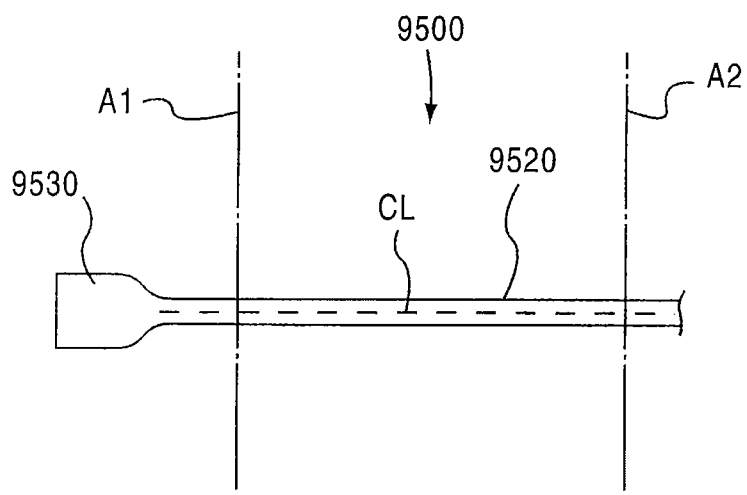

Although the insertion tool 8500 is shown and described as having a single radius of curvature R1, in some embodiments, an insertion tool can have multiple radii of curvature and/or geometrically complex shapes. For example, FIGS. 79 and 80 show a side view and a top plan view of an insertion tool 9500 according to an embodiment of the invention. The insertion tool 9500 includes a curved portion 9520 and an implant support portion 9530. A center line CL of the curved portion 9520 defines a first radius of curvature R1 about a first axis A1 that is substantially normal to the center line CL. The center line CL of the curved portion 9520 also defines a second radius of curvature R2 about a second axis A2 that is substantially parallel to the first axis A1 and substantially normal to the center line CL. As described above, the radii of curvature R1 and R2 can be any value suitable to define the passageway P such that the implant is aligned with the lateral axis $L_L$ during insertion. Moreover, as shown in FIG. 79, a portion of the elongate member 9500 is disposed between the first axis A1 and the second axis A2. Said another way, the first axis A1 and the second axis A2 are positioned such that the curved portion 9520 forms an "S" shape.

Although the insertion tool 9500 is shown and described as defining axis A1 and axis A2 with insertion tool 9500 therebetween, in other embodiments, an insertion tool can be on the same side of these axes. Similarly, although the insertion tool 9500 is described as defining axes A1 and A2 that are substantially parallel to each other, in other embodiments, an insertion tool can define axes A1 and A2 that are not substantially parallel to each other. Said another way, although the insertion tool 9500 is shown as having a two-dimensional curve, in other embodiments, an insertion tool can have a three-dimensional curve.

Figure 81:
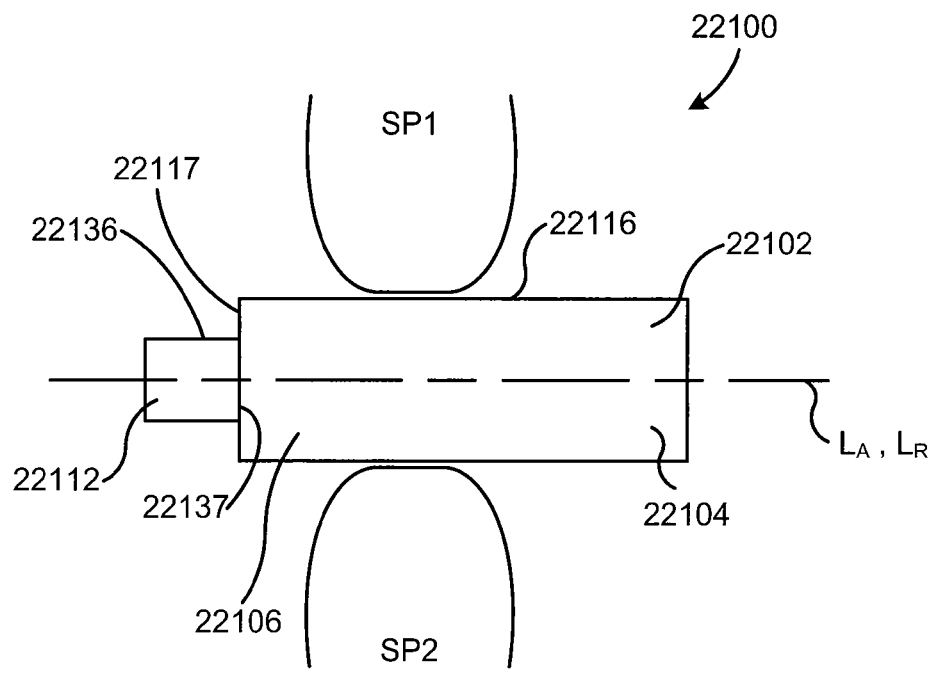
FIG. 81 is a schematic illustration of a posterior view of an implant in a first configuration according to an embodiment of the invention disposed between a first spinous process and second spinous process.
Figure 82:
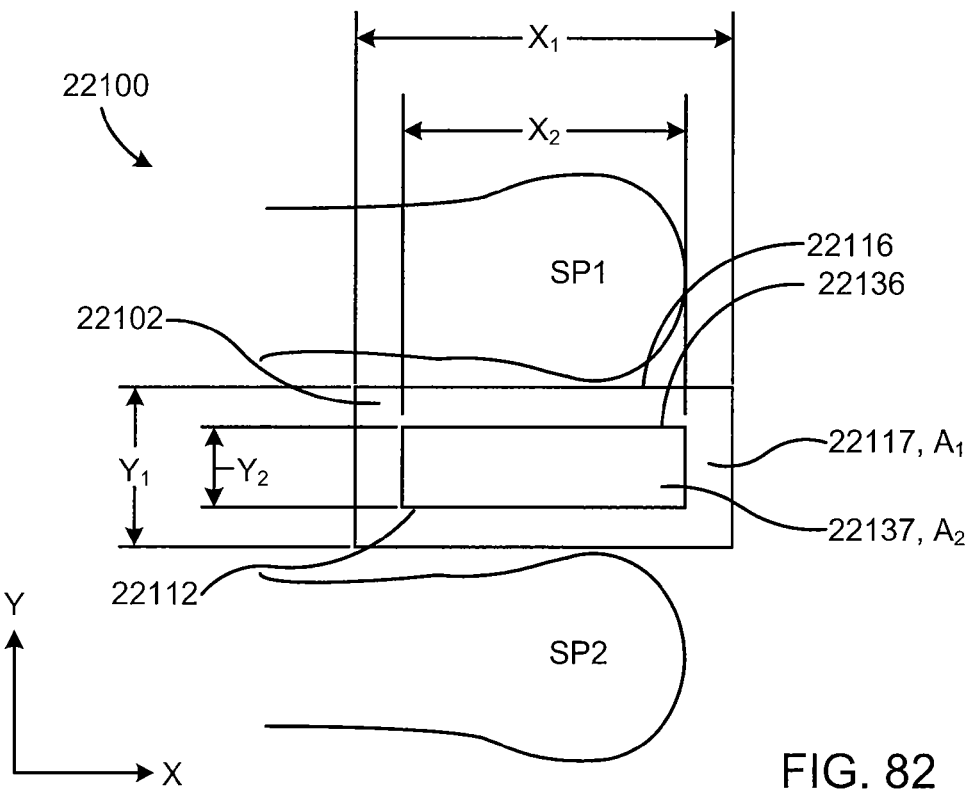
FIG. 82 is a schematic illustration of a lateral view of the implant shown in FIG. 81 in the first configuration.
Figure 83:
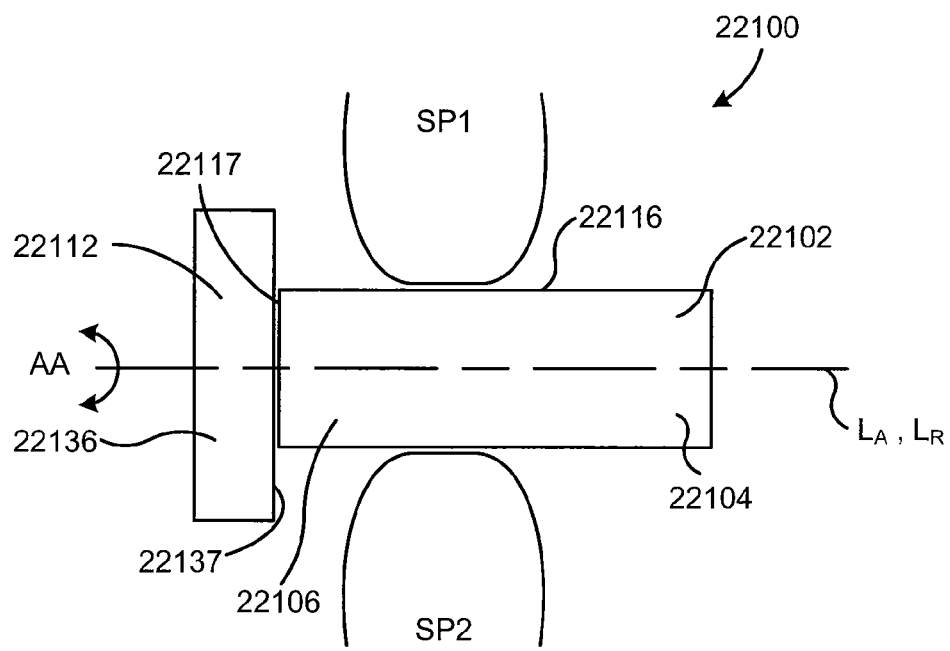
FIG. 83 is a schematic illustration of a posterior view of the implant shown in FIG. 81 in a second configuration.
Figure 84:
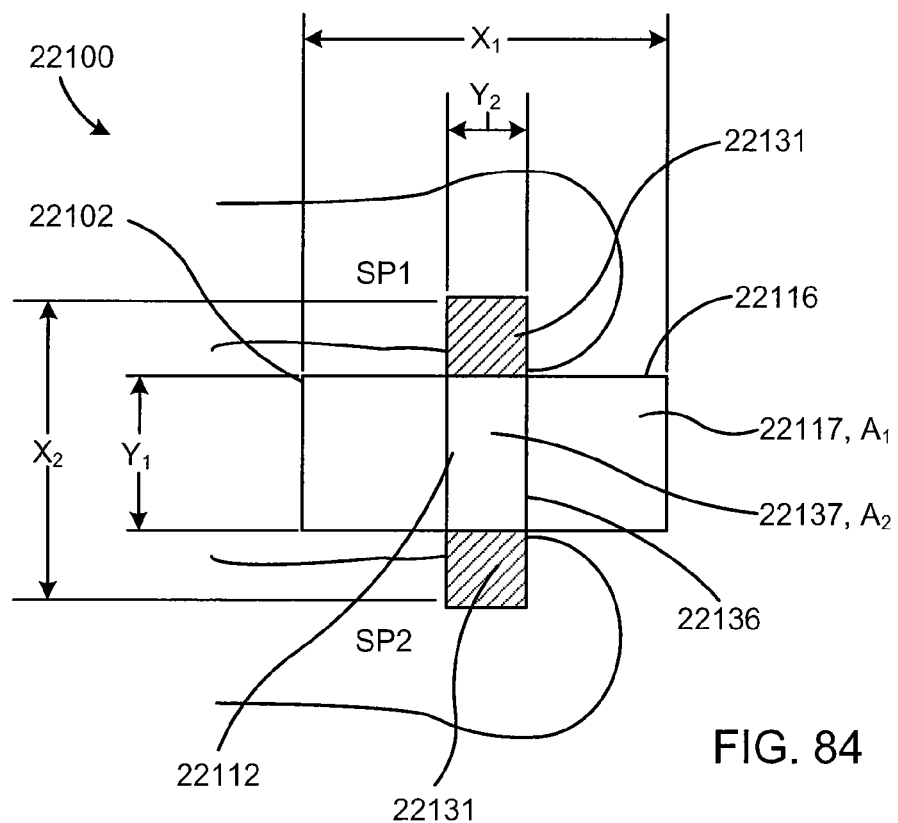
FIG. 84 is a schematic illustration of a lateral view of the implant shown in FIG. 81 in a second first configuration.

FIGS. 81-84 are schematic illustrations of an implant 22100 according to an embodiment of the invention. FIGS. 81 and 83 are posterior views of the implant 22100 in a first configuration and a second configuration, respectively, disposed between a first spinous process SP1 and a second spinous process SP2 adjacent the first spinous process SP1. FIGS. 82 and 84 are lateral views of the implant 22100 in the first configuration and the second configuration, respectively, disposed between the first spinous process SP1 and the second spinous process SP2. The implant 22100 includes a first member 22102 and a second member 22112 movably coupled to the first member 22102.

The first member 22102 has a proximal portion 22104, a distal portion 22106, a first surface 22116, and a second surface 22117. The first surface 22116 of the first member 22102 is substantially parallel to a longitudinal axis $L_A$ of the first member 22102. Said another way, the longitudinal axis $L_A$ and a line defined to include a portion of the first surface 22116 of the first member 22102 are non-intersecting as they extend to infinity. Said yet another way, in embodiments in which the first surface 22116 of the first member 22102 includes at least a planar portion, every point along the longitudinal axis $L_A$ is spaced apart from the nearest portion of a plane defined to include the planar portion of the first surface 22116 of the first member 22102 by a substantially equal distance. The longitudinal axis $L_A$ can, for example, pass lengthwise (e.g., from the proximal portion 22104 to the distal portion 22106) through the centroid of the first member 22102 (e.g., the longitudinal axis $L_A$ can be a centroidal axis of the first member 22102). As shown, when the implant 22100 is disposed between the first spinous process SP1 and the second spinous process SP2, the longitudinal axis $L_A$ can be substantially parallel and/or coincident with a lateral axis defined by the spinal column.

As shown, at least a portion of the first surface 22116 of the first member 22102 is disposed between the first spinous process SP1 and the second spinous process SP2. In this manner, the implant 22100 can maintain a minimal spacing between the adjacent spinous processes SP1 and SP2 during extension of the spinal column (not shown FIGS. 81-84) while allowing flexion of the spinal column. Moreover, in some embodiments, the implant 22100 can distract a prior spacing of the adjacent spinous processes SP1 and SP2.

The second surface 22117 is disposed at the distal portion 22106 of the first member 22102 and intersects the longitudinal axis $L_A$ at an angle of approximately 90 degrees. Said another way, the second surface 22117 of the first member 22102 is substantially normal to the first surface 22116 of the first member 22102. Although the second surface 22117 of the first member 22102 is shown as intersecting the longitudinal axis $L_A$ of the first member 22102 at an angle of approximately 90 degrees, in other embodiments, the second surface of the first member can intersect the longitudinal axis of the first member by any non-zero angle.

The second member 22112 has a first surface 22136 and a second surface 22137. The first surface 22136 is substantially parallel to the longitudinal axis $L_A$ of the first member 22102. Said another way, the longitudinal axis $L_A$ and a line defined to include a portion of the first surface 22136 of the second member 22112 are non-intersecting as they extend to infinity. Said yet another way, in embodiments in which the first surface 22136 of the second member 22112 includes at least a planar portion, every point along the longitudinal axis $L_A$ is spaced apart from the nearest portion of a plane defined to include the planar portion of the first surface 22136 of the second member 22112 by a substantially equal distance. Although the first surface 22136 of the second member 22112 is shown as being substantially parallel to the longitudinal axis $L_A$ of the first member 22102, in other embodiments, the first surface of the second member can intersect the longitudinal axis of the first member by any non-zero angle.

The second surface 22137 intersects the longitudinal axis $L_A$ at an angle of approximately 90 degrees. Said another way, the second surface 22137 of the second member 22112 is substantially parallel to the second surface 22117 of the first member 22102, substantially normal to the first surface 22136 of the second member 22112, and substantially normal to the first surface 22116 of the first member 22102. Although the second surface 22137 of the second member 22112 is shown as intersecting the longitudinal axis $L_A$ of the first member 22102 at an angle of approximately 90 degrees, in other embodiments, the second surface of the second member can intersect the longitudinal axis of the first member by any non-zero angle.

As shown in FIGS. 81 and 83, the second member 22112 is coupled to the distal portion 22106 of the first member 22102 such that at least a portion of the second surface 22137 of the second member 22112 is in contact with at least a portion of the second surface 22117 of the first member 22102. In other embodiments, however, the second member can be coupled to the distal portion of the first member such that the second surface of the second member is spaced apart from the second surface of the first member 22102.

As shown in FIGS. 82 and 84, the first member 22102 has a first dimension $X_1$ along an axis X substantially normal to the longitudinal axis $L_A$ (e.g., a length of the second surface 22117) and a second dimension $Y_1$ along an axis Y substantially normal to both the longitudinal axis $L_A$ and the axis X (e.g., a height of the second surface 22117). Similarly, the second member 22112 has a first dimension $X_2$ along the axis X (e.g., a length of the second surface 22137) and a second dimension $Y_2$ along the axis Y (e.g., a height of the second surface 22137). The first dimension $X_2$ of the second member 22112 is greater than the second dimension $Y_1$ of the first member 22102 and is no greater than the first dimension $X_1$ of the first member 22102. The second dimension $Y_2$ of the second member 22112 is no greater than the second dimension $Y_1$ of the first member 22102. Said another way, when the second member 22112 is in a first position, as shown in FIG. 82, the footprint of the second member 22112 (e.g., a projected area having the first dimension $X_2$ and the second dimension $Y_2$) is within the footprint of the first member 22102 (e.g., a projected area having the first dimension $X_1$ and the second dimension $Y_1$).

The second member 22112 is coupled to the first member 22102 such that the second member 22112 can rotate relative to the first member 22102 about an axis of rotation $L_R$ substantially parallel to the longitudinal axis $L_A$. As indicated by the arrows AA in FIGS. 83 and 84, the second member 22112 can rotate relative to the first member 22102 between a first position (FIGS. 81 and 82) and a second position (FIGS. 83 and 84). When the second member 22112 is in the first position, the implant 22100 can be inserted such that at least a portion of the first surface 22116 of the first member 22102 is disposed between the first spinous process SP1 and the second spinous process SP2. When the second member 22112 is in the second position, the second member 22112 limits movement of the first member 22102 in the proximal direction along the longitudinal axis $L_A$ and relative to the adjacent spinous processes SP1 and SP2. The second member 22112 can limit movement of the first member 22102, for example, by contacting and/or engaging the spinous processes SP1 and SP2 (e.g., either directly or through surrounding tissue).

As shown in FIG. 81, when the second member 22112 is in the first position, the second surface 22137 of the second member 22112 is in contact with and/or adjacent to at least a portion of the second surface 22117 of the first member 22102. When the second member 22112 is in the second position, at least a portion 22131 of the second surface 22137 (indicated by the shaded region in FIG. 84) is spaced apart from the portion of the second surface 22117 of the first member 22102. In this manner, the portion 22131 of the second surface 22137 can limit movement of the first member 22102 by contacting and/or engaging the spinous processes SP1 and/or SP2 (e.g., either directly or through surrounding tissue). Although the second surface 22137 of the second member 22112 is shown in FIG. 81 as being in continuous contact with at least a portion of the second surface 22117 of the first member 22102, it is understood that portions of the second surface 22137 of the second member 22112 can be spaced apart from the second surface 22117 of the first member 22102. For example, in some embodiments, portions of the second surface 22137 of the second member 22112 can be spaced apart from the second surface 22117 of the first member 22102 as a result of surface roughness, corrugation and/or waviness of the second surface 22137 of the second member 22112 and/or the second surface 22117 of the first member 22102.

Similarly stated, when the second member 22112 is in the first position, a cross-sectional area $A_2$ bounded by an outer surface of the second member 22112 (e.g., the area bounded by the second surface 22137) is within a cross-sectional area $A_1$ bounded by an outer surface of the first member 22102 (e.g., the area bounded by the second surface 22117) when the areas $A_1$ and $A_2$ are projected on a plane substantially normal to the longitudinal axis $L_A$ (see FIG. 82). When the second member 22112 is in the second position, a portion of the cross-sectional area $A_2$ bounded by the outer surface of the second member 22112 (e.g., the area bounded by the portion 22131 of the second surface 22137) is outside of the cross-sectional area $A_1$ bounded by an outer surface of the first member 22102 when the areas $A_1$ and $A_2$ are projected on a plane substantially normal to the longitudinal axis $L_A$ (see FIG. 84).

Said another way, when the second member 22112 is in the first position, the first dimension $X_2$ of the second member 22112 is aligned with (e.g., is substantially parallel to) the first dimension $X_1$ of the first member 22102. Because the first dimension $X_2$ of the second member 22112 is no greater than the first dimension $X_1$ of the first member 22102 and the second dimension $Y_2$ of the second member 22112 is no greater than the second dimension $Y_1$ of the first member 22102, when the second member 22112 is in the first position, the footprint of the second member 22112 (e.g., the shape of a portion of the second member 22112, such as for example, the shape corresponding to the area $A_2$ bounded by the outer surface of the second member 22112) is within the footprint of the first member 22102 (e.g., the shape of a portion of the first member 22102, such as for example, the shape corresponding to the area $A_1$ bounded by the outer surface of the first member (22102).

When the second member 22112 is in the second position, the second dimension $Y_2$ of the second member 22112 is aligned with the first dimension $X_1$ of the first member 22102 (i.e., the second member 22112 is rotated approximately 90 degrees relative to the first member 22102). Because the first dimension $X_2$ of the second member 22112 is greater than the second dimension $Y_1$ of the first member 22102, a portion of the footprint of the second member 22112 is disposed outside of the footprint of the first member 22102. In this manner, when the second member 22112 is in the first position, the implant 22100 can be inserted between the spinous processes SP1 and SP2 unimpeded by the second member 22112 (i.e., the second member 22112 does not limit movement of the first member 22102 relative to the spinous processes SP1 and SP2). Conversely, when the second member 22112 is in the second position, a portion of the second member 22112 can contact and/or engage the first spinous process SP1 and/or the second spinous process SP2 to limit longitudinal movement of the first member 22102 relative to the spinous processes SP1 and SP2.

In use, the adjacent spinous processes SP1 and SP2 can be distracted prior to inserting the implant 22100 into the patient. An access passageway can then be defined to allow insertion of the implant 22100. The passageway can have any suitable shape (e.g., curved in two dimensions, curved in multiple planes or the like) and can be formed by any suitable method and by any suitable tool, as discussed herein. After the access passageway is defined, the implant 22100 is inserted percutaneously and advanced along the longitudinal axis $L_A$ until it is positioned between the spinous processes SP1 and SP2. The implant 22100 is inserted with the second member 22112 first and in the first position. Once the implant 22100 is in place, the second member 22112 is moved to the second position to limit lateral movement of the first member 22102 in the proximal direction the longitudinal axis $L_A$ and relative to the spinous processes SP1 and SP2.

If or when it is desirable to change the position of the implant 22100 and/or remove the implant 22100, the second member 22112 can be moved back to the first position, thereby allowing the first member 22102 to be moved laterally. Once the first member 22102 is repositioned as desired, the second member 22112 can be moved back to the second position, if desired.

Although the axis of rotation $L_R$ is shown as being coincident with the longitudinal axis $L_A$, in other embodiments, the axis of rotation $L_R$ can be offset from and parallel to the longitudinal axis $L_A$. In other embodiments, the axis of rotation $L_R$ can be angularly offset from the longitudinal axis $L_A$ (i.e., the axis of rotation $L_R$ and the longitudinal axis $L_A$ intersect). Similarly, although the second member 22112 is shown and described as being rotatably coupled to the first member 22102, in other embodiments, the second member 22112 can movably coupled to the first member 22102 such that the second member 22112 translates relative to the first member 22102 between the first position and the second position.

Although the first dimension $X_2$ of the second member 22112 is shown in FIG. 82 as being less than the first dimension $X_1$ of the first member 22102, in some embodiments the first dimension $X_2$ of the second member 22112 can be substantially equal to the first dimension $X_1$ of the first member 22102. Similarly, although the second dimension $Y_2$ of the second member 22112 is shown in FIG. 82 as being less than the second dimension $Y_1$ of the first member 22102, in some embodiments the second dimension $Y_2$ of the second member 22112 can be substantially equal to the second dimension $Y_1$ of the first member 22102. In this manner, the first surface 22116 of the first member 22102 and the first surface 22136 of the second member 22112 can collectively form a continuous surface.

Although a portion 22131 of the second surface 22137 of the second member 22112 is shown and described as being in contact with at least a portion of the second surface 22117 of the first member 22102 when the second member 22112 is in the first position, in other embodiments the entire second surface 22137 of the second member 22112 can be spaced apart from the second surface 22117 of the first member 22102 when the second member 22112 is in the first position. For example, in some embodiments, the second surface of the second member can be complementarily disposed adjacent at least a portion of the second surface of the first member when the second member is in the first position. The second surface of the second member can be disposed apart from (e.g., out of alignment with) the portion of the second surface of the first member when the second member is in the second position. In this manner the first member and the second member can be spaced apart to allow the second member to move relative to the first member without touching the first member.

Figure 85:
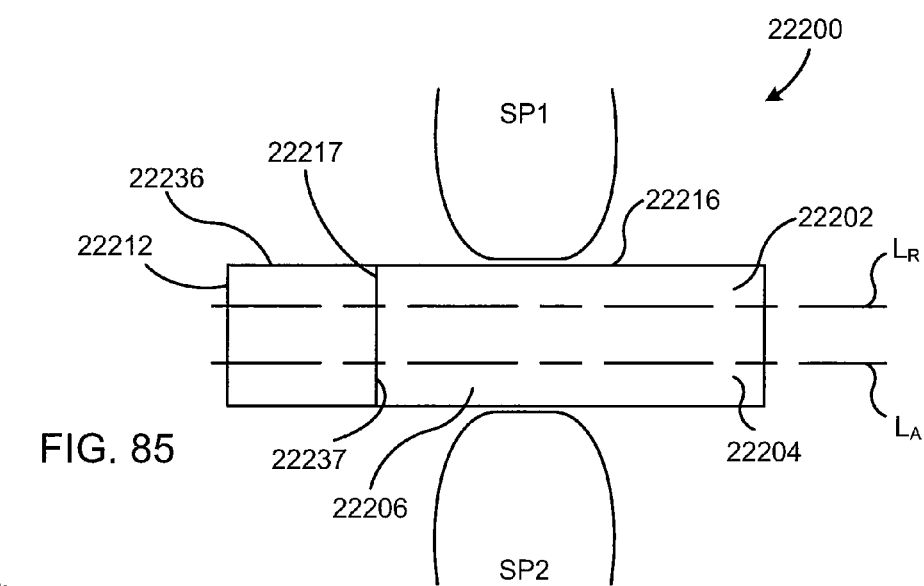
FIG. 85 is a schematic illustration of a posterior view of an implant in a first configuration according to an embodiment of the invention disposed between a first spinous process and second spinous process.
Figure 86:
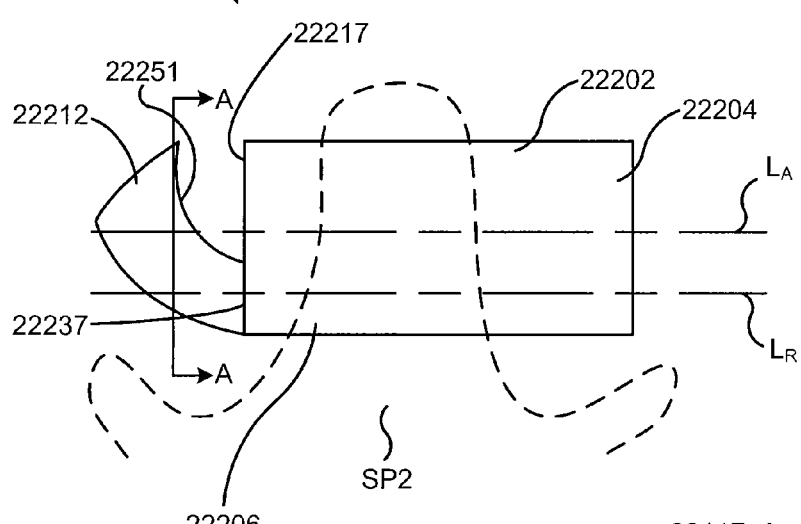
FIG. 86 is a schematic illustration of a side view of the implant shown in FIG. 85 in the first configuration.
Figure 87:
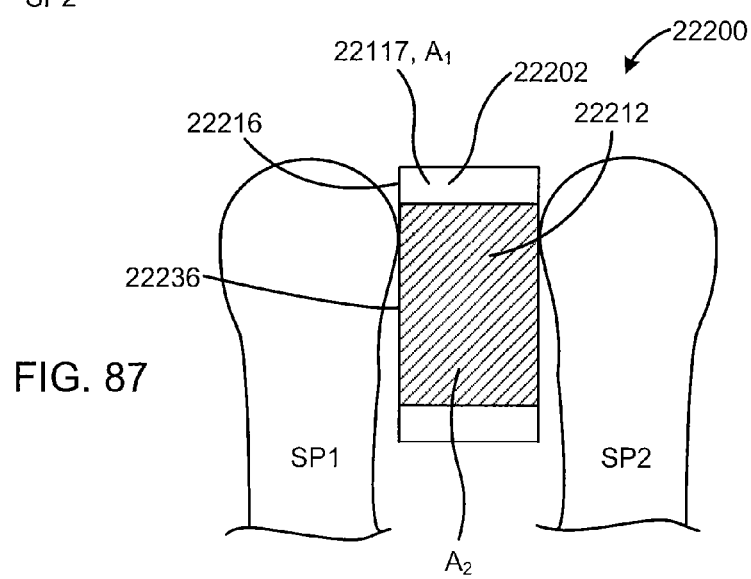
FIG. 87 is a schematic illustration of a lateral cross-sectional view of the implant shown in FIG. 85 in the first configuration taken along line A-A as shown in FIG. 86.

Although a portion 22131 of the second surface 22137 of the second member 22112 is shown and described as being spaced apart from the second surface 22117 of the first member 22102 when the second member 22112 is in the second position, in other embodiments the entire second surface 22137 of the second member 22112 can remain in contact with the second surface 22117 of the first member 22102 when the second member 22112 is in the second position. For example, FIGS. 85-90 are schematic illustrations of an implant 22200 according to an embodiment of the invention. FIGS. 85 and 88 are posterior views of the implant 22200 in a first configuration and a second configuration, respectively, disposed between a first spinous process SP1 and a second spinous process SP2 adjacent the first spinous process SP1. FIGS. 86 and 89 are side views of the implant 22200 in the first configuration and the second configuration, respectively disposed between the spinous processes SP1 and SP2. FIGS. 87 and 90 are cross-sectional views of the implant 22200 taken along lines A-A in FIGS. 86 and 89, respectively.

The implant 22200 includes a first member 22202 and a second member 22212 movably coupled to the first member 22202. The first member 22202 has a proximal portion 22204, a distal portion 22206, a first surface 22216, and a second surface 22217. The first surface 22216 of the first member 22202 is substantially parallel to a longitudinal axis $L_A$ of the first member 22202. Said another way, the longitudinal axis $L_A$ and a line defined to include a portion of the first surface 22216 of the first member 22202 are non-intersecting as they extend to infinity. Said yet another way, in embodiments in which the first surface 22216 of the first member 22202 includes at least a planar portion, every point along the longitudinal axis $L_A$ is spaced apart from the nearest portion of a plane defined to include the planar portion of the first surface 22216 of the first member 22202 by a substantially equal distance. The longitudinal axis $L_A$ can, for example, pass lengthwise (e.g., from the proximal portion 22204 to the distal portion 22206) through the centroid of the first member 22202. As shown, when the implant 22200 is disposed between the first spinous process SP1 and the second spinous process SP2, the longitudinal axis $L_A$ can be substantially parallel and/or coincident with a lateral axis defined by the spinal column.

As shown, at least a portion of the first surface 22216 of the first member 22202 is disposed between the first spinous process SP1 and the second spinous process SP2. In this manner, the implant 22200 can maintain a minimal spacing between the adjacent spinous processes SP1 and SP2 during extension of the spinal column (not shown FIGS. 81-84) while allowing flexion of the spinal column.

The second surface 22217 is disposed at the distal portion 22206 of the first member 22202 and intersect the longitudinal axis $L_A$ at an angle of approximately 90 degrees. Said another way, the second surface 22217 of the first member 22202 is substantially normal to the first surface 22216 of the first member 22202.

The second member 22212 has a first surface 22236, a second surface 22237 and a saddle surface 22251. The first surface 22236 is substantially parallel to the longitudinal axis $L_A$ of the first member 22202. Said another way, the longitudinal axis $L_A$ and a line defined to include a portion of the first surface 22236 of the second member 22212 are non-intersecting as they extend to infinity. Said yet another way, in embodiments in which the first surface 22236 of the second member 22212 includes at least a planar portion, every point along the longitudinal axis $L_A$ is spaced apart from the nearest portion of a plane defined to include the planar portion of the first surface 22236 of the second member 22212 by a substantially equal distance. The second surface 22237 intersects the longitudinal axis $L_A$ at an angle of approximately 90 degrees. Said another way, the second surface 22237 of the second member 22212 is substantially parallel to the second surface 22217 of the first member 22202, substantially normal to the first surface 22236 of the second member 22212, and substantially normal to the first surface 22216 of the first member 22202. The saddle surface 22251 is adjacent the second surface 22237 and has a curved shape that can form a portion of a saddle 22252, as discussed in more detail herein.

The second member 22212 is coupled to the distal portion 22206 of the first member 22202 such that the second surface 22237 of the second member 22212 is in contact with a portion of the second surface 22217 of the first member 22202. The second member 22212 is rotatably coupled to the first member 22202 about an axis of rotation $L_R$ substantially parallel to and offset from the longitudinal axis $L_A$. As indicated by the arrows BB in FIGS. 88-90, the second member 22212 can rotate relative to the first member 22202 between a first position (FIGS. 85-87) and a second position (FIGS. 88-90).

As shown in FIGS. 85-87, when the second member 22212 is in the first position, a cross-sectional area $A_2$ bounded by an outer surface of the second member 22212 (i.e., the cross-sectional area of the second member 22212 taken along line A-A in FIG. 86) is within a cross-sectional area $A_1$ bounded by an outer surface of the first member 22202 (i.e., the area of the second surface 22217) when projected on a plane substantially normal to the longitudinal axis $L_A$ (see FIG. 87). As shown in FIGS. 88-90, when the second member 22212 is in the second position, a portion of the cross-sectional area $A_2$ of the second member 22212 is outside of the cross-sectional area $A_1$ of the first member 22202 when the areas $A_1$ and $A_2$ are projected on a plane substantially normal to the longitudinal axis $L_A$ (see FIG. 90). As shown in FIG. 86, the cross-sectional area $A_2$ of the second member 22212 need not coincide with the second surface 22237 of the second member 22212, but rather can be considered at any longitudinal location along the second member 22212 (e.g., at the widest point of the second member 22212). Similarly, although the cross-sectional area $A_1$ of the first member 22202 is shown as being the area of the second surface 22217, in other embodiments, the cross-sectional area $A_1$ of the first member 22202 can be considered at any longitudinal location along the first member 22202.

As shown in FIG. 88, when the second member 22212 is in the second position, the first surface 22216 of the first member 22202 and the saddle surface 22251 of the second member 22212 collectively form a portion of a saddle 22252 configured to receive a portion of the spinous process SP1. In this manner, the saddle 22252 can receive and/or engage a portion of the spinous process SP1 and/or its surrounding tissue to limit movement of the first member 22202 along the longitudinal axis $L_A$ and relative to the spinous processes SP1 and SP2. In some embodiments, the saddle 22252 and/or the saddle surface 22251 can have a curved surface that substantially corresponds to a shape and/or a size of the spinous process SP1 (e.g., the spinous process SP1 and/or the surrounding tissue). In some embodiments, the shape and/or size of the saddle surface 22251 can be configured to more evenly distribute forces between the saddle 22252 and the spinous process SP1. In some embodiments, the saddle surface 22251 and the first surface 22216 of the first member 22202 can form a substantially smooth and/or continuous surface.

Figure 91:
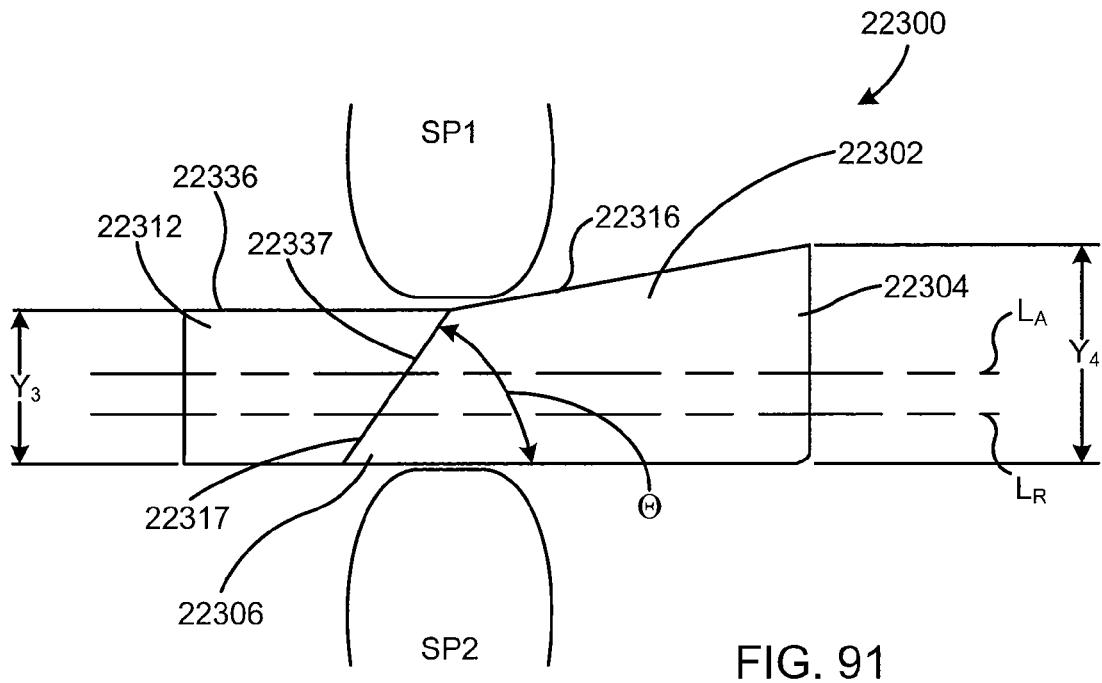
FIG. 91 is a schematic illustration of a posterior view of an implant in a first configuration according to an embodiment of the invention disposed between a first spinous process and second spinous process.
Figure 92:
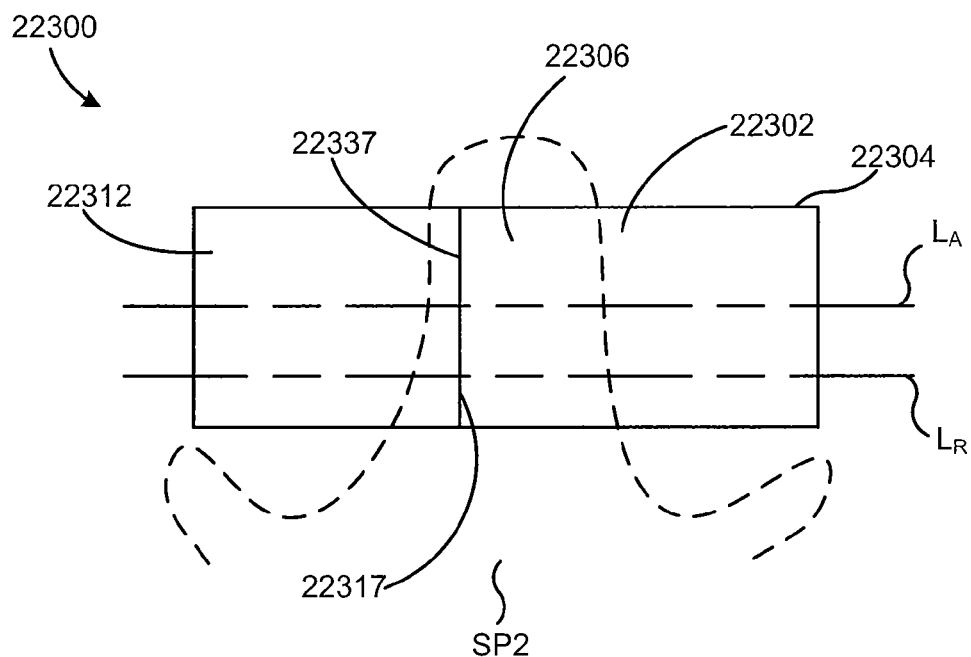
FIG. 92 is a schematic illustration of a side view of the implant shown in FIG. 91 in the first configuration.
Figure 93:
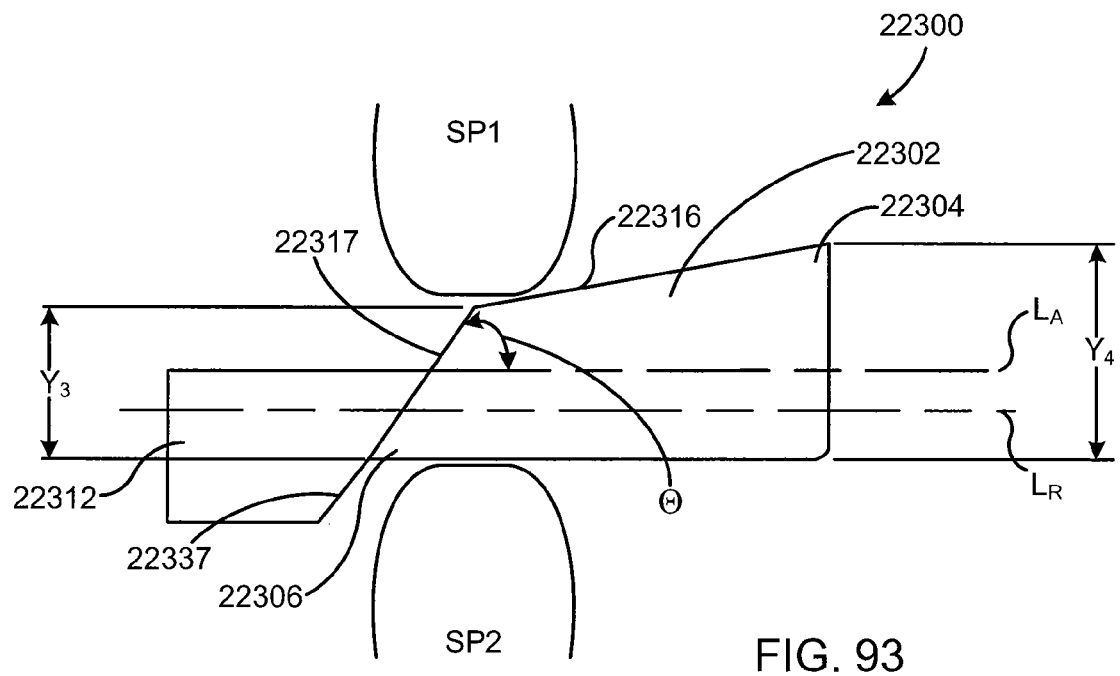
FIG. 93 is a schematic illustration of a posterior view of the implant shown in FIG. 91 in a second configuration.
Figure 94:
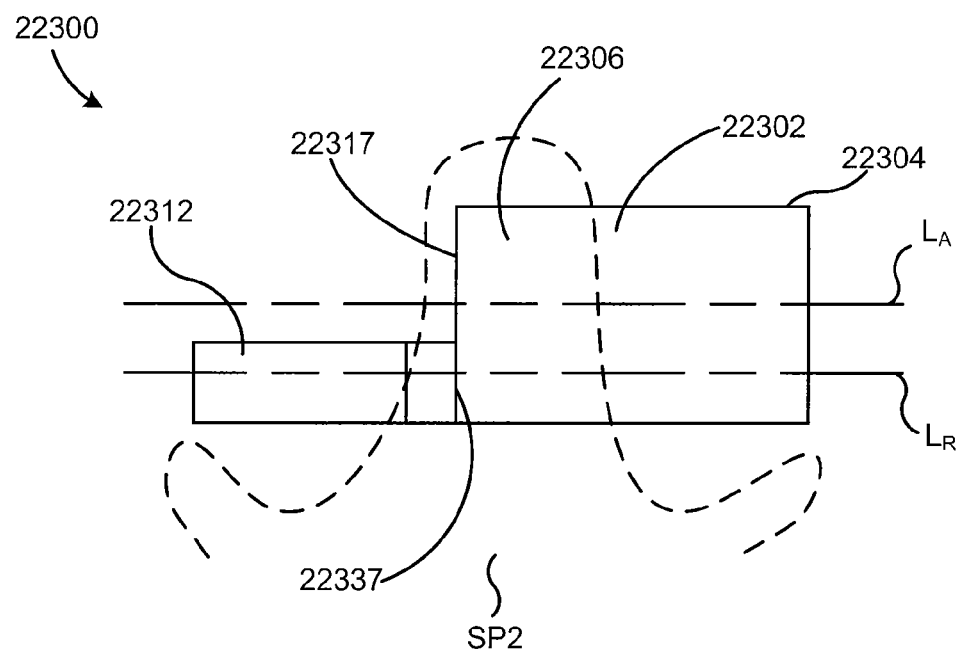
FIG. 94 is a schematic illustration of a side view of the implant shown in FIG. 91 in the second configuration.

Returning to FIGS. 81-84, although the first surface 22116 of the first member 22102 and the first surface 22136 of the second member 22112 are shown and described as being substantially parallel to the longitudinal axis $L_A$, the first surface 22116 of the first member 22102 and/or the first surface 22136 of the second member 22112 can have any suitable shape, contour and/or orientation. For example, in some embodiments, the first surface 22116 of the first member 22102 can have a curved shape to form a portion of a saddle, as described above. In other embodiments, a first surface of a first member can be tapered. For example, FIGS. 91-94 are schematic illustrations of an implant 22300 according to an embodiment of the invention. FIGS. 91 and 93 are posterior views of the implant 22300 in a first configuration and a second configuration, respectively, disposed between a first spinous process SP1 and a second spinous process SP2. FIGS. 92 and 94 are side views of the implant 22300 in the first configuration and the second configuration, respectively, disposed between the spinous processes SP1 and SP2.

The implant 22300 includes a first member 22302 and a second member 22312 movably coupled to the first member 22302. The first member 22302 has a proximal portion 22304, a distal portion 22306, a first surface 22316, and a second surface 22317. The first surface 22316 of the first member 22302 is tapered in a direction substantially parallel to a longitudinal axis $L_A$ of the first member 22302 such that a size $Y_3$ of the distal portion 22306 is less than a size $Y_4$ of the proximal portion 22304. In this manner, when a portion of the first surface 22316 of the first member 22202 is disposed between the first spinous process SP1 and the second spinous process SP2, the tapered of the first member 22302 can contact and/or engage the spinous process SP1 (either directly or indirectly through its surrounding tissue) to limit movement of the first member 22302 along the longitudinal axis $L_A$ and relative to the adjacent spinous processes SP1 and SP2.

The distal portion 22306 of the first member 22302 includes the second surface 22317, which intersects the longitudinal axis $L_A$ at an acute angle $\Theta$. Said another way, the second surface 22317 of the first member 22302 is angularly offset from the longitudinal axis $L_A$ by an angle greater than zero degrees and less than 90 degrees.

The second member 22312 has a first surface 22336 and a second surface 22337. The first surface 22336 is substantially parallel to the longitudinal axis $L_A$ of the first member 22302. Said another way, the longitudinal axis $L_A$ and a line defined to include a portion of the first surface 22336 of the second member 22112 are non-intersecting as they extend to infinity. Said yet another way, in embodiments in which the first surface 22336 of the second member 22312 includes at least a planar portion, every point along the longitudinal axis $L_A$ is spaced apart from the nearest portion of a plane defined to include the planar portion of the first surface 22136 of the second member 22112 by a substantially equal distance. The second surface 22337 intersects the longitudinal axis $L_A$ at the acute angle $\Theta$. Said another way, the second surface 22237 of the second member 22212 is substantially parallel to the second surface 22217 of the first member 22202.

As described above, the second member 22312 is rotatably coupled to the distal portion 22306 of the first member 22302 about an axis of rotation $L_R$ such that the second member 22312 can rotate relative to the first member 22302 between a first position (FIGS. 91 and 92) and a second position (FIGS. 93 and 94). When the second member 22312 is in the first position, the second surface 22337 of the second member 22312 is in contact with at least a portion of the second surface 22317 of the first member 22302. When the second member 22312 is in the second position, at least a portion of the second surface 22337 is spaced apart from the portion of the second surface 22317 of the first member 22302. In this manner, the portion of the second surface 22337 can limit movement of the first member 22302 by contacting and/or engaging the spinous process SP2 (either directly or indirectly through its surrounding tissue).

Although the first member 22302 is shown as being asymmetrically tapered along the longitudinal axis $L_A$ (i.e., tapered on the first surface 22316 without being tapered on at least one other surface), in some embodiments, the first member 22302 can be symmetrically tapered along the longitudinal axis $L_A$. In other embodiments, the first member 22302 can be tapered along the longitudinal axis $L_A$ in two dimensions (i.e., a height and a width).

Figure 95:
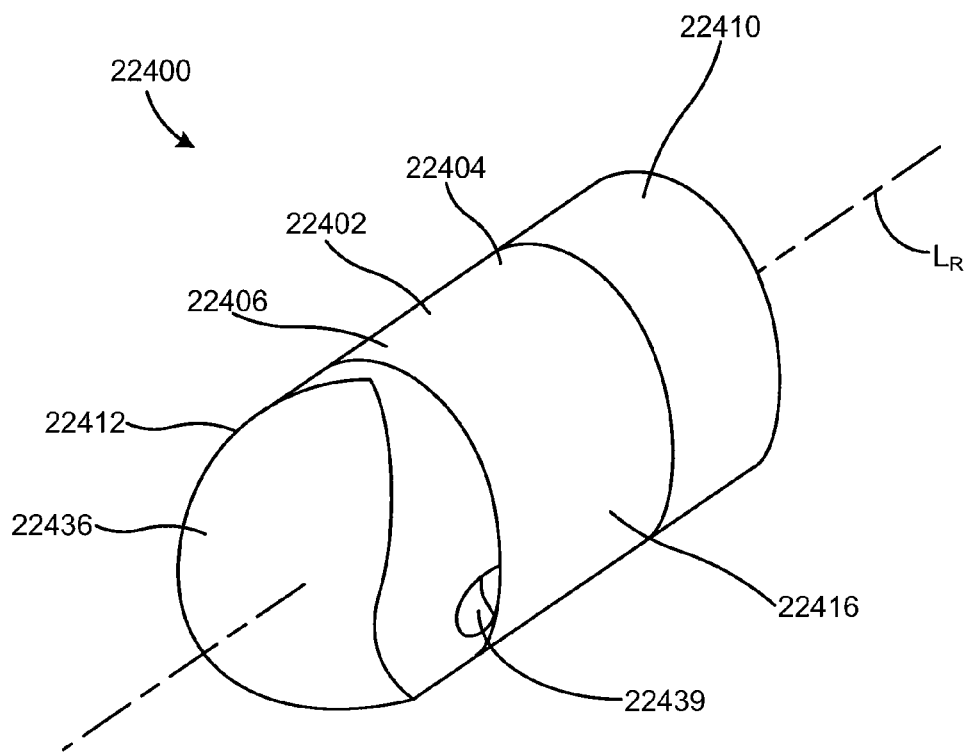
FIG. 95 is a perspective view of an implant according to an embodiment of the invention in a first configuration.
Figure 96:
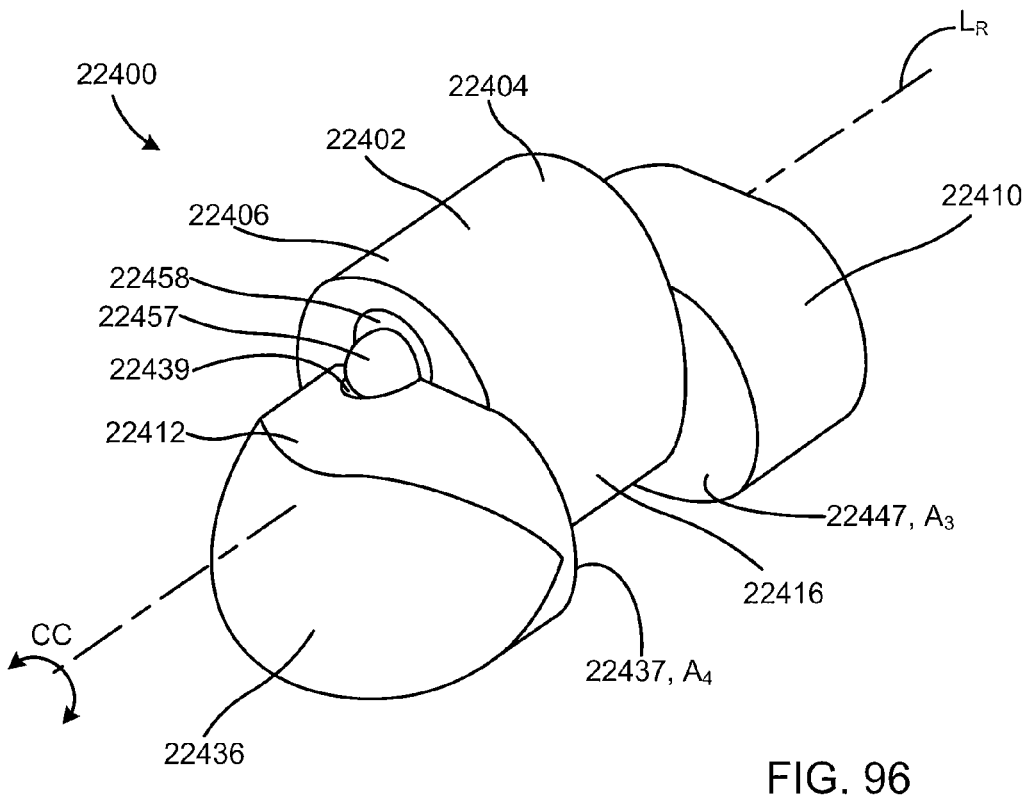
FIG. 96 is a perspective view of the implant shown in FIG. 95 in a second configuration.
Figure 97:
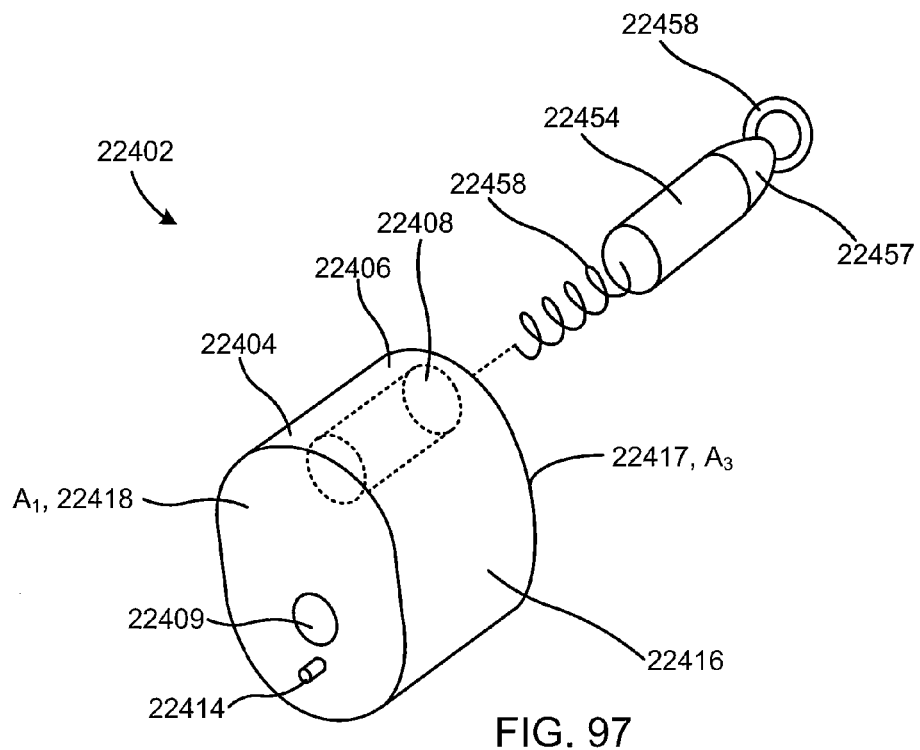
FIG. 97 is a perspective view of a support member of the implant shown in FIG. 95.
Figure 98:
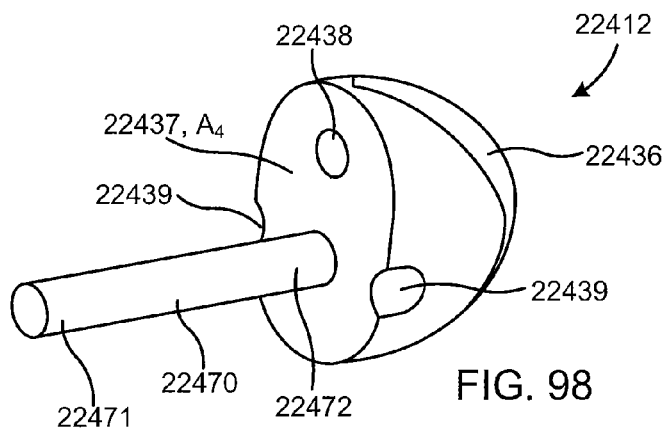
FIG. 98 is a perspective view of a distal retention member of the implant shown in FIG. 95.
Figure 99:
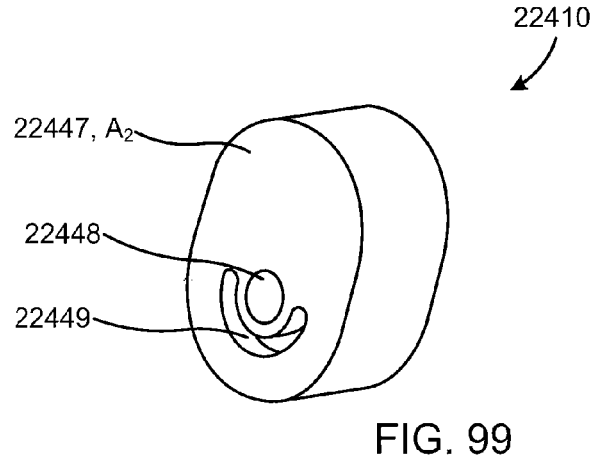
FIG. 99 is a perspective view of a proximal retention member of the implant shown in FIG. 95.

FIGS. 95-99 show an implant 22400 according to an embodiment of the invention. FIGS. 95 and 96 are perspective views of the implant 22400 in a first configuration and a second configuration, respectively. FIGS. 97-99 are perspective views of portions of the implant 22400. The implant 22400 includes a support member 22402, a proximal retention member 22410 and a distal retention member 22412.

The support member 22402 has a proximal portion 22404, a distal portion 22406 and a support surface 22416. The support surface 22416 is configured to be disposed between adjacent spinous processes (not shown in FIGS. 95-99) to maintain a minimal spacing between the spinous processes during extension of the spinal column. Accordingly, the support member 22402 can be constructed from any biocompatible material having sufficient strength, such as, for example, stainless steel, plastic, polyetheretherketone (PEEK), carbon fiber, ultra-high molecular weight (UHMW) polyethylene, and the like.

The proximal portion 22404 of the support member 22402 includes a proximal end surface 22418 substantially normal to the support surface 22416 of the support member 22402. Similarly, the distal portion 22406 of the support member 22402 includes a distal end surface 22417 substantially normal to the support surface 22416 of the support member 22402. As shown in FIG. 97, the proximal end surface 22418 includes a protrusion 22414 and defines a first opening 22409 that extends through the support member 22402 and receives a pivot rod 22470, as described in more detail herein. The distal end surface 22417 defines a second opening 22408 (shown in hidden lines) that receives a portion of a locking member 22454 and a biasing member 22458, as described in more detail herein.

As shown in FIG. 99, the proximal retention member 22410 includes a retention surface 22447 that is substantially parallel to the proximal end surface 22418 of the support member 22402. The retention surface 22447 of the proximal retention member 22410 defines a first opening 22448 and a second opening 22449. The first opening 22448 receives the proximal end portion 22471 of the pivot rod 22470. The second opening 22449 has an arcuate shape and receives a portion of the protrusion 22414 of the support member 22402. In this manner, as described in more detail herein, when the proximal retention member 22410 rotates relative to the support member 22402, the protrusion 22414 moves within second opening 22449 to limit end positions of the rotation of the proximal retention member 22410 relative to the support member 22402.

Similarly, as shown in FIG. 98, the distal retention member 22412 includes an outer surface 22436 and a retention surface 22437. The outer surface 22436 of the distal retention member 22412 has a curved shape to facilitate insertion of the implant 22400 into the body. For example, in some embodiments, the outer surface 22436 of the distal retention member 22412 can be configured to displace a bodily tissue, dilate a bodily tissue and/or distract a space between adjacent spinous processes. The outer surface 22436 of the distal retention member 22412 also defines two recesses 22439, one of which receives an end portion 22457 of the locking member 22454 when the implant 22400 is in the second configuration (see FIG. 96).

The retention surface 22437 of the distal retention member 22412 is substantially parallel to the distal end surface 22417 of the support member 22402. The retention surface 22437 of the distal retention member 22412 defines a recess 22438 that receives the end portion 22457 of the locking member 22454.

The proximal retention member 22410 and the distal retention member 22412 are rotatably coupled to the support member 22402 by the pivot rod 22470. As shown in FIG. 98, a distal end portion 22472 of the pivot rod 22470 is affixed to the retention surface 22437 of the distal retention member 22412. In some embodiments, for example, the distal end portion 22472 of the pivot rod 22470 can be affixed to the retention surface 22437 by disposing a portion of the distal end portion 22472 of the pivot rod 22470 within an opening (not shown in FIG. 98) defined by the retention surface 22437. In such embodiments, the opening and the distal end portion 22472 of the pivot rod 22470 can be configured to produce an interference fit. Similarly, in such embodiments, the distal end portion 22472 of the pivot rod 22470 can be welded to the retention surface 22437.

The pivot rod 22470 extends through the first opening 22409 of the support member 22402 such that the proximal end portion 22471 of the pivot rod 22470 is received within the first opening 22448 of the proximal retention member 22410 and is fixedly coupled to the proximal retention member 22410. In this manner, the proximal retention member 22410 and the distal retention member 22412 are coupled together and can collectively rotate relative to the support member 22402 about an axis of rotation $L_R$ (which is coincides with the center line of the pivot rod 22470), as indicated by the arrows CC in FIG. 96.

The proximal retention member 22410 and the distal retention member 22412 can collectively rotate relative to the support member 22402 between a first position (i.e., the first configuration of the implant 22400, as shown in FIG. 95) and a second position (i.e., the second configuration of the implant 22400, as shown in FIG. 96). When the proximal retention member 22410 and the distal retention member 22412 are in the first position, the retention surface 22447 of the proximal retention member 22410 is in contact with and/or adjacent to the proximal end surface 22418 of the support member 22402 and the retention surface 22437 of the distal retention member 22412 is in contact with and/or adjacent to the distal end surface 22417 of the support member 22402. In this manner, the implant 22400 can be inserted between adjacent spinous processes unimpeded by the proximal retention member 22410 and/or the distal retention member 22412 (i.e., the proximal retention member 22410 and/or the distal retention member 22412 do not limit movement of the support member 22402 relative to the spinous processes). As described above, it is understood that portions of the retention surface 22447 and the retention surface 22437 can be spaced apart from the proximal end surface 22418 and the distal end surface 22417, respectively. For example, in some embodiments, portions of the retention surface 22447 and/or the retention surface 22437 of the second member 22412 can be spaced apart from the proximal end surface 22418 and/or the distal end surface 22417, respectively, as a result of surface roughness, corrugation and/or waviness of the mating surfaces.

Similarly stated, when the proximal retention member 22410 and the distal retention member 22412 are in the first position, the area $A_2$ of the proximal retention surface 22447 is within the area $A_1$ of the proximal end surface 22418 of the support member 22402 when the areas $A_1$ and $A_2$ are projected on a plane substantially parallel to the proximal end surface 22418 of the support member 22402. Similarly, the area $A_4$ of the distal retention surface 22437 is within the area $A_3$ of the distal end surface 22417 of the support member 22402 when the areas $A_3$ and $A_4$ are projected on a plane substantially parallel to the distal end surface 22417 of the support member 22402.

Moreover, when the implant 22400 is in the first configuration, the biasing member 22458 exerts a force against the locking member 22454 such that the end portion 22457 of the locking member 22454 is disposed outside of the support member 22402 and is received within the recess 22438 of the retention surface 22437 of the distal retention member 22412. Accordingly, when the implant 22400 is in the first configuration, the locking member 22454 temporarily maintains the distal retention member 22412 and the proximal retention member 22410 in the first position. The recess 22438 of the retention surface 22437 has a curved shape that substantially corresponds to a shape of the end portion 22457 of the locking member 22454. When a rotational force is applied to the proximal retention member 22410 and/or the distal retention member 22412, as shown by the arrow CC in FIG. 96, a resulting force is produced that moves the end portion 22457 of the locking member 22454 into the opening 22408 of the support member 22402. In this manner, the implant 22400 can be moved into the second configuration when disposed between adjacent spinous processes. Although the locking member 22454 is shown as being a cylindrical pin, in other embodiments, any suitable detent can used to maintain the implant 22400 in the first configuration.

When the proximal retention member 22410 and the distal retention member 22412 are in the second position, at least a portion of the proximal retention surface 22447 and at least a portion of the distal retention surface 22437 are spaced apart from the proximal end surface 22418 of the support member 22402 and the distal end surface 22417 of the support member 22402, respectively. In this manner, when implant 22400 is in the second configuration, the portion of the proximal retention surface 22447 and/or the portion of the distal retention surface 22437 can contact and/or engage the spinous processes to limit lateral movement of the support member 22402 relative to the spinous processes.

When the proximal retention member 22410 and the distal retention member 22412 are in the second position, a portion of the area $A_2$ of the proximal retention surface 22447 is outside of the area $A_1$ of the proximal end surface 22418 of the support member 22402 when projected on a plane substantially parallel to the proximal end surface 22418 of the support member 22402. Similarly, a portion of the area $A_4$ of the distal retention surface 22437 is outside of the area $A_3$ of the distal end surface 22417 of the support member 22402 when projected on a plane substantially parallel to the distal end surface 22417 of the support member 22402.

Moreover, when the implant 22400 is in the second configuration, the biasing member 22458 exerts a force against the locking member 22454 such that the end portion 22457 of the locking member 22454 is received, at least partially, within one of the recesses 22439 of the outer surface 22436 of the distal retention member 22412. Accordingly, when the implant 22400 is in the second configuration, the locking member 22454 maintains the distal retention member 22412 and the proximal retention member 22410 in the second position. The recesses 22439 of the outer surface 22437 are configured to receive, at least partially, the end portion 22457 of the locking member 22454 such that the distal retention member 22412 and the proximal retention member 22410 are releasably locked in the second position. In this manner, in some embodiments, a deployment tool, of the types shown and described herein, is used to move the locking member 22454 into the opening 22408 of the support member 22402 so that the implant 22400 can be moved from the second configuration to the first configuration. The locking member 22454 is retained within the second opening 24408 by the retainer 22458. The retainer 22458 can be coupled within the opening 24408, for example, by an interference fit, a weld, a swaged fit or the like.

Moreover, when the implant 22400 is in the second configuration, the protrusion 22414 of the proximal end surface 22418 can be in contact with the retention surface 22447 of the proximal retention member 22410 that defines an end portion of the arcuate opening 22449. In this manner, the proximal retention member 22410 is prevented from being rotated more than approximately 90 degrees from the first position. Said another way, the protrusion 22414 and the surfaces defining the arcuate opening 22449 limit the rotation of the proximal retention member 22410 relative to the support member 22402.

Although the locking member 22454 is shown as being disposed within the support member 22402 such that an end portion 22457 of the locking member 22454 is received within the recesses 22438 and/or 22439, in other embodiments, a locking member can be disposed within a proximal retention member and/or a distal retention member such that an end portion of the locking member is received within a recess in the proximal end surface of the support member and/or the distal end surface of the support member to temporarily maintain the implant in a first and/or a second configuration. In other embodiments, a locking member can be coupled to an outer surface of the support member such that a portion of the locking member is received within recesses defined by an outer surface of a proximal retention member and/or a distal retention member. In yet other embodiments, an implant can include a first locking member or detent to temporarily maintain the implant in a first configuration and a second locking member or detent to temporarily maintain the implant in a second configuration.

Although the proximal retention member 22410 and the distal retention member 22412 are shown and described as being disposed adjacent the proximal end surface 22417 and the distal end surface 22418 of the support member 22402, in other embodiments, an implant can include a retention member disposed at a location other than at a proximal end surface or a distal end surface. For example, in some embodiments, an implant can include a retention member disposed in a central portion of a support member. In some embodiments, a retention member can be movably coupled to a support member such that the retention member is disposed within the support member when the retention member is in a first position and at least a portion of the retention member is disposed outside of the support member when the retention member is in a second position.

Figure 100:
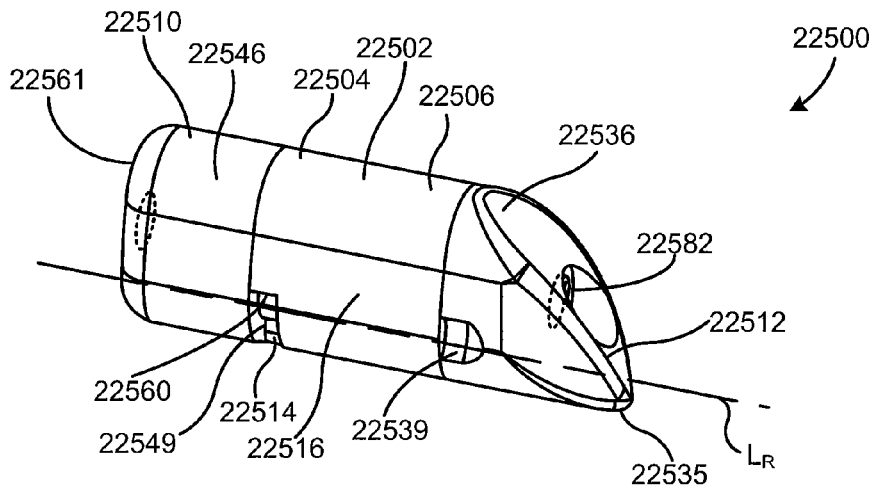
FIG. 100 is a perspective view of an implant according to an embodiment of the invention in a first configuration.
Figure 101:
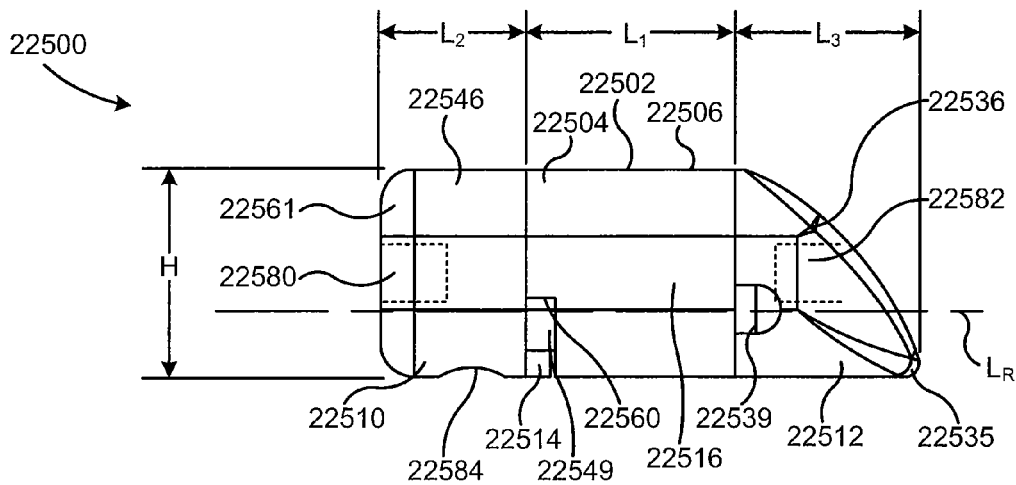
FIG. 101 is a front view of the implant shown in FIG. 100 in the first configuration.
Figure 102:
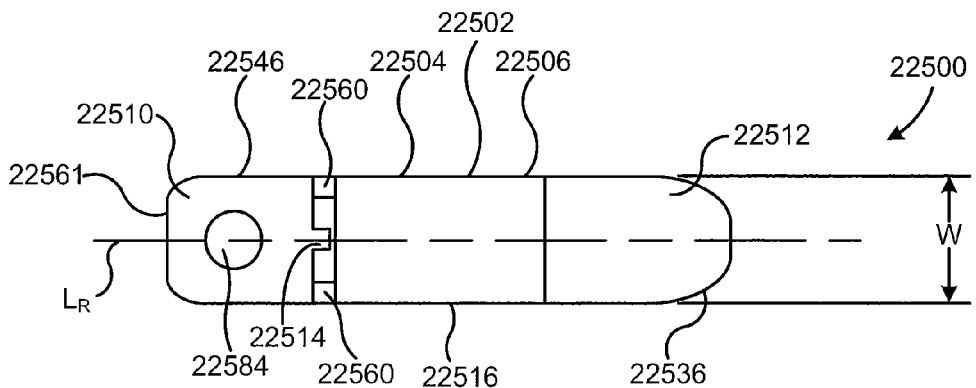
FIG. 102 is a bottom view of the implant shown in FIG. 100 in the first configuration.
Figure 103:
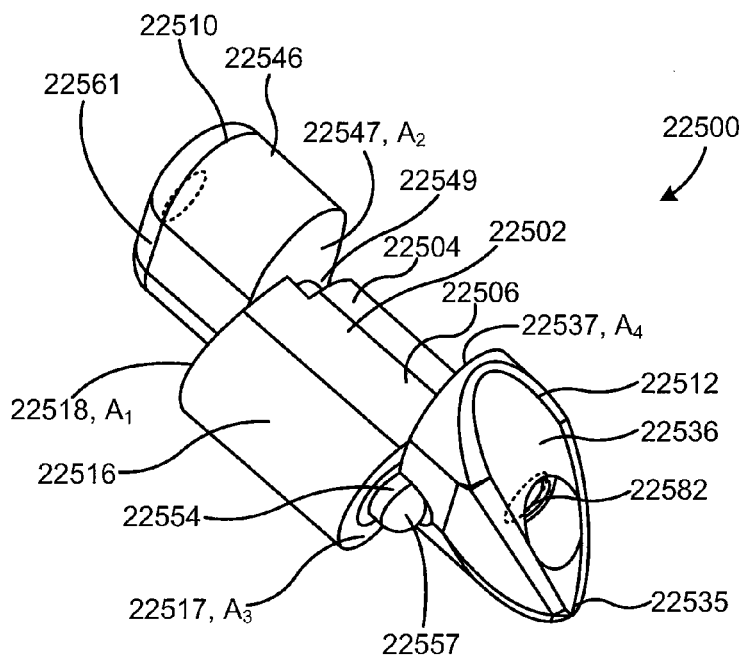
FIG. 103 is a perspective view of the implant shown in FIG. 100 in a second configuration.
Figure 104:
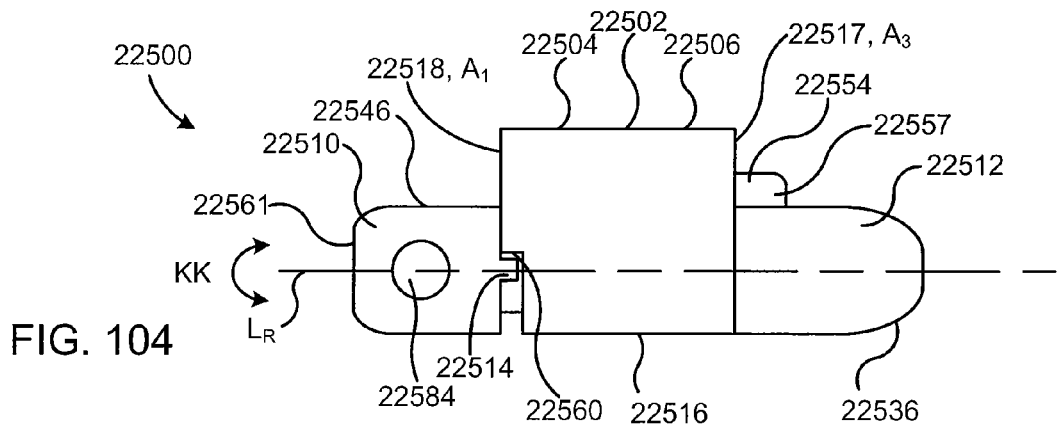
FIG. 104 is a front view of the implant shown in FIG. 100 in the second configuration.
Figure 105:
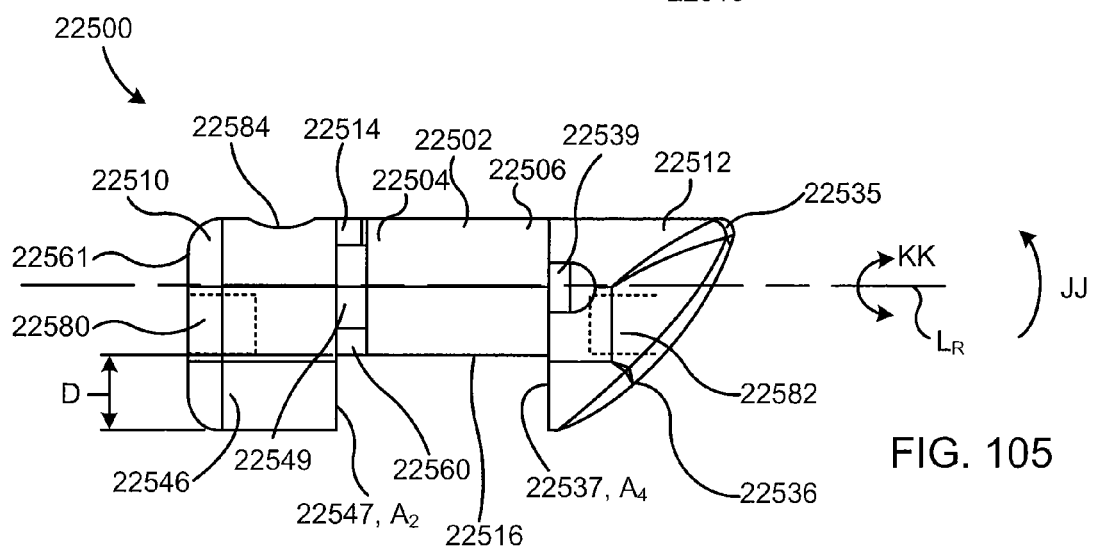
FIG. 105 is a bottom view of the implant shown in FIG. 100 in the second configuration.
Figure 106:
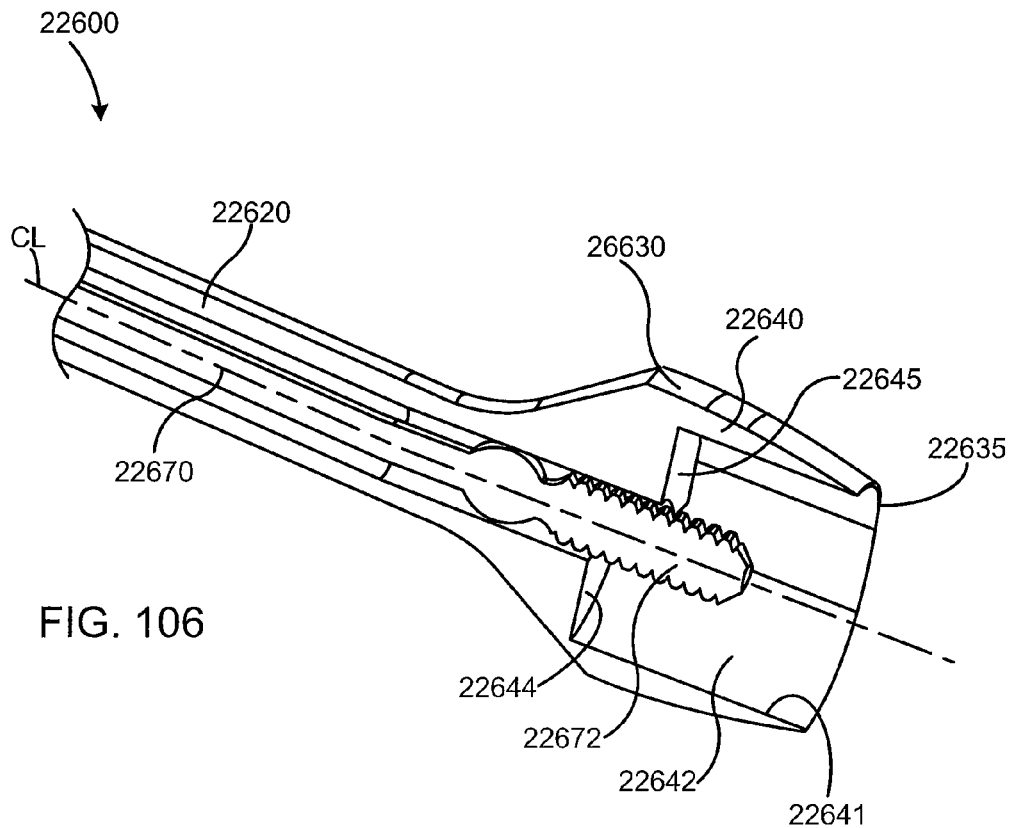
FIG. 106 is a cross-sectional perspective view of a deployment tool according to an embodiment of the invention.

FIGS. 100-105 show an implant 22500 according to an embodiment of the invention. FIGS. 100-102 show a perspective view, a front view and a bottom view, respectively, of the implant 22500 in a first configuration. FIGS. 103-105 show a perspective view, a front view and a bottom view, respectively, of the implant 22500 in a second configuration. The implant 22500 includes a support member 22502, a proximal retention member 22510 and a distal retention member 22512.

The support member 22502 has a proximal portion 22504, a distal portion 22506 and a support surface 22516. The support surface 22516 is configured to be disposed between adjacent spinous processes (not shown in FIGS. 100-105) to maintain a minimal spacing between the spinous processes during extension of the spinal column. The support surface 22516 defines a recess 22549 having two shoulder surfaces 22560. As described in more detail herein, the shoulder surfaces 22560 are configured to engage a protrusion 22514 of the proximal retention member 22510 to limit the end positions of the rotation of the proximal retention member 22510 relative to the support member 22502.

Figure 107:
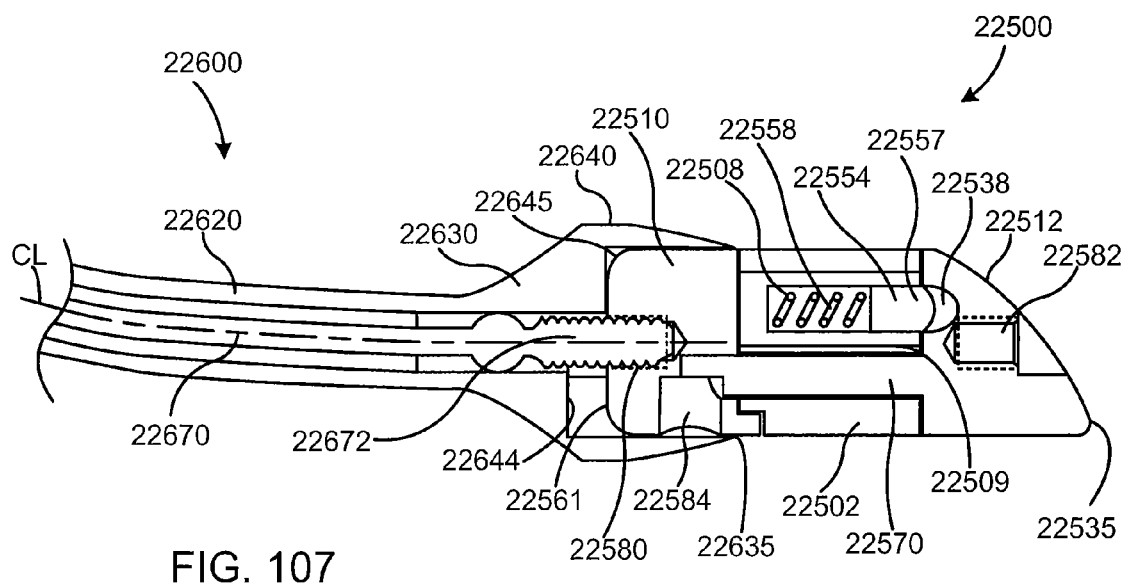
FIG. 107 is a cross-sectional front view of the deployment tool shown in FIG. 106 engaging a proximal portion of the implant shown in FIG. 100.
Figure 110:
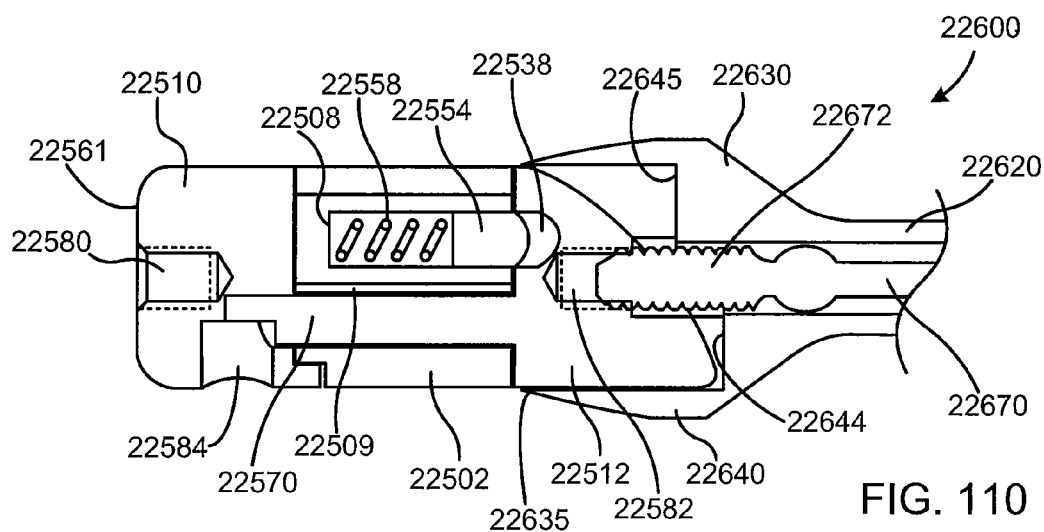
FIG. 110 is a cross-sectional front view of the deployment tool shown in FIG. 106 engaging a distal portion the implant shown in FIG. 100.

The proximal portion 22504 of the support member 22502 includes a proximal end surface 22518 substantially normal to the support surface 22516 of the support member 22502. Similarly, the distal portion 22506 of the support member 22502 includes a distal end surface 22517 substantially normal to the support surface 22516 of the support member 22502. As shown in FIGS. 107 and 110, the proximal end surface 22518 defines a first opening 22509 that extends through the support member 22502 and receives a pivot rod 22570. As shown in FIGS. 107 and 110, the distal end surface 22517 defines a second opening 22508 that receives a portion of a locking member 22554 and a biasing member 22558, as described in more detail herein.

The proximal retention member 22510 includes an outer surface 22546, a proximal end surface 22561 and retention surface 22547. The outer surface 22546 has a curved surface that substantially corresponds to a shape and/or a size of the support surface 22516 of the support member 22502. In this manner, the outer surface 22546 of the proximal retention member 22510 and the support surface 22516 of the support member 22502 can form a substantially smooth and/or continuous surface when the implant 22500 is in the first configuration.

Figure 108:
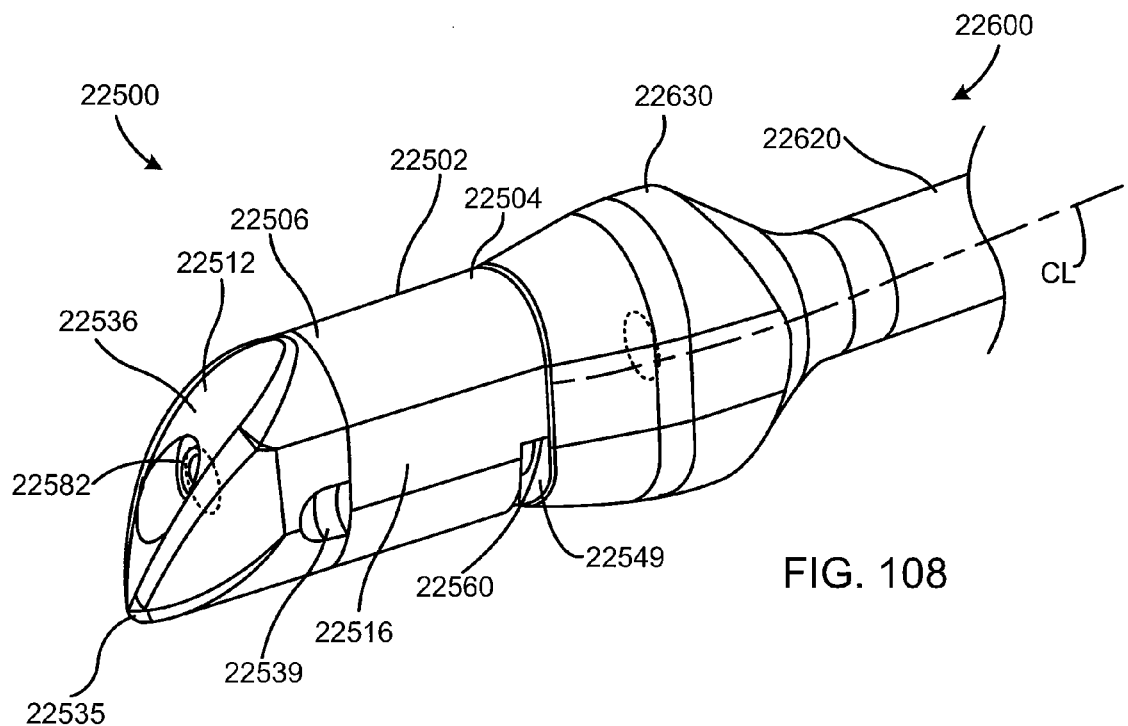
FIG. 108 is a perspective view of the deployment tool shown in FIG. 106 engaging the proximal portion of the implant shown in FIG. 100 in the first configuration.
Figure 109:
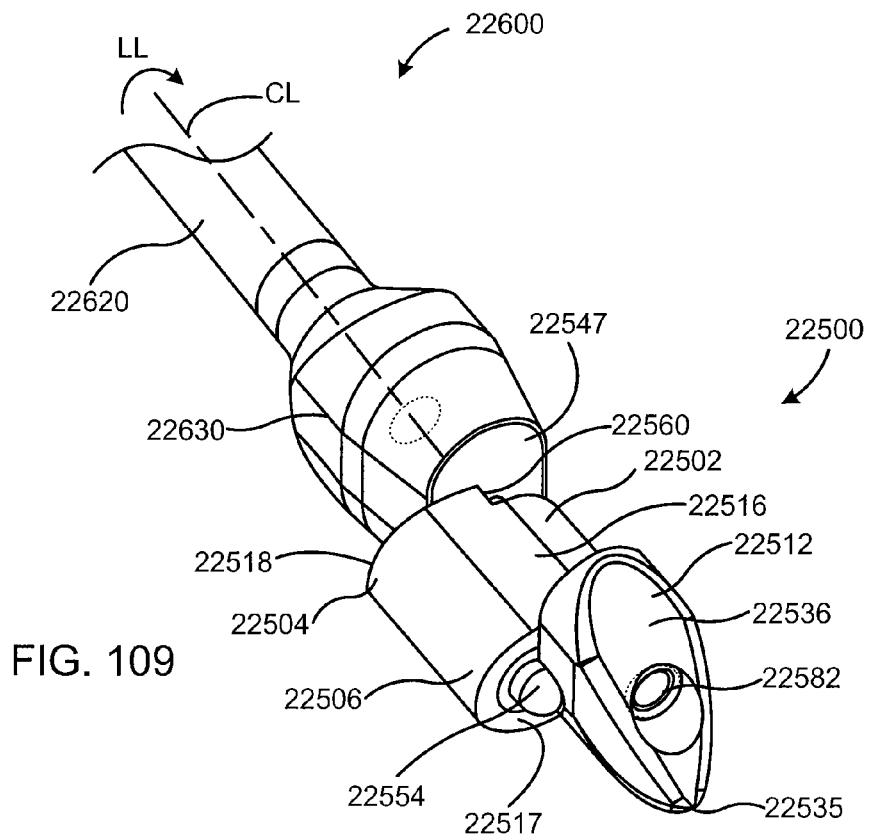
FIG. 109 is a perspective view of the deployment tool shown in FIG. 106 engaging the proximal portion the implant shown in FIG. 100 in the second configuration.

As shown in FIGS. 107-109, the proximal end surface 22561 of the proximal retention member 22510 is configured to be received within a receiving area 22642 of a deployment tool 22600. The proximal end surface 22561 defines a threaded opening 22580 configured engage a threaded portion 22672 of a rod 22670 of the deployment tool 22600.

The retention surface 22547 of the proximal retention member 22510 is substantially parallel to the proximal end surface 22518 of the support member 22502. The retention surface 22547 of the proximal retention member 22510 defines an opening 22548 and a protrusion 22514. As shown in FIGS. 107 and 110, the opening 22548 receives the proximal end portion 22471 of the pivot rod 22570. The outer surface 22546 also defines an opening 25584. The opening 25584 can be used, for example, during the assembly of the implant 22500 to ensure that the proximal end portion 22471 of the pivot rod 22570 is properly positioned and/or affixed within the opening 22509. In some embodiments, the opening 22584 can be welded closed.

The protrusion 22514 of the proximal retention member 22510 is received within the recess 22549 defined by the support surface 22516. When the proximal retention member 22510 rotates relative to the support portion 22502, the protrusion 22514 contacts the shoulder surfaces 22560 (see e.g., FIGS. 104 and 105) to limit the end positions of the rotation of the proximal retention member 22510 relative to the support member 22502.

Similarly, the distal retention member 22512 includes an outer surface 22536 and a retention surface 22537. The outer surface 22536 of the distal retention member 22512 has a curved shape (e.g., a tapered end portion) and includes a tip 22535 to facilitate insertion of the implant 22500 into the body. In some embodiments, for example, the outer surface 22436 and/or the tip 22535 can displace a bodily tissue when the implant 22500 is inserted into the body. In some embodiments, the outer surface 22436 and/or the tip 22535 can dilate a bodily tissue, such as the supraspinous ligament, when the implant 22500 is inserted into the body. In some embodiments, the outer surface 22436 and/or the tip 22535 can distract a space between adjacent spinous processes when the implant 22500 is inserted into the body.

The shape of the outer surface 22536 of the distal retention member 22512 is asymmetrical such that when the implant 22500 is in the second configuration, a portion of the support surface 22516 of the support member 22502 and a portion of the outer surface 22536 of the distal retention member 22512 form a substantially continuous and/or linear surface (see e.g., FIG. 105). In this manner, when the implant 22500 is in the second configuration, the substantially continuous and/or linear surface formed by the support surface 22516 of the support member 22502 and the outer surface 22536 of the distal retention member 22512 can limit rotational movement of the implant 22500 about an axis normal to the axis $L_R$ (e.g., in a direction as indicated by the arrow JJ in FIG. 105). Said another way, the substantially continuous and/or linear surface formed by the support surface 22516 of the support member 22502 and the outer surface 22536 of the distal retention member 22512 can prevent the implant 22500 from rotating out of its position between the adjacent spinous processes.

The outer surface 22536 of the distal retention member 22512 defines two recesses 22539, one of which receives an end portion 22557 of the locking member 22454 when the implant 22500 is in the second configuration (see FIG. 103). The outer surface 22536 of the distal retention member 22512 also defines a threaded opening 22582 configured engage the threaded portion 22672 of a rod 22670 of the deployment tool 22600.

The retention surface 22537 of the distal retention member 22512 is substantially parallel to the distal end surface 22517 of the support member 22502. The retention surface 22537 of the distal retention member 22512 defines a recess 22538 that receives the end portion 22557 of the locking member 22554.

The proximal retention member 22510 and the distal retention member 22512 are rotatably coupled to the support member 22502 by the pivot rod 22570, as described above. As shown in FIG. 107, the pivot rod 22570 extends through the first opening 22509 of the support member 22502 such that the proximal end portion 22571 of the pivot rod 22570 is received within the first opening 22548 of the proximal retention member 25510 and is fixedly coupled to the proximal retention member 22510. In this manner, the proximal retention member 22510 and the distal retention member 22512 are coupled together and can collectively rotate relative to the support member 22502 about an axis of rotation $L_R$ (which is coincides with the center line of the pivot rod 22570), as indicated by the arrows KK in FIG. 105.

The proximal retention member 22510 and the distal retention member 22512 can collectively rotate relative to the support member 22502 between a first position (i.e., the first configuration of the implant 22500, as shown in FIGS. 100-102) and a second position (i.e., the second configuration of the implant 22500, as shown in FIG. 103-105). When the implant 22500 is in the first configuration, the retention surface 22547 of the proximal retention member 22510 is in contact with and/or adjacent to the proximal end surface 22518 of the support member 22502 and the retention surface 22537 of the distal retention member 22512 is in contact with and/or adjacent to the distal end surface 22517 of the support member 22502. In this manner, the implant 22500 can be inserted between adjacent spinous processes unimpeded by the proximal retention member 22510 and/or the distal retention member 22512 (i.e., the proximal retention member 22510 and/or the distal retention member 22512 do not limit movement of the support member 22502 relative to the spinous processes). As described above, it is understood that portions of the retention surface 22547 and the retention surface 22537 can be spaced apart from the proximal end surface 22518 and the distal end surface 22517, respectively. For example, in some embodiments, portions of the retention surface 22547 and/or the retention surface 22537 of the second member 22512 can be spaced apart from the proximal end surface 22518 and/or the distal end surface 22517, respectively, as a result of surface roughness, corrugation and/or waviness of the mating surfaces.

Similarly stated, when the implant 22500 is in the first configuration, the area $A_2$ of the proximal retention surface 22547 is within the area $A_1$ of the proximal end surface 22518 of the support member 22502 when the areas $A_1$ and $A_2$ are projected on a plane substantially parallel to the proximal end surface 22518 of the support member 22502. Similarly, when the implant 22500 is in the first configuration, the area $A_4$ of the distal retention surface 22537 is within the area $A_3$ of the distal end surface 22517 of the support member 22502 when the areas $A_3$ and $A_4$ are projected on a plane substantially parallel to the distal end surface 22517 of the support member 22502.

Moreover, when the implant 22500 is in the first configuration, the biasing member 22558 exerts a force against the locking member 22554 such that the end portion 22557 of the locking member 22554 is disposed outside of the support member 22502 and is received within the recess 22538 of the retention surface 22537 of the distal retention member 22512. Accordingly, when the implant 22500 is in the first configuration, the locking member 22554 temporarily maintains the distal retention member 22512 and the proximal retention member 22510 in the first position, as described above.

When the implant 22500 is in the second configuration, at least a portion of the proximal retention surface 22547 and at least a portion of the distal retention surface 22537 are spaced apart from the proximal end surface 22518 of the support member 22502 and the distal end surface 22517 of the support member 22502, respectively. In this manner, when implant 22500 is in the second configuration, the portion of the proximal retention surface 22547 and/or the portion of the distal retention surface 22537 can contact and/or engage the spinous processes (or the associated surrounding tissue) to limit lateral movement of the support member 22502 relative to the spinous processes.

When the proximal retention member 22510 and the distal retention member 22512 are in the second position, a portion of the area $A_2$ of the proximal retention surface 22547 is outside of the area $A_1$ of the proximal end surface 22518 of the support member 22502 when projected on a plane substantially parallel to the proximal end surface 22518 of the support member 22502. Similarly, a portion of the area $A_4$ of the distal retention surface 22537 is outside of the area $A_3$ of the distal end surface 22517 of the support member 22502 when projected on a plane substantially parallel to the distal end surface 22517 of the support member 22502.

Moreover, when the implant 22500 is in the second configuration, the biasing member 22558 exerts a force against the locking member 22554 such that the end portion 22557 of the locking member 22554 is received, at least partially, within one of the recesses 22539 of the outer surface 22536 of the distal retention member 22512. Accordingly, when the implant 22500 is in the second configuration, the locking member 22554 maintains the distal retention member 22512 and the proximal retention member 22510 in the second position, as described above.

Moreover, when the implant 22500 is in the second configuration, the protrusion 22514 of the proximal retention member 22510 can be in contact with one of the shoulder surfaces 22560 of the support member 22502. In this manner, the proximal retention member 22510 is prevented from being rotated more than approximately 90 degrees from the first position. Said another way, the protrusion 22514 and the shoulder surfaces 22560 limit the rotation of the proximal retention member 22510 relative to the support member 22502.

The implant 22500 can be inserted into and/or removed from the body by a deployment tool 22600, as shown in FIGS. 106-112. The deployment tool 22600 includes a shaft 22620 and a rod 22670 movably disposed within the shaft 22620. The distal end of the shaft 22620 includes an implant support portion 26630. The implant support portion 26630 has a side wall 22640 having an inner surface 22641, a first end face 22644 and a second end face 22645. The inner surface 22641, the first end face 22644 and the second end face 22645 collectively define a receiving area 22642. As shown, the inner surface 22641 of the side wall 22640 is configured to complementarily receive the proximal retention member 22510 and the distal retention member 22512 of the implant 22500. Moreover, the first end face 22644 is set back proximally from the second end face 22645 to accommodate the curved outer surface 22536 of the distal retention member 22512. In this manner, as described in more detail herein, the proximal retention member 22510 and/or the distal retention member 22512 can be received within the receiving area 22642 of the deployment tool 22600.

The rod 22670 includes a threaded portion 22672 that is positioned within the receiving area 22642. The rod 22670 is rotatable within the shaft 22620 such that the threaded portion 22672 of the rod 22670 can be threadedly engaged with the threaded opening 22580 of the proximal retention member 22510 (see e.g., FIG. 107) and/or the threaded opening 22582 of the distal retention member 22512 (see e.g., FIG. 110). In this manner, the implant 22500 can be removably secured within the receiving area 22642 of the deployment tool 22600. The rod 22670 can be rotated within the shaft 22620 by any suitable mechanism, such as a knob assembly (not shown in FIGS. 106-112) of the type shown and described above with reference to FIGS. 11-16.

In use, with the implant 22500 in the first configuration, the proximal retention member 22510 of the implant 22500 can be secured within the receiving area 22642 of the deployment tool 22600, as described above. As shown in FIG. 107, the proximal end surface 22561 of the proximal retention member 22510 can be in contact with the second end face 22645 of the deployment tool 22600.

The implant 22500 can then be inserted percutaneously until at least a portion of the support surface 22516 of the support member 22502 is between adjacent spinous processes (not shown in FIGS. 106-112). In some embodiments, the implant 22500 can be deployed via a lateral access path. The path can have any suitable curvature and/or size, such as those described herein.

When the implant 22500 is positioned between the adjacent spinous processes, the shaft 22620 is rotated about its center line CL, as indicated by the arrow LL in FIG. 109. When the shaft 22620 is rotated, the position of the support member 22502 is maintained by the adjacent spinous processes. In this manner, the proximal retention member 22510 and the distal retention member 22512 are rotated relative support member 22502, thereby moving the implant 22500 from the first configuration (FIG. 108) to the second configuration (FIG. 109). The deployment tool 22600 is decoupled from the implant 22500 by rotating the rod 22670 within the shaft 22620 until the threaded portion 22672 of the rod 22670 is no longer engaged with the threaded opening 22580 of the proximal retention member 22510.

Figure 111:
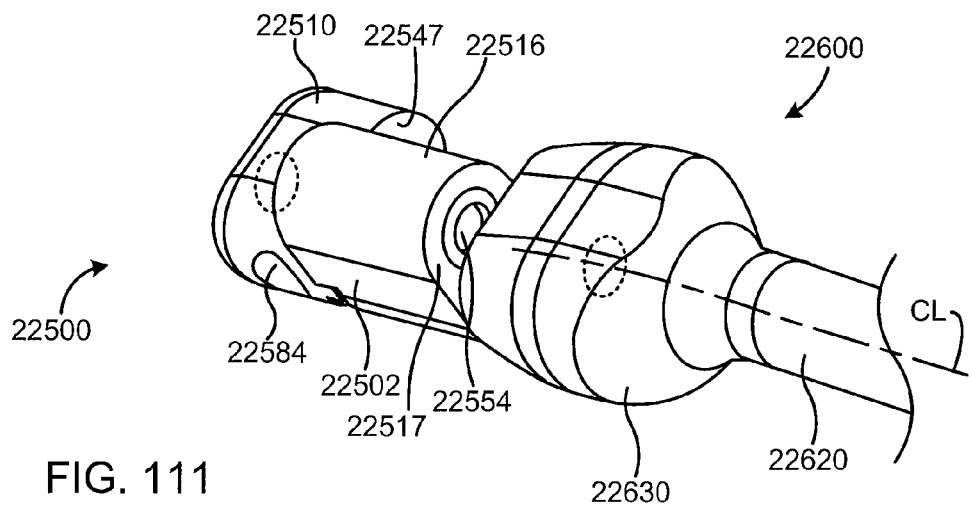
FIG. 111 is a perspective view of the deployment tool shown in FIG. 106 engaging the distal portion the implant shown in FIG. 100 in the second configuration.
Figure 112:
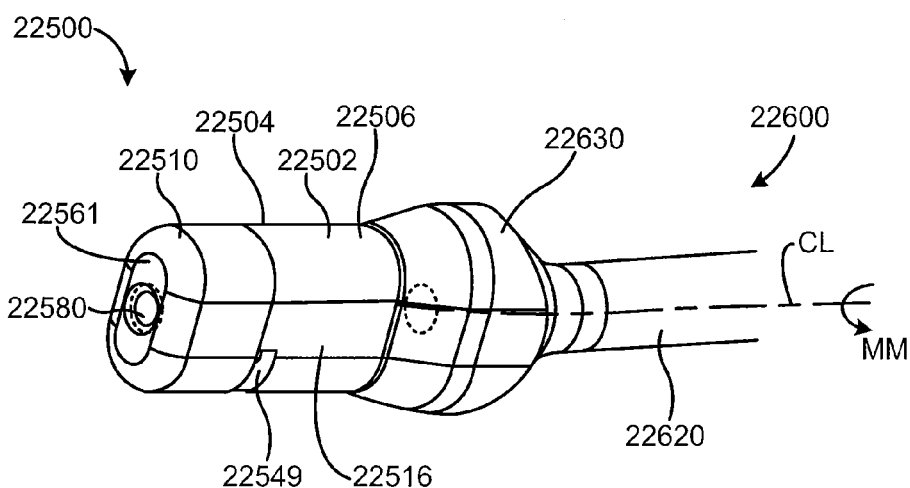
FIG. 112 is a perspective view of the deployment tool shown in FIG. 106 engaging the distal portion of the implant shown in FIG. 100 in the first configuration.

The implant 22500 can be removed from and/or repositioned within the body by positioning the deployment tool 22600 such that the distal retention member 22512 of the implant 22500 is within the receiving area 22642, as shown in FIGS. 110-112. As shown in FIG. 111, when the distal retention member 22512 is within the receiving area 22642, the distal end surface 22635 of the implant support portion 26630 engages the portion 22557 of the locking member 22554 and moves the locking member 22554 into the opening 22508. In this manner, the implant 22500 is "unlocked" and can be moved from the second configuration (FIG. 111) back to the first configuration (FIG. 112). As described above, the implant 22500 can be moved to the first configuration by rotating the shaft 22620 about its center line CL, as indicated by the arrow MM in FIG. 112.

Although the rod 22670 is shown as being rotatable within the shaft 22620, in other embodiments, the rod 22670 can both rotate and translate within the shaft 22620. For example, in some embodiments, a deployment tool can have a knob assembly similar to the knob assembly shown and described above with reference to FIGS. 11-16.

Although the implant 22500 is shown and described without reference to any specific dimensions, the implant 22500 can have any suitable size to be disposed between any set of adjacent spinous processes within a patients body (ranging, for example, from the L4/L5 spinous processes to the C1/C2 spinous processes). Referring to the dimensions shown in FIGS. 101 and 102, in some embodiments, for example, the length $L_1$ of the support member 22502 can be between 8 mm and 16 mm. In some embodiments, the length $L_1$ of the support member 22502 can be approximately 12 mm. Similarly, in some embodiments, the length $L_2$ of the proximal retention member 22510 can be between 6 mm and 12 mm. In some embodiments, the length $L_2$ of the proximal retention member 22510 can be approximately 9 mm. Similarly, in some embodiments, the length $L_3$ of the distal retention member 22512 can be between 8 mm and 16 mm. In some embodiments, the length $L_3$ of the distal retention member 22512 can be approximately 11 mm.

In some embodiments, the height H of the implant 22500 can be between 9 mm and 22 mm. Similarly, in some embodiments, the width W of the implant 22500 can be between 6 mm and 16 mm. In some embodiments, for example, the height H of the implant 22500 can be approximately 12 mm and the width W of the implant 22500 can be approximately 8 mm. As shown in FIG. 105, the difference between the height H and the width W is the distance D that the outermost edge of the proximal retention member 22510 and/or the distal retention member 22512 are spaced apart from the support surface 22516 of the support member 22502 when the implant is in the second configuration. Said another way, the aspect ratio of the implant 22500 (H divided by W) is associated with the distance D. In some embodiments, the aspect ratio of the implant 22500 is between approximately 1.2 and 1.6.

Figure 113:
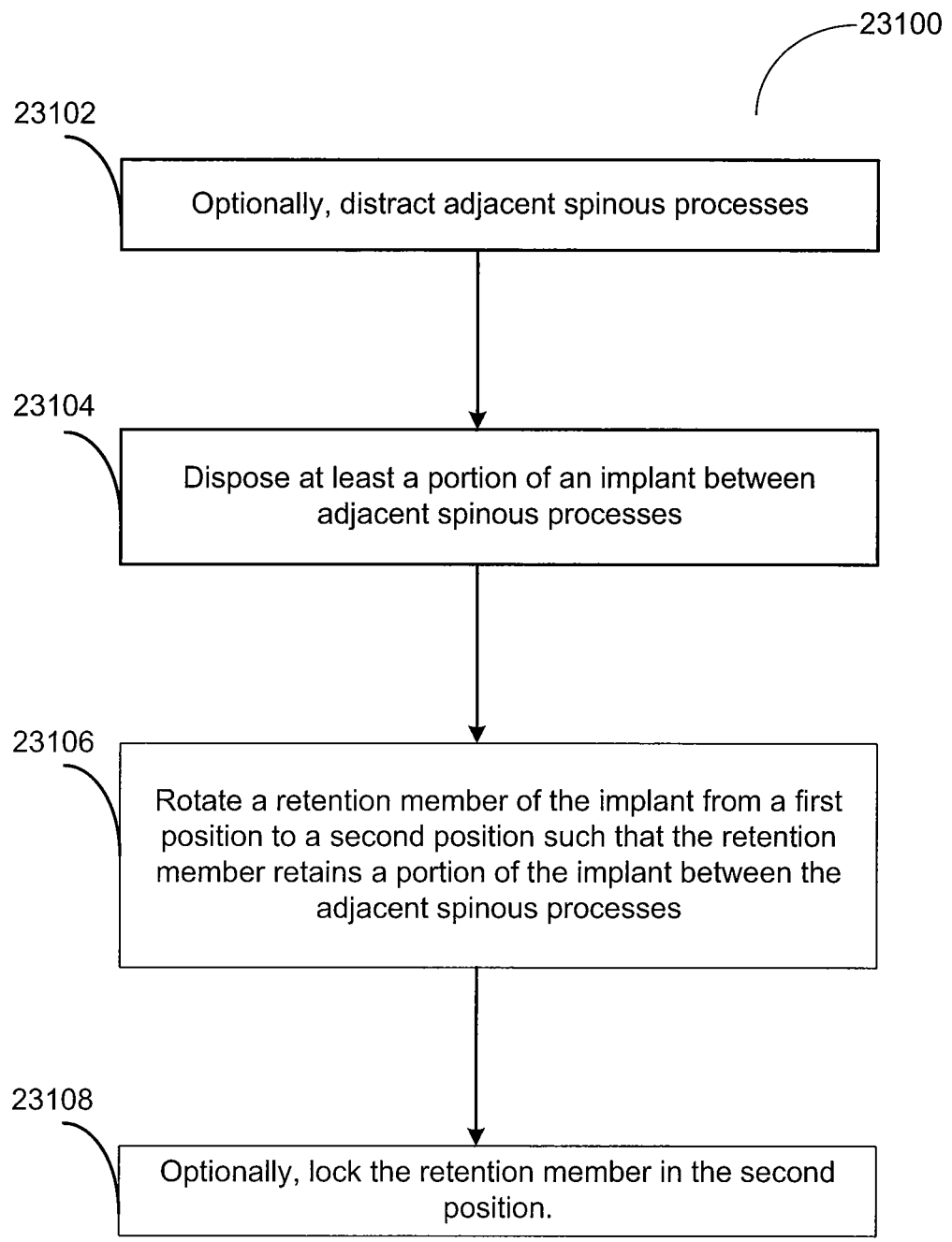
FIG. 113 is a flow chart illustrating a method of treating a spinal condition according to an embodiment of the invention.

FIG. 113 shows a method 23100 according to an embodiment of the invention. The method includes disposing at least a portion of an implant between adjacent spinous processes, 23104. The implant includes a support member having a longitudinal axis, and a retention member movably coupled to the support member. The implant can be any suitable implant of the types shown and described above, such as for example, the implant 22100.

In some embodiments, the disposing can include inserting the implant percutaneously via a lateral access path. In some embodiments, the disposing can include inserting the implant using a curved tool and/or a guide member, as described herein. In some embodiments, the method can include optionally distracting the adjacent spinous processes before the disposing, 23102.

The retention member of the implant is then rotated from a first position to a second position such that the retention member retains a portion of the implant between the adjacent spinous processes, 23106. In some embodiments, the retention member can be rotated about an axis substantially parallel to the longitudinal axis of the support member. In some embodiments, for example, the support member has an end portion having a cross-sectional area normal to the longitudinal axis of the support member. The retention member also has a cross-sectional area normal to the longitudinal axis of the support member. The cross-sectional area of the retention member being within the cross-sectional area of the distal end of the support member projected on a plane substantially normal to the longitudinal axis and when the retention member is in the first position. In such embodiments, the rotating can include rotating the retention member such that a portion of the cross-sectional area of the retention member is outside of the cross-sectional area of the distal end of the support member when projected on the plane substantially normal to the longitudinal axis.

In some embodiments, the method can include optionally locking the retention member in the second position, 23108. The locking can include, for example, moving a locking member such that a portion of the locking member is received within a recess defined by the support member and/or the retention member, as described above.

Figure 114:
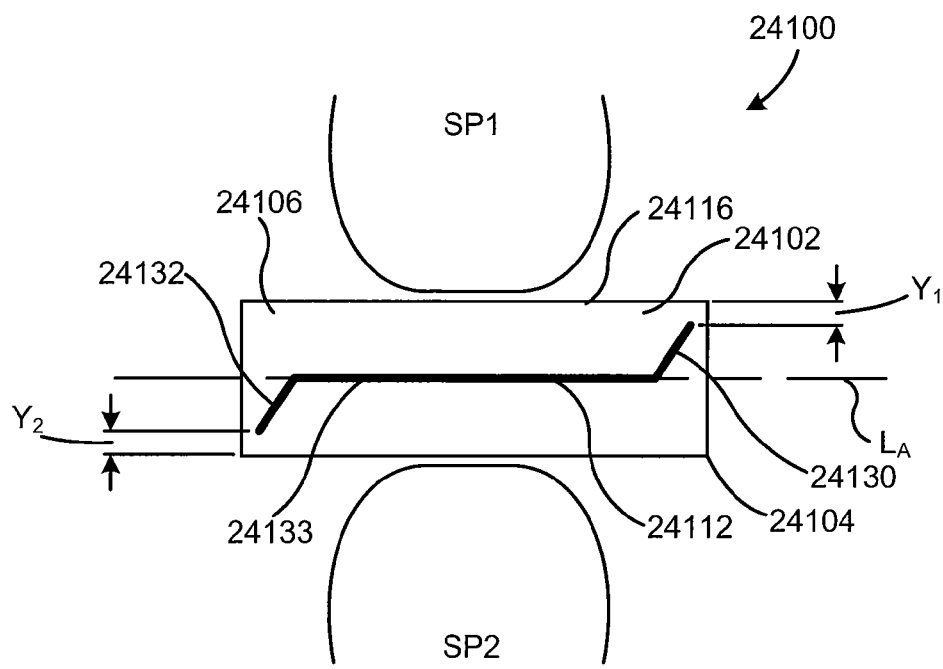
FIG. 114 is a schematic illustration of a posterior view of an implant in a first configuration according to an embodiment of the invention disposed between a first spinous process and second spinous process.
Figure 115:
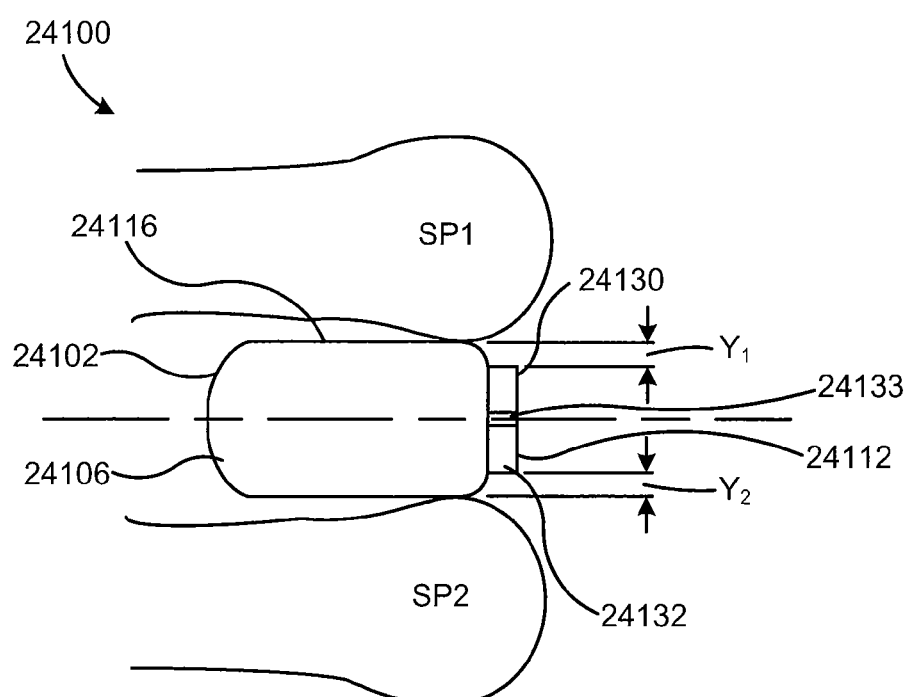
FIG. 115 is a schematic illustration of a lateral view of the implant shown in FIG. 114 in the first configuration.
Figure 116:
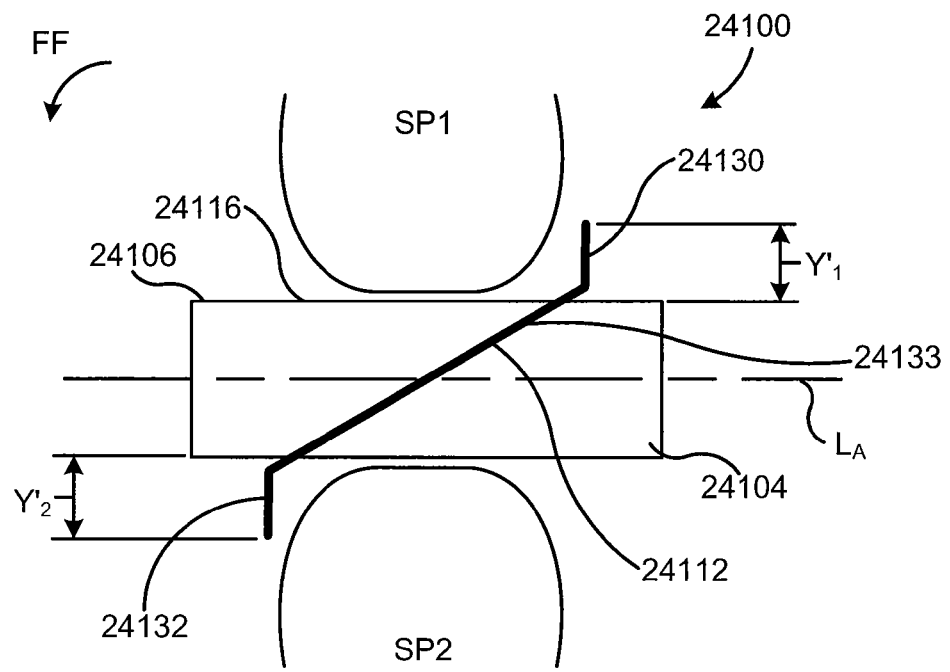
FIG. 116 is a schematic illustration of a posterior view of the implant shown in FIG. 114 in a second configuration.
Figure 117:
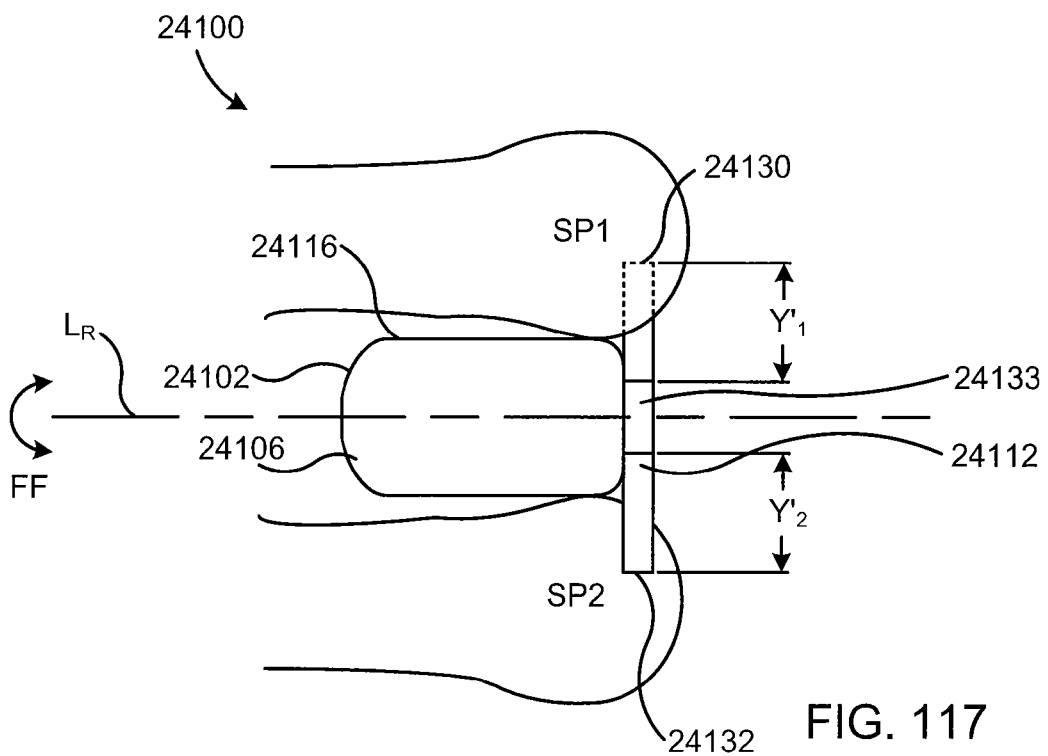
FIG. 117 is a schematic illustration of a lateral view of the implant shown in FIG. 114 in the second configuration.

FIGS. 114-117 are schematic illustrations of an implant 24100 according to an embodiment of the invention. FIGS. 114 and 116 are posterior views of the implant 24100 in a first configuration and a second configuration, respectively, disposed between a first spinous process SP1 and a second spinous process SP2 adjacent the first spinous process SP1. FIGS. 115 and 117 are lateral views of the implant 24100 in the first configuration and the second configuration, respectively, disposed between the first spinous process SP1 and the second spinous process SP2. The implant 24100 includes a support member 24102 and a retention member 24112 rotatably coupled to the support member 24102.

The support member 24102 has a proximal portion 24104, a distal portion 24106 and an outer surface 24116. The outer surface 24116 of the support member 24102 is substantially parallel to a longitudinal axis $L_A$ of the support member 24102. Said another way, the longitudinal axis $L_A$ and a line defined to include a portion of the outer surface 24116 of the support member 24102 are non-intersecting as they extend to infinity. Said yet another way, in embodiments in which the first surface 24116 of the support member 24102 includes at least a planar portion, every point along the longitudinal axis $L_A$ is spaced apart from the nearest portion of a plane defined to include the planar portion of the first surface 24116 of the first member 22402 by a substantially equal distance. The longitudinal axis $L_A$ can, for example, pass lengthwise (e.g., from the proximal portion 24104 to the distal portion 24106) through the centroid of the support member 24102 (e.g., the longitudinal axis $L_A$ can be a centroidal axis of the support member 24102). As shown, when the implant 24100 is disposed between the first spinous process SP1 and the second spinous process SP2, the longitudinal axis $L_A$ can be substantially parallel and/or coincident with a lateral axis defined by the spinal column.

As shown, at least a portion of the outer surface 24116 of the support member 24102 is disposed between the first spinous process SP1 and the second spinous process SP2. In this manner, the implant 24100 can maintain a minimal spacing between the adjacent spinous processes SP1 and SP2 during extension of the spinal column (not shown FIGS. 114-117) while allowing flexion of the spinal column. Moreover, in some embodiments, the implant 24100 can distract the adjacent spinous processes SP1 and SP2.

The retention member 24112 has a first end portion 24130, a second end portion 24132 and a central portion 24133 disposed between the first end portion 24130 and the second end portion 24132. The retention member 24112 is rotatably coupled to the support member 24102 such that the retention member 24112 can rotate relative to the support member 24102 about an axis of rotation $L_R$ substantially normal to the longitudinal axis $L_A$. As indicated by the arrows FF in FIGS. 116 and 117, the retention member 24112 can rotate relative to the support member 24102 between a first position (FIGS. 114 and 115) and a second position (FIGS. 116 and 117). When the retention member 24112 is in the first position, the implant 24100 can be inserted such that at least a portion of the first surface 24116 of the support member 24102 is disposed between the first spinous process SP1 and the second spinous process SP2. When the retention member 24112 is in the second position, the retention member 24112 limits lateral movement of the support member 24102 along the longitudinal axis $L_A$ and relative to the adjacent spinous processes SP1 and SP2. The retention member 24112 can limit lateral movement of the support member 24102, for example, by contacting the spinous processes SP1 and SP2 (e.g., either directly or through surrounding tissue).

As shown in FIGS. 114 and 115, when the retention member 24112 is in the first position, the outermost portion of the first end portion 24130 is spaced apart from the outer surface 24116 of the support member 24102 by a distance $Y_1$ along an axis substantially normal to the longitudinal axis $L_A$ and substantially normal to the axis of rotation $L_R$. The distance $Y_1$ is such that the distance between the first end portion 24130 and the longitudinal axis $L_A$ is less than the distance between the outer surface 24116 of the support member 24102 and the longitudinal axis $L_A$ (i.e., the first end portion 24130 of the retention member 24112 is "below" the outer surface 24116 of the support member 24102 relative to the longitudinal axis $L_A$). Similarly, when the retention member 24112 is in the first position, the outermost portion of the second end portion 24132 is spaced apart from the outer surface 24116 of the support member 24102 by a distance $Y_2$ along the axis substantially normal to the longitudinal axis $L_A$ and substantially normal to the axis of rotation $L_R$. The distance $Y_2$, which, in some embodiments, can be equal to the distance $Y_1$, is such that the distance between the second end portion 24132 and the longitudinal axis $L_A$ is less than the distance between the outer surface 24116 of the support member 24102 and the longitudinal axis $L_A$ (i.e., the second end portion 24132 of the retention member 24112 is "below" the outer surface 24116 of the support member 24102 relative to the longitudinal axis $L_A$). In this manner, when the retention member 24112 is in the first position, the implant 24100 can be inserted between the spinous processes SP1 and SP2 unimpeded by first end portion 24130 of the retention member 24112 and/or the second end portion 24132 of the retention member 24112

(i.e., the retention member 24112 does not limit movement of the support member 24102 relative to the spinous processes SP1 and SP2).

As shown in FIGS. 116 and 117, when the retention member 24112 is in the second position, the outermost portion of the first end portion 24130 is spaced apart from the outer surface 24116 of the support member 24102 by a distance $Y'_1$ along the axis substantially normal to the longitudinal axis $L_A$ and substantially normal to the axis of rotation $L_R$. The distance $Y'_1$ is such that the distance between the first end portion 24130 and the longitudinal axis $L_A$ is greater than the distance between the outer surface 24116 of the support member 24102 and the longitudinal axis $L_A$ (i.e., the first end portion 24130 of the retention member 24112 is "above" the outer surface 24116 of the support member 24102 relative to the longitudinal axis $L_A$). Similarly, when the retention member 24112 is in the second position, the outermost portion of the second end portion 24132 is spaced apart from the outer surface 24116 of the support member 24102 by a distance $Y'_2$ along the axis substantially normal to the longitudinal axis $L_A$ and substantially normal to the axis of rotation $L_R$. The distance $Y'_2$, which in some embodiments can be equal to the distance $Y'_1$, is such that the distance between the second end portion 24132 and the longitudinal axis $L_A$ is greater than the distance between the outer surface 24116 of the support member 24102 and the longitudinal axis $L_A$ (i.e., the second end portion 24132 of the retention member 24112 is "above" the outer surface 24116 of the support member 24102 relative to the longitudinal axis $L_A$). In this manner, when the retention member 24112 is in the second position, the first end portion 24130 can contact the first spinous process SP1 and/or the second end portion 24132 can contact the second spinous process SP2 to limit movement of the support member 24102 relative to the spinous processes SP1 and SP2.

In use, the adjacent spinous processes SP1 and SP2 can be distracted prior to inserting the implant 24100 into the patient. An access passageway can be then defined to allow insertion of the implant 24100. The passageway can have any suitable shape and can be formed by any suitable method, as discussed herein. After the access passageway is defined, the implant 24100 can be inserted percutaneously and advanced along the longitudinal axis $L_A$ until it is positioned between the spinous processes SP1 and SP2. The implant 24100 is inserted distal portion 24106 first and with the retention member 24112 in the first position. Once the implant 24100 is in place, the retention member 24112 is moved to the second position to limit lateral movement of the support member 24102 with respect to the spinous processes SP1 and SP2.

If or when it is desirable to change the position of the implant 24100 and/or remove the implant 24100, the retention member 24112 can be moved back to the first position, thereby allowing the support member 24102 to be moved laterally. Once the support member 24102 is repositioned as desired, the retention member 24112 can be moved back to the second position, if desired.

Although the first end portion 24130 and the second end portion 24132 are shown and described as being "below" the outer surface 24116 of the support member 24102 relative to the longitudinal axis $L_A$, in other embodiments, the first end portion 24130 and/or the second end portion 24132 can be flush with the outer surface 24116 of the support member 24102 (i.e., the distance $Y_1$ and/or the distance $Y_2$ can be zero). In other embodiments, the first end portion 24130 and/or the second end portion 24132 can be above the outer surface 24116 of the support member 24102 by a distance that does not interfere with the insertion of the implant 24100.

Figure 118:
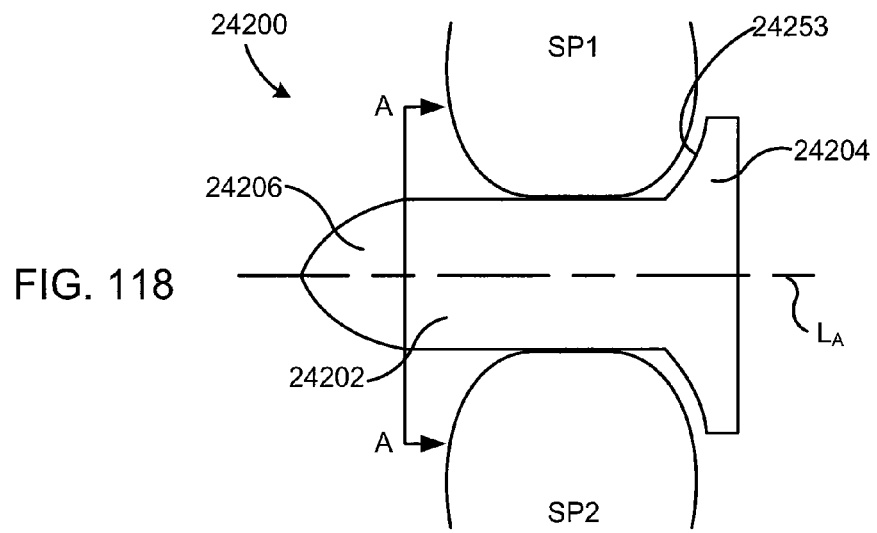
FIG. 118 is a posterior view of an implant in a first configuration according to an embodiment of the invention disposed between a first spinous process and second spinous process.
Figure 119:
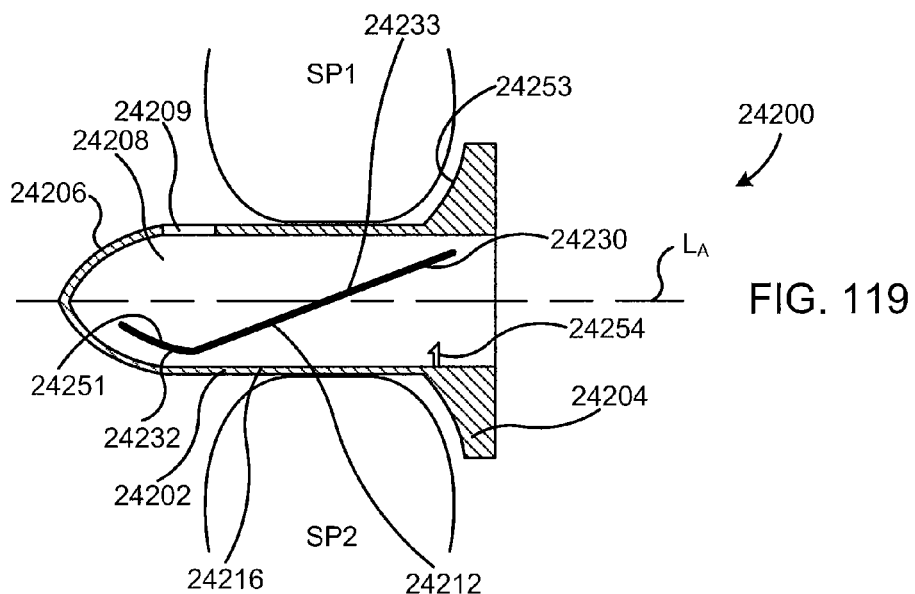
FIG. 119 is a cross-sectional posterior view of the implant shown in FIG. 118 in the first configuration.
Figure 120:
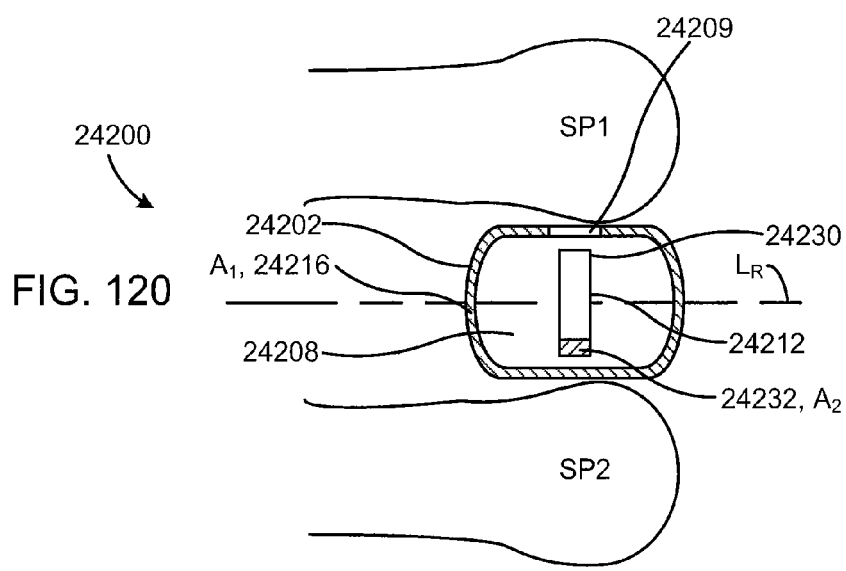
FIG. 120 is a cross-sectional of the implant shown in FIG. 118 in the first configuration taken along line A-A.
Figure 121:
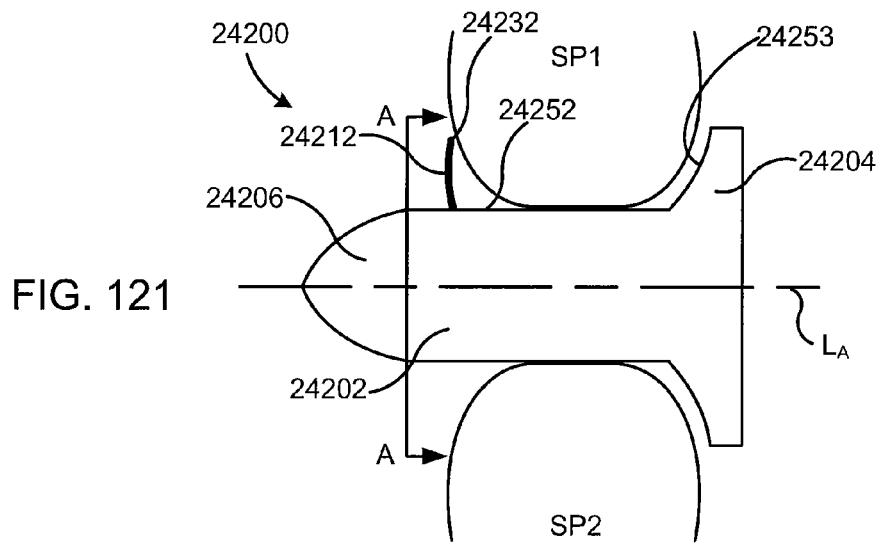
FIG. 121 is a posterior view of the implant shown in FIG. 118 in the second configuration.
Figure 122:
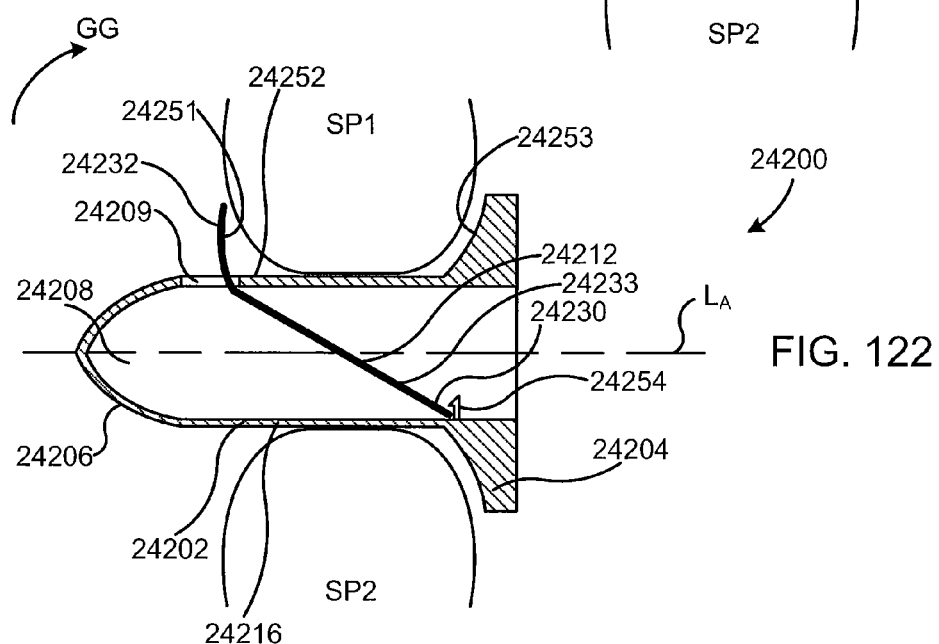
FIG. 122 is a cross-sectional posterior view of the implant shown in FIG. 118 in the second configuration.
Figure 123:
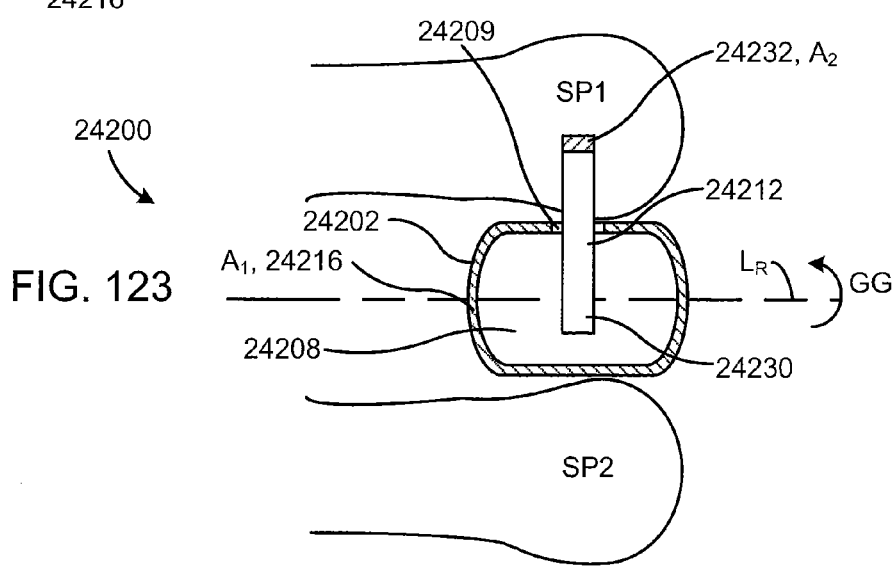
FIG. 123 is a cross-sectional of the implant shown in FIG. 105 in the second configuration taken along line A-A.

Although the retention member 24112 is shown as being coupled to the outer surface 24116 of the support member 24102, in some embodiments, at least a portion of a retention member can be disposed within a support member. For example, FIGS. 118-123 show an implant 24200 according to an embodiment of the invention. FIGS. 118 and 121 are posterior views of the implant 24200 in a first configuration and a second configuration, respectively, disposed between a first spinous process SP1 and a second spinous process SP2 adjacent the first spinous process SP1. FIGS. 119 and 122 are posterior cross-sectional views of the implant 24200 in the first configuration and the second configuration, respectively, disposed between the spinous processes SP1 and SP2. FIGS. 120 and 123 are cross-sectional views of the implant 24200 taken along lines A-A in FIGS. 118 and 121, respectively.

The implant 24200 includes a support member 24202 and a retention member 24212 movably coupled to the support member 24202. The support member 24202 has a proximal portion 24204, a distal portion 24206 and a side wall 24216. The side wall 24216 defines a lumen 24208 having a longitudinal axis $L_A$. As shown, at least a portion of the outer surface of the side wall 24216 is in contact with and/or adjacent to the first spinous process SP1 and/or the second spinous process SP2 when the support member 24202 is disposed between the first spinous process SP1 and the second spinous process SP2. In this manner, the implant 24200 can maintain a minimal spacing between the adjacent spinous processes SP1 and SP2 during extension of the spinal column while allowing flexion of the spinal column, as described herein.

The proximal portion 24204 of the support member 24202 includes a saddle surface 24253 having a curved shape that can form a portion of a saddle 24252, as discussed in more detail herein. The proximal portion 24204 also includes a locking member 24254 disposed within the lumen 24208 adjacent the side wall 24216. The distal portion 24206 of the support member 24202 has a curved shape to facilitate insertion of the implant 24200 into the body.

The retention member 24212 has a first end portion 24230, a second end portion 24232 and a central portion 24233 disposed between the first end portion 24230 and the second end portion 24232. The central portion 24233 of the retention member 24212 is disposed within the lumen 24208 of the support member 24202. The second end portion 24232 includes a saddle surface 24251 having a curved shape that can form a portion of a saddle 24252, as discussed in more detail herein.

The retention member 24212 is rotatably coupled to the support member 24202 such that the retention member 24212 can rotate relative to the support member 24202 about an axis of rotation $L_R$ substantially normal to the longitudinal axis $L_A$. As indicated by the arrows GG in FIGS. 122 and 123, the retention member 24212 can rotate relative to the support member 24202 between a first position (FIGS. 118-120) and a second position (FIGS. 121-123). When the retention member 24212 is in the first position, the implant 24200 can be inserted such that at least a portion of the side wall 24216 of the support member 24202 is disposed between the first spinous process SP1 and the second spinous process SP2. When the retention member 24212 is in the second position, the retention member 24212 limits movement of the support member 24202 along the longitudinal axis $L_A$ and relative to the adjacent spinous processes SP1 and SP2. The second end portion 24232 of the retention member 24212 can limit movement of the support member 24202, for example, by contacting and/or engaging the spinous processes SP1.

As shown in FIGS. 119 and 120, when the retention member 24212 is in the first position, the second end portion 24232 of the retention member 24212 is disposed within the lumen 24208 of the support member 24202. When the retention member 24212 is in the first position, the implant 24200 can be inserted such that a portion of the support member 22202 is disposed between the first spinous process SP1 and the second spinous process SP2.

As shown in FIGS. 121-123, when the retention member 24212 is in the second position, the second end portion 24232 is disposed through an opening 24209 in the side wall 24208 and outside of the distal end portion 24206 of the support member 24202. When the retention member 24212 is in the second position, the outer surface of the side wall 22216 of the support member 24202 and the saddle surface 22251 of the second end portion 24232 of the retention member 24212 collectively form a portion of a saddle 24252 configured to receive a portion of the spinous process SP1. The saddle 24252 can receive and/or engage a portion of the spinous process SP1 and/or its surrounding tissue to limit movement of the support member 24202 along the longitudinal axis $L_A$ and relative to the spinous processes SP1 and SP2. In some embodiments, the saddle 24252 and/or the saddle surface 24251 can have a curved surface that substantially corresponds to a shape and/or a size of the spinous process SP1. In some embodiments, the shape and/or size of the saddle surface 24251 can be configured to more evenly distribute forces between the saddle 24252 and the spinous process SP1. In some embodiments, the saddle surface 24251 and the outer surface of the side wall 24216 of the can form a substantially continuous surface.

Moreover, when the retention member 24212 is in the second position, the first end portion 24230 of the retention member 24212 engages with the locking member 24254 to maintain the retention member 24212 in the second position. In some embodiments, the locking member 24254 can be configured to temporarily maintain the retention member 24212 in the second position. In other embodiments, the locking member 24254 can be configured to fixedly maintain the retention member 24212 in the second position. In some embodiments, the locking member 24254 can be, for example, a protrusion defining a recess configured to receive and/or releasably retain the first end portion 24230 of the retention member 24212. In other embodiments, the locking member 24254 can be monolithically formed as part of the side wall 24216. In such embodiments, for example, the locking member 24254 can be a recess configured to matingly receive (e.g., via an interference fit) the first end portion 24230 of the retention member 24212 to maintain the retention member 24212 in the second position.

Said another way, when the retention member 24212 is in the first position, a cross-sectional area $A_2$ of the second end portion 24232 of the retention member 24212 is within a cross-sectional area $A_1$ of the support member 24202 when projected on a plane substantially normal to the longitudinal axis $L_A$ (see FIG. 120). When the retention member 24212 is in the second position, at least a portion of the cross-sectional area $A_2$ of the retention member 24212 is outside of the cross-sectional area $A_1$ of the support member 24202 when projected on a plane substantially normal to the longitudinal axis $L_A$ (see FIG. 123). Although the cross sectional area $A_2$ of the retention member 24212 and the cross-sectional area $A_1$ of the support member 24202 are shown as being within a plane normal to the longitudinal axis $L_A$ when viewed from a lateral view (e.g., FIGS. 120 and 123), the cross sectional areas $A_2$ and $A_1$ can be within a plane normal to the longitudinal axis $L_A$ when viewed from a posterior view (e.g., FIGS. 119 and 122).

In some embodiments, the implant 24200 can include a biasing member, such as, for example, a torsional spring, disposed between the retention member 24212 and the support member 24202. In this manner, the retention member 24212 can be biased in the second position (i.e., such that the second end portion 24232 of the retention member 24212 is maintained in engagement with the first spinous process SP1 and/or its surrounding tissue). In other embodiments, the retention member 24212 can be biased in the first position (i.e., such that the second end portion 24232 of the retention member 24212 is maintained within the lumen 24208 of the support member 24202).

Although the first end portion 24230 of the retention member 24212 and the second end portion 24232 of the retention member 24212 are shown as being within the lumen 24208 of the support member 24202 when the retention member 24212 is in the first position, in other embodiments, at least a portion of the first end portion 24230 and/or the second end portion 24232 can be disposed outside of the support member 24202 when the retention member 24212 is in the first position. For example, in some embodiments, a second end portion of a retention member can extend outside of a distal end portion of a support member along a longitudinal axis of the support member when the retention member is in a first position. In such embodiments, for example, a cross-sectional area of the second end portion of the retention member can be within a cross-sectional area of the support member when projected on a plane substantially normal to the longitudinal axis and when the retention member is in the first position, as described above.

Figure 126:
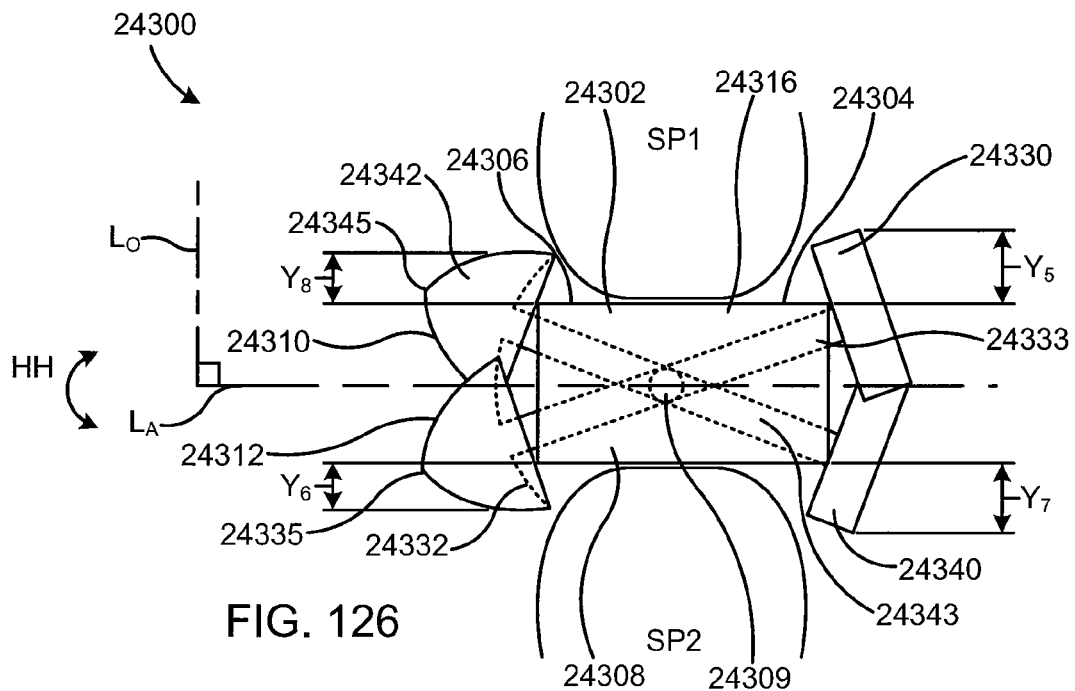
FIG. 126 is a posterior view of the implant shown in FIG. 111 in a second configuration.
Figure 127:
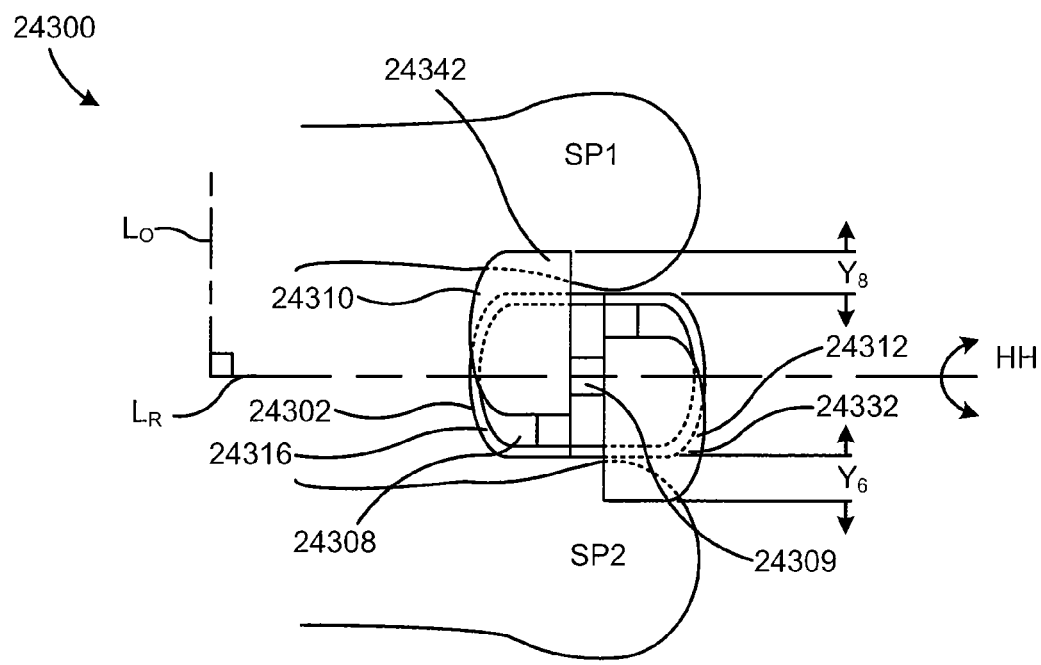
FIG. 127 is a lateral view of the implant shown in FIG. 111 in the second configuration.

Although the implant 24200 is shown and described as including a retention member 24212, in other embodiments, an implant can include multiple retention members. For example, FIGS. 124-127 show an implant 24300 according to an embodiment of the invention in a first configuration (FIGS. 124 and 125) and a second configuration (FIGS. 126 and 127). The implant 24300 includes a support member 24302, a first retention member 24312 and a second retention member 24310. The first retention member 24312 and the second retention member 24310 are rotatably coupled to the support member by a pin 24309.

As described above, the support member 24302 has a proximal portion 24304, a distal portion 24306 and a side wall 24316. The side wall 24316 defines a lumen 24308 having a longitudinal axis $L_A$. As shown, at least a portion of the outer surface of the side wall 24316 is in contact the first spinous process SP1 and/or the second spinous process SP2 when the support member 24302 is disposed between the first spinous process SP1 and the second spinous process SP2.

The first retention member 24312 has a proximal end portion 24330, a distal end portion 24332 and a central portion 24333 disposed between the proximal end portion 24330 and the distal end portion 24332. The central portion 24333 of the first retention member 24312 is disposed within the lumen 24308 of the support member 24302. The proximal end portion 24330 of the first retention member 24312 and the distal end portion 24332 of the first retention member 24312 are disposed outside of the lumen 24308. The distal end portion 24332 of the first retention member 24312 has a curved shape (e.g., a tapered end portion) to facilitate insertion of the implant 24300 into the body. The distal end portion 24332 of the first retention member 24312 also includes a tip 24335 to facilitate insertion of the implant 24300 into the body. In some embodiments, for example, the distal end portion 24332 of the first retention member 24312 can displace a bodily tissue when the implant 24300 is inserted into the body. In some embodiments, the distal end portion 24332 of the first retention member 24312 can dilate a bodily tissue, such as the supraspinous ligament, when the implant 24300 is inserted into the body. In some embodiments, the distal end portion 24332 of the first retention member 24312 can distract a space between adjacent spinous processes when the implant 24300 is inserted into the body.

Similarly, the second retention member 24310 (not shown in FIG. 111) has a proximal end portion 24340, a distal end portion 24342 and a central portion 24343 disposed between the proximal end portion 24340 and the distal end portion 24342. The central portion 24343 second retention member 24310 is disposed within the lumen 24308 of the support member 24302. The proximal end portion 24340 of the second retention member 24310 and the distal end portion 24342 of the second retention member 24310 are disposed outside of the lumen 24308. The distal end portion 24342 of the second retention member 24310 has a curved shape (e.g., a tapered end portion) to facilitate insertion of the implant 24300 into the body.

The distal end portion 24342 of the second retention member 24310 also includes a tip 24345 to facilitate insertion of the implant 24300 into the body. In some embodiments, for example, the distal end portion 24342 of the second retention member 24310 can displace a bodily tissue when the implant 24300 is inserted into the body. In some embodiments, the distal end portion 24342 of the second retention member 24310 can dilate a bodily tissue, such as the supraspinous ligament, when the implant 24300 is inserted into the body. In some embodiments, the distal end portion 24342 of the second retention member 24310 can distract a space between adjacent spinous processes when the implant 24300 is inserted into the body.

In some embodiments, the shape of the distal end portion 24342 of the second retention member 24310 can be similar (e.g., a mirror image) to the shape of the distal end portion 24332 of the first retention member 24312. Said another way, in some embodiments, the distal end portion 24342 of the second retention member 24310 and the distal end portion 24332 of the first retention member 24312 can cooperatively form a substantially continuous surface.

The first retention member 24312 and the second retention member 24310 are rotatably coupled to the support member 24302 about an axis of rotation $L_R$ substantially normal to the longitudinal axis $L_A$. As indicated by the arrows HH in FIGS. 126 and 127, the first retention member 24312 and/or the second retention member 24310 can rotate relative to the support member 24202 to place the implant 24300 in a first configuration (FIGS. 124 and 125) and a second configuration (FIGS. 126 and 127). When in the first configuration, the implant 24300 can be inserted such that at least a portion of the side wall 24316 of the support member 24302 is disposed between the first spinous process SP1 and the second spinous process SP2. When in the second configuration, first retention member 24312 and/or the second retention member 24310 limit lateral movement of the support member 24302 along the longitudinal axis $L_A$ and relative to the adjacent spinous processes SP1 and SP2.

Figure 124:
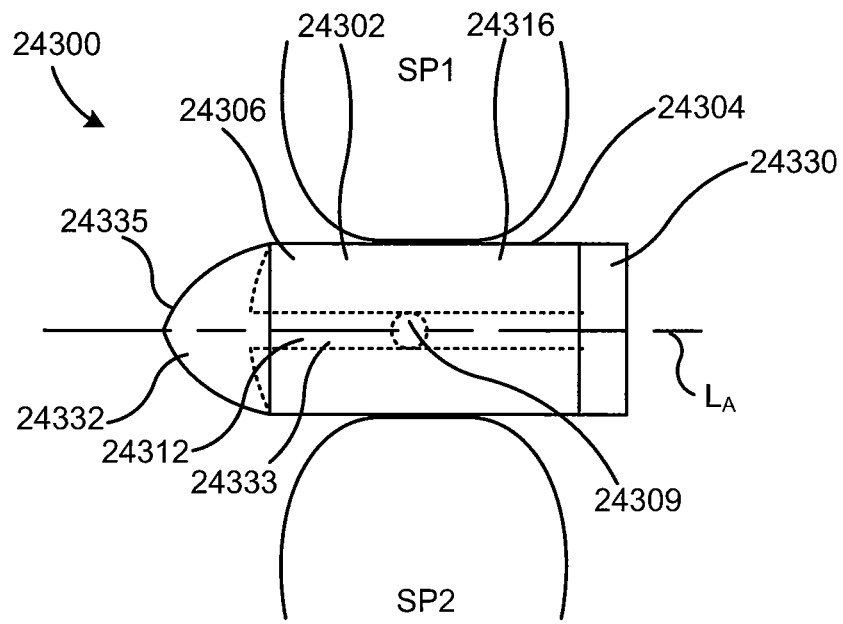
FIG. 124 is a posterior view of an implant in a first configuration according to an embodiment of the invention disposed between a first spinous process and second spinous process.
Figure 125:
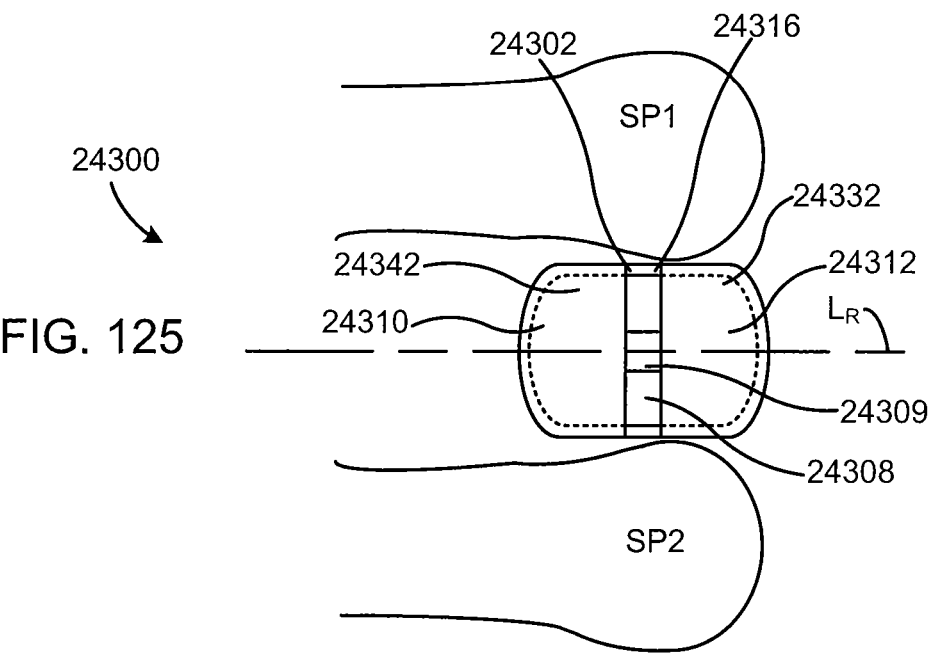
FIG. 125 is a lateral view of the implant shown in FIG. 111 in the first configuration.

As shown in FIGS. 124 and 125, when the implant 24300 is in the first configuration, the outer surface of the proximal end portion 24330 of the first retention member 24312 is flush with the outer surface 24316 of the support member 24302 (i.e., the outer surface of the proximal end portion 24330 is spaced apart from the outer surface 24316 of support member 24302 by a nominal gap along a direction normal to the longitudinal axis $L_A$). Additionally, the outer surface of the distal end portion 24332 of the first retention member 24312 is flush with the outer surface 24316 of the support member 24302 (i.e., the outer surface of the distal end portion 24332 is spaced apart from the outer surface 24316 of support member 24302 by a nominal gap along a direction normal to the longitudinal axis $L_A$). Said another way, when the implant 24300 is in the first configuration, the proximal end portion 24330 of the first retention member 24312, the distal end portion 24332 of the first retention member 24312 and the outer surface 24316 of the support member 24302 collectively form a substantially continuous surface.

Similarly, when the implant 24300 is in the first configuration, the outer surface of the proximal end portion 24340 of the second retention member 24310 is flush with the outer surface 24316 of the support member 24302 (i.e., the outer surface of the proximal end portion 24340 is spaced apart from the outer surface 24316 of support member 24302 by a nominal gap along an offset axis $L_O$ normal to the longitudinal axis $L_A$ and substantially normal to the axis of rotation $L_R$). Additionally, the outer surface of the distal end portion 24342 of the second retention member 24310 is flush with the outer surface 24316 of the support member 24302 (i.e., the outer surface of the distal end portion 24342 is spaced apart from the outer surface 24316 of support member 24302 by a nominal gap along the offset axis $L_O$). Said another way, when the implant 24300 is in the first configuration, the proximal end portion 24340 of the second retention member 24310, the distal end portion 24342 of the second retention member 24310 and the outer surface 24316 of the support member 24302 collectively form a substantially continuous surface.

As shown in FIGS. 126 and 127, when the implant 24300 is in the second configuration, the outermost edge of the proximal end portion 24330 of the first retention member 24312 is spaced apart from the outer surface 24316 of the support member 24302 by a distance $Y_5$ along the offset axis $L_O$. The distance $Y_5$ is such that the distance between the outermost edge of the proximal end portion 24330 and the longitudinal axis $L_A$ is greater than the distance between the outer surface 24316 of the support member 24302 and the longitudinal axis $L_A$ (i.e., the proximal end portion 24330 of the first retention member 24312 is "outside" the outer surface 24316 of the support member 24302 relative to the longitudinal axis $L_A$).

Similarly, when the implant 24300 is in the second configuration, the outermost edge of the distal end portion 24332 of the first retention member 24312 is spaced apart from the outer surface 24316 of the support member 24302 by a distance $Y_6$ along the offset axis $L_O$. The distance $Y_6$ is such that the distance between the outermost edge of the distal end portion 24332 and the longitudinal axis $L_A$ is greater than the distance between the outer surface 24316 of the support member 24302 and the longitudinal axis $L_A$ (i.e., the distal end portion 24332 of the first retention member 24312 is "outside" the outer surface 24316 of the support member 24302 relative to the longitudinal axis $L_A$). In this manner, when the implant 24300 is in the second configuration, the proximal end portion 24330 of the first retention member 24312 and/or the distal end portion 24332 of the first retention member 24312 can contact the first spinous process SP1, the second spinous process SP2 and/or the surrounding tissue to limit lateral movement of the support member 24302 relative to the spinous processes SP1 and SP2.

Similarly, when the implant 24300 is in the second configuration, the outermost edge of the proximal end portion 24340 of the second retention member 24310 is spaced apart from the outer surface 24316 of the support member 24302 by a distance $Y_7$ along the offset axis $L_O$. Said another way, the proximal end portion 24340 of the second retention member 24312 is "outside" the outer surface 24316 of the support member 24302 relative to the longitudinal axis $L_A$. The outermost edge of the distal end portion 24342 of the second retention member 24310 is spaced apart from the outer surface 24316 of the support member 24302 by a distance $Y_8$ along the offset axis $L_O$. Said another way, the distal end portion 24342 of the second retention member 24310 is "outside" the outer surface 24316 of the support member 24302 relative to the longitudinal axis $L_A$. In this manner, when the implant 24300 is in the second configuration, the proximal end portion 24340 of the second retention member 24310 and/or the distal end portion 24342 of the second retention member 24310 can contact the first spinous process SP1, the second spinous process SP2 and/or the surrounding tissue to limit lateral movement of the support member 24302 relative to the spinous processes SP1 and SP2.

In some embodiments, the first retention member 24312 and the second retention member 24310 can be moved relative to the support member 24302 serially. In other embodiments, the first retention member 24312 and the second retention member 24310 can be moved relative to the support member 24302 simultaneously. In yet other embodiments, only one of the first retention member 24312 or the second retention member 24310 can be moved relative to the support member 24302.

Figure 128:
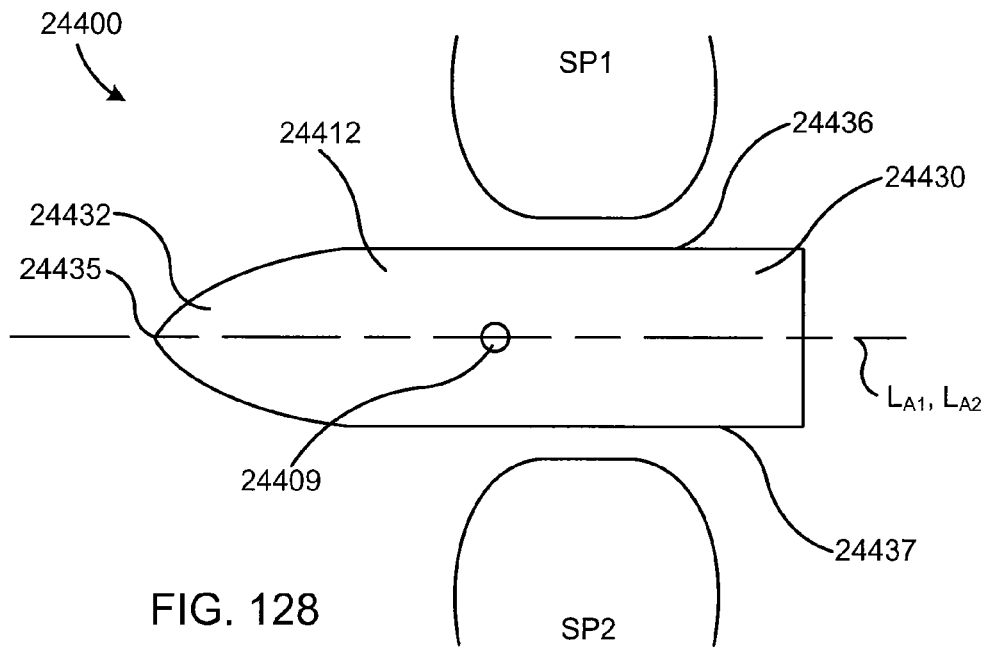
FIG. 128 is a posterior view of an implant in a first configuration according to an embodiment of the invention disposed between a first spinous process and second spinous process.
Figure 129:
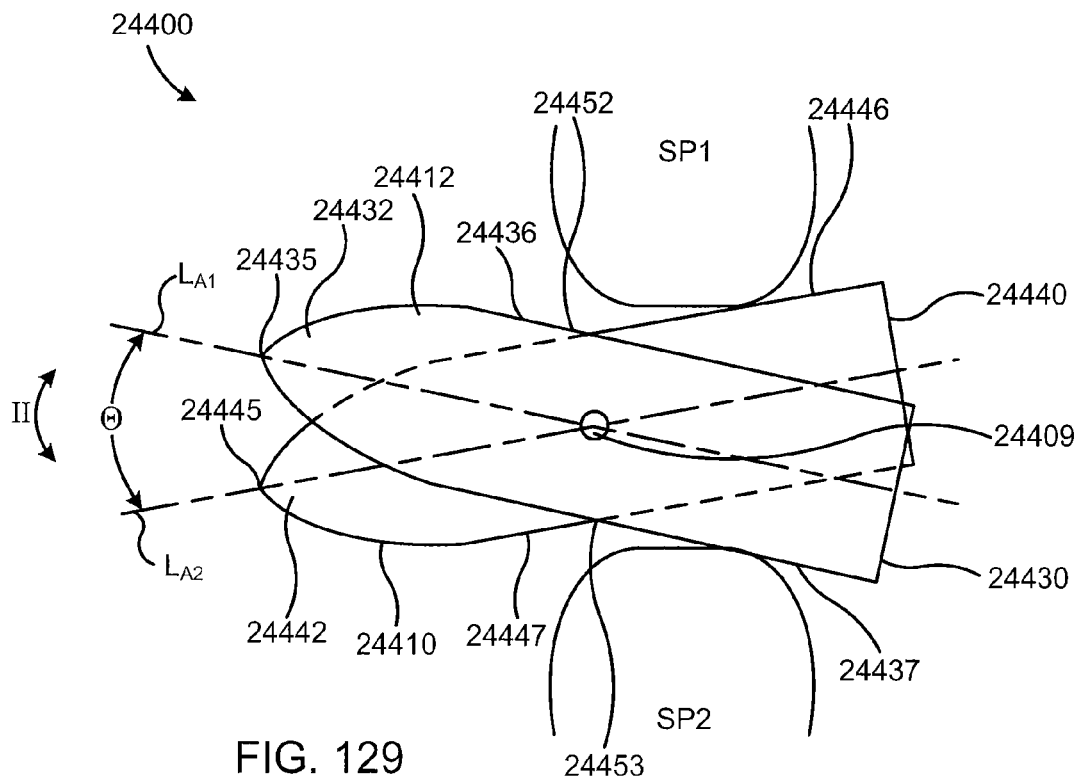
FIG. 129 is a posterior view of the implant shown in FIG. 115 in a second configuration.

FIGS. 128 and 129 show an implant 24400 according to an embodiment of the invention in a first configuration (FIG. 128) and a second configuration (FIG. 129). The implant 24400 includes a first elongate member 24412 and a second elongate member 24410. As shown, the implant 24400 is configured to be disposed between a first spinous process SP1 and a second spinous process SP2 to maintain a minimal spacing between the spinous processes during extension of the spinal column. The first elongate member 24412 and the second elongate member 24410 are rotatably coupled together by a pin 24409.

The first elongate member 24412 has a proximal end portion 24430 and a distal end portion 24432 and defines a longitudinal axis $L_{A1}$. The distal end portion 24432 of the first elongate member 24412 has a curved shape (e.g., a tapered end portion) to facilitate insertion of the implant 24400 into a body. The distal end portion 24432 of the first retention member 24412 also includes a tip 24435 to facilitate insertion of the implant 24400 into the body. In some embodiments, for example, the distal end portion 24432 of the first retention member 24412 can displace a bodily tissue when the implant 24400 is inserted into the body. In some embodiments, the distal end portion 24432 of the first retention member 24412 can dilate a bodily tissue, such as the supraspinous ligament, when the implant 24400 is inserted into the body. In some embodiments, the distal end portion 24432 of the first retention member 24412 can distract a space between adjacent spinous processes when the implant 24400 is inserted into the body.

The first elongate member 24412 also has a first surface 24436 and a second surface 24437 opposite the first surface 24436. As described in more detail herein, the first surface 24436 and the second surface 24437 are configured to contact and/or engage the first spinous process SP1 and/or the second spinous process SP2, respectively to limit movement of the implant 24400 along the longitudinal axis $L_{A1}$ and relative to the adjacent spinous processes SP1 and SP2. Although the first surface 24436 and the second surface 24437 are shown and described as being substantially parallel to each other and substantially parallel to the longitudinal axis $L_{A1}$, in other embodiments, the first surface 24436 and/or the second surface 24437 can be angularly offset from each other and/or angularly offset from the longitudinal axis $L_{A1}$. Similarly, although the first surface 24436 and the second surface 24437 are shown as being linear when viewed from the posterior view, in some embodiments, the first surface 24436 and/or the second surface 24437 can have a non-linear shape.

Similarly, as shown in FIG. 129, the second elongate member 24410 also has a proximal end portion 24440 and a distal end portion 24442 and defines a longitudinal axis $L_{A2}$. The distal end portion 24442 of the second elongate member 24410 has a curved shape (e.g., a tapered end portion) to facilitate insertion of the implant 24400 into the body. The distal end portion 24442 of the second retention member 24410 also includes a tip 24445 to facilitate insertion of the implant 24400 into the body. In some embodiments, for example, the distal end portion 24442 of the second retention member 24410 can displace a bodily tissue when the implant 24400 is inserted into the body. In some embodiments, the distal end portion 24442 of the second retention member 24410 can dilate a bodily tissue, such as the supraspinous ligament, when the implant 24400 is inserted into the body. In some embodiments, the distal end portion 24442 of the second retention member 24410 can distract a space between adjacent spinous processes when the implant 24400 is inserted into the body.

The second elongate member 24410 also has a first surface 24446 and a second surface 24447 opposite the first surface 24446. As described in more detail herein, the first surface 24446 and the second surface 24447 are configured to contact and/or engage the first spinous process SP1 and the second spinous process SP2, respectively, either directly or indirectly, to limit movement of the implant 24400 along the longitudinal axis $L_{A1}$ and relative to the adjacent spinous processes SP1 and SP2. Although the first surface 24446 and the second surface 24447 are shown and described as being substantially parallel to each other and substantially parallel to the longitudinal axis $L_{A2}$, in other embodiments, the first surface 24446 and/or the second surface 24447 can be angularly offset from each other and/or angularly offset from the longitudinal axis $L_{A2}$. Similarly, although the first surface 24446 and the second surface 24447 are shown as being linear when viewed from the posterior view, in some embodiments, the first surface 24446 and/or the second surface 24447 can have a non-linear shape.

As indicated by the arrow II in FIG. 129, the first elongate member 24412 and the second elongate member 24410 can rotate relative to each other about an axis of rotation substantially normal to the longitudinal axis $L_A$ to move the implant 24400 between a first configuration (FIG. 128) and a second configuration (FIG. 129). When the implant 24400 is in the first configuration, the longitudinal axis $L_{A1}$ of the first elongate member 24412 is substantially parallel to the longitudinal axis $L_{A2}$ of the second elongate member 24410. Similarly stated, when the implant 24400 is in the first configuration, the first surface 24436 of the first elongate member 24412 is aligned with the first surface 24446 of the second elongate member 24410 (i.e., the first surface 24436 and the first surface 24446 form a substantially continuous surface) and the second surface 24437 of the first elongate member 24412 is aligned with the second surface 24447 of the second elongate member 24410 (i.e., the second surface 24437 and the second surface 24447 form a substantially continuous surface). Accordingly, when in the first configuration, the implant 24400 can be disposed between the first spinous process SP1 and the second spinous process SP2.

As shown in FIG. 129, when the implant 24400 is in the second configuration, the longitudinal axis $L_{A1}$ of the first elongate member 24412 intersects the longitudinal axis $L_{A2}$ of the second elongate member 24410 at an angle Θ. Moreover, when the implant 24400 is in the second configuration, the first surface 24436 of the first elongate member 24412 and the first surface 24446 of the second elongate member 24410 collectively form a portion of a first saddle 24452 configured to receive a portion of the spinous process SP1. Similarly, the second surface 24437 of the first elongate member 24412 and the second surface 24447 of the second elongate member 24410 collectively form a portion of a second saddle 24453 configured to receive a portion of the spinous process SP2. The first saddle 24452 and the second saddle 24453 can be of any suitable shape and size, as discussed above. In this manner, when the implant 24400 is in the second configuration, the first saddle 24452 and/or the second saddle 24453 limit movement of the implant relative to the adjacent spinous processes SP1 and SP2.

Figure 130:
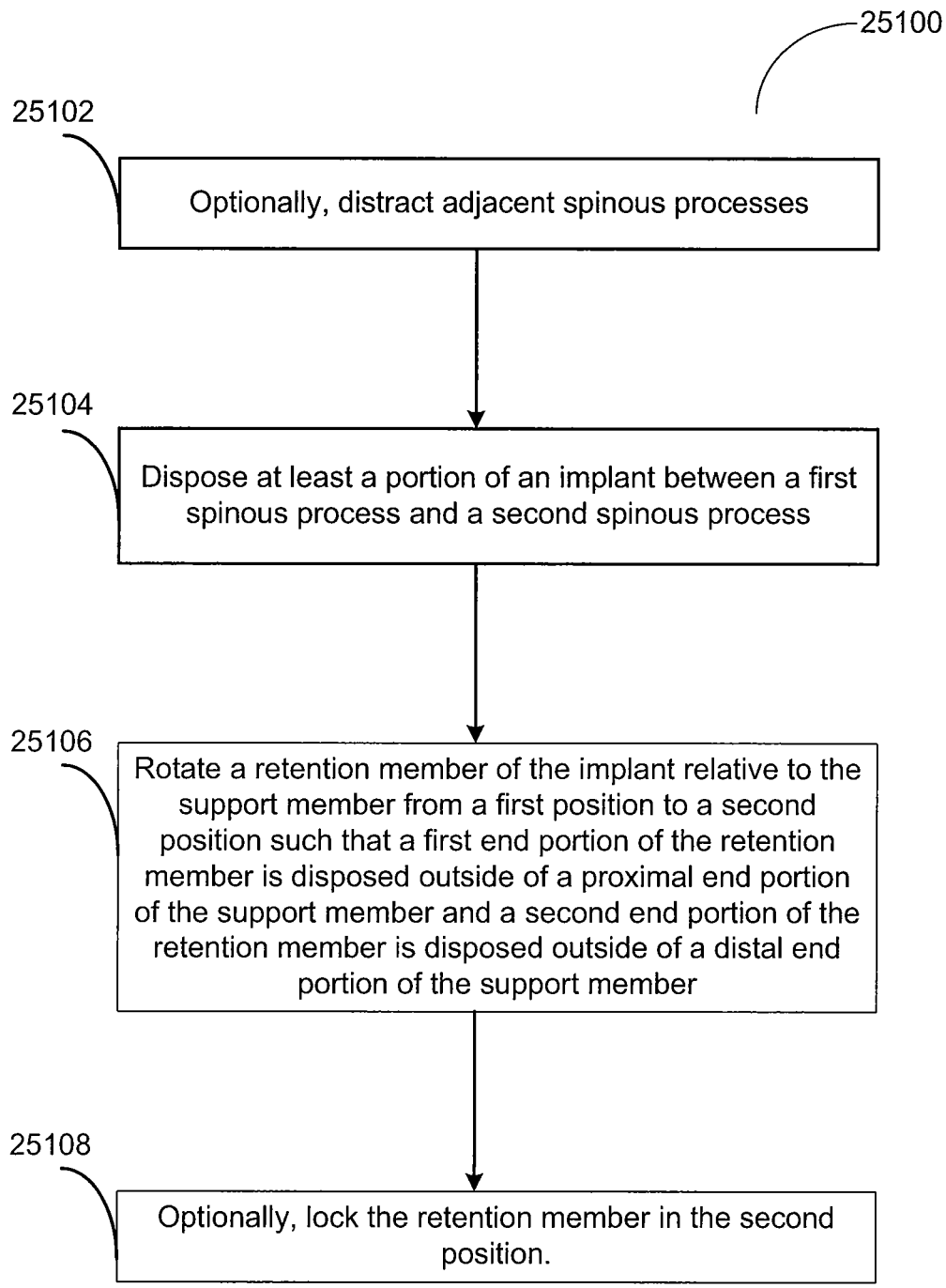
FIG. 130 is a flow chart illustrating a method according to an embodiment of the invention.

FIG. 130 shows a method 25100 according to an embodiment of the invention. The method includes disposing at least a portion of an implant between a first spinous process and a second spinous process, 23104. The implant includes a support member and a retention member rotatably coupled to the support member. The implant can be any suitable implant of the types shown and described above, such as for example, the implant 24100.

In some embodiments, the disposing can include inserting the implant percutaneously via a lateral access path. In some embodiments, the disposing can include inserting the implant using a curved tool and/or a guide member, as described herein. In some embodiments, the method can include optionally distracting the adjacent spinous processes before the disposing, 25102.

The retention member of the implant is rotated relative to the support member from a first position to a second position such that a first end portion of the retention member is disposed outside of a proximal end portion of the support member and a second end portion of the retention member is disposed outside a distal end portion of the support member, 25106. In this manner, the first end portion of the retention member and the second end portion of the retention member can cooperatively limit movement of the support member along the longitudinal axis and relative to the first spinous process and the second spinous process. In some embodiments, the retention member can be rotated about an axis substantially normal to a longitudinal axis of the support member.

In some embodiments, the method can include optionally locking the retention member in the second position, 25108. The locking can include, for example, moving a portion of the retention member into engagement with a locking member, as described above.

Figure 131:
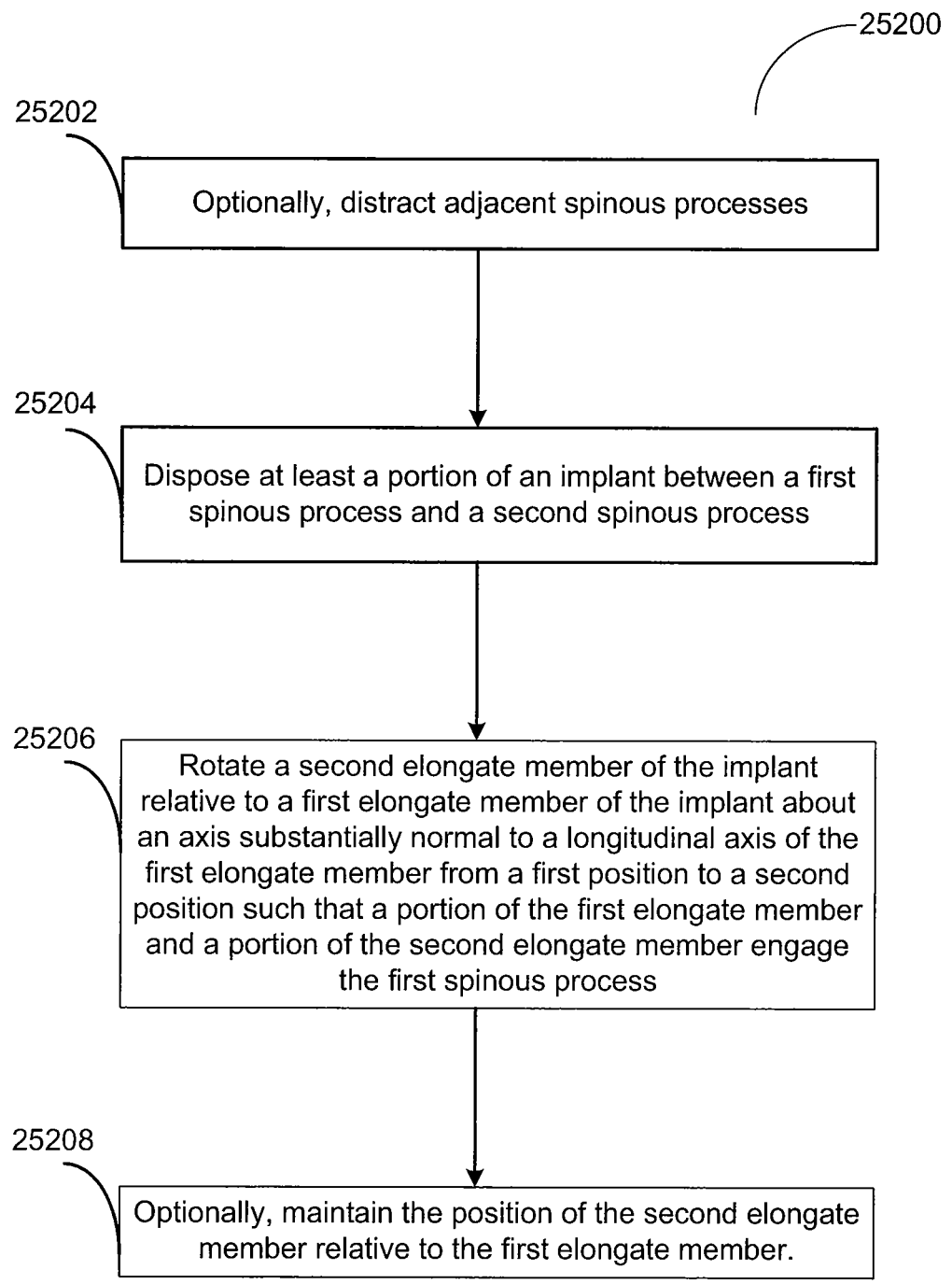
FIG. 131 is a flow chart illustrating a method according to an embodiment of the invention.

FIG. 131 shows a method 25200 according to an embodiment of the invention. The method includes disposing at least a portion of an implant between a first spinous process and a second spinous process, 25204. The implant includes a first elongate member and a second elongate member rotatably coupled to the first elongate member. The implant can be any suitable implant of the types shown and described above, such as for example, the implant 24400.

In some embodiments, the disposing can include inserting the implant percutaneously via a lateral access path. In some embodiments, the disposing can include inserting the implant using a curved tool and/or a guide member, as described herein. In some embodiments, the method can include optionally distracting the adjacent spinous processes before the disposing, 25202.

The second elongate member is rotated relative to the first elongate member about an axis substantially normal to a longitudinal axis of the first elongate member from a first position to a second position such that a portion of the first elongate member and a portion of the second elongate member engage the first spinous process, 25206. In this manner, the first elongate member and the second elongate member cooperatively limit movement of the first elongate member along the longitudinal axis and relative to the first spinous process and the second spinous process.

In some embodiments, the method can include optionally maintaining the position of the second elongate member relative to the first elongate member after the rotating, 25208. The maintaining can include, for example, moving a portion of the first elongate member and/or a portion of the second elongate member into engagement with a locking member, as described above.

Figure 132:
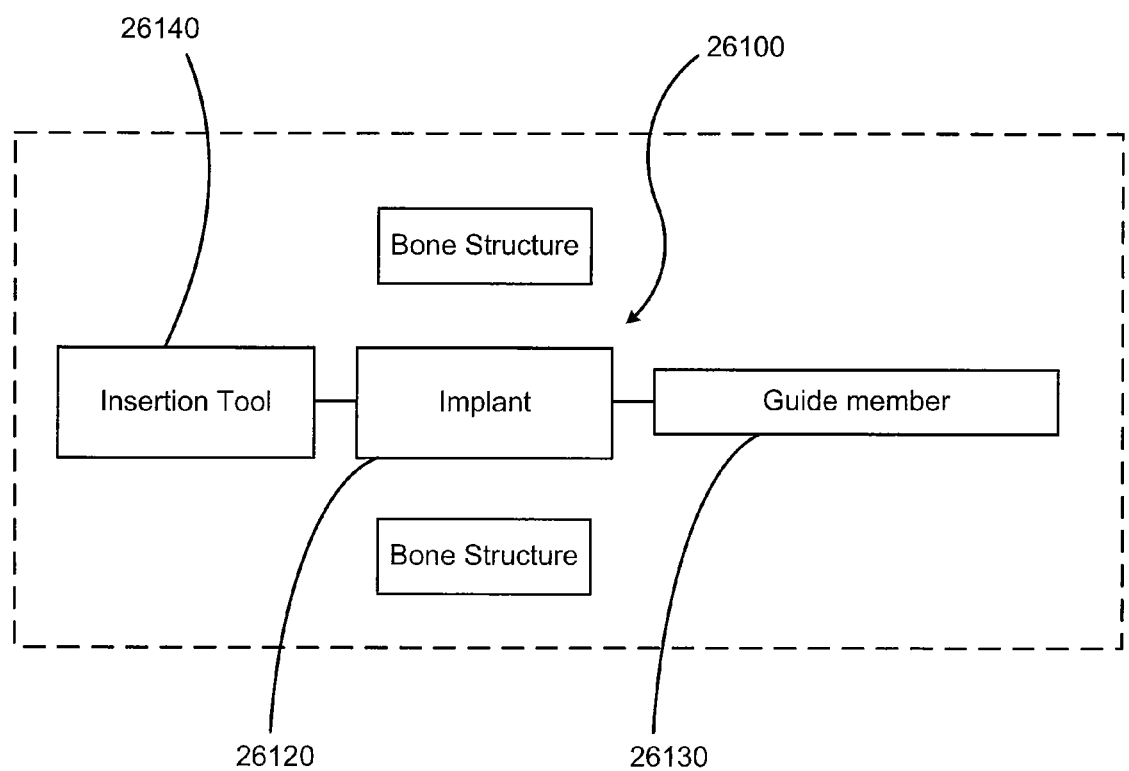
FIG. 132 is a schematic illustration of an embodiment of a medical device shown within a schematic representation of a body.

FIG. 132 is a schematic illustration of an example of a medical device that can be used to perform the methods described herein. A medical device can include an implant, a guide member and/or an insertion tool, as described herein. The various components of the medical device can be provided in some embodiments, for example, as a kit. Such a kit can include one or more implants, one or more guide members, and/or one or more insertion tools as described herein. A medical device 26100 includes an implant 26120 and a guide member 26130 that can be releasably coupled to the implant 26120. The guide member 26130 can be percutaneously inserted into a body and the implant 26120 can be inserted into the body and moved within the body using an insertion tool 26140 that can be releasably coupled to the implant 26120. The insertion tool 26140 can be, for example, coupled to a proximal end portion of the implant 26120. The insertion tool 26140 can apply a longitudinal force to a proximal end of the implant 26120 to move the implant 26120 through a portion of a body. In some embodiments, the medical device 26100 can be inserted through a cannula (not shown). The guide member 26130 can be releasably coupled to a distal end portion of the implant 26120 and can be used to guide the implant 26120 as the implant 26120 is moved by the insertion tool 26140. For example, the guide member 26130 can lead the implant 26120 along a path defined by a shape of the guide member 26130 as described in more detail below.

The guide member 26130 can include a distal end having a sharp tip (not shown in FIG. 132) that can be percutaneously inserted into a body through an exterior location on the body. The guide member 26130 can have a curved shape to allow the guide member 26130 to define a curved path as the guide member 26130 is maneuvered through a body. A proximal end portion of the guide member 26130 can have a connector or connector portion configured to releasably couple the guide member 26130 to the implant 26120. A separate connector member can be coupled to the guide member 26130, or the guide member 26130 can have a connector portion formed monolithically with the guide member 26130. For example, the guide member 26130 can include a threaded portion configured to threadedly couple to a threaded portion of a distal end portion of the implant 26120. In other embodiments, a proximal end portion of the guide member 26130 can include a key member (not shown) that can be received in, and releasably locked, within a keyway or opening at a distal end portion of the implant 26120. In some embodiments, a proximal end portion of the guide member 26130 is received within an opening in the distal end portion of the implant 26120 and held in place within the opening, in part, by a longitudinal force exerted on the implant 26120 by an insertion tool 26140.

The guide member 26130 can be formed, for example, as a flexible wire or a flexible needle having a lumen there through. The guide member can be formed such that it is sufficiently flexible about an axis normal to a longitudinal axis of the guide member 26130 and is sufficiently rigid when a force along the longitudinal axis such that the guide member 26130 substantially maintains its shape when percutaneously inserted into a body.

The insertion tool 26140 includes a distal end portion configured to be releasably coupled to the implant 26120. For example, the distal end portion of the insertion tool 26140 can define an opening and an interior space that can receive the proximal end portion of the implant 26120 therein. The proximal end portion of the implant 26120 can be sized to fit within the interior space of the distal end portion of the insertion tool 26140. When the insertion tool 26140 moves within a body in a direction toward the implant 26120, the implant 26120 will move in the same direction, but when the insertion tool 26140 is moved in an opposite direction, away from the implant 26120, the insertion tool 26140 will be removed from the proximal end portion of the implant 26120.

The insertion tool 26140 can have various different, shapes, sizes and configurations and include different coupling means to releasably couple the insertion tool 26140 to the implant 26120. Likewise, the proximal end portion of the implant 26120 can include various coupling means for coupling the implant 26120 to an insertion tool 26140. For example, in some embodiments, the insertion tool can be releasably coupled to the implant via a quick-connect coupling as shown and described in U.S. patent application Ser. No. 11/693,496, incorporated herein by reference. In some embodiments, the insertion tool is releasably coupled to the implant via a locking member disposed on the insertion tool also as shown and described in the above-mentioned application. In some embodiments, the insertion tool is releasably coupled to the implant using a key and keyway as shown and described herein with reference to FIGS. 15 and 16. For example, the distal end portion of the implant can include multiple notches that can matingly receive corresponding protrusions on the distal end portion of the insertion tool.

In use, a distal end of the guide member 26130 is percutaneously inserted into a body through a first location on the body. The implant 26120 can be coupled to the guide member 26130 before or after at least the distal end of the guide member 26130 has been inserted into the body. For example, the guide member 26130 can be inserted partially into the body and then the implant 26120 inserted into the body thereafter.

In some embodiments, the guide member 26130 has a length such that the guide member 26130 can be inserted into the body at a first location, and moved or pushed through the body along a curved path until the distal end of the guide member 26130 exits the body at a second location. In such an embodiment, the implant 26120 is inserted into the body after the distal end of the guide member 26130 exits the body at the second location.

In some embodiments, the distal end of the guide member 26130 is inserted through a first opening in a body at a first distance from a centerline of the body. The guide member 26130 can then be advanced, either with or without the implant 26120 being advanced within the body, until the distal end of the guide member 26130 exits the body at a second opening at a second distance from the centerline of the body and on a second side of the centerline of the body. In some embodiments, the first distance is substantially equal to the second distance. In other embodiments, the first distance is not equal to the second distance.

With the distal end portion of the implant 26120 coupled to the proximal end portion of the guide member 26130, the insertion tool 26140 can be used to push or advance the implant 26120 through the body to a selected position within the body. In some embodiments, an imaging device is used to assist in the positioning of the implant 26120 at a desired location within the body. As the implant 26120 is advanced in the body, the implant 26120 will move or advance the guide member 26130 through the body along a path defined by the guide member 26130. The implant 26120 can be moved, for example, to a position between two adjacent bone structures, such as, between two adjacent spinous processes. In doing so, the distal end of the guide member 26130 will exit the body at a second location, if not already exited prior to inserting or moving the implant 26120. After the implant 26120 is positioned in the desired location within the body (e.g., between bone structures), the guide member 26130 can be released from the implant 26120. For example, the distal end of the guide member 26130 positioned outside of the body at the second location can be grasped, and the releasable coupling between the guide member 26130 and the implant 26120 can be decoupled to release the guide member 26130 from the implant 26120.

The insertion tool 26140 can also be released from the implant 26120 and removed from the body before, after or simultaneously with the removal of the guide member 26130. After removing both the guide member 26130 and the insertion tool 26149, the implant 26120 will be left within the body at the desired implantation site.

FIG. 133 is an exploded view of an embodiment of a medical device including an implant, a guide member and insertion tool. The various components of the medical device can be provided, for example, as a kit. The kit can include one or more implants, and/or one or more guide members, and/or one or more insertion tools. A medical device 26200 includes an implant 26220 having a proximal end portion 26222 and distal end portion 26224. The distal end portion 26224 of the implant 26220 defines an opening 26228. The implant 26220 also includes a threaded portion 26226 disposed at the distal end portion 26224 as illustrated in FIGS. 133 and 134.

A guide member 26230 has a proximal end portion 26236, a distal end portion 26234 and a distal end 26238 having a sharpened or tapered shape. The proximal end portion 26232 of the guide member 26230 includes a threaded portion 26236. The threaded portion 26236 is configured to matingly couple to the corresponding threaded portion 26226 of the implant 26220. The distal end 26238 can be percutaneously inserted through an exterior location of a body and passed through the body until the distal end 26238 exits the body at a second exterior location of the body.

An insertion tool 26240 includes a middle portion 26242, a proximal end portion (not shown) and a distal end portion 26244. In some embodiments, the proximal end portion, the distal end portion 26244, and the middle portion 26242 are monolithically formed. In some embodiments, some or all of the proximal end portion, the distal end portion 26244, and the middle portion 26242 are formed as separate components and coupled together. The distal end portion 26244 defines an opening 26248 that is in communication with an interior space 26250 as best shown in FIG. 135. The proximal end portion 26222 of the implant 26220 can be received through the opening 26248 and disposed within the interior space 26250 to releasably couple the implant 26220 to the insertion tool 26240.

Figure 137:
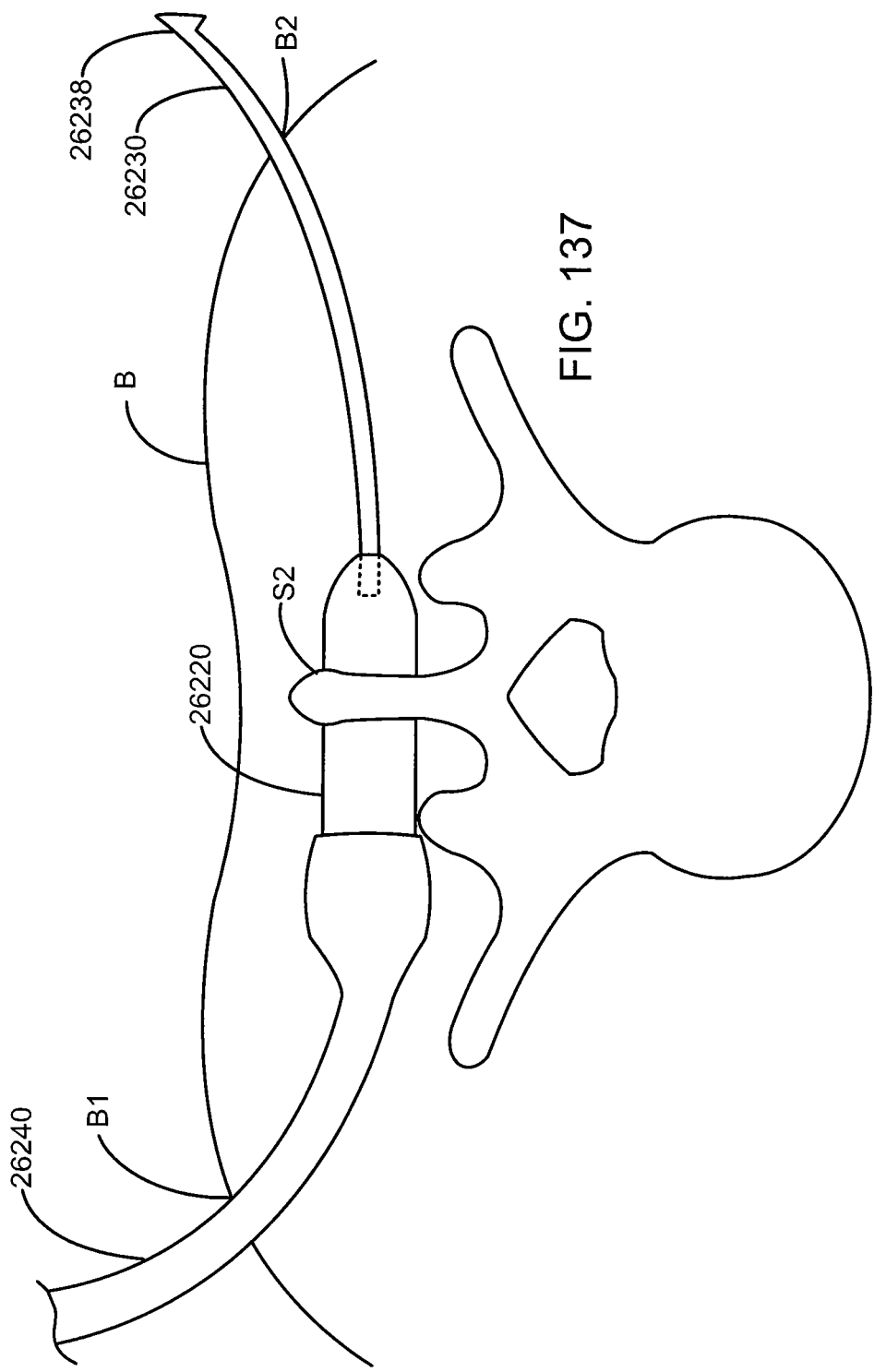
FIG. 137 is a top view of a portion of the medical device of FIG. 133 shown partially disposed within a body in a second position.

The guide member 26230 and the insertion tool 26240 can be used to deliver the implant 26220 to an implantation site within a body. FIGS. 136 and 137 illustrate an example of a procedure to deliver the implant 26220 to a location between adjacent spinous processes. As shown in FIG. 136, the guide member 26230 is percutaneously inserted through a first exterior location B1 in a body B. As described above, the implant 26220 can be coupled to the guide member 26230 before or after the guide member 26230 is inserted into a body. To couple the guide member 26230 to the implant 26220, the threaded portion 26236 of the guide member 26230 is rotated with respect to the mating threaded portion 26226 of the implant 26220. The curved shape of the guide member 26230 defines a curved path through the body as the guide member 26230 is moved through the body, indicated by the dashed-line path in FIG. 136. In this example procedure, the path of the guide member 26230 passes between adjacent spinous processes (only the inferior spinous process S1 is shown in FIG. 136). In this embodiment, the length of the guide member 26230 is such that the implant 26220 is still disposed outside the body B when the guide member 26230 is passed between the spinous processes.

The insertion tool 26240 is coupled to the proximal end portion of the implant 2620 to push or move the implant 26220 through the body B, as shown in FIG. 137. FIG. 137 is a top view illustrating a view above a second spinous process S2 superior to the spinous process S1. As the insertion tool 26240 moves or advances the implant 26220 to a position between the inferior spinous process S1 and the superior spinous process S2, the guide member 26230 will be advanced along the curved path defined by the curve of the guide member 26230. The guide member 26230 will be advanced until the distal tip 26238 exits a second exterior location B2 on the body B.

Once the implant 26220 is positioned in the desired location within the body, the insertion tool 26240 can be decoupled from the implant 26220 by pulling the insertion tool 26240 proximally and out of the body B. The guide member 26230 can also be removed from the implant 26220 by turning the guide member counter-clockwise to decouple the threaded coupling between the implant 26220 and the guide member 26230. It may be desirable to remove the guide member 26230 before removing the insertion tool 26240 so that the insertion tool 26240 can be held to stabilize the implant 26220 while decoupling the guide member 26230 from the implant 26220. After removing both the guide member 26230 and the insertion tool 26240, the implant 26220 will remain implanted between the two spinous processes S1 and S2.

Figure 138:
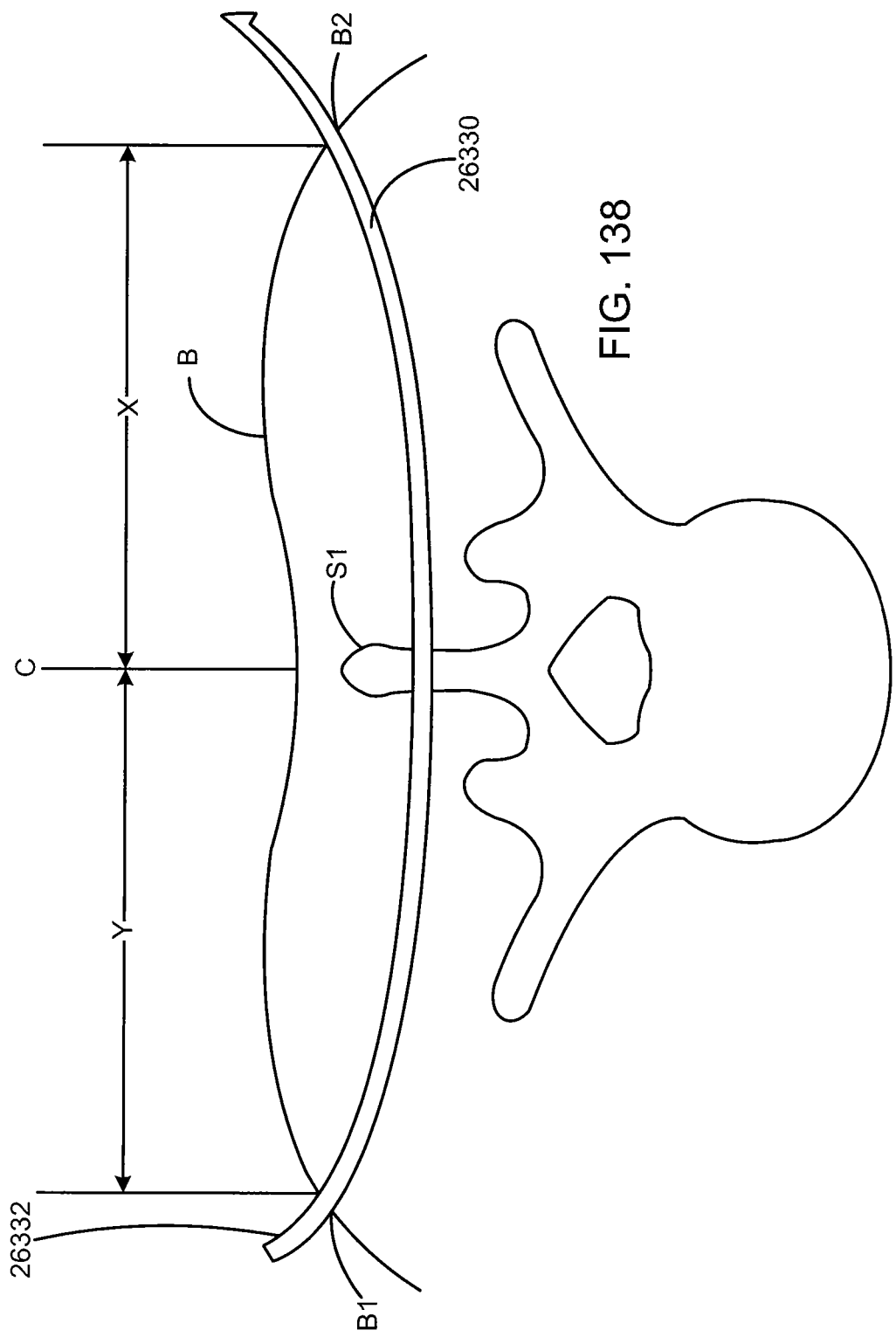
FIG. 138 is a top view of a portion of a medical device according to an embodiment of the inventions shown partially disposed within a body.

FIG. 138 illustrates an embodiment of a guide member that has sufficient length to extend within a body between an ingress location and an egress location before inserting an implant into the body. A guide member 26330 is shown percutaneously inserted through a first location B1 on a body B, passing between adjacent spinous processes (only an inferior spinous process S1 is shown), and a distal end 26338 of the guide member 26330 exiting the body B at an exit location B2. The ingress location B1 is at a distance Y from a centerline C of the body B, and the egress location B2 is at a distance X from the centerline C of the body B on an opposite side of the centerline C. In this embodiment, the distance X and the distance Y is substantially equal. In other embodiments, the distance X and the distance Y are not equal.

As stated previously, a distal end portion of an implant (not shown) can be releasably coupled to a proximal end portion 26332 of the guide member 26330, either before or after the guide member 26330 has been inserted into the body B. Although not needed for all embodiments, an optional insertion tool (not shown) can be used to advance the implant and guide member 26330 along a curved path defined by the guide member 26330 as described previously. Alternatively, after the distal end 26338 is positioned outside of the egress location B2, the distal end 26338 of the guide member 26330 can be grasped (e.g., by hand, with forceps, or using another instrument) and pulled such that the implant is moved (e.g., pulled) through the body B and to a desired implantation site. For example, the implant can be pulled through the body B along the curved path defined by the guide member 26330 and is positioned between adjacent spinous processes.

FIGS. 139-141 illustrate another embodiment of a medical device. A medical device 26400 includes an implant 26420 and guide member 26430. The implant 26420 and guide member 26430 are similar to the embodiments illustrated in FIG. 133 except in this embodiment the coupling between the implant 26420 and the guide member 26430 includes a key configured to be received within a keyway. The implant 26420 has a proximal end portion 26426 and a distal end portion 26424. The distal end portion 26424 defines an opening 26428 and a slot or keyway 26458, as shown in the distal end view of the implant 26420 of FIG. 140. The slot 26458 is in fluid communication with an interior space 26460 within the implant 26420. The guide member 26430 has a distal end portion 26434 that includes a sharp distal end or tip 26438. The guide member 26430 also has a proximal end portion 26432 that includes a key 26456. The key 26456 can be received through the opening 26428 and the slot 26458 to releasably couple the guide member 26430 to the implant 26420.

For example, to couple the guide member 26430 to the implant 26420, the guide member 26430 is initially turned or oriented such that the key 26456 is substantially aligned with the opening 26428 and slot 26458. The key 26456 is then placed through the slot 26458 and then turned (e.g., 90 degrees) such that the key 26456 is at least partially misaligned with the slot 26458 and disposed within the interior region 26460 of the implant 26420, as shown in FIG. 141.

After the implant 26420 coupled to the guide member 26430, the implant 26420 can be inserted within a body in the same manner as described previously, using an insertion tool (not shown) releasably coupled to the proximal end portion 26426 of the implant 26420. For example, the insertion tool can apply a longitudinal force on a proximal end of the implant 26420 to move or advance the implant 26420 within a body. This will in turn move or advance the guide member 26430 coupled to the implant 26420. As with the previous embodiments, the implant 26420 will be advanced along a curved path defined by the guide member 26430. Once the implant 26420 is positioned at an implantation site, the guide member 26430 can be decoupled from the implant 26420 and removed from the body. To decouple the guide member 26430 from the implant 26420, the guide member 26430 is turned such that the key 26456 is substantially aligned with the slot 26458. This will allow the guide member 26430 to be moved out of the interior region 26460 of the implant 26420 through the slot 26458, and removed from the body. The insertion tool can also be removed as previously described.

FIGS. 142 and 143 illustrate another embodiment of guide member and implant. A medical device 26500 includes a guide member 26530 and an implant 26520. The implant 26520 and guide member 26530 are similar to the previous embodiments, except in this embodiment, the guide member 26530 is coupled to the implant 26520 in a manner similar to the coupling between the implant 26220 and insertion tool 26240 illustrated in FIG. 143. The implant 26520 has a proximal end portion 26522 and a distal end portion 26524 that defines an opening 26528. The distal end portion 26524 includes a surface 26562 disposed within the opening 26528.

The guide member 26530 has a distal end portion 26534 that includes a distal end 26538, and a proximal end portion 26532 that can be received within the opening 26528. As shown in FIG. 143, the implant 26520 can be advanced through a body B using an insertion tool 26540 as previously described. As a force is applied by the insertion tool 26540 and translated to a proximal end the implant 26520 in the direction of arrow D, the implant 26520 and the guide member 26530 will be advanced along a path defined by the guide member 26530. A longitudinal force is applied by the implant 26520 on the proximal end portion 26532 of the guide member 26530 to move the implant 2620 in a direction toward the distal end 26538 of the guide member 26530. This force will advance the guide member 26530 within the body, and maintain the position of the proximal end portion 26532 of the guide member 26530 within the opening 26528 of the implant 26520. In addition, internal walls of the implant 26520 that define the opening 26528 help maintain the position of the proximal end portion 26532 of the guide member 26530 within the opening 26528 of the implant 26520. After the implant 26520 is positioned at a desired location within the body (e.g., between adjacent spinous processes), and the distal tip 26538 of the guide member 26530 has exited the body at a location B2, the guide member 26530 can be removed by pulling the guide member 26530 out through the exit location 26554.

The guide members described above can be used in the deployment of a variety of different types of implants. The guide members can be configured to be releasably coupled to any of the implants, extension limiting devices, extraction devices described herein or with other devices not specifically described. For example, a guide member as described herein can be configured to be releasably coupled to an implant 6610 illustrated with references to FIGS. 17-23. A distal end portion of the implant 6610 can be configured with an opening that can receive a proximal end of a guide member as described herein. Various different coupling methods can also be included on an implant 6610, such as the key and keyway coupling or the threaded coupling described above. Thus, the implants and guide members described herein are merely example embodiments to illustrate and described the use of a guide member in the deployment of an implant within a body.

Further, the various coupling methods described herein to releasably couple a guide member to a distal end portion of an implant can also be used to couple an implant to an insertion tool. Likewise, the various coupling methods described herein to releasably couple an implant to an insertion tool can be used to couple a guide member to an implant. For example, a guide member and implant can each be configured to include a quick-connect coupling to releasably couple the guide member to the implant. In another example, a guide member can include one or more protrusions configured to be received in one or more notches formed in the distal end portion of the implant as described herein with reference to the implant and insertion tool of FIGS. 15 and 16.

Figure 144:
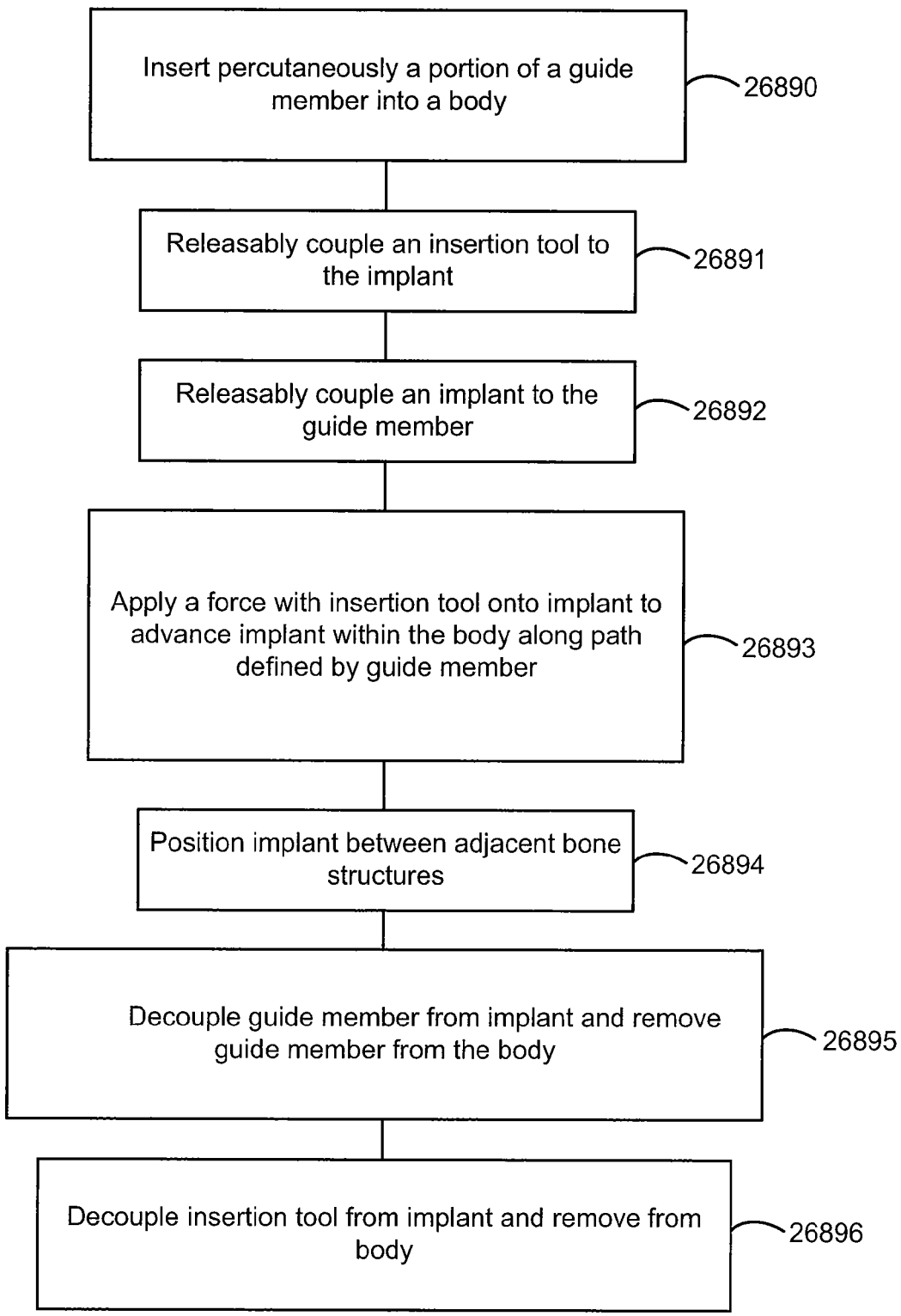

FIG. 144 is a flowchart of a method of using a guide member to deliver an implant between spinous processes. At 26890, at least a portion of a guide member as described herein is inserted percutaneously into a body through at a first exterior location on the body. A distal end portion of an implant is releasably coupled to a proximal end portion of the guide member at 26891. The implant can be coupled to the guide member either before or after the guide member is inserted into the body. At 26892, an insertion tool is releasably coupled to a proximal end portion of the implant. The insertion tool can be coupled to the implant either before or after the implant is coupled to the guide member. At 26893, the insertion tool applies a force to the implant to move or advance the implant such that the guide member is advanced within the body along a path defined by the guide member. A trajectory of the path is defined by the shape of the guide member. For example, the guide member can have a curved shape and will define a curved path.

At 26894, the implant is positioned between adjacent bone structures, such as between a superior and inferior spinous process. The guide member is advanced such that a distal end of the guide member exits the body at a second location. As stated previously, the guide member can be advanced such that a distal end of the guide member extends from the body at a second location either before or after the implant has been inserted into the body. Thus, the guide member can be so advanced simultaneously with the positioning of the implant between adjacent bone structures. After the implant is positioned between the bone structures, at 26895, the guide member is decoupled from the implant and removed from the body at a second location on the body. At 26896 the insertion tool is decoupled from the implant and removed from the body.

Figure 145:
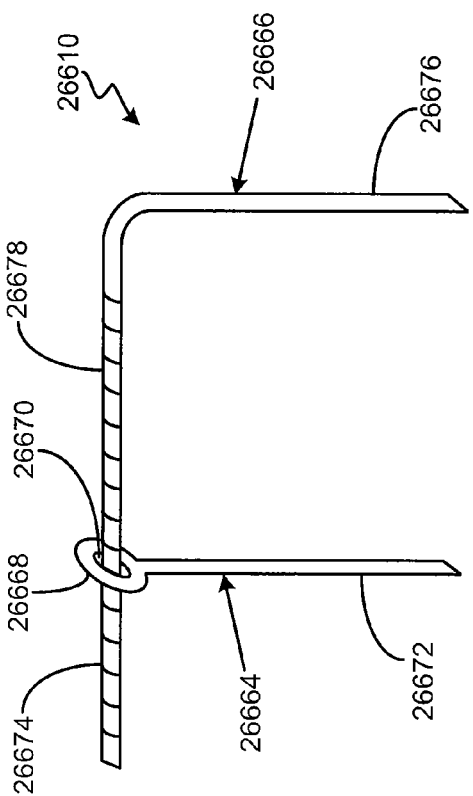

FIG. 145 illustrates a device according to another embodiment of the invention. A measurement device 26610 can be used in conjunction with a procedure to deliver an implant between adjacent bone structures, or a procedure to distract adjacent bone structures, such as, for example, a procedure to distract adjacent spinous processes as described herein. For example, the measurement device 26610 can be used to measure the relative movement between the adjacent bone structures being distracted and to measure the amount of correction achieved by a distraction procedure. The measurement device 26610 can be used independent of an implant or other device used to distract the adjacent bone structures, and without the use of an imaging device, such as a fluoroscopy device. In addition, the measurement device 26610 is not limited to use in conjunction with any particular type of distraction or extension limiting device. The measurement device 26610 can also increase the reliability and accuracy of a procedure to measure the amount of distraction by reducing the potential variability of the interface between, for example, a distraction device and an imaging device. In addition, the measurement device 26610 extends outside of a body, which allows a physician to visualize the physical correction (e.g., distraction) being made to the bone structures external from the patient rather than measuring the correction on an imaging screen. Thus, the variability and/or error factor of the electronic interface is eliminated.

As shown in FIG. 145, the measurement device 26610 includes a first anchor member 26664 and a second anchor member 26666 that can be coupled together such that the relative movement between the first anchor member 26664 and the second anchor member 26666 can be viewed and/or measured. The first anchor 26664 includes a first portion 26668 that defines an opening 26670, and a second portion 26672 that can be driven or nailed to a bone structure. The second anchor member 26666 includes a first portion 26674 that can be received through the opening 26670 of the first anchor member 26664, and a second portion 26676 that can be driven or nailed to a bone structure. The second portion 26672 of the first anchor member 26664, and the second portion 26676 of the second anchor member 26666 can alternatively include a threaded portion to screw or threadedly couple each of the second portion 26672 and the second portion 26676 to a bone structure.

The first portion 26674 of the second anchor member 26666 can move or slide relative to the first anchor member 26664 via the opening 26670. The second anchor member 26666 also includes markings 26678 along a longitudinal length of the first portion 26674. The markings 26678 can be measurement graduations and can be used to determine an amount of movement between the first anchor member 26664 and the second anchor member 26666 as described in more detail below.

Figure 146:
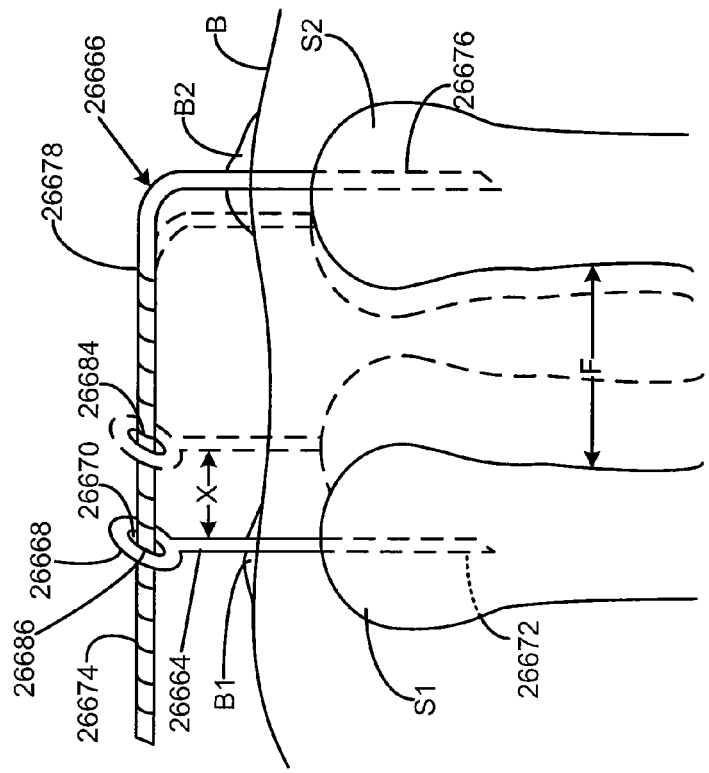

FIG. 146 illustrates an example use of the measurement device 26610 to measure the distraction achieved between adjacent spinous processes after insertion and/or use of a distraction device such as an implant or distraction device as described herein. Prior to the insertion of the distraction device, the second portion 26672 of first anchor member 26664 is percutaneously inserted through a first opening B1 of a body B, and removably secured to a first spinous process S1 (e.g., nailed or driven into the first spinous process S1). The first portion 26674 of the second anchor member 26666 is disposed through the opening 26670 of the first anchor member 26664, and the second portion 26676 of the second anchor member 26666 is inserted through an opening B2 of the body B, and removably secured to a second spinous process S2 (e.g., nailed or driven into the second spinous process S2). The dashed-line illustration of a portion of the first anchor member 26664 and a portion of the second anchor member 26666 is shown to indicate a position of the first spinous process S1 and the second spinous process S2, before being distracted. A first measurement can be taken using the markings 26678. For example, a first measurement can be taken where the 26674 passes through the opening 26670 of the first anchor member 26664 as indicated at 26684, prior to distracting the adjacent spinous processes.

A distraction device such as, for example, an implant or distraction device described herein (not shown) can be placed between the spinous process S1 and the spinous process S2. A force F can be exerted on the spinous process S1 and the spinous process S2 to move the first spinous process S1 and second spinous process S2 apart a distance X. A second measurement can be taken where the first portion 26674 of the second anchor member 26666 passes through the opening 26670 of the first anchor member 26664 at 26686, after distracting the adjacent spinous processes. The distance X can be calculated as the difference between the first measurement and the second measurement.

Figure 147:
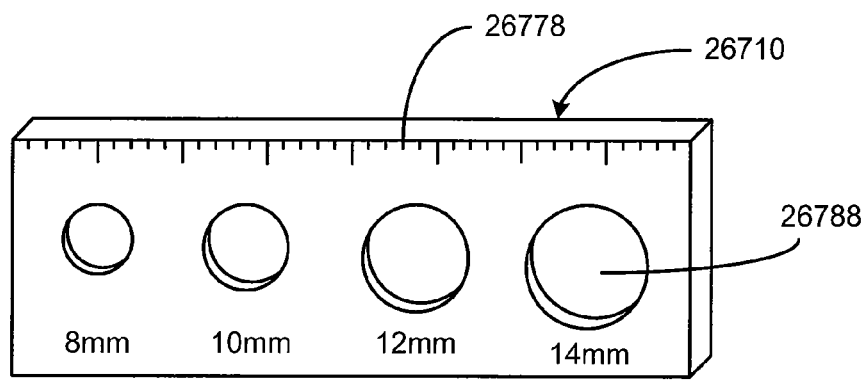

FIG. 147 illustrates a measurement device according to another embodiment. A measurement device 26710 is similar to a template that can be used to determine the size of an implant that is appropriate for implantation in the space between bone structures. For example, the measurement device 26710 can be used to measure the size of an implant to be placed between adjacent spinous processes. Rather than approximating the size of an appropriate implant when, for example, a patient is under anesthesia and unable to provide feedback to the physician as to whether their pain has been relieved, the measurement device 26710 can be used when the patient is awake. For example, an x-ray of a patient's spine can be taken while the patient bends over. A determination can be made as to the amount of distraction needed, based on the level of pain relief the patient feels as the patient bends over. The physician can place the measurement device 26710 adjacent an x-ray image, to measure the amount of distraction necessary and the size of implant needed to be placed between the adjacent spinous processes.

The measurement device 26710 is a substantially planar device similar to a ruler or template. The measurement device 26710 can be formed of transparent material to allow the physician to see an image, for example, from an x-ray, through. The measurement device 26710 includes markings 26778, and defines multiple openings 26788. The markings 26778 are measurement graduations that can be scaled to correspond to the type of image (e.g., x-ray) being used during the measurement process. The openings 26788 can be sized, for example, to correspond to various sizes of interspinous implants. The scale of the markings 26788 to the size of the openings 26788 can vary depending on the particular imaging device. For example, the markings 26788 used to measure the image can be a 1:1 scale to the dimensions used for the openings 26788. For example, for a 1:1 scale, 10 graduations of the markings 26788 equals a 10 mm diameter opening 26788. Other scales can alternatively be used.

Figure 148:
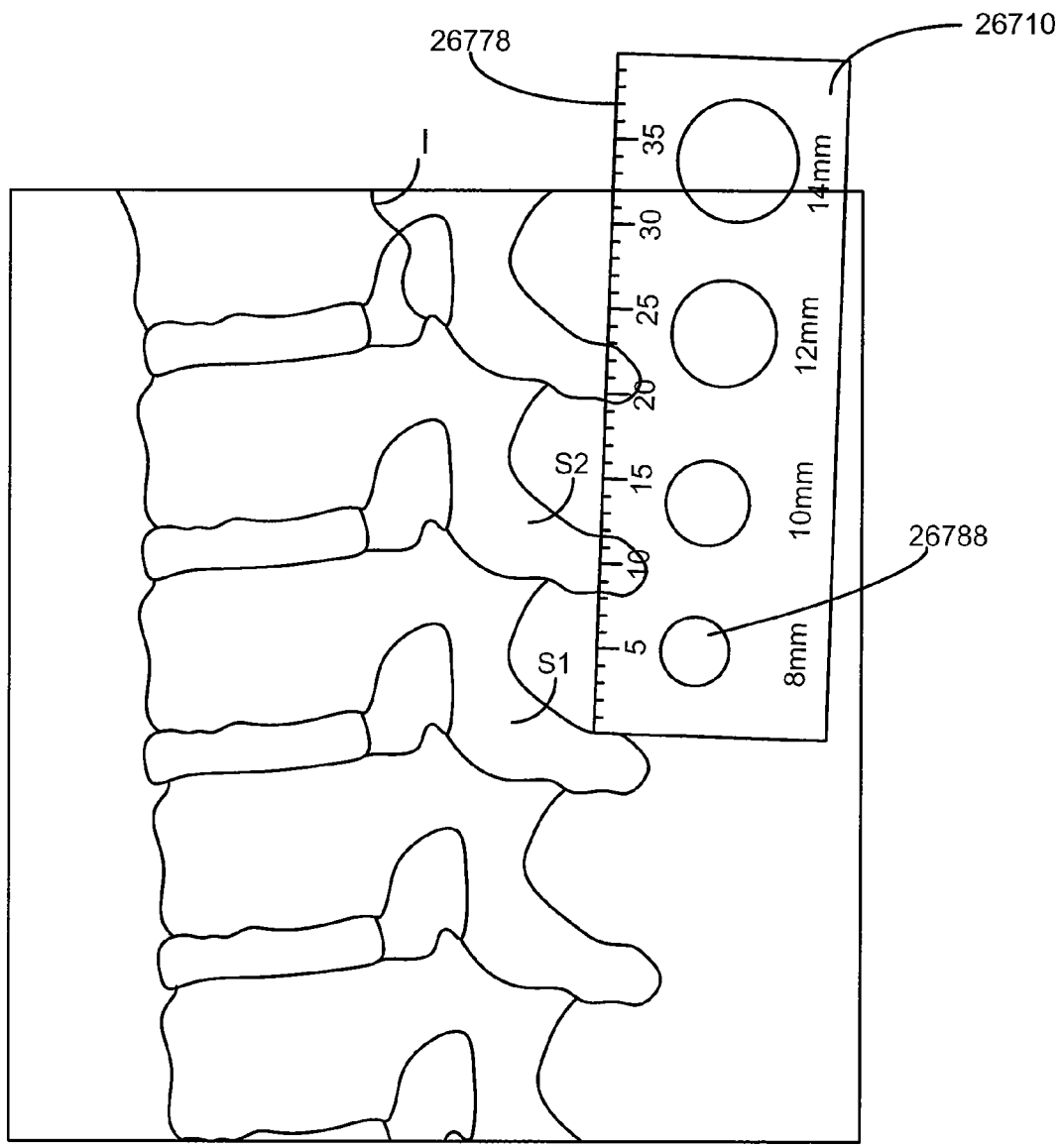

FIG. 148 illustrates an example use of the measurement device 26710. The measurement device 26710 is placed adjacent to, or in contact with an image I, which is a side view of a portion of a patient's spine. A visual of the spinal components can be viewed through the measurement device 26710. To determine a size of an implant needed to be placed between a spinous process S1 and a spinous process S2, a distance between the spinous processes is measured using the markings 26778. The size of implant appropriate for implantation is then determined by the opening 26788 that corresponds to the measurement of the markings 26778. In the example shown in FIG. 148, a distance between the spinous processes S1 and S2 is approximately 6 graduations as indicated on markings 26778, and the appropriate implant size would be 8 mm as indicated by the opening 26788 that corresponds to the 6 mm graduation.

Figure 149:
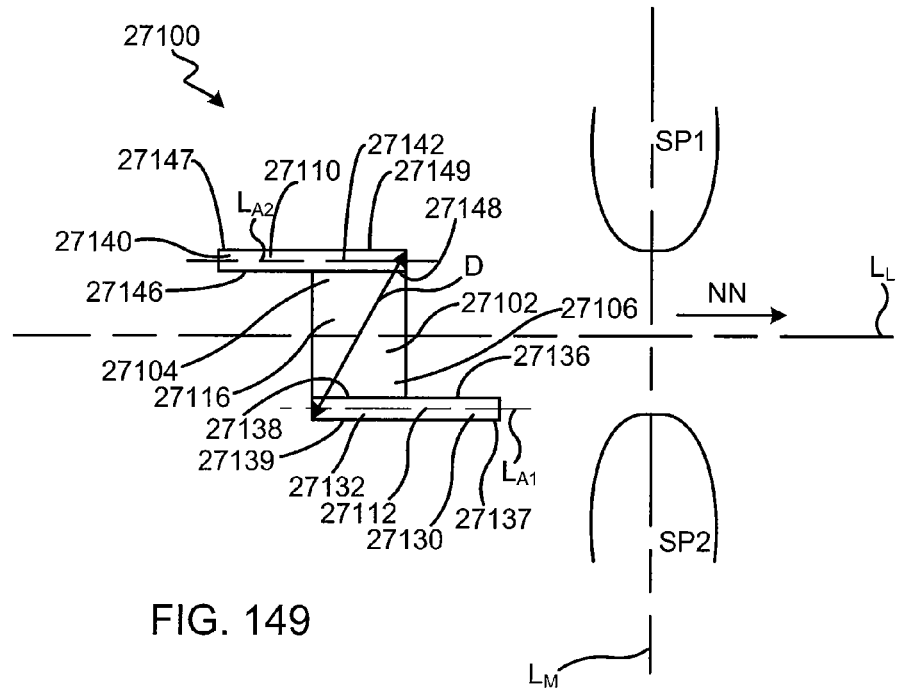
Figure 150:
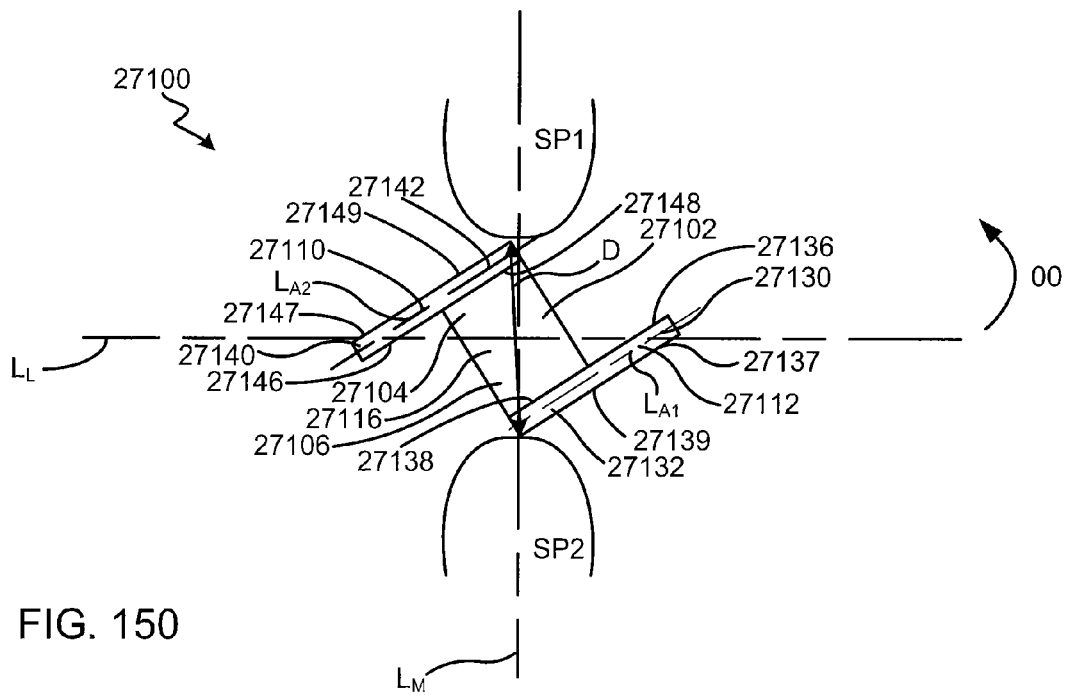
Figure 151:
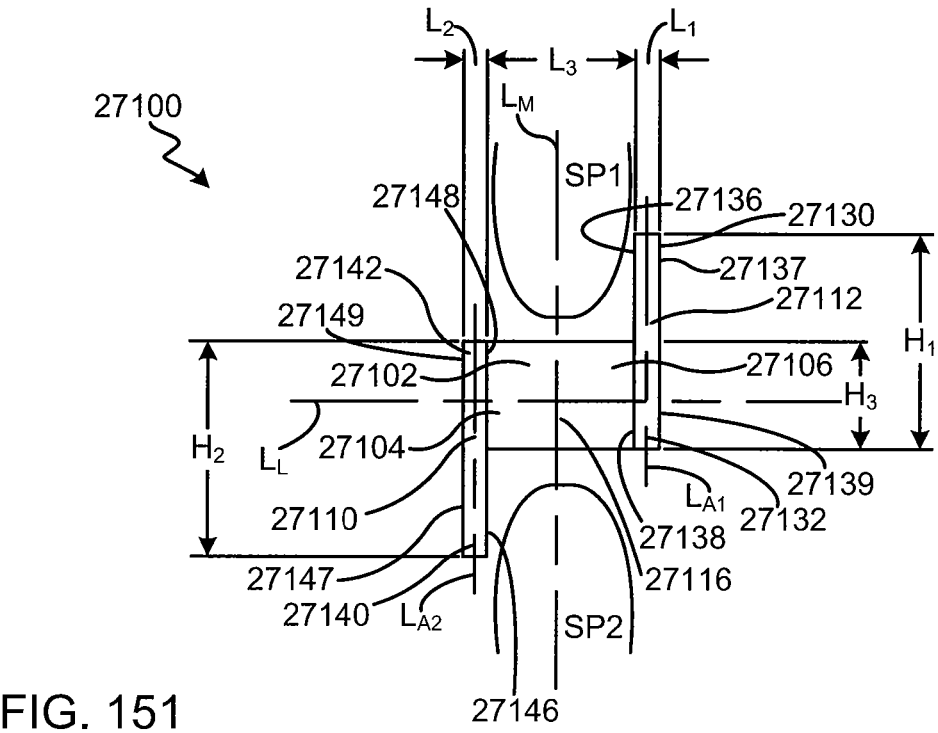
Figure 152:
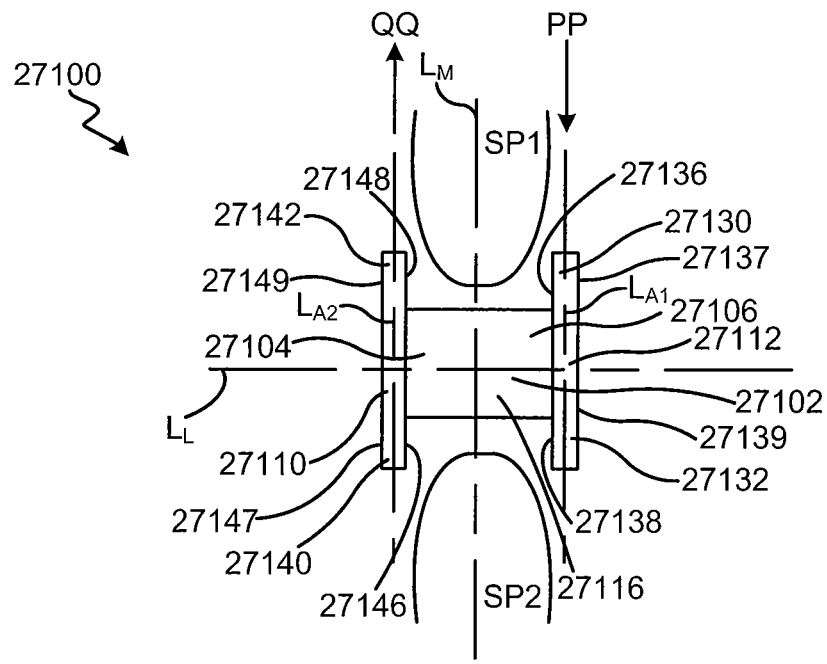

FIGS. 149-152 are schematic illustrations of an implant 27100 according to an embodiment of the invention in a first configuration, a second configuration, a third configuration and a fourth configuration, respectively. The implant 27100 includes a support member 27102, a first retention member 27112 and a second retention member 27110. The support member 27102 has a first end portion 27106, a second end portion 27104 and an outer surface 27116. As shown in FIGS. 151 and 152, at least a portion of the outer surface 27116 is configured to be disposed between a first spinous process SP1 and a second spinous process SP2.

The first retention member 27112 has a first end portion 27130, a second end portion 27132 and defines a longitudinal axis $L_{A1}$. The first end portion 27130 of the first retention member 27112 has an inner surface 27136 and an outer surface 27137 opposite the inner surface 27136. Similarly, the second end portion 27132 of the first retention member 27112 has an inner surface 27138 and an outer surface 27139 opposite the inner surface 27138. Although the inner surface 27136 of the first end portion 27130 and the inner surface 27138 of the second end portion 27132 are shown as forming a continuous, co-planar surface, in other embodiments, the inner surface 27136 of the first end portion 27130 can be discontinuous or in a plane different than the inner surface 27138 of the second end portion 27132. Similarly, in some embodiments, the outer surface 27137 of the first end portion 27130 can be discontinuous or in a plane different than the outer surface 27139 of the second end portion 27132.

The second retention member 27110 has a first end portion 27140, a second end portion 27142 and defines a longitudinal axis $L_{A2}$. The first end portion 27140 of the second retention member 27110 has an inner surface 27146 and an outer surface 27147 opposite the inner surface 27146. Similarly, the second end portion 27142 of the second retention member 27110 has an inner surface 27148 and an outer surface 27149 opposite the inner surface 27148. Although the inner surface 27146 of the first end portion 27140 and the inner surface 27148 of the second end portion 27142 are shown as forming a continuous, co-planar surface, in other embodiments, the inner surface 27146 of the first end portion 27140 can be discontinuous or in a plane different than the inner surface 27148 of the second end portion 27142. Similarly, in some embodiments, the outer surface 27147 of the first end portion 27140 can be discontinuous or in a plane different than the outer surface 27149 of the second end portion 27142.

The first retention member 27112 is slidably coupled to the first end portion 27106 of the support member 27102. As indicated by the arrow PP in FIG. 152, the first retention member 27112 can translate along its longitudinal axis $L_{A1}$ between a first position (FIGS. 149-151) and a second position (FIG. 152). When the first retention member 27112 is in the first position, the first end portion 27130 is spaced apart from the support member 27102 and the second end portion 27132 is adjacent the first end portion 27106 of the support member 27102. Moreover, as described in more detail herein, when the first retention member 27112 is in the first position, the first end portion 27130 can contact and/or engage the first spinous process SP1 (or its associated surrounding tissue) to limit lateral movement of the support member 27102 along the lateral axis $L_L$ and relative to the adjacent spinous processes SP1 and SP2. When the first retention member 27112 is in the second position, the first end portion 27130 is spaced apart from the support member 27102 and the second end portion 27132 is spaced apart from the support member 27102. Moreover, as described in more detail herein, when the first retention member 27112 is in the second position, the first end portion 27130 can contact and/or engage the first spinous process SP1 (or its associated surrounding tissue) and the second end portion 27132 can contact and/or engage the second spinous process SP2 (or its associated surrounding tissue). In this manner, when the first retention member 27112 is in its second position, the first retention member 27112 can limit lateral movement of the support member 27102 along the lateral axis $L_L$ and relative to the adjacent spinous processes SP1 and SP2.

Similarly, the second retention member 27110 is slidably coupled to the second end portion 27104 of the support member 27102. As indicated by the arrow QQ in FIG. 152, the second retention member 27110 can translate along its longitudinal axis $L_{A2}$ between a first position (FIGS. 149-151) and a second position (FIG. 152). When the second retention member 27112 is in the first position, the first end portion 27140 is spaced apart from the support member 27102 and the second end portion 27142 is adjacent the second end portion 27104 of the support member 27102. Moreover, as described in more detail herein, when the second retention member 27110 is in the first position, the first end portion 27140 can contact and/or engage the second spinous process SP2 (or its associated surrounding tissue) to limit lateral movement of the support member 27102 along the lateral axis $L_L$ and relative to the adjacent spinous processes SP1 and SP2. When the second retention member 27110 is in the second position, the first end portion 27140 is spaced apart from the support member 27102 and the second end portion 27142 is spaced apart from the support member 27102. Moreover, as described in more detail herein, when the second retention member 27110 is in the second position, the first end portion 27140 can contact and/or engage the second spinous process SP2 (or its associated surrounding tissue) and the second end portion 27142 can contact and/or engage the first spinous process SP1 (or its associated surrounding tissue). In this manner, when the second retention member 27110 is in its second position, the second retention member 27110 can limit lateral movement of the support member 27102 along the lateral axis $L_L$ and relative to the adjacent spinous processes SP1 and SP2.

In use, the adjacent spinous processes SP1 and SP2 can be distracted prior to inserting the implant 27100 into the patient. An access passageway can be defined to allow insertion of the implant 27100. The passageway can have any suitable shape and can be formed by any suitable method, as discussed herein. After the access passageway is defined, the implant 27100 can be inserted percutaneously along a lateral access passageway, as shown by the arrow NN in FIG. 149. As shown in FIG. 149, during insertion, the implant 27100 is placed in a first configuration in which the first retention member 27112 is in the first position, the second retention member 27110 is in the first position, the longitudinal axis $L_{A1}$ of the first retention member 27112 is substantially parallel to the lateral axis $L_L$, and the longitudinal axis $L_{A2}$ of the second retention member 27110 is substantially parallel to the lateral axis $L_L$. The overall length of the implant 27100 (i.e., the sum of lengths $L_1$, $L_2$ and $L_3$ as shown in FIG. 151) is such that the implant 27100 can be disposed between the first spinous process SP1 and the second spinous process SP2 when the implant is in the first configuration.

Although the implant 27100 is described as being inserted after an access passageway is defined, in some embodiments, an access passageway can be defined by the implant when it is being inserted. For example, in some embodiments, the first end portion 27130 of the first retention member 27112 can include a sharp tip suitable for defining a passageway. Similarly, in some embodiments, portions of the retention members 27112, 27110 and/or the support member 27102 can be tapered such that a passageway can be defined when the implant 27100 is being inserted.

When the implant 27100 is between the first spinous process SP1 and the second spinous process SP2, the implant 27100 can be rotated into the second configuration. As shown by the arrow OO in FIG. 150, the implant 27100 can be rotated relative to the adjacent spinous processes SP1 and SP2 about an axis substantially normal to a mid-line axis $L_M$ defined by the spinal column. The diagonal dimension D across the support member 27102 and including a portion of the first retention member 27112 and the second retention member 27110 is such that the implant 27100 can be disposed between the first spinous process SP1 and the second spinous process SP2 when the implant is in the second configuration. Said another way, the diagonal dimension D is sized such that the implant 27100 can be rotated as shown in FIG. 150. Although the diagonal dimension D is shown as being less than the spacing between the first spinous process SP1 and the second spinous process SP2 such that the implant 27100 can be rotated without contacting the first spinous process SP1 and/or the second spinous process SP2, in other embodiments, the diagonal dimension D can be greater than the spacing between the adjacent spinous processes SP1 and SP2. In such embodiments, the implant can distract the adjacent spinous processes SP1 and SP2 when in the second configuration (i.e., when rotating relative to the adjacent spinous processes SP1 and SP2).

As shown in FIG. 151, the implant 27100 can be rotated relative to the adjacent spinous processes SP1 and SP2 approximately ninety degrees into the third configuration (i.e., the implant can be moved from the first configuration shown in FIG. 149 to the third configuration shown in FIG. 151). When the implant 27100 is in the third configuration, the first retention member 27112 is in its first position and the second retention member 27110 is in its first position. Additionally, when the implant 27100 is in the third configuration, the inner surface 27136 of the first end portion 27130 of the first retention member 27112 is disposed adjacent the first spinous process SP1. Said another way, when the implant 27100 is in the third configuration, the inner surface 27136 of the first end portion 27130 of the first retention member 27112 is between the outer surface 27137 of the first end portion 27130 of the first retention member 27112 and the first spinous process SP1. In some embodiments, the inner surface 27136 of the first end portion 27130 can substantially contact a portion of the first spinous process SP1 (either directly or indirectly through surrounding tissue) when the implant 27100 is in the third configuration.

Similarly, when the implant 27100 is in the third configuration, the inner surface 27146 of the first end portion 27140 of the second retention member 27110 is disposed adjacent the second spinous process SP2. Said another way, when the implant 27100 is in the third configuration, the inner surface 27146 of the first end portion 27140 of the second retention member 27110 is between the outer surface 27147 of the first end portion 27140 of the second retention member 27110 and the second spinous process SP2. In some embodiments, the inner surface 27146 of the first end portion 27140 can substantially contact a portion of the second spinous process SP2 (either directly or indirectly through surrounding tissue) when the implant 27100 is in the third configuration.

After the implant 27100 is placed in the third configuration, the first retention member 27112 can be moved along its longitudinal axis $L_{A1}$ from the first position to the second position, as indicated by the arrow PP in FIG. 152. Said another way, the first retention member 27112 can be moved from the first position to the second position along an axis substantially parallel to the mid-line axis $L_M$. Similarly, the second retention member 27110 can be moved along its longitudinal axis $L_{A2}$ from the first position to the second position, as indicated by the arrow QQ in FIG. 152. Said another way, the second retention member 27110 can be moved from the first position to the second position along an axis substantially parallel to the mid-line axis $L_M$. As indicated by the arrows PP and QQ, the first retention member 27112 can be moved in a first direction (downward) and the second retention member 27110 can be moved in a second direction (upward), opposite the first direction. In this manner, the implant can be placed into the fourth configuration, as shown in FIG. 152.

When the implant 27100 is in the fourth configuration, the first end portion 27130 of the first retention member 27112 is spaced apart from the support member 27102 and the second end portion 27132 of the first retention member 27112 is spaced apart from the support member 27102. Moreover, when the implant 27100 is in the fourth configuration, the first end portion 27130 is disposed adjacent the first spinous process SP1 and the second end portion 27132 is disposed adjacent the second spinous process SP2. Said another way, when the implant 27100 is in the fourth configuration, the inner surface 27136 of the first end portion 27130 of the first retention member 27112 is between the outer surface 27137 of the first end portion 27130 of the first retention member 27112 and the first spinous process SP1. Similarly, the inner surface 27138 of the second end portion 27132 of the first retention member 27112 is between the outer surface 27139 of the second end portion 27132 of the first retention member 27112 and the second spinous process SP2. In this manner, when the implant 27100 is in the fourth configuration, the first retention member 27112 can limit lateral movement of the support member 27102 along the lateral axis $L_L$ and relative to the adjacent spinous processes SP1 and SP2. In some embodiments, the inner surface 27136 of the first end portion 27130 and/or the inner surface 27138 of the second end portion 27132 can substantially contact a portion of the first spinous process SP1 and/or the second spinous process SP2, respectively (either directly or indirectly through surrounding tissue) when the implant 27100 is in the fourth configuration.

When the implant 27100 is in the fourth configuration, the first end portion 27140 of the second retention member 27110 is spaced apart from the support member 27102 and the second end portion 27142 of the second retention member 27110 is spaced apart from the support member 27102. Moreover, when the implant 27100 is in the fourth configuration, the first end portion 27140 is disposed adjacent the second spinous process SP2 and the second end portion 27142 is disposed adjacent the first spinous process SP1. Said another way, when the implant 27100 is in the fourth configuration, the inner surface 27146 of the first end portion 27140 of the second retention member 27110 is between the outer surface 27147 of the first end portion 27140 of the second retention member 27110 and the second spinous process SP2. Similarly, the inner surface 27148 of the second end portion 27142 of the second retention member 27110 is between the outer surface 27149 of the second end portion 27142 of the second retention member 27110 and the first spinous process SP1. In this manner, when the implant 27100 is in the fourth configuration, the second retention member 27110 can limit lateral movement of the support member 27102 along the lateral axis $L_L$ and relative to the adjacent spinous processes SP1 and SP2. In some embodiments, the inner surface 27146 of the first end portion 27140 and/or the inner surface 27148 of the second end portion 27142 can substantially contact a portion of the second spinous process SP2 and/or the first spinous process SP1, respectively (either directly or indirectly through surrounding tissue) when the implant 27100 is in the fourth configuration.

If or when it is desirable to change the position of the implant 27100 and/or remove the implant 27100, the first retention member 27112 can be moved back to its first position and the second retention member 27110 can be moved back to its first position, thereby allowing the implant 27100 to be rotated (in direction opposite from that indicated by the arrow OO in FIG. 150) to place the implant 27100 back in the second configuration. Once the implant 27100 is in the second configuration, the implant 27100 can be repositioned and/or removed. If or when the implant 27100 is repositioned as desired, the implant can be moved to the fourth configuration, as described above.

In some embodiments, the first retention member 27112 and the second retention member 27110 can be moved relative to the support member 27102 serially. In other embodiments, the first retention member 27112 and the second retention member 27110 can be moved relative to the support member 27102 simultaneously. In yet other embodiments, only one of the first retention member 27112 or the second retention member 27110 can be moved relative to the support member 27102.

In some embodiments, the first retention member 27112 can be temporarily maintained in its first position and/or its second position by a locking mechanism as shown and described above in connection with other embodiments (see e.g., FIGS. 95-99). Similarly, in some embodiments, the first retention member 27112 can be biased in its first position and/or its second position by a biasing member as shown and described above in connection with other embodiments (see e.g., FIGS. 118-123). In some embodiments, the second retention member 27110 can be temporarily maintained in its first position and/or its second position by a locking mechanism as shown and described above in connection with other embodiments (see e.g., FIGS. 95-99). Similarly, in some embodiments, the second retention member 27110 can be biased in its first position and/or its second position by a biasing member as shown and described above in connection with other embodiments (see e.g., FIGS. 118-123).

Although the implant 27100 is shown and described without reference to any specific dimensions, the implant 27100 can have any suitable size to be disposed between the adjacent spinous processes SP1 and SP2 as described above. In some embodiments, for example, the implant 27100 can be sized such that the diagonal dimension D is less than the distance between the first spinous process SP1 and the second spinous process SP2 such that the implant 27100 can be rotated without substantially contacting the first spinous process SP1 and/or the second spinous process SP2. In other embodiments, the implant 27100 can be sized such that the diagonal dimension D can be greater than the spacing between the adjacent spinous processes SP1 and SP2.

Referring to the dimensions shown in FIG. 151, in some embodiments, for example, the length $L_3$ of the support member 27102 can be between 5 mm and 16 mm. In some embodiments, the length $L_3$ of the support member 27102 can be approximately 8 mm. In some embodiments, the length $L_1$ of the first retention member 27112 can be between 1 mm and 4 mm. In some embodiments, the length $L_1$ of the first retention member 27112 can be approximately 2 mm. Similarly, in some embodiments, the length $L_2$ of the second retention member 27110 can be between 1 mm and 4 mm. In some embodiments, the length $L_2$ of the second retention member 27110 can be approximately 2 mm.

In some embodiments, the height $H_3$ of the support member 27102 can be between 6 mm and 16 mm. In some embodiments, the height $H_3$ of the support member 27102 can be approximately 8 mm. In some embodiments, the height $H_1$ of the first retention member 27112 can be between 14 mm and 32 mm. In some embodiments, the height $H_1$ of the first retention member 27112 can be approximately 18 mm. Similarly, in some embodiments, the height $H_2$ of the second retention member 27110 can be between 14 mm and 32 mm. In some embodiments, the height $H_2$ of the second retention member 27110 can be approximately 18 mm. Although the height $H_1$ and the height $H_2$ are shown as being substantially equal, in other embodiments, the height $H_1$ of the first retention member 27112 can be different than the height $H_2$ of the second retention member 27110. Similarly, although the first retention member 27112 and the second retention member 27110 are shown as being positioned symmetrically about the lateral axis $L_L$ when in their respective second positions (see FIG. 152), in some embodiments, the first retention member 27112 and/or the second retention member 27110 can be positioned asymmetrically about the lateral axis $L_L$ when in their respective second positions.

Although the first retention member 27112 and the second retention member 27110 are shown as being coupled to and disposed outside of the support member 27102, in some embodiments, the first retention member 27112 and/or the second retention member 27110 can be arranged such that at least a portion thereof is disposed within the support member 27102. For example, in some embodiments, a support member can define an opening in which a portion of a first retention member and/or a second retention member is disposed. In such embodiments, the opening of the support member can be, for example, a slot at an end portion of the support member configured to receive a portion of the first retention member and/or the second retention member. In this manner, the first retention member and/or the second retention member can translate within the slot between a first position and a second position, as described above. For example, in some embodiments, an end portion of a retention member can be disposed within the support member (e.g., within the slot defined by the support member) when the retention member is in the first position. The end portion of the retention member can be disposed outside of the support member when the retention member is in the second position.

Although the implant 27100 is shown and described above as being rotated relative to the adjacent spinous processes SP1 and SP2 approximately ninety degrees into the third configuration, in some embodiments, an implant can be rotated any suitable amount to during insertion. For example, in some embodiments, an implant can be rotated between 45 degrees and 135 degrees. In other embodiments, an implant can be rotated between 5 degrees and 90 degrees. In yet other embodiments, an implant can be rotated between 5 and 175 degrees. Similarly, in some embodiments, an implant can be rotated incrementally when a retention member is translated relative to a support member of the implant.

Although the implant 27100 is shown and described as including a first retention member 27112 and a second retention member 27110, in other embodiments and implant can include only one retention member. For example, FIGS. 153-156 are schematic illustrations of an implant 27200 according to an embodiment of the invention in a first configuration, a second configuration, a third configuration and a fourth configuration, respectively. The implant 27200 includes a support member 27202 and a retention member 27212. The support member 27202 has a first end portion 27206, a second end portion 27204 and an outer surface 27216. The support member 27202 is tapered such that a size of the first end portion 27206 (e.g., the height $H_1$ as shown in FIG. 156) is less than a size of the second end portion 27204 (e.g., the height $H_2$ as shown in FIG. 156). In this manner, the outer surface 27216 of the support member 27202 includes a tapered portion 27217. As shown in FIGS. 155 and 156, at least a portion of the outer surface 27216 is configured to be disposed between a first spinous process SP1 and a second spinous process SP2.

The retention member 27212 has a first end portion 27230, a second end portion 27232 and defines a longitudinal axis $L_A$. The first end portion 27230 of the retention member 27212 has an inner surface 27236 and an outer surface 27237 opposite the inner surface 27236. Similarly, the second end portion 27232 of the retention member 27212 has an inner surface 27238 and an outer surface 27239 opposite the inner surface 27238. Although the inner surface 27236 of the first end portion 27230 and the inner surface 27238 of the second end portion 27232 are shown as forming a continuous, co-planar surface, in other embodiments, the inner surface 27236 of the first end portion 27230 can be discontinuous or in a plane different than the inner surface 27238 of the second end portion 27232. Similarly, in some embodiments, the outer surface 27236 of the first end portion 27230 can be discontinuous or in a plane different than the outer surface 27238 of the second end portion 27232.

The retention member 27212 is slidably coupled to the first end portion 27206 of the support member 27202. As indicated by the arrow RR in FIG. 153, the retention member 27212 can translate along its longitudinal axis $L_A$ between a first position (FIGS. 153-155) and a second position (FIG. 156). When the retention member 27212 is in the first position, the first end portion 27230 is spaced apart from the support member 27202 and the second end portion 27232 is adjacent the first end portion 27206 of the support member 27202. Moreover, as described in more detail herein, when the retention member 27212 is in the first position, the first end portion 27230 can contact and/or engage the first spinous process SP1 (either directly or indirectly through its surrounding tissue) to limit lateral movement of the support member 27202 along the lateral axis $L_L$ and relative to the adjacent spinous processes SP1 and SP2. When the retention member 27212 is in the second position, the first end portion 27230 is spaced apart from the support member 27202 and the second end portion 27232 is spaced apart from the support member 27202. Moreover, as described in more detail herein, when the retention member 27212 is in the second position, the first end portion 27230 can contact and/or engage the first spinous process SP1 (either directly or indirectly through its surrounding tissue) and the second end portion 27232 can be contact and/or engage the second spinous process SP2 (either directly or indirectly through its surrounding tissue). In this manner, when the retention member 27212 is in its second position, the retention member 27212 can limit lateral movement of the support member 27202 along the lateral axis $L_L$ and relative to the adjacent spinous processes SP1 and SP2.

In use, the implant 27200 can be inserted percutaneously along a lateral access passageway, as shown by the arrow RR in FIG. 153. As shown in FIG. 153, during insertion, the implant 27200 is placed in a first configuration in which the retention member 27212 is in the first position and the longitudinal axis $L_A$ of the retention member 27212 is substantially parallel to the lateral axis $L_L$. As described above, the implant 27200 is sized such that the implant 27200 can be disposed between the first spinous process SP1 and the second spinous process SP2 when the implant is in the first configuration. In other embodiments, the implant 27200 can be sized such that the implant 27200 can distract the adjacent spinous processes SP1 and SP2 during insertion.

When the implant 27200 is between the first spinous process SP1 and the second spinous process SP2, the implant 27200 can be rotated into the second configuration. As shown by the arrow SS in FIG. 154, the implant 27200 can be rotated relative to the adjacent spinous processes SP1 and SP2 about an axis substantially normal to a mid-line axis $L_M$ defined by the spinal column. The diagonal dimension D across the support member 27202 and including a portion of the retention member 27212 is such that the implant 27200 can be disposed between the first spinous process SP1 and the second spinous process SP2 when the implant is in the second configuration. Said another way, the diagonal dimension D is sized such that the implant 27200 can be rotated as shown in FIG. 154.

As shown in FIG. 155, the implant 27200 can be rotated relative to the adjacent spinous processes SP1 and SP2 approximately ninety degrees into the third configuration. When the implant 27200 is in the third configuration, the retention member 27212 is in its first position and the longitudinal axis $L_A$ of the retention member 27212 is substantially parallel to the mid-line axis $L_M$. Additionally, when the implant 27200 is in the third configuration, the inner surface 27236 of the first end portion 27230 of the retention member 27212 can contact and/or engage the first spinous process SP1, either directly or through surrounding tissue. Said another way, when the implant 27200 is in the third configuration, the inner surface 27236 of the first end portion 27230 of the retention member 27212 is between the outer surface 27237 of the first end portion 27230 of the retention member 27212 and the first spinous process SP1.

Moreover, when the implant 27200 is in the third configuration, the tapered portion 27217 of the outer surface 27216 of the support member 27202 is adjacent the first spinous process SP1 and/or the second spinous process SP2. In some embodiments, the tapered portion 27217 of the outer surface 27216 can substantially contact a portion of the first spinous process SP1 and/or the second spinous process SP2 (either directly or indirectly through surrounding tissue) when the implant 27200 is in the third configuration.

After the implant 27200 is placed in the third configuration, the retention member 27212 can be moved along its longitudinal axis $L_A$ from the first position to the second position, as indicated by the arrow TT in FIG. 156. Said another way, the retention member 27212 can be moved from the first position to the second position along an axis substantially parallel to the mid-line axis $L_M$. In this manner, the implant can be placed into the fourth configuration, as shown in FIG. 156.

When the implant 27200 is in the fourth configuration, the first end portion 27230 of the retention member 27212 is spaced apart from the support member 27202 and the second end portion 27232 of the retention member 27212 is spaced apart from the support member 27202. Moreover, when the implant 27200 is in the fourth configuration, the first end portion 27230 can contact and/or engage the first spinous process SP1 and the second end portion 27232 can contact and/or engage the second spinous process SP2. Said another way, when the implant 27200 is in the fourth configuration, the inner surface 27236 of the first end portion 27230 of the retention member 27212 is between the outer surface 27237 of the first end portion 27230 of the retention member 27212 and the first spinous process SP1. Similarly, the inner surface 27238 of the second end portion 27232 of the retention member 27212 is between the outer surface 27239 of the second end portion 27232 of the retention member 27212 and the second spinous process SP2. Additionally, when the implant 27200 is in the fourth configuration, the tapered portion 27217 of the outer surface 27216 remains between the first spinous process SP1 and the second spinous process SP2. In this manner, when the implant 27200 is in the fourth configuration, the retention member 27212 and/or the tapered portion 27217 can limit lateral movement of the support member 27202 along the lateral axis $L_L$ and relative to the adjacent spinous processes SP1 and SP2.

Although the support member 27206 is shown and described as being asymmetrically tapered, in other embodiments, a support member can be symmetrically tapered. Said another way, although the portion of the outer surface 27216 adjacent the first spinous process SP1 (see FIGS. 155 and 156) is shown as having a different amount of taper than the tapered portion 27217, in other embodiments, the portion of the support member adjacent the first spinous process SP1 can have the same taper as the portion of the support member adjacent the second spinous process SP2.

Although the support member 27206 is shown and described as being tapered linearly, in other embodiments, a support member can have a curved taper. Similarly, in some embodiments, an end portion of a retention member can be tapered. For example, in some embodiments an end portion of a retention member can include a pointed tip such that the implant can define its own access passageway when inserted into the body.

FIG. 157 is a flow chart illustrating a method 27300 according to an embodiment of the invention. The method includes inserting at least a portion of an implant between a first spinous process and a second spinous process, 27304. The implant includes a support member and a retention member movably coupled to the support member. The implant can be any suitable implant of the types shown and described above, such as for example, the implant 27100.

In some embodiments, the inserting can include inserting the implant percutaneously via a lateral access path. In some embodiments, the inserting can include positioning the implant such that a longitudinal axis of the retention member is substantially parallel to a lateral axis defined between the spinous processes. In some embodiments, the implant can be inserted using a curved tool and/or a guide member, as described herein. In some embodiments, the method can include optionally distracting the adjacent spinous processes before the disposing, 27302.

The implant is then rotated relative to the first spinous process and the second spinous process about an axis substantially normal to a mid-line axis defined by a spinal column, 27306. In some embodiments, for example, the implant is rotated approximately ninety degrees relative to the first spinous process and the second spinous process. In some embodiments, for example, the implant is rotated such that an inner surface of an end portion of the retention member is between an outer surface of the end portion of the retention member and the first spinous process.

The retention member is translated relative to the support member, 27308. In some embodiments, the retention member is translated relative to the support member in a direction substantially parallel to the mid-line axis defined by a spinal column. In some embodiments, the retention member is translated relative to the support member along the longitudinal axis of the retention member. In some embodiments, the retention member is translated such that an inner surface of a second end portion of the retention member is between an outer surface of the second end portion of the retention member and the second spinous process.

In some embodiments, the method can include optionally maintaining a position of the retention member relative to the support member, 27310. The position of the retention member can be maintained, for example, by moving a locking member such that a portion of the locking member is received within a recess defined by the support member and/or the retention member, as described above.

FIG. 158 is a flow chart illustrating a method 27400 according to an embodiment of the invention. The method includes inserting an implant having a first member, a second member and a third member such that at least a portion of the first member is disposed between a first spinous process and a second spinous process, 27404. The implant can be any suitable implant of the types shown and described above, such as for example, the implant 27100.

In some embodiments, the inserting can include inserting the implant percutaneously via a lateral access path. In some embodiments, the inserting can include positioning the implant such that a longitudinal axis of the retention member is substantially parallel to a lateral axis defined between the spinous processes. In some embodiments, the implant can be inserted using a curved tool and/or a guide member, as described herein. In some embodiments, the method can include optionally distracting the adjacent spinous processes before the disposing, 27402.

The implant is then rotated relative to the first spinous process and the second spinous process such that an inner surface the second member is between an outer surface the second member and the first spinous process and an inner surface of the third member is between an outer surface of the third member and the second spinous process, 27406. In some embodiments, for example, the implant is rotated about an axis substantially normal to a mid-line axis defined by a spinal column. In some embodiments, for example, the implant is rotated approximately ninety degrees relative to the first spinous process and the second spinous process.

The second member is translated relative to the first member, 27408. In some embodiments, the second member is translated along a longitudinal axis of the second member substantially parallel to the mid-line axis defined by a spinal column. In some embodiments, the second member is translated such that an inner surface of the second member is between an outer surface of the second member and the second spinous process.

In some embodiments, the method optionally includes translating the third member relative to the first member, 27410. In some embodiments, the third member is translated along a longitudinal axis of the third member substantially parallel to the mid-line axis. In some embodiments, the third member is translated such that an inner surface of the third member is between an outer surface of the third member and the first spinous process.

In some embodiments, the method can include optionally maintaining a position of the second member and/or the third member relative to the support member, 27412. The position of the second member and/or the third member can be maintained by a locking mechanism, as described above.

The various implants, deployment/insertion tools, and guide members described herein can be constructed with various biocompatible materials such as, for example, titanium, titanium alloyed, surgical steel, biocompatible metal alloys, stainless steel, plastic, polyetheretherketone (PEEK), carbon fiber, ultra-high molecular weight (UHMW) polyethylene, biocompatible polymeric materials, etc. The material of a central portion of the implant can have, for example, a compressive strength similar to or higher than that of bone. In one embodiment, the central portion of the implant, which is placed between the two adjacent spinous processes, is configured with a material having an elastic modulus higher than the elastic modulus of the bone, which forms the spinous processes. In another embodiment, the central portion of the implant is configured with a material having a higher elastic modulus than the materials used to configure the distal and proximal portions of the implant. For example, the central portion of the implant may have an elastic modulus higher than bone, while the proximal and distal portions have a lower elastic modulus than bone. In yet another embodiment, where the implant is configured with an outer shell and an inner core. The outer shell can be configured with material having a higher elastic modulus than the inner core (e.g., outer shell is made with titanium alloyed, while the inner core is made with a polymeric material). Alternatively, the outer shell can be configured with a material having a lower elastic modulus than the inner core (e.g., the outer shell is made with a polymeric material while the inner core is made with a titanium alloyed material).

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

For example, although the embodiments above are primarily described as being spinal implants configured to be positioned between adjacent spinous processes, in alternative embodiments, the implants are configured to be positioned adjacent any bone, tissue or other bodily structure where it is desirable to maintain spacing while preventing axial or longitudinal movement of the implant.

Although the medical devices are shown and described as including an implant and/or a deployment tool, in some embodiments a kit can include any number of implants and/or any number of deployment tools and/or any number of guide members as described above. For example, a kit can include an implant and two deployment tools, one deployment tool configured to be used to move the implant from a collapsed configuration to an expanded configuration, and another deployment tool configured to be used to move the implant from the expanded configuration to the collapsed configuration. Alternatively, a kit can include a single deployment tool have multiple engaging portions as described herein, that can be releasably coupled to an elongate member of a deployment tool. For example, one type or style of engaging portion can be used to move the implant from a collapsed configuration to an expanded configuration, and another type or style of engaging portion can be used to move the implant from the expanded configuration to the collapsed configuration. The kit can include engaging portions having one of a variety of different shapes and sizes, such that a user can select a particular engaging portion(s) for use in a particular application. In another example, a kit can include more than one guide member, each having a different length to accommodate different needs and/or uses.

Similarly, although various embodiments have been described as having particular features and/or combinations of components, other embodiments are possible having a combination of any features and/or components from any of embodiments as discussed above. For example, one such embodiment includes an implant having a locking mechanism of the type shown and described above with reference to FIGS. 95-99 and two retention members configured to rotate about an axis of rotation substantially normal to a longitudinal axis of the implant, as shown and described above with reference to FIGS. 124-127.

Although various implants have been shown and described above as having a first configuration and a second configuration, in some embodiments, an implant can include three or more configurations. For example, in some embodiments, an implant can have a first configuration, in which the implant can be inserted between the spinous processes unimpeded by a retention member of the implant, a second configuration, in which lateral movement of the implant is limited by the retention member and a third configuration in which the implant can move in one lateral direction, but not the other.

Similarly, in some embodiments, a deployment tool, an expansion device and/or an insertion tool can be configured to perform any combination of functions described herein. For example, in some embodiments, a deployment tool, an expansion devices and/or an insertion tool can be configured to insert a spinal implant into a body, move a spinal implant between a retracted configuration and an expanded configuration within a body, reposition a spinal implant within the body and/or remove a spinal implant within the body. In some embodiments, a deployment tool, an expansion device and/or an insertion tool can be configured to perform only a single function, such as, for example, removing a spinal implant from body. In other embodiments, a kit can include a deployment tool, an expansion device and/or an insertion tool along with various implements so that the deployment tool, expansion device and/or insertion tool can be re-configured to perform any combination of functions described herein.

What is claimed is:

1. An apparatus, comprising:
a support member extending between a first end surface and a second end surface and including a portion configured to be disposed between adjacent spinous processes;
a first retention member having a first end portion, a second end portion, and a central portion; the first retention member movable relative to the support member between a retracted configuration and a deployed configuration; the first retention member configured to limit lateral movement of the support member relative to the adjacent spinous processes in at least one direction when the first retention member is in the deployed configuration; the central portion being spaced apart from the first end surface of the support member when the first retention member is in its retracted configuration; at least one of the first end portion and the second end portion being in contact with the first end surface of the support member when the first retention member is in its retracted configuration;
the central portion being in contact with the first end surface of the support member when the first retention member is in its deployed configuration; the at least one of the first end portion and the second end portion being spaced apart from the first end surface of the support member when the first retention member is in its deployed configuration;
a second retention member movable relative to the support member between a retracted configuration and a deployed configuration; the second retention member configured to limit lateral movement of the support member relative to the adjacent spinous processes in a second direction, opposite the first direction, when the second retention member is in its deployed configuration; the second retention member disposed proximally relative to the support member and spaced from the first retention member by the support member;
wherein the first end portion and the second end portion are spaced apart by a first distance when the first retention member is in its retracted configuration and spaced apart by a second distance when the first retention member is in its deployed configuration; the second distance being greater than the first distance;
a biasing member disposed within the support member and extending between the first end surface and the second end surface of the support member and operatively connected to the first and second retention members and biasing the first and second retention members toward their deployed configurations when the first and second retention members are in their retracted configurations.

2. The apparatus of claim 1, wherein a central portion of the second retention member is in contact with the second end surface of the support member when the second retention member is in its deployed configuration.

3. The apparatus of claim 1, wherein the second distance is greater than a width of the support member.

4. The apparatus of claim 1, wherein the first end surface of the support member includes a retention portion configured to engage at least one of the first end portion and the second end portion when the first and second retention members are in their retracted configurations.

5. The apparatus of claim 1, wherein the first end portion of the first retention member is rotatably coupled to the second end portion of the first retention member.

6. The apparatus of claim 1, wherein the biasing member has a first portion and a second portion; the first portion coupled to the central portion of the first retention member; the second portion disposed through an aperture formed in the second end surface of the support member.

7. The apparatus of claim 1, wherein the central portion of the first retention member is configured to receive a portion of an insertion tool configured to move the first and second retention members between their retracted configurations and their deployed configurations.

8. The apparatus of claim 1, wherein the support member and the first and second retention members are configured to be collectively inserted percutaneously via a lateral incision when the first and second retention members are in their retracted configurations.

9. The apparatus of claim 1, wherein the first and second retention members are configured to be moved between their retracted configurations and their deployed configurations when the portion of the support member is disposed between the adjacent spinous processes.

10. The apparatus of claim 1:
wherein the support member has a longitudinal axis;
wherein the first end surface is a first distal longitudinal endface and the second end surface is a second distal longitudinal endface;
wherein the first and second retention members, when in their retracted configurations, are disposed partially distally of the first and second distal longitudinal endface, respectively, but entirely inside an area of the distal longitudinal endface projected on a plane normal to the longitudinal axis;
wherein the first and second retention members, when in their deployed configurations, are disposed partially outside the area of the first and second distal longitudinal endface, respectively and projected on the plane normal to the longitudinal axis.

11. The apparatus of claim 1 wherein the support member has a longitudinal axis and wherein the biasing member comprises a lumen extending parallel to the longitudinal axis.

12. An apparatus, comprising:
a support member including a portion configured to be disposed between adjacent spinous processes;
a first retention member movable relative to the support member between a retracted configuration and a deployed configuration; the first retention member configured to limit lateral movement of the support member relative to the adjacent spinous processes in a first direction when the first retention member is in its deployed configuration; the first retention member disposed distally relative to the support member; the first retention member has a first end portion, a second end portion, and a central portion disposed therebetween; the central portion being spaced apart from a distal end surface of the support member when the first retention member is in its retracted configuration; at least one of the first end portion and the second end portion being in contact with the distal end surface of the support member when the retention member is in its retracted configuration;
the central portion being in contact with the distal end surface of the support member when the first retention member is in its deployed configuration; the at least one of the first end portion and the second end portion being spaced apart from the distal end surface of the support member when the first retention member is in its deployed configuration;
a second retention member movable relative to the support member between a retracted configuration and a deployed configuration; the second retention member configured to limit lateral movement of the support member relative to the adjacent spinous processes in a second direction, opposite the first direction, when the second retention member is in its deployed configuration; the second retention member disposed proximally relative to the support member and spaced from the first retention member by the support member;
a biasing member having a first portion and a second portion; the first portion coupled to the first retention member; the second portion disposed within the support member; the biasing member configured to bias the first and second retention members toward each other and toward their deployed configurations when the retention members are in their retracted configurations.

13. The apparatus of claim 12, wherein the support member and the first and second retention members are collectively configured to receive a portion of an insertion tool configured to move the first and second retention members between their retracted configurations and their deployed configurations.

14. The apparatus of claim 12, wherein the support member extends between a first end surface and a second end surface.

15. The apparatus of claim 14, wherein the support member has a longitudinal axis, wherein the first end surface is a first distal longitudinal endface and the second end surface is a second distal longitudinal endface.

16. The apparatus of claim 15, wherein each distal longitudinal endface of the support member comprises first and second slots spaced from one another; wherein the first retention member extends into the first slot when the first retention member is in its retracted configuration; wherein the second retention member extends into the second slot when the second retention member is in its retracted configuration.

17. The apparatus of claim 12, wherein the support member and the first and second retention members are configured to be collectively inserted percutaneously via a lateral incision when the first and second retention members are in their retracted configurations.

* * * * *